United States Patent [19]

Hlavka et al.

[11] Patent Number: 5,530,117

[45] Date of Patent: Jun. 25, 1996

[54] 7-SUBSTITUTED-9-SUBSTITUTED AMINO-6-DEMETHYL-6-DEOXYTETRACYCLINES

[75] Inventors: Joseph J. Hlavka, Tuxedo Park; Phaik-Eng Sum, Pomona, both of N.Y.; Yakov Gluzman, Upper Saddle River, N.J.; Ving J. Lee, Monsey; Adma A. Ross, Airmont, both of N.Y.

[73] Assignee: American Cyanamid Company, Wayne, N.J.

[21] Appl. No.: 455,923

[22] Filed: May 31, 1995

Related U.S. Application Data

[62] Division of Ser. No. 286,096, Aug. 4, 1994, which is a continuation of Ser. No. 926,091, Aug. 13, 1992, abandoned, which is a continuation-in-part of Ser. No. 771,576, Oct. 4, 1991, abandoned.

[51] Int. Cl.$^6$ ............ C07D 205/08; C07D 265/30; C07D 211/06; C07D 293/10

[52] U.S. Cl. ............ 540/362; 544/106; 544/162; 546/195; 548/124; 548/125; 548/126; 548/127; 548/146; 548/152; 548/207; 548/206; 548/214; 548/215; 548/217; 548/255; 548/257; 548/121; 548/247; 548/248; 548/356.5; 548/262.2; 548/268.2; 548/300.4; 548/528; 549/70; 549/72; 549/75; 549/487; 549/491; 549/496; 552/205

[58] Field of Search ............ 540/362; 544/106, 544/162; 546/195; 548/124, 125, 126, 127, 214, 215, 217, 146, 152, 255, 257, 300.4, 262.2, 268.2, 206, 207, 121, 247, 248, 356.5, 528; 549/70, 72, 75, 487, 491, 496; 552/205

[56] References Cited

U.S. PATENT DOCUMENTS

| | | | |
|---|---|---|---|
| Re. 26,253 | 8/1967 | Petisi | 260/559 |
| Re. 26,271 | 9/1967 | Boothe | 260/559 |
| 2,482,055 | 9/1949 | Duggar | 552/203 |
| 2,997,471 | 8/1961 | Cheney et al. | 260/247.2 |
| 3,007,965 | 11/1961 | Crowich | 260/559 |
| 3,043,875 | 7/1962 | Beereboom | 260/559 |
| 3,200,149 | 8/1965 | Blackwood | 260/559 |
| 3,226,436 | 12/1965 | Petisi | 552/205 |
| 3,338,963 | 8/1967 | Petisi | 260/559 |
| 3,341,585 | 9/1967 | Bitha | 260/559 |
| 3,345,410 | 10/1967 | Winterbottom et al. | 260/559 |
| 3,360,557 | 12/1967 | Shu | 260/559 |
| 3,360,561 | 12/1967 | Zambrano | 260/559 |
| 3,502,696 | 3/1970 | Conover | 260/351 |
| 3,509,184 | 4/1970 | Conover et al. | 260/351 |
| 3,515,731 | 6/1970 | Conover | 260/351 |
| 3,518,306 | 6/1970 | Martell | 260/559 |
| 3,697,552 | 10/1972 | Conover et al. | 260/351 |
| 3,772,363 | 11/1973 | Conover et al. | 260/351 |
| 3,829,453 | 8/1974 | Conover et al. | 260/351 |
| 3,849,493 | 11/1974 | Conover et al. | 260/559 |
| 3,862,225 | 1/1975 | Conover et al. | 260/559 |
| 5,021,407 | 6/1991 | Levy | 514/154 |
| 5,240,272 | 5/1995 | Sum, et al. | 544/63 |
| 5,248,797 | 9/1993 | Sum | 552/205 |
| 5,281,628 | 1/1994 | Hlavka, et al. | 514/510 |
| 5,284,963 | 2/1994 | Sum et al. | 552/205 |
| 5,328,902 | 7/1994 | Sum et al. | 514/152 |
| 5,380,888 | 1/1995 | Sum et al. | 552/205 |
| 5,386,041 | 1/1995 | Sum et al. | 552/205 |
| 5,401,729 | 3/1995 | Sum et al. | 514/152 |
| 5,430,162 | 7/1995 | Sum et al. | 552/205 |

OTHER PUBLICATIONS

Chopra, Handbook of Experimental Pharmacology, 78, pp. 317–392, Springer–Verlag (1985).
Levy, Antimicrobial Agents & Chemotherapy, 33(8), pp. 1373–1374 (Aug. 1989).
Salyers, Molecular Microbiology, 4(1), pp. 151–156 (1990).
Boothe, et al, J. Am. Chem. Soc., 82, pp. 1253–1254 (1960).
Spencer, et al, J. Med. Chem., 6, pp. 405–407 (1963).

Primary Examiner—Kimberly J. Prior
Attorney, Agent, or Firm—T. S. Szatkowski

[57] ABSTRACT

The disclosure is drawn to novel 7-substituted-9-(substituted amino)-6-demethyl-6-deoxytetracycline compounds. These compounds are useful to treat infections caused by a wide spectrum of bacterial organisms, including those which are resistant to tetracycline.

8 Claims, No Drawings

7-SUBSTITUTED-9-SUBSTITUTED AMINO-6-DEMETHYL-6-DEOXYTETRACYCLINES

This is a divisional of copending application Ser. No. 08/286,096 filed on Aug. 4, 1994 which is a continuation of Ser. No. 07/926,091 filed Aug. 13, 1992 now abandoned which is a continuation in part of Ser. No. 07/771,576, filed on Oct. 4, 1991 now abandoned for NOVEL 7-SUBSTITUTED-9-SUBSTITUTED AMINO-6-DEMETHYL-6-DEOXYTETRACYCLINES.

BACKGROUND OF THE INVENTION

1. Field of the Invention

The invention relates to novel [4S-(4,12aα)]-4-(dimethylamino)-7-(substituted)-9 -(substituted amino)-1,4,4a,5,5a, 6,11,12a-octahydro-3,10,12,12a-tetrahydroxy-1,11-dioxo-2 -naphthacenecarboxamides hereinafter called 7-(substituted)-9-(substituted amino)-6-demethyl-6-deoxytetracyclines, which exhibit antibiotic activity against a wide spectrum of organisms including organisms which are resistant to tetracyclines and are useful as antibiotic agents. The invention also relates to novel 7-(substituted)-9-(substituted amino)-6-demethyl-6-deoxytetracycline intermediates useful for making the novel compounds of the present invention and to novel methods for producing the novel compounds and intermediate compounds.

2. Description of the Prior Art

A variety of tetracycline antibiotics have been synthesized and described for the treatment of infectious diseases in man and animals since 1947. Tetracyclines inhibit protein synthesis by binding to the 30S subunit of the bacterial ribosome preventing binding of aminoacyl RNA (Chopra, Handbook of Experimental Pharmacology, Vol. 78, 317–392, Springer-Verlag, 1985). Resistance to tetracyclines has emerged among many clinically important microorganisms which limit the utility of these antibiotics. There are two major mechanisms of bacterial resistance to tetracyclines: a) energy-dependent efflux of the antibiotic mediated by proteins located in the cytoplasmic membrane which prevents intracellular accumulation of tetracycline (S. B. Levy, et al., Antimicrob. Agents Chemotherapy 33, 1373–1374 (1989); and b) ribosomal protection mediated by a cytoplasmic protein which interacts with the ribosome such that tetracycline no longer binds or inhibits protein synthesis (A. A. Salyers, B. S. Speers and N. B. Shoemaker, Mol. Microbiol, 4:151–156, 1990). The efflux mechanism of resistance is encoded by resistance determinants designated tetA-tetL. They are common in many Gram-negative bacteria (resistance genes Class A–E), such as Enterobacteriaceae, Pseudomonas, Haemophilus and Aeromonas, and in Gram-positive bacteria (resistance genes Class K and L), such as Staphylococcus, Bacillus and Streptococcus. The ribosomal protection mechanism of resistance is encoded by resistance determinants designated TetM, N and O, and is common in Staphylococcus, Streptococcus, Campylobacter, Gardnerella, Haemophilus and Mycoplasma (A. A. Salyers, B. S. Speers and N. B. Shoemaker, Mol. Microbiol, 4:151–156 1990).

A particularly useful tetracycline compound is 7-(dimethylamino)-6-demethyl-6-deoxytetracycline, known as minocycline (see U.S. Pat. Nos. 3,148,212, Re. 26,253 and 3,226,436 discussed below). However, strains harboring the tetB (efflux in gram-negative bacteria) mechanism, but not tetK (efflux in Staphylococcus) are resistant to minocycline. Also, strains carrying tetM (ribosomal protection) are resistant to minocycline. This invention describes the synthesis of novel tetracycline compounds which demonstrate significant in vitro and in vivo activity vs. tetracycline and minocycline susceptible strains and some tetracycline and minocycline resistant strains, that is, those harboring the tetM (ribosomal protection) resistance determinants.

Duggar, U.S. Pat. No. 2,482,055, discloses the preparation of Aureomycin® (I) by fermentation which have antibacterial activity. Growich et al., U.S. Pat. No. 3,007,965, disclose improvements to the fermentation preparation of I. Neither of these patents teaches or suggests the 6-demethyl-6-deoxytetracyclines.

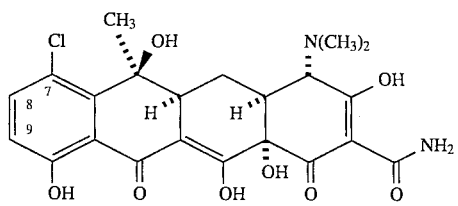

Beereboom et al., U.S. Pat. No. 3,043,875 discloses tetracycline derivatives of the formulae (II) and (III) where R is H or CH$_3$; R$_1$ is H and when R is CH$_3$, OH; R$_2$ is H and N(CH$_3$)$_2$; X and Y are halogen; Z is H and halogen and B is bromo, chloro and iodo, which have antibacterial activity. This patent does not teach or suggest the inclusion of both di(lower alkyl)amino or mono(lower alkyl)amino substituents (at Y or Z) and an amino function (at B).

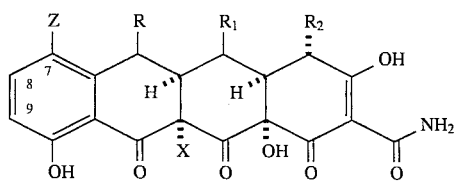

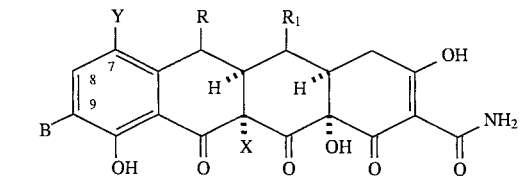

Boothe et al., U.S. Pat. No. 3,148,212, reissued as U.S. Pat. No. Re. 26,253, and Petisi et al., U.S. Pat. No. 3,226, 436, discloses tetracycline derivatives of the formula (IV) wherein R is hydrogen or methyl and R$_1$ and R$_2$ is hydrogen, mono(lower alkyl)amino or di(lower alkyl)amino with the proviso that R$_1$ and R$_2$ cannot both be hydrogen, which are useful for treating bacterial infections. This patent does not teach or suggest the inclusion of a 9-amino functionality (at R$_2$).

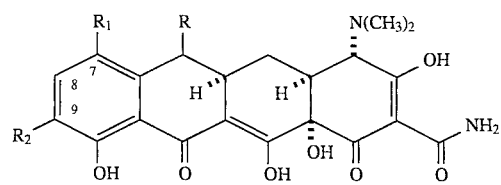

Blackwood et al., U.S. Pat. No. 3,200,149 discloses tetracycline derivatives of the formulae (V) and (VI) and reduction products thereof wherein Y may be hydrogen or hydroxyl, X may be hydrogen, chloro, iodo, or bromo, X$_1$ may be hydrogen, amino, and lower alkanoylamino, X$_2$ may be hydrogen or nitro and Z is chloro or fluoro which possess microbiological activity. This patent does not teach or suggest the inclusion of both a di(lower alkyl)amino group (at X) and another nitrogen functionality (at $X_1$) on the 6-demethyl-6-deoxytetracycline nucleus.

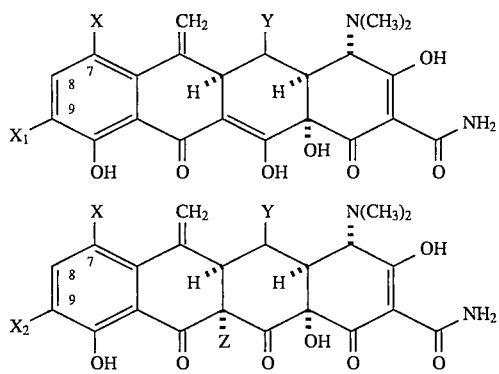

Petisi et al., U.S. Pat. No. 3,338,963 discloses tetracycline compounds of the formula (VII) wherein $R_1$ and $R_2$ are hydrogen, nitro, amino, formylamino, acetylamino, p-(dihydroxyboryl)benzoylamino, p-(aminobenzenesulfonyl)amino, chlorine, bromine or diazonium with the proviso that $R_1$ and $R_2$ may not both be hydrogen and with the further proviso that when $R_1$ is chlorine or bromine, $R_2$ may not be hydrogen and vice versa, $R_3$ is hydrogen or methyl and $R_4$ is hydrogen or hydroxy, which have broad-spectrum antibacterial activity. This patent does not teach or suggest the inclusion of both di(lower alkyl)amino or mono(lower alkyl)amino substituents (at $R_1$) and amino substituents (at $R_2$).

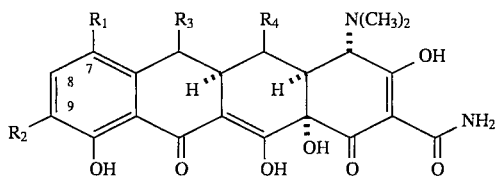

Bitha et al., U.S. Pat. No. 3,341,585 discloses tetracycline compounds of the formula (VIII) wherein $R_5$ is hydrogen, α-hydroxy or β-hydroxy, $R_6$ is α-methyl or β-methyl, and $R_7$ and $R_9$ are each hydrogen, mono(lower alkyl)amino or di(lower alkyl)amino with the proviso that $R_7$ and $R_9$ cannot both be hydrogen and with the further proviso that when $R_5$ is hydrogen then $R_6$ is α-methyl. A preferred embodiment of the general formula (VIII) is when $R_5$ is α-hydroxy or β-hydroxy, $R_6$ is α-methyl or β-methyl, $R_7$ is di(lower alkyl)amino and $R_9$ is hydrogen, which have broad-spectrum antibacterial activity. This patent does not teach or suggest the inclusion of both di(lower alkyl)amino or mono-(lower alkyl)amino substituents (at $R_7$) and amino substituents (at $R_9$).

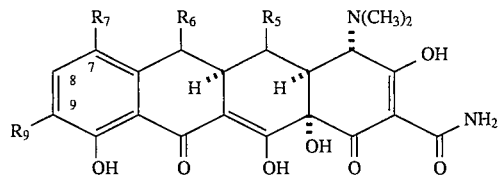

Shu, U.S. Pat. No. 3,360,557 discloses 9-hydroxytetracyclines of the formula (IX) wherein $R_1$ is hydrogen or hydroxy, $R_2$ is hydrogen or hydroxy, $R_3$ is hydrogen or methyl, $R_2$ and $R_3$ taken together is methylene, and $R_4$ is hydrogen, halogen, nitro, amino, mono(lower alkyl)amino or di(lower alkyl)amino, which have been found to possess antibacterial activity. This patent is restricted to 9-hydroxytetracyclines and does not teach or suggest the presently claimed compounds.

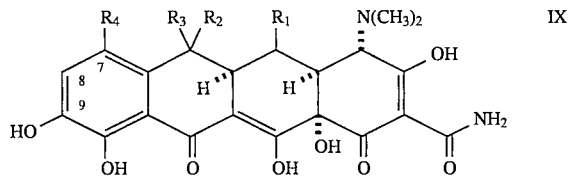

Zambrano, U.S. Pat. No. 3,360,561 discloses a process for preparing 9-nitrotetracyclines of the formula (X) wherein $R_5$ is hydrogen or hydroxy, $R_1$ is hydrogen or hydroxy, $R_6$ is hydrogen or methyl, $R_1$ and $R_6$ taken together is methylene, $R_7$ is hydrogen, chloro or nitro and $R_9$ is hydrogen or nitro with the proviso that $R_7$ and $R_9$ cannot both be hydrogen. This patent does not teach or suggest the inclusion of both a di(lower alkyl)amino or mono(lower alkyl)amino substituent (at $R_7$) and an amino functionality (at $R_9$).

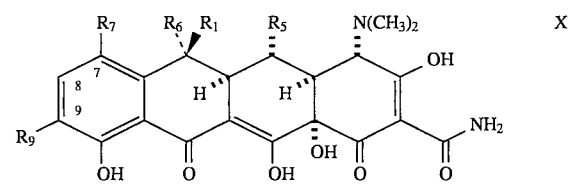

Martell et al., U.S. Pat. No. 3,518,306 discloses 7-and/or 9-(N-nitrosoalkylamino)-6-demethyl-6-deoxytetracyclines of the formula (XI) which possess in vivo antibacterial activity. This patent does not teach or suggest the inclusion of both a di(lower alkyl)amino or mono(lower alkyl)amino substituent (at C-7) and an amino functionality (at C-9).

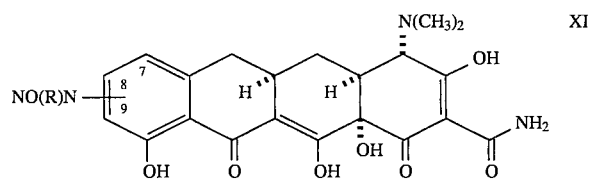

In U.S. Pat. No. 5,021,407, a method of overcoming the resistance of tetracycline resistant bacteria is disclosed. The method involves utilizing a blocking agent compound in conjunction with a tetracycline type antibiotic. This patent does not disclose novel tetracycline compounds which themselves have activity against resistant organisms.

In summary, none of the above patents teach or suggest the novel compounds of this application. In addition, none of the above patents teach or suggest novel tetracycline compounds having activity against tetracycline and minocycline resistant strains as well as strains which are normally susceptible to tetracyclines.

SUMMARY OF THE INVENTION

This invention is concerned with novel 7-(substituted)-9-(substituted amino)-6-demethyl-6-deoxytetracyclines, represented by formula I and II, which have antibacterial activity; with method of treating infectious diseases in warm blooded animals employing these new compound; with methods of treating or controlling veterinary diseases; with pharmaceutical preparations containing these compounds; with novel intermediate compounds and processes for the production of these compounds. More particularly, this invention is concerned with compounds of formula I and II which have enhanced in vitro and in vivo antibiotic activity against tetracycline resistant strains as well as a high level of activity against strains which are normally susceptible to tetracyclines.

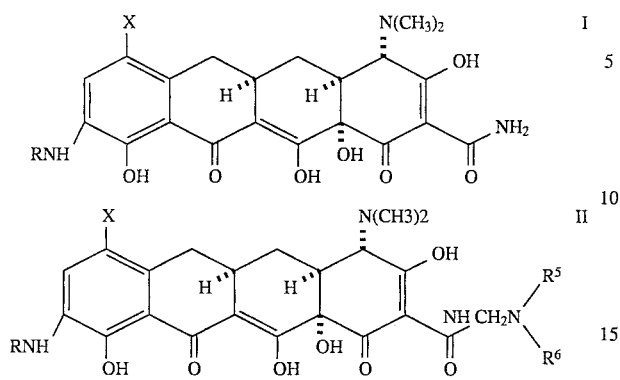

In formula I and II, X is selected from amino, $NR^1R^2$, or halogen; the halogen is selected from bromine, chlorine, fluorine or iodine; and when $X=NR^1R^2$ and $R^1$=hydrogen, $R^2$=methyl, ethyl, n-propyl, 1-methylethyl, n-butyl, 1-methylpropyl, 2-methylpropyl or 1,1-dimethylethyl; and when $R^1$=methyl or ethyl, $R^2$=methyl, ethyl, n-propyl, 1-methylethyl, n-butyl, 1-methylpropyl or 2-methylpropyl; and when $R^1$=n-propyl, $R^2$=n-propyl, 1-methylethyl, n-butyl, 1-methylpropyl or 2-methylpropyl; and when $R^1$=1-methylethyl, $R^2$=n-butyl, 1-methylpropyl or 2-methylpropyl; and when $R^1$=n-butyl, $R^2$=n-butyl, 1-methylpropyl or 2-methylpropyl; and when $R^1$=1-methylpropyl, $R^2$=2-methylpropyl; R is selected from $R^4(CH_2)_nCO—$ or $R^4(CH_2)_nSO_2—$; and when $R=R^4(CH_2)_nCO—$ and n=0, $R^4$ is selected from hydrogen; amino; monosubstituted amino selected from straight or branched ($C_1$–$C_6$)alkylamino, cyclopropylamino, cyclobutylamino, benzylamino or phenylamino; disubstituted amino selected from dimethylamino, diethylamino, ethyl(1-methylethyl)amino, monomethylbenzylamino, piperidinyl, morpholinyl, 1-imidazolyl, 1-pyrrolyl, 1-(1,2,3-triazolyl) or 4-(1,2,4-triazolyl); straight or branched ($C_1$–$C_4$)alkyl group selected from methyl, ethyl, n-propyl, 1-methylethyl, n-butyl, 1-methylpropyl, 2-methylpropyl or 1,1-dimethylethyl; ($C_3$–$C_6$)cycloalkyl group selected from cyclopropyl, cyclobutyl, cyclopentyl or cyclohexyl; substituted ($C_3$–$C_6$)cycloalkyl group (substitution selected from ($C_1$–$C_3$)alkyl, cyano, amino or ($C_1$–$C_3$)acyl); ($C_6$–$C_{10}$)aryl group selected from phenyl, α-naphthyl or β-naphthyl; substituted ($C_6$–$C_{10}$)aryl group (substitution selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino or carboxy); ($C_7$–$C_9$)aralkyl group selected from benzyl, 1-phenylethyl, 2-phenylethyl or phenylpropyl; α-amino-($C_1$–$C_4$)alkyl group selected from aminomethyl, α-aminoethyl, α-aminopropyl or α-aminobutyl; carboxy($C_2$–$C_4$)alkylamino group selected from aminoacetic acid, α-aminobutyric acid or α-aminopropionic acid and their optical isomers; ($C_7$–$C_9$)aralkylamino group such as phenylglycyl; ($C_1$–$C_4$)alkoxycarbonylamino substituted ($C_1$–$C_4$)alkyl group, substitution selected from phenyl or p-hydroxyphenyl; α-hydroxy($C_1$–$C_3$)alkyl group selected from hydroxymethyl, α-hydroxyethyl or α-hydroxy-1-methylethyl or α-hydroxypropyl; α-mercapto($C_1$–$C_3$)alkyl group selected from mercaptomethyl, α-mercaptoethyl, α-mercapto-1-methylethyl or α-mercaptopropyl; halo($C_1$–$C_3$)alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-bromoethyl or 2-iodoethyl; a heterocycle group selected from a five membered aromatic or saturated ring with one N, O, S or Se heteroatom optionally having a benzo or pyrido ring fused thereto:

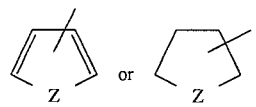

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

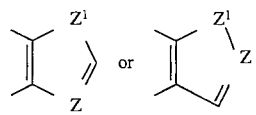

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

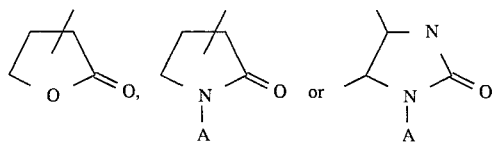

(A is selected from hydrogen; straight or branched ($C_1$–$C_4$)alkyl; $C_6$-aryl; substituted $C_6$-aryl (substitution selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino or carboxy); ($C_7$–$C_9$)aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N, O, S or Se heteroatoms such as pyridyl, pyridazinyl, pyrazinyl, sym-triazinyl, unsym-triazinyl, pyrimidinyl or ($C_1$–$C_3$)alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl; acyl or haloacyl group selected from acetyl, propionyl, chloroacetyl, trifluoroacetyl, ($C_3$–$C_6$)cycloalkylcarbonyl such as cyclopropylcarbonyl, cyclobutylcarbonyl, cyclopentylcarbonyl, cyclohexylcarbonyl, (2,3-dimethylcyclopropyl)carbonyl, (1,2-dimethylcyclopropyl)carbonyl, (2-ethylcyclopropyl)carbonyl, (2-methylcyclopentyl)carbonyl or (3-ethylcyclobutyl)carbonyl, ($C_6$–$C_{10}$)aroyl selected from benzoyl or naphthoyl, halo substituted ($C_6$–$C_{10}$)aroyl such as pentafluorobenzoyl, 4-chlorobenzoyl, 3-bromobenzoyl or 3,4-difluorobenzoyl, ($C_1$–$C_4$)alkylbenzoyl such as 4-toluoyl, 2-toluoyl or 4-(1-methylethyl)benzoyl, or (heterocycle)carbonyl, the heterocycle selected from a five membered aromatic or saturated ring with one N, O, S or Se heteroatom optionally having a benzo or pyrido ring fused thereto:

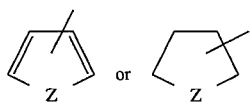

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

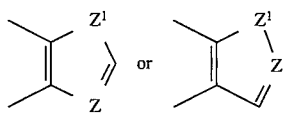

Z or Z¹ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

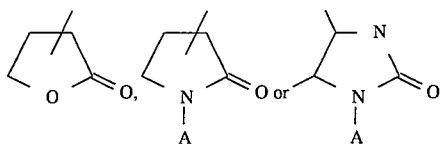

(A is selected from hydrogen; straight or branched $(C_1–C_4)$alkyl; $C_6$-aryl; substituted $C_6$-aryl (substitution selected from halo, $(C_1–C_4)$alkoxy, trihalo$(C_1–C_3)$alkyl, nitro, amino, cyano, $(C_1–C_4)$alkoxycarbonyl, $(C_1–C_3)$alkylamino or carboxy); $(C_7–C_9)$aralkyl group selected from benzyl, 1-phenylethyl, 2-phenylethyl or phenylpropyl) such as γ-butyrolactam, γ-butyrolactone, imidazolidinone or N-aminoimidazolidinone, or a six membered aromatic ring with one to three N, O, S or Se heteroatoms such as pyridyl, pyridazinyl, pyrazinyl, sym-triazinyl, unsym-triazinyl, pyrimidinyl or $(C_1–C_3)$alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl; $(C_1–C_4)$alkoxycarbonyl group selected from methoxycarbonyl, ethoxycarbonyl, straight or branched propoxylcarbonyl, straight or branched butoxycarbonyl or allyloxycarbonyl; vinyl or substituted vinyl group [substitution selected from $(C_1–C_3)$alkyl group, halogen, $(C_6–C_{10})$aryl group selected from phenyl, α-naphthyl, β-naphthyl, substituted $(C_6–C_{10})$aryl group (substitution selected from halo, $(C_1–C_4)$alkoxy, trihalo$(C_1–C_3)$alkyl, nitro, amino, cyano, $(C_1–C_4)$alkoxycarbonyl, $(C_1–C_3)$alkylamino or carboxy), halo$(C_1–C_3)$alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-bromoethyl or 2-iodoethyl, a heterocycle group selected from a five membered aromatic or saturated ring with one N, O, S or Se heteroatom optionally having a benzo or pyrido ring fused thereto:

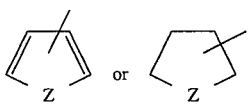

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl]; $(C_1–C_4)$alkoxy group such as allyloxy, methoxy, ethoxy, n-propoxy, n-butoxy or tert-butoxy; $C_6$-aryloxy group selected from phenoxy or substituted phenoxy (substitution selected from halo, $(C_1–C_4)$alkyl, nitro, cyano, thiol, amino, carboxy, di$(C_1–C_3)$alkylamino); $(C_7–C_{10})$aralkyloxy group such as benzyloxy, 1-phenylethyloxy or 2-phenylethyloxy; vinyloxy or substituted vinyloxy group (substitution selected from $(C_1–C_4)$alkyl, cyano, carboxy, or $(C_6–C_{10})$aryl selected from phenyl, α-naphthyl or β-naphthyl); $R^aR^b$amino$(C_1–C_4)$alkoxy group, wherein $R^aR^b$ is a straight or branched $(C_1–C_4)$alkyl selected from methyl, ethyl, n-propyl, 1-methylethyl, n-butyl, 1-methylpropyl, 2-methylpropyl or 1,1-dimethylethyl or $R^aR^b$ is $(CH_2)_n$, n=2–6, or —$(CH_2)_2W(CH_2)_2$— wherein W is selected from —$N(C_1–C_3)$alkyl [straight or branched], —NH, —NOB [B is selected from hydrogen or $(C_1–C_3)$alkyl], O or S; or $R^aR^b$aminoxy group, wherein $R^aR^b$ is a straight or branched $(C_1–C_4)$alkyl selected from methyl, ethyl, n-propyl, 1-methylethyl, n-butyl, 1-methylpropyl, or 2-methylpropyl or $R^aR^b$ is $(CH_2)_n$, n=2–6, or —$(CH_2)_2W(CH_2)_2$— wherein W is selected from —$N(C_1–C_3)$alkyl [straight or branched], —NH, —NOB [B is selected from hydrogen or $(C_1–C_3)$alkyl], O or S; and when $R=R^4(CH_2)_nCO$— and n=1–4, $R^4$ is selected from hydrogen; amino; straight or branched $(C_1–C_4)$alkyl group selected from methyl, ethyl, n-propyl, 1-methylethyl, n-butyl, 1-methylpropyl, 2-methylpropyl or 1,1-dimethylethyl; $(C_3–C_6)$cycloalkyl group selected from cyclopropyl, cyclobutyl, cyclopentyl or cyclohexyl; substituted $(C_3–C_6)$cycloalkyl group (substitution selected from $(C_1–C_3)$alkyl, cyano, amino or $(C_1–C_3)$acyl); $(C_6–C_{10})$aryl group selected from phenyl, α-naphthyl or β-naphthyl; substituted$(C_6–C_{10})$aryl group (substitution selected from halo, $(C_1–C_4)$alkoxy, trihalo$(C_1–C_3)$alkyl, nitro, amino, cyano, $(C_1–C_4)$alkoxycarbonyl, $(C_1–C_3)$alkylamino or carboxy); $(C_7–C_9)$aralkyl group such as benzyl, 1-phenylethyl, 2-phenylethyl or phenylpropyl; acyloxy or haloacyloxy group, selected from acetyl, propionyl, chloroacetyl, trichloroacetyl, $(C_3–C_6)$cycloalkylcarbonyl, $(C_6–C_{10})$aroyl selected from benzoyl or naphthoyl, halo substituted $(C_6–C_{10})$aroyl such as pentafluorobenzoyl, 4-chlorobenzoyl, 3-bromobenzoyl or 3,4-difluorobenzoyl, $(C_1–C_4)$alkylbenzoyl such as 4-toluoyl, 2-toluoyl or 4-(1-methylethyl)benzoyl, (heterocycle)carbonyl, the heterocycle selected from a five membered aromatic or saturated ring with one N, O, S or Se heteroatom optionally having a benzo or pyrido ring fused thereto:

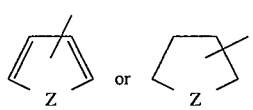

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

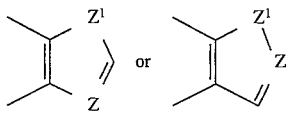

Z or Z¹ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

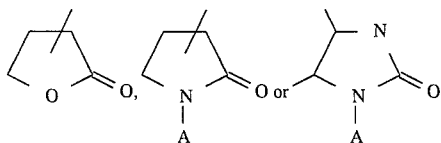

(A is selected from hydrogen; straight or branched $(C_1-C_4)$alkyl; $C_6$-aryl; substituted $C_6$-aryl (substitution selected from halo, $(C_1-C_4)$alkoxy, trihalo$(C_1-C_3)$alkyl, nitro, amino, cyano, $(C_1-C_4)$alkoxycarbonyl, $(C_1-C_3)$alkylamino or carboxy); $(C_7-C_9)$aralkyl group selected from benzyl, 1-phenylethyl, 2-phenylethyl or phenylpropyl)
such as γ-butyrolactam, γ-butyrolactone, imidazolidinone or N-aminoimidazolidinone, or a six membered aromatic ring with one to three N, O, S or Se heteroatoms such as pyridyl, pyridazinyl, pyrazinyl, sym-triazinyl, unsym-triazinyl, pyrimidinyl or $(C_1-C_3)$alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl; $(C_1-C_4)$alkoxy group such as allyloxy, methoxy, ethoxy, n-propoxy, n-butoxy or tert-butoxy; $C_6$-aryloxy group selected from phenoxy or substituted phenoxy (substitution selected from halo, $(C_1-C_4)$alkyl, nitro, cyano, thiol, amino, carboxy, di$(C_1-C_3)$alkylamino); $(C_7-C_{10})$aralkyloxy group such as benzyloxy, 1-phenylethyloxy or 2-phenylethyloxy; $(C_1-C_3)$alkylthio group selected from methylthio, ethylthio, propylthio or allylthio; $C_6$-arylthio group selected from phenylthio or substituted phenylthio (substitution selected from halo, $(C_1-C_4)$alkyl, nitro, cyano, thiol, amino, carboxy, di$(C_1-C_3)$alkylamino); $C_6$-arylsulfonyl group selected from phenylsulfonyl or substituted phenylsulfonyl (substitution selected from halo, $(C_1-C_4)$alkoxy, trihalo$(C_1-C_3)$alkyl, nitro, amino, cyano, $(C_1-C_4)$alkoxycarbonyl, $(C_1-C_3)$alkylamino or carboxy); $(C_7-C_8)$aralkylthio group such as benzylthio, 1-phenylethylthio or 2-phenylethylthio; a heterocycle group selected from a five membered aromatic or saturated ring with one N, O, S or Se heteroatom optionally having a benzo or pyrido ring fused thereto:

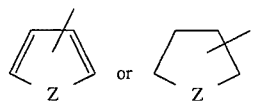

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

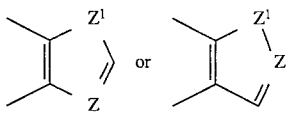

Z or Z¹ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

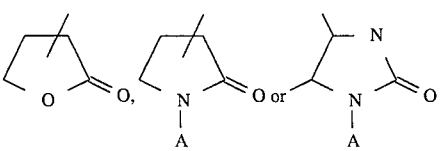

(A is selected from hydrogen; straight or branched $(C_1-C_4)$alkyl; $C_6$-aryl; substituted $C_6$-aryl (substitution selected from halo, $(C_1-C_4)$alkoxy, trihalo$(C_1-C_3)$alkyl, nitro, amino, cyano, $(C_1-C_4)$alkoxycarbonyl, $(C_1-C_3)$alkylamino or carboxy); $(C_7-C_9)$aralkyl group selected from benzyl, 1-phenylethyl, 2-phenylethyl or phenylpropyl)
such as γ-butyrolactam, γ-butyrolactone, imidazolidinone or N-aminoimidazolidinone, or a six membered aromatic ring with one to three N, O, S or Se heteroatoms such as pyridyl, pyridazinyl, pyrazinyl, sym-triazinyl, unsym-triazinyl, pyrimidinyl or $(C_1-C_3)$alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl; hydroxy group; mercapto group; mono- or di-straight or branched chain $(C_1-C_6)$alkylamino group selected from methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl or 1-methyl-1-ethylpropylamino; $(C_2-C_5)$azacycloalkyl group such as aziridinyl, azetidinyl, pyrrolidinyl, piperidinyl, morpholinyl or 2-methylpyrrolidinyl; carboxy$(C_2-C_4)$alkylamino group selected from aminoacetic acid, α-aminopropionic acid, α-aminobutyric acid and their optical isomers; α-hydroxy$(C_1-C_3)$alkyl group selected from hydroxymethyl, α-hydroxyethyl or α-hydroxy-1-methylethyl or α-hydroxypropyl; halo$(C_1-C_3)$alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoromethyl, 2-bromoethyl or 2-iodoethyl; acyl or haloacyl group selected from acetyl, propionyl, chloroacetyl, trifluoroacetyl, $(C_3-C_6)$cycloalkylcarbonyl, $(C_6-C_{10})$-aroyl selected from benzoyl or naphthoyl, halo substituted $(C_6-C_{10})$aroyl such as pentafluorobenzoyl, 4-chlorobenzoyl, 3-bromobenzoyl, 3,4-difluorobenzoyl, $(C_1-C_4)$alkylbenzoyl such as 4-toluoyl, 2-toluoyl or 4-(1-methylethyl)benzoyl, or (heterocycle)carbonyl, the heterocycle selected from a five membered aromatic or saturated ring with one N, O, S or Se heteroatom optionally having a benzo or pyrido ring fused thereto:

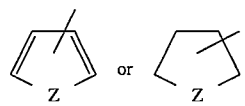

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

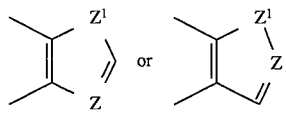

Z or Z¹ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

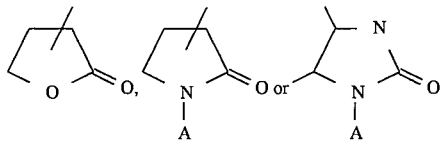

(A is selected from hydrogen; straight or branched $(C_1-C_4)$alkyl; $C_6$-aryl; substituted $C_6$-aryl (substitution selected from halo, $(C_1-C_4)$alkoxy, trihalo$(C_1-C_3)$alkyl, nitro, amino, cyano, $(C_1-C_4)$alkoxycarbonyl, $(C_1-C_3)$alkylamino or carboxy); $(C_7-C_9)$aralkyl group selected from benzyl, 1-phenylethyl, 2-phenylethyl or phenylpropyl) such as γ-butyrolactam, γ-butyrolactone, imidazolidinone or N-aminoimidazolidinone, or a six membered aromatic ring with one to three N, O, S or Se heteroatoms such as pyridyl, pyridazinyl, pyrazinyl, sym-triazinyl, unsym-triazinyl, pyrimidinyl or $(C_1-C_3)$alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl; $(C_1-C_4)$alkoxycarbonylamino group selected from tert-butoxycarbonylamino, allyloxycarbonylamino, methoxycarbonylamino, ethoxycarbonylamino or propoxycarbonylamino; $(C_1-C_4)$alkoxycarbonyl group selected from methoxycarbonyl, ethoxycarbonyl, straight or branched propoxycarbonyl, allyloxycarbonyl or straight or branched butoxycarbonyl; $R^aR^b$amino$(C_1-C_4)$alkoxy group, wherein $R^aR^b$ is a straight or branched $(C_1-C_4)$alkyl selected from methyl, ethyl, n-propyl, 1-methylethyl, n-butyl, 1-methylpropyl, or 2-methylpropyl or $R^aR^b$ is $(CH_2)_n$, n=2–6, or $-(CH_2)_2W(CH_2)_2-$ wherein W is selected from $-N(C_1-C_3)$alkyl [straight or branched], $-NH$, $-NOB$ [B is selected from hydrogen or $(C_1-C_3)$alkyl], O or S; or $R^aR^b$aminoxy group, wherein $R^aR^b$ is a straight or branched $(C_1-C_4)$alkyl selected from methyl, ethyl, n-propyl, 1-methylethyl, n-butyl, 1-methylpropyl, or 2-methylpropyl or $R^aR^b$ is $(CH_2)_n$, n=2–6, or $-(CH_2)_2W(CH_2)_2-$ wherein W is selected from $-N(C_1-C_3)$alkyl [straight or branched], $-NH$, $-NOB$ [B is selected from hydrogen or $(C_1-C_3)$alkyl], O or S; and when $R=R^{4'}(CH_2)_nSO_2-$ and n=0, $R^{4'}$ is selected from amino; monosubstituted amino selected from straight or branched $(C_1-C_6)$alkylamino, cyclopropylamino, cyclobutylamino, benzylamino or phenylamino; disubstituted amino selected from dimethylamino, diethylamino, ethyl(1-methylethyl)amino, monomethylbenzylamino, piperidinyl, morpholinyl, 1-imidazolyl, 1-pyrrolyl, 1-(1,2,3-triazolyl) or 4-(1,2,4-triazolyl); straight or branched $(C_1-C_4)$alkyl group selected from methyl, ethyl, n-propyl, 1-methylethyl, n-butyl, 1-methylpropyl, 2-methylpropyl or 1,1-dimethylethyl; $(C_3-C_6)$cycloalkyl group selected from cyclopropyl, cyclobutyl, cyclopentyl or cyclohexyl; substituted $(C_3-C_6)$cycloalkyl group (substitution selected from $(C_1-C_3)$alkyl, cyano, amino or $(C_1-C_3)$acyl); $(C_6-C_{10})$aryl group selected from phenyl, α-naphthyl or β-naphthyl; substituted $(C_6-C_{10})$aryl group (substitution selected from halo, $(C_1-C_4)$alkoxy trihalo$(C_1-C_3)$alkyl, nitro, amino, cyano, $(C_1-C_4)$alkoxycarbonyl, $(C_1-C_3)$alkylamino or carboxy); $(C_7-C_9)$aralkyl group such as benzyl, 1-phenylethyl, 2-phenylethyl or phenylpropyl; halo$(C_1-C_3)$alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-chloroethyl, 2,2-dichloroethyl, 2,2,2-trichloroethyl, 2-bromoethyl or 2-iodoethyl; a heterocycle group selected from a five membered aromatic or saturated ring with one N, O, S or Se heteroatom optionally having a benzo or pyrido ring fused thereto:

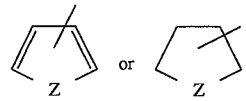

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

Z or Z¹ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

(A is selected from hydrogen; straight or branched $(C_1-C_4)$alkyl; $C_6$-aryl; substituted $C_6$-aryl (substitution selected from halo, $(C_1-C_4)$alkoxy, trihalo$(C_1-C_3)$alkyl, nitro, amino, cyano, $(C_1-C_4)$alkoxycarbonyl, $(C_1-C_3)$alkylamino or carboxy); $(C_7-C_9)$aralkyl group selected from benzyl, 1-phenylethyl, 2-phenylethyl or phenylpropyl) such as γ-butyrolactam, γ-butyrolactone, imidazolidinone or N-aminoimidazolidinone, or a six membered aromatic ring with one to three N, O, S or Se heteroatoms such as pyridyl, pyridazinyl, pyrazinyl, sym-triazinyl, unsym-triazinyl, pyrimidinyl or $(C_1-C_3)$alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl; $R^aR^b$amino$(C_1-C_4)$alkoxy group, wherein $R^aR^b$ is a straight or branched $(C_1-C_4)$alkyl selected from methyl, ethyl, n-propyl, 1-methylethyl, n-butyl, 1-methylpropyl, or 2-methylpropyl or $R^aR^b$ is $(CH_2)_n$, n=2–6, or —$(CH_2)_2W(CH_2)_2$— wherein W is selected from —$N(C_1-C_3)$alkyl [straight or branched], —NH, —NOB [B is selected from hydrogen or $(C_1-C_3)$alkyl], O or S; or $R^aR^b$aminoxy group, wherein $R^aR^b$ is a straight or branched $(C_1-C_4)$alkyl selected from methyl, ethyl, n-propyl, 1-methylethyl, n-butyl, 1-methylpropyl, or 2-methylpropyl or $R^aR^b$ is $(CH_2)_n$, n=2–6, or —$(CH_2)_2W(CH_2)_2$— wherein W is selected from —$N(C_1-C_3)$alkyl [straight or branched], —NH, —NOB [B is selected from hydrogen or $(C_1-C_3)$alkyl], O or S; and when R=R'$(CH_2)_nSO_2$— and n=1–4, $R^{4'}$ is selected from hydrogen; amino; straight or branched $(C_1-C_4)$alkyl group selected from methyl, ethyl, n-propyl, 1-methylethyl, n-butyl, 1-methylpropyl, 2-methylpropyl or 1,1-dimethylethyl; $(C_1-C_4)$carboxyalkyl group; $(C_3-C_6)$cycloalkyl group selected from cyclopropyl, cyclobutyl, cyclopentyl or cyclohexyl; substituted $(C_3-C_6)$cycloalkyl group (substitution selected from $(C_1-C_3)$alkyl, cyano, amino or $(C_1-C_3)$acyl); $(C_6-C_{10})$aryl group selected from phenyl, α-naphthyl or β-naphthyl; substituted $(C_6-C_{10})$aryl group (substitution selected from halo, $(C_1-C_4)$alkoxy, trihalo$(C_1-C_3)$alkyl, nitro, amino, cyano, $(C_1-C_4)$alkoxycarbonyl, $(C_1-C_3)$alkylamino or carboxy); $(C_7-C_9)$aralkyl group selected from benzyl, 1-phenylethyl, 2-phenylethyl or phenylpropyl; $(C_1-C_4)$alkoxy group such as allyloxy, methoxy, ethoxy, n-propoxy or tert-butoxy; $C_6$-aryloxy group selected from phenoxy or substituted phenoxy (substitution selected from halo, $(C_1-C_3)$alkyl, nitro, cyano, thiol, amino, carboxy, di$(C_1-C_3)$alkylamino); $(C_7-C_{10})$aralkyloxy group such as benzyloxy, 1-phenylethyloxy or 2-phenylethyloxy; $R^aR^b$amino$(C_1-C_4)$alkoxy group, wherein $R^aR^b$ is a straight or branched $(C_1-C_4)$alkyl selected from methyl, ethyl, n-propyl, 1-methylethyl, n-butyl, 1-methylpropyl, or 2-methylpropyl or $R^aR^b$ is $(CH_2)_n$, n=2–6, or —$(CH_2)_2W(CH_2)_2$— wherein W is selected from —$N(C_1-C_3)$alkyl [straight or branched], —NH, —NOB [B is selected from hydrogen or $(C_1-C_3)$alkyl], O or S; $R^aR^b$aminoxy group, wherein $R^aR^b$ is a straight or branched $(C_1-C_4)$alkyl selected from methyl, ethyl, n-propyl, 1-methylethyl, n-butyl, 1-methylpropyl, or 2-methylpropyl or $R^aR^b$ is $(CH_2)_n$, n=2–6, or —$(CH_2)_2W(CH_2)_2$— wherein W is selected from —$N(C_1-C_3)$alkyl [straight or branched], —NH, —NOB [B is selected from hydrogen or $(C_1-C_3)$alkyl], O or S; $(C_1-C_3)$alkylthio group selected from methylthio, ethylthio or n-propylthio; $C_6$-arylthio group selected from phenylthio or substituted phenylthio (substitution selected from halo, $(C_1-C_3)$alkyl, nitro, cyano, thiol, amino, carboxy, di$(C_1-C_3)$alkylamino); $(C_7-C_8)$aralkylthio group such as benzylthio, 1-phenylethylthio or 2-phenylethylthio; a heterocycle group selected from a five membered aromatic or saturated ring with one N, O, S or Se heteroatom optionally having a benzo or pyrido ring fused thereto:

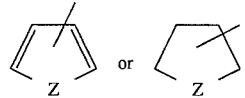

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

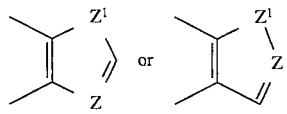

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

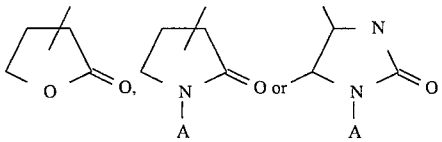

(A is selected from hydrogen; straight or branched $(C_1-C_4)$alkyl; $C_6$-aryl; substituted $C_6$-aryl (substitution selected from halo, $(C_1-C_4)$alkoxy, trihalo$(C_1-C_3)$alkyl, nitro, amino, cyano, $(C_1-C_4)$alkoxycarbonyl, $(C_1-C_3)$alkylamino or carboxy); $(C_7-C_9)$aralkyl group selected from benzyl, 1-phenylethyl, 2-phenylethyl or phenylpropyl) such as γ-butyrolactam, γ-butyrolactone, imidazolidinone or N-aminoimidazolidinone, or a six membered aromatic ring with one to three N, O, S or Se heteroatoms such as pyridyl, pyridazinyl, pyrazinyl, sym-triazinyl, unsym-triazinyl, pyrimidinyl or $(C_1-C_3)$alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl; hydroxy group, mercapto group; mono- or di- straight or branched $(C_1-C_6)$alkylamino group selected from methyl, ethyl, n-propyl, 1-methylethyl, n-butyl, 1-methylpropyl, 2-methylpropyl, 1,1-dimethylethyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 2-methylpentyl, 1,2-dimethylbutyl, 1,3-dimethylbutyl or 1-methyl-1-ethylpropyl amino; halo$(C_1-C_3)$alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-chloroethyl, 2,2-dichloroethyl, 2,2,2-trichloroethyl, 2-bromoethyl or 2-iodoethyl; acyl or haloacyl group selected from acetyl, propionyl, chloroacetyl, trifluoroacetyl, ($C_3$–$C_6$)cycloalkylcarbonyl, ($C_6$–$C_{10}$)aroyl selected from benzoyl or naphthoyl, halo substituted ($C_6$–$C_{10}$)aroyl such as pentafluorobenzoyl, 4-chlorobenzoyl, 3-bromobenzoyl or 3,4-difluorobenzoyl, ($C_1$–$C_4$)alkylbenzoyl such as 4-toluoyl, 2-toluoyl or 4-(1-methylethyl)benzoyl, or (heterocycle)carbonyl, the heterocycle selected from a five membered aromatic or saturated ring with one N, O, S or Se heteroatom optionally having a benzo or pyrido ring fused thereto:

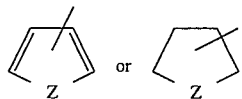

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

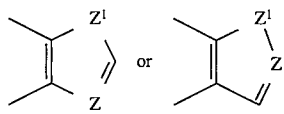

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

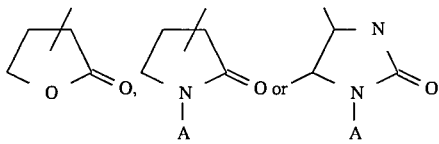

(A is selected from hydrogen; straight or branched ($C_1$–$C_4$)alkyl; $C_6$-aryl; substituted $C_6$-aryl (substitution selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino or carboxy); ($C_7$–$C_9$)aralkyl group selected from benzyl, 1-phenylethyl, 2-phenylethyl or phenylpropyl)
such as γ-butyrolactam, γ-butyrolactone, imidazolidinone or N-aminoimidazolidinone, or a six membered aromatic ring with one to three N, O, S or Se heteroatoms such as pyridyl, pyridazinyl, pyrazinyl, sym-triazinyl, unsym-triazinyl, pyrimidinyl or ($C_1$–$C_3$)alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl; ($C_1$–$C_4$)alkoxycarbonyl group selected from methoxycarbonyl, ethoxycarbonyl, straight or branched propoxycarbonyl, allyloxycarbonyl or straight or branched butoxycarbonyl; $R^5$ is selected from hydrogen; straight or branched ($C_1$–$C_3$)alkyl group selected from methyl, ethyl, n-propyl or 1-methylethyl; ($C_6$–$C_{10}$)aryl group selected from phenyl, α-naphthyl or β-naphthyl; ($C_7$–$C_9$)aralkyl group such as benzyl, 1-phenylethyl, 2-phenylethyl or phenylpropyl; a heterocycle group selected from a five membered aromatic or saturated ring with one N, O, S or Se heteroatom optionally having a benzo or pyrido ring fused thereto:

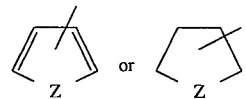

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

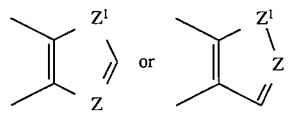

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

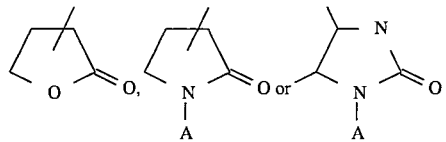

(A is selected from hydrogen; straight or branched ($C_1$–$C_4$)alkyl; $C_6$-aryl; substituted $C_6$-aryl (substitution selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino or carboxy); ($C_7$–$C_9$)aralkyl group selected from benzyl, 1-phenylethyl, 2-phenylethyl or phenylpropyl)
such as γ-butyrolactam, γ-butyrolactone, imidazolidinone or N-aminoimidazolidinone, or a six membered aromatic ring with one to three N, O, S or Se heteroatoms such as pyridyl, pyridazinyl, pyrazinyl, sym-triazinyl, unsym-triazinyl, pyrimidinyl or ($C_1$–$C_3$) alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl, 2-dioxothiomorpholinyl; or —$(CH_2)_n COOR^7$ where n=0–4 and $R^7$ is selected from hydrogen; straight or branched ($C_1$–$C_3$)alkyl group selected from methyl, ethyl, n-propyl or 1-methylethyl; or ($C_6$–$C_{10}$)aryl group selected from phenyl, α-naphthyl, β-naphthyl; $R^6$ is selected from hydrogen; straight or branched ($C_1$–$C_3$)alkyl group selected from methyl, ethyl, n-propyl or 1-methylethyl; ($C_6$–$C_{10}$)aryl group selected from phenyl, α-naphthyl or β-naphthyl; ($C_7$–$C_9$)aralkyl group such as benzyl, 1-phenylethyl, 2-phenylethyl or phenylpropyl; a heterocycle group selected from a five membered aromatic or saturated ring with one N, O, S or Se heteroatom optionally having a benzo or pyrido ring fused thereto:

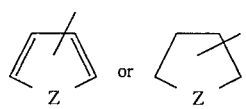

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

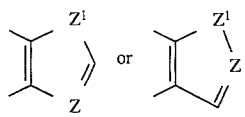

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

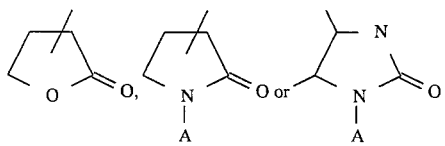

(A is selected from hydrogen; straight or branched $(C_1-C_4)$alkyl; $C_6$-aryl; substituted $C_6$-aryl (substitution selected from halo, $(C_1-C_4)$alkoxy, trihalo$(C_1-C_3)$alkyl, nitro, amino, cyano, $(C_1-C_4)$alkoxycarbonyl, $(C_1-C_3)$alkylamino or carboxy); $(C_7-C_9)$aralkyl group selected from benzyl, 1-phenylethyl, 2-phenylethyl or phenylpropyl)
such as γ-butyrolactam, γ-butyrolactone, imidazolidinone or N-aminoimidazolidinone, or a six membered aromatic ring with one to three N, O, S or Se heteroatoms such as pyridyl, pyridazinyl, pyrazinyl, sym-triazinyl, unsym-triazinyl, pyrimidinyl or $(C_1-C_3)$alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl, 2-dioxothiomorpholinyl; or —$(CH_2)_n COOR^{7'}$ where n=0–4 and $R^{7'}$ is selected from hydrogen; straight or branched $(C_1-C_3)$alkyl selected from methyl, ethyl, n-propyl or 1-methylethyl; or $(C_6-C_{10})$aryl selected from phenyl, α-naphthyl or β-naphthyl; with the proviso that $R^5$ and $R^6$ cannot both be hydrogen; or $R^5$ and $R^6$ taken together are —$(CH_2)_2 W(CH_2)_2$—, wherein W is selected from $(CH_2)_n$ and n=0–1, —NH, —N$(C_1-C_3)$alkyl [straight or branched], —N$(C_1-C_4)$alkoxy, oxygen, sulfur or substituted congeners selected from (L or D)proline, ethyl(L or D)prolinate, morpholine, pyrrolidine or piperidine; and the pharmacologically acceptable organic and inorganic salts or metal complexes.

Preferred compounds are compounds according to the above formula I and II in which X is selected from amino $NR^1R^2$, or halogen; the halogen is selected from bromine, chlorine, fluorine or iodine; and when X=$NR^1R^2$ and $R^1$=hydrogen, $R^2$=methyl, ethyl, n-propyl, 1-methylethyl, n-butyl, 1-methylpropyl, 2-methylpropyl or 1,1-dimethylethyl; and when $R^1$=methyl or ethyl, $R^2$=methyl, ethyl, n-propyl, 1-methylethyl, n-butyl, 1-methylpropyl or 2-methylpropyl; R is selected from $R^4(CH_2)_n CO$— or $R_4$-$(CH_2)_n SO_2$—; and when R=$R^4(CH_2)_n CO$— and n=0, $R^4$ is selected from hydrogen; amino; monosubstituted amino selected from straight or branched $(C_1-C_6)$alkylamino, cyclopropylamino, cyclobutylamino, benzylamino or phenylamino; disubstituted amino selected from dimethylamino, diethylamino, ethyl(1-methylethyl)amino, monomethylbenzylamino, piperidinyl, morpholinyl, 1-imidazolyl, 1-pyrrolyl, 1-(1,2,3-triazolyl) or 4-(1,2,4-triazolyl); straight or branched $(C_1-C_3)$alkyl group selected from methyl, ethyl, n-propyl or 1-methylethyl; $(C_3-C_6)$cycloalkyl group selected from cyclopropyl, cyclobutyl, cyclopentyl or cyclohexyl; substituted $(C_3-C_6)$cycloalkyl group (substitution selected from $(C_1-C_3)$alkyl, cyano, amino or $(C_1-C_3)$acyl); $(C_6-C_{10})$aryl group selected from phenyl, α-naphthyl or β-naphthyl; substituted $(C_6-C_{10})$aryl group (substitution selected from halo, $(C_1-C_4)$alkoxy, trihalo$(C_1-C_3)$alkyl, nitro, amino, cyano, $(C_1-C_4)$alkoxycarbonyl, $(C_1-C_3)$alkylamino or carboxy); α-amino$(C_1-C_4)$alkyl group selected from aminomethyl, α-aminoethyl, α-aminopropyl or α-aminobutyl; carboxy$(C_2-C_4)$alkylamino group selected from aminoacetic acid, β-aminobutyric acid or α-aminopropionic acid and their optical isomers; $(C_7-C_9)$aralkylamino group such as phenylglycyl; $(C_1-C_4)$alkoxycarbonylamino substituted $(C_1-C_4)$alkyl group, substitution selected from phenyl or p-hydroxyphenyl; α-hydroxy$(C_1-C_3)$alkyl group selected from hydroxymethyl, α-hydroxyethyl or α-hydroxy-1-methylethyl or α-hydroxypropyl; halo$(C_1-C_3)$alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-bromoethyl or 2-iodoethyl; a heterocycle group selected from a five membered aromatic or saturated ring with one N, O, S or Se heteroatom optionally having a benzo or pyrido ring fused thereto:

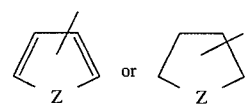

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

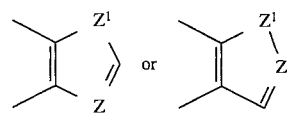

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

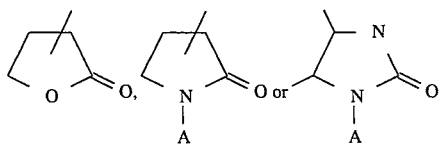

(A is selected from hydrogen; straight or branched ($C_1$–$C_4$)alkyl; $C_6$-aryl; substituted $C_6$-aryl (substitution selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino or carboxy); ($C_7$–$C_9$)aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N, O, S or Se heteroatoms such as pyridyl, pyridazinyl, pyrazinyl, sym-triazinyl, unsym-triazinyl, pyrimidinyl or ($C_1$–$C_3$)alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl; acyl or haloacyl group selected from acetyl, propionyl, chloroacetyl, trifluoroacetyl, ($C_3$–$C_6$)cycloalkylcarbonyl such as cyclopropylcarbonyl, cyclobutylcarbonyl, cyclopentylcarbonyl, cyclohexylcarbonyl, (2,3-dimethylcyclopropyl)carbonyl, (1,2-dimethylcyclopropyl)carbonyl, (2-ethylcyclopropyl)carbonyl, (2-methylcyclopentyl)carbonyl or (3-ethylcyclobutyl)carbonyl, ($C_6$–$C_{10}$)aroyl selected from benzoyl or naphthoyl, halo substituted ($C_6$–$C_{10}$)aroyl such as pentafluorobenzoyl, 4-chlorobenzoyl, 3-bromobenzoyl or 3,4-difluorobenzoyl, ($C_1$–$C_4$)alkylbenzoyl such as 4-toluoyl, 2-methyltoluoyl or 4-(1-methylethyl)benzoyl, or (heterocycle)carbonyl, the heterocycle selected from a five membered aromatic or saturated ring with one N, O, S or Se heteroatom optionally having a benzo or pyrido ring fused thereto:

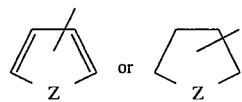

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

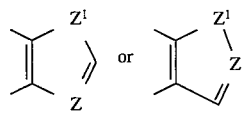

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

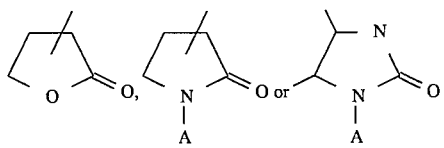

(A is selected from hydrogen; straight or branched ($C_1$–$C_4$)alkyl; $C_6$-aryl; substituted $C_6$-aryl (substitution selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino or carboxy); ($C_7$–$C_9$)aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N, O, S or Se heteroatoms such as pyridyl, pyridazinyl, pyrazinyl, sym-triazinyl, unsym-triazinyl, pyrimidinyl or ($C_1$–$C_3$)alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl; ($C_1$–$C_4$)alkoxycarbonyl group selected from methoxycarbonyl, ethoxycarbonyl, straight or branched propoxylcarbonyl, straight or branched butoxycarbonyl or allyloxycarbonyl; vinyl or substituted vinyl group [substitution selected from ($C_1$–$C_3$)alkyl group, halogen, ($C_6$–$C_{10}$)aryl group selected from phenyl, α-naphthyl, β-naphthyl, substituted ($C_6$–$C_{10}$)aryl group (substitution selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino or carboxy), halo($C_1$–$C_3$)alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-bromoethyl or 2-iodoethyl, a heterocycle group selected from a five membered aromatic or saturated ring with one N, O, S or Se heteroatom optionally having a benzo or pyrido ring fused thereto:

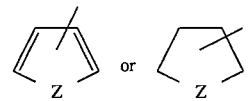

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl]; ($C_1$–$C_4$)alkoxy group such as allyloxy, methoxy, ethoxy, n-propoxy, n-butoxy or tert-butoxy; $C_6$-aryloxy group selected from phenoxy or substituted phenoxy (substitution selected from halo, ($C_1$–$C_4$)alkyl, nitro, cyano, thiol, amino, carboxy, di($C_1$–$C_3$)alkylamino); ($C_7$–$C_{10}$)aralkyloxy group such as benzyloxy, 1-phenylethyloxy or 2-phenylethyloxy; vinyloxy or substituted vinyloxy group (substitution selected from ($C_1$–$C_4$)alkyl, cyano, carboxy, or ($C_6$–$C_{10}$)aryl selected from phenyl, α-naphthyl or β-naphthyl); $R^a R^b$amino($C_1$–$C_4$)alkoxy group, wherein $R^a R^b$ is a straight or branched ($C_1$–$C_4$)alkyl selected from methyl, ethyl, n-propyl, 1-methylethyl, n-butyl, 1-methylpropyl, or 2-methylpropyl or $R^a R^b$ is $(CH_2)_n$, n=2–6, or —$(CH_2)_2 W(CH_2)_2$— wherein W is selected from —N($C_1$–$C_3$)alkyl [straight or branched], —NH, —NOB [B is selected from hydrogen or ($C_1$–$C_3$)alkyl], O or S; or $R^a R^b$aminoxy group, wherein $R^a R^b$ is a straight or branched ($C_1$–$C_4$)alkyl selected from methyl, ethyl, n-propyl, 1-methylethyl, n-butyl, 1-methylpropyl, or 2-methylpropyl or $R^aR^b$ is $(CH_2)_n$, n=2–6, or —$(CH_2)_2W(CH_2)_2$— wherein W is selected from —N($C_1$–$C_3$)alkyl [straight or branched], —NH, —NOB [B is selected from hydrogen or ($C_1$–$C_3$)alkyl], O or S; and when R=$R^4$ $(CH)_nCO$— and n=1–4, $R^4$ is selected from hydrogen; ($C_1$–$C_3$)alkyl group selected from methyl, ethyl, n-propyl or 1-methylethyl; amino; monosubstituted amino selected from straight or branched ($C_1$–$C_6$)alkylamino, cyclopropylamino, cyclobutylamino, benzylamino or phenylamino; disubstituted amino selected from dimethylamino, diethylamino, ethyl(1-methylethyl)amino, monomethylbenzylamino, piperidinyl, morpholinyl, 1-imidazolyl, 1-pyrrolyl, 1-(1,2,3-triazolyl) or 4-(1,2,4-triazolyl); ($C_6$–$C_{10}$)aryl group selected from phenyl, α-naphthyl or β-naphthyl; substituted ($C_6$–$C_{10}$)aryl group (substitution selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino or carboxy); acyloxy or haloacyloxy group, selected from acetyl, propionyl, chloroacetyl, trichloroacetyl, ($C_3$–$C_6$)cycloalkylcarbonyl, ($C_6$–$C_{10}$)aroyl selected from benzoyl or naphthoyl, halo substituted ($C_6$–$C_{10}$)aroyl such as pentafluorobenzoyl, 4-chlorobenzoyl, 3-bromobenzoyl or 3,4-difluorobenzoyl, ($C_1$–$C_4$)alkylbenzoyl such as 4-toluoyl, 2-toluoyl, 4-(1-methylethyl)benzoyl or (heterocycle)carbonyl, the heterocycle selected from a five membered aromatic or saturated ring with one N, O, S or Se heteroatom opionally having a benzo or pyrido ring fused thereto:

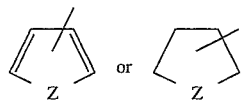

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

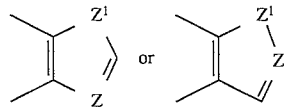

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

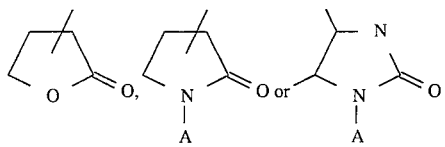

(A is selected from hydrogen; straight or branched ($C_1$–$C_4$)alkyl; $C_6$-aryl; substituted $C_6$-aryl (substitution selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino or carboxy); ($C_7$–$C_9$)aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N, O, S or Se heteroatoms such as pyridyl, pyridazinyl, pyrazinyl, sym-triazinyl, unsym-triazinyl, pyrimidinyl or ($C_1$–$C_3$)alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl; ($C_1$–$C_4$)alkoxy group such as allyloxy, methoxy, ethoxy, n-propoxy, n-butoxy or tert-butoxy; $R^aR^b$amino($C_1$–$C_4$)alkoxy group, wherein $R^aR^b$ is a straight or branched ($C_1$–$C_4$)alkyl selected from methyl, ethyl, n-propyl, 1-methylethyl, n-butyl, 1-methylpropyl, or 2-methylpropyl or $R^aR^b$ is $(CH_2)_n$, n=2–6, or —$(CH_2)_2W(CH_2)_2$— wherein W is selected from —N($C_1$–$C_3$)alkyl [straight or branched], —NH, —NOB [B is selected from hydrogen or ($C_1$–$C_3$)alkyl], O or S; or $R^aR^b$aminoxy group, wherein $R^aR^b$ is a straight or branched ($C_1$–$C_4$)alkyl selected from methyl, ethyl, n-propyl, 1-methylethyl, n-butyl, 1-methylpropyl, or 2-methylpropyl or $R^aR^b$ is $(CH_2)_n$, n=2–6, or —$(CH_2)_2W(CH_2)_2$— wherein W is selected from —N($C_1$–$C_3$)alkyl [straight or branched], —NH, —NOB [B is selected from hydrogen or ($C_1$–$C_3$)alkyl], O or S; $C_6$-aryloxy group selected from phenoxy or substituted phenoxy (substitution selected from halo, ($C_1$–$C_4$)alkyl, nitro, cyano, thiol, amino, carboxy, di($C_1$–$C_3$)alkylamino); ($C_1$–$C_3$)alkylthio group selected from methylthio, ethylthio, propylthio or allylthio; $C_6$-arylthio group selected from phenylthio or substituted phenylthio (substitution selected from halo, ($C_1$–$C_4$)alkyl, nitro, cyano, thiol, amino, carboxy, di($C_1$–$C_3$)alkylamino); $C_6$-arylsulfonyl group selected from phenylsulfonyl or substituted phenylsulfonyl (substitution selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino or carboxy); a heterocycle group selected from a five membered aromatic or saturated ring with one N, O, S or Se heteroatom optionally having a benzo or pyrido ring fused thereto:

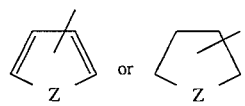

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

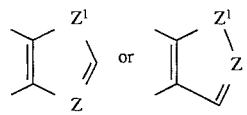

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

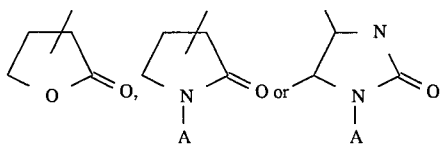

(A is selected from hydrogen; straight or branched ($C_1$–$C_4$)alkyl; $C_6$-aryl; substituted $C_6$-aryl (substitution selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino or carboxy); ($C_7$–$C_9$)aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N, O, S or Se heteroatoms such as pyridyl, pyridazinyl, pyrazinyl, sym-triazinyl, unsym-triazinyl, pyrimidinyl or ($C_1$–$C_3$)alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl; hydroxy group; α-hydroxy($C_1$–$C_3$)alkyl group selected from hydroxymethyl, α-hydroxyethyl or α-hydroxy-1-methylethyl or α-hydroxypropyl; halo($C_1$–$C_3$)alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoromethyl, 2-bromoethyl or 2-iodoethyl; acyl or haloacyl group selected from acetyl, propionyl, chloroacetyl, trifluoroacetyl, ($C_3$–$C_6$)cycloalkylcarbonyl, ($C_6$–$C_{10}$)aroyl selected from benzoyl or naphthoyl, halo substituted ($C_6$–$C_{10}$)aroyl such as pentafluorobenzoyl, 4-chlorobenzoyl, 3-bromobenzoyl or 3,4-difluorobenzoyl, ($C_1$–$C_4$)alkylbenzoyl such as 4-toluoyl, 2-toluoyl, or 4-(1-methylethyl)benzoyl, or (heterocycle)carbonyl, the heterocycle selected from a five membered aromatic or saturated ring with one N, O, S or Se heteroatom optionally having a benzo or pyrido ring fused thereto:

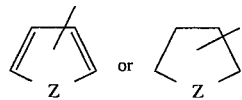

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

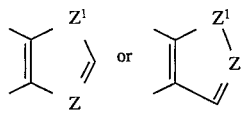

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

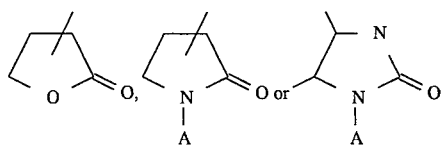

(A is selected from hydrogen; straight or branched ($C_1$–$C_4$)alkyl; $C_6$-aryl; substituted $C_6$-aryl (substitution selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino or carboxy); ($C_7$–$C_9$)aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N, O, S or Se heteroatoms such as pyridyl, pyridazinyl, pyrazinyl, sym-triazinyl, unsym-triazinyl, pyrimidinyl or ($C_1$–$C_3$)-alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl; ($C_1$–$C_4$)alkoxycarbonylamino group selected from tert-butoxycarbonylamino, allyloxycarbonylamino, methoxycarbonylamino, ethoxycarbonylamino or propoxycarbonylamino; and when R=$R^{4'}$($CH_2$)$_n$$SO_2$— and n=0, $R^{4'}$ is selected from amino; monosubstituted amino selected from as straight or branched ($C_1$–$C_6$)alkylamino, cyclopropylamino, cyclobutylamino, benzylamino or phenylamino; disubstituted amino selected from dimethylamino, diethylamino, ethyl(1-methylethyl)amino, monomethylbenzylamino, piperidinyl, morpholinyl, 1-imidazolyl, 1-pyrrolyl, 1-(1,2,3-triazolyl) or 4-(1,2,4-triazolyl); straight or branched ($C_1$–$C_3$)alkyl group selected from methyl, ethyl, n-propyl or 1-methylethyl; ($C_6$–$C_{10}$)aryl group selected from phenyl, α-naphthyl or β-naphthyl; substituted ($C_6$–$C_{10}$)aryl group (substitution selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino or carboxy); a heterocycle group selected from a five membered aromatic or saturated ring with one N, O, S or Se heteroatom optionally having a benzo or pyrido ring fused thereto:

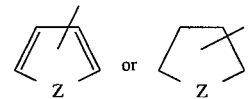

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

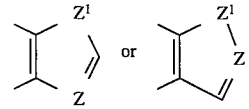

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl- 3H-imidazo[4,5-b]pyridyl or pyridylimidazolyl, or a five membered saturated ring with one or two N, O, S or Se heteroatoms and an adjacent appended O heteroatom:

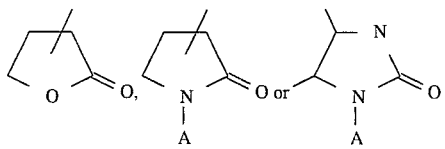

(A is selected from hydrogen; straight or branched $(C_1-C_4)$alkyl; $C_6$-aryl; substituted $C_6$-aryl (substitution selected from halo, $(C_1-C_4)$alkoxy, trihalo$(C_1-C_3)$alkyl, nitro, amino, cyano, $(C_1-C_4)$alkoxycarbonyl, $(C_1-C_3)$alkylamino or carboxy); $(C_7-C_9)$aralkyl group selected from benzyl, 1-phenylethyl, 2-phenylethyl or phenylpropyl) such as γ-butyrolactam, γ-butyrolactone, imidazolidinone or N-aminoimidazolidinone, or a six membered aromatic ring with one to three N, O, S or Se heteroatoms such as pyridyl, pyridazinyl, pyrazinyl, sym-triazinyl, unsym-triazinyl, pyrimidinyl or $(C_1-C_3)$alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl; and when $R=R^{4'}(CH_2)_nSO_2$— and n=1–4, $R^{4'}$ is selected from hydrogen; amino; monosubstituted amino selected from straight or branched $(C_1-C_6)$alkylamino, cyclopropylamino, cyclobutylamino, benzylamino or phenylamino; disubstituted amino selected from dimethylamino, diethylamino, ethyl(1-methylethyl)amino, monomethylbenzylamino, piperidinyl, morpholinyl, 1-imidazolyl, 1-pyrrolyl, 1-(1,2,3-triazolyl) or 4-(1,2,4-triazolyl); straight or branched $(C_1-C_3)$alkyl group selected from methyl, ethyl, n-propyl or 1-methylethyl; $(C_6-C_{10})$aryl group selected from phenyl, α-naphthyl or β-naphthyl; substituted $(C_6-C_{10})$aryl group (substitution selected from halo, $(C_1-C_4)$alkoxy, trihalo$(C_1-C_3)$alkyl, nitro, amino, cyano, $(C_1-C_4)$alkoxycarbonyl, $(C_1-C_3)$alkylamino or carboxy); $(C_1-C_4)$alkoxy group such as allyloxy, methoxy, ethoxy, n-propoxy, n-butoxy, isobutoxy or tert-butoxy; $C_6$-aryloxy group selected from phenoxy or substituted phenoxy (substitution selected from halo, $(C_1-C_4)$alkyl, nitro cyano, thiol, amino, carboxy, di$(C_1-C_3)$alkylamino; $(C_7-C_{10})$aralkyloxy group such as benzyloxy, 1-phenylethyloxy or 2-phenylethyloxy; $(C_1-C_4)$carboxyalkyl group; $R^5$ is selected from hydrogen; straight or branched $(C_1-C_3)$alkyl group selected from methyl, ethyl, n-propyl or 1-methylethyl; $(C_6-C_{10})$aryl group selected from phenyl, α-naphthyl or β-naphthyl; $(C_7-C_9)$aralkyl group such as benzyl, 1-phenylethyl, 2-phenylethyl or phenylpropyl; a heterocycle group selected from a five membered aromatic or saturated ring with one N, O, S or Se heteroatom optionally having a benzo or pyrido ring fused thereto:

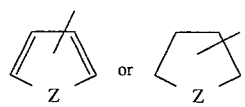

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

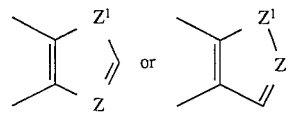

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

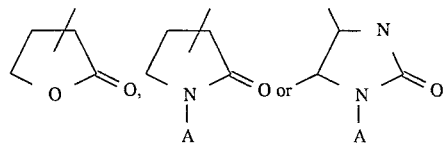

(A is selected from hydrogen;.straight or branched $(C_1-C_4)$alkyl; $C_6$-aryl; substituted $C_6$-aryl (substitution selected from halo,$(C_1-C_4)$alkoxy, trihalo$(C_1-C_3)$alkyl, nitro, amino, cyano, $(C_1-C_4)$-alkoxycarbonyl, $(C_1-C_3)$alkylamino or carboxy); $(C_7-C_9)$-aralkyl group selected from benzyl, 1-phenylethyl, 2-phenylethyl or phenylpropyl) such as γ-butyrolactam, γ-butyrolactone, imidazolidinone or N-aminoimidazolidinone, or a six membered aromatic ring with one to three N, O, S or Se heteroatoms such as pyridyl, pyridazinyl, pyrazinyl, sym-triazinyl, unsym-triazinyl, pyrimidinyl or $(C_1-C_3)$alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl- 2-dioxo-1-piperazinyl, 2-dioxomorpholinyl, 2-dioxothiomorpholinyl; or $—(CH_2)_nCOOR^7$ where n=0–4 and $R^7$ is selected from hydrogen; straight or branched $(C_1-C_3)$-alkyl group selected from methyl, ethyl, n-propyl or 1-methylethyl; or $(C_6-C_{10})$aryl group selected from phenyl, α-naphthyl or β-naphthyl; $R^6$ is selected from hydrogen; straight or branched $(C_1-C_3)$alkyl group selected from methyl, ethyl, n-propyl or 1-methylethyl; $(C_6-C_{10})$aryl group selected from phenyl, α-naphthyl or β-naphthyl; $(C_7-C_9)$-aralkyl group such as benzyl, 1-phenylethyl, 2-phenylethyl or phenylpropyl; a heterocycle group selected from a five membered aromatic or saturated ring with one N, O, S or Se heteroatom optionally having a benzo or pyrido ring fused thereto:

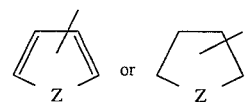

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

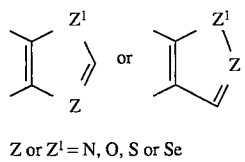

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended heteroatom:

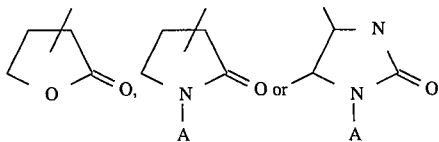

(A is selected from hydrogen; straight or branched $(C_1-C_4)$alkyl; $C_6$-aryl; substituted $C_6$-aryl (substitution selected from halo,$(C_1-C_4)$alkoxy, trihalo$(C_1-C_3)$alkyl, nitro, amino, cyano, $(C_1-C_4)$-alkoxycarbonyl, $(C_1-C_3)$alkylamino or carboxy); $(C_7-C_9)$-aralkyl group selected from benzyl, 1-phenylethyl, 2-phenylethyl or phenylpropyl)
such as γ-butyrolactam, γ-butyrolactone, imidazolidinone or N-aminoimidazolidinone, or a six membered aromatic ring with one to three N, O, S or Se heteroatoms such as pyridyl, pyridazinyl, pyrazinyl, sym-triazinyl, unsym-triazinyl, pyrimidinyl or $(C_1-C_3)$alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl, 2-dioxothiomorpholinyl; or $(CH_2)_nCOOR^{7'}$ where n=0–4 and $R^{7'}$ is selected from hydrogen; straight or branched $(C_1-C_3)$alkyl selected from methyl, ethyl, n-propyl or 1-methylethyl; or $(C_6-C_{10})$aryl selected from phenyl, α-naphthyl or β-naphthyl; with the proviso that $R^5$ and $R^6$ cannot both be hydrogen; or $R^5$ and $R^6$ taken together are —$(CH_2)_2W(CH_2)_2$—, wherein W is selected from $(CH_2)_n$ and n=0–1, —NH, —N$(C_1-C_3)$alkyl [straight or branched], —N$(C_1-C_4)$alkoxy, oxygen, sulfur or substituted congeners selected from (L or D)proline, ethyl(L or D)prolinate, morpholine, pyrrolidine or piperidine; and the pharmacologically acceptable organic and inorganic salts or metal complexes.

Particularly preferred compounds are compounds according to the above formula I and II in which X is selected from amino, $NR^1R^2$, or halogen; the halogen is selected from bromine, chlorine, fluorine or iodine; and when $X=NR^1R^2$ and $R^1$=hydrogen, $R^2$=methyl, ethyl, n-propyl, 1-methylethyl, n-butyl, 1-methylpropyl, 2-methylpropyl or 1,1-dimethylethyl; and when $R^1$=methyl or ethyl, $R^2$=methyl, ethyl, n-propyl, 1-methylethyl, n-butyl, 1-methylpropyl or 2-methylpropyl; R is selected from $R^4(CH_2)_nCO$— or $R^{4'}(CH_2)_nSO_2$—; and when $R=R^4(CH_2)_nCO$— and n=0, $R^4$ is selected from hydrogen; amino; monosubstituted amino selected from straight or branched $(C_1-C_6)$alkylamino, cyclopropylamino, cyclobutylamino, benzylamino or phenylamino; disubstituted amino selected from dimethylamino, diethylamino, ethyl(1-methylethyl)amino, monomethylbenzylamino, piperidinyl, morpholinyl, 1-imidazolyl, 1-pyrrolyl, 1-(1,2,3-triazolyl) or 4-(1,2,4-triazolyl); straight or branched $(C_1-C_3)$alkyl group selected from methyl, ethyl, n-propyl or 1-methylethyl; $(C_3-C_6)$cycloalkyl group selected from cyclopropyl, cyclobutyl, cyclopentyl or cyclohexyl; substituted $(C_3-C_6)$cycloalkyl group (substitution selected from $(C_1-C_3)$alkyl, cyano, amino or $(C_1-C_3)$acyl); $(C_6-C_{10})$aryl group selected from phenyl, α-naphthyl or β-naphthyl; substituted $(C_6-C_{10})$aryl group (substitution selected from halo,$(C_1-C_4)$alkoxy, trihalo $(C_1-C_3)$alkyl, nitro, amino, cyano, $(C_1-C_4)$alkoxycarbonyl, $(C_1-C_3)$alkylamino or carboxy); α-amino-$(C_1-C_4)$alkyl group selected from aminomethyl, α-aminoethyl, α-aminopropyl or α-aminobutyl; carboxy$(C_2-C_4)$alkylamino group selected from aminoacetic acid, α-aminobutyric acid or α-aminopropionic acid and their optical isomers; $(C_7-C_9)$aralkylamino group such as phenylglycyl; $(C_1-C_4)$alkoxycarbonylamino substituted $(C_1-C_4)$alkyl group, substitution selected from phenyl or p-hydroxyphenyl; α-hydroxy$(C_1-C_3)$alkyl group selected from hydroxymethyl, α-hydroxyethyl or α-hydroxy-1,methylethyl or α-hydroxypropyl; halo$(C_1-C_3)$alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-bromoethyl or 2-iodoethyl; a heterocycle group selected from a five membered aromatic or saturated ring with one N, O, S or Se heteroatom optionally having a benzo or pyrido ring fused thereto:

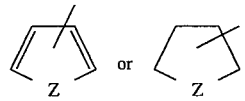

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

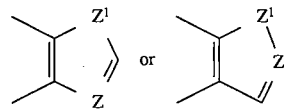

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended heteroatom:

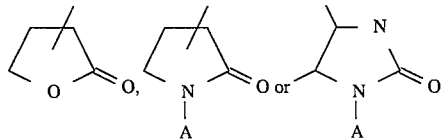

(A is selected from hydrogen; straight or branched $(C_1-C_4)$alkyl; $C_6$-aryl; substituted $C_6$-aryl (substitution selected from halo,$(C_1-C_4)$alkoxy, trihalo$(C_1-C_3)$alkyl, nitro, amino, cyano, $(C_1-C_4)$-alkoxycarbonyl, $(C_1-C_3)$alkylamine or carboxy); $(C_7-C_9)$-aralkyl group selected from benzyl, 1-phenylethyl, 2-phenylethyl or phenylpropyl)
such as γ-butyrolactam, γ-butyrolactone, imidazolidinone or N-aminoimidazolidinone, or a six membered aromatic ring with one to three N, O, S or Se heteroatoms such as pyridyl, pyridazinyl, pyrazinyl, sym-triazinyl, unsym-triazinyl, pyrimidinyl or ($C_1$–$C_3$)-alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl- 2-dioxo-1-piperazinyl, 2-dioxomorpholinyl or 2-dioxothiomorpholinyl; acyl or haloacyl group selected from acetyl, propionyl, chloroacetyl, trifluoroacetyl, ($C_3$–$C_6$)cycloalkylcarbonyl such as cyclopropylcarbonyl, cyclobutylcarbonyl, cyclopentylcarbonyl, cyclohexylcarbonyl, (2,3-dimethylcyclopropyl)carbonyl, (1,2-dimethylcyclopropyl)carbonyl, (2-ethylcyclopropyl)carbonyl, (2-methylcyclopentyl)carbonyl or (3-ethylcyclobutyl)carbonyl, ($C_6$–$C_{10}$)aroyl selected from benzoyl or naphthoyl, halo substituted ($C_6$–$C_{10}$)aroyl such as pentafluorobenzoyl, 4-chlorobenzoyl, 3-bromobenzoyl or 3,4-difluorobenzoyl, ($C_1$–$C_4$)alkylbenzoyl such as 4-toluoyl, 2-methylbenzoyl or 4-(1-methylethyl)benzoyl, or (heterocycle)carbonyl, the heterocycle selected from a five membered aromatic or saturated ring with one N, O, S or Se heteroatom optionally having a benzo or pyrido ring fused thereto:

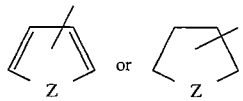

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

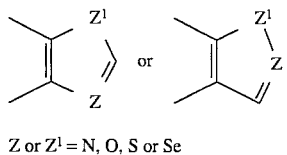

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

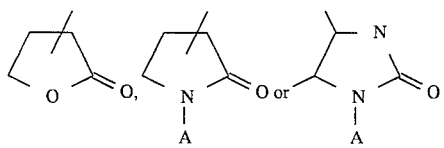

(A is selected from hydrogen; straight or branched ($C_1$–$C_4$)alkyl; $C_6$-aryl; substituted $C_6$-aryl (substitution selected from halo,($C_1$–$C_4$)alkoxy, trihalo($C_1$–$C_3$)alkyl, nitro, amino, cyano, ($C_1$–$C_4$)-alkoxycarbonyl, ($C_1$–$C_3$)alkylamino or carboxy); ($C_7$–$C_9$)-aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N, O, S or Se heteroatoms such as pyridyl, pyridazinyl, pyrazinyl, sym-triazinyl, unsym-triazinyl, pyrimidinyl or ($C_1$–$C_3$)-alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl; ($C_1$–$C_4$)alkoxycarbonyl group selected from methoxycarbonyl, ethoxycarbonyl, straight or branched propoxylcarbonyl, straight or branched butoxycarbonyl or allyloxycarbonyl; vinyl or substituted vinyl group [substitution selected from ($C_1$–$C_3$)alkyl group, halogen, ($C_6$–$C_{10}$)aryl group selected from phenyl, α-naphthyl, β-naphthyl, substituted ($C_6$–$C_{10}$)aryl group (substitution selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino, amino or carboxy), halo($C_1$–$C_3$)alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-bromoethyl or 2-iodoethyl, a heterocycle group selected from a five membered aromatic or saturated ring with one N, O, S or Se heteroatom optionally having a benzo or pyrido ring fused thereto:

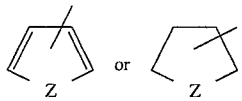

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl]; ($C_1$–$C_4$)alkoxy group such as allyloxy, methoxy, ethoxy, n-propoxy,n-butoxy or tert-butoxy; $C_6$-aryloxy group selected from phenoxy or substituted phenoxy (substitution selected from halo, ($C_1$–$C_4$)alkyl, nitro, cyano, thiol, amino, carboxy, di($C_1$–$C_3$)alkylamino); ($C_7$–$C_{10}$)aralkyloxy group such as benzyloxy, 1-phenylethyloxy or 2-phenylethyloxy; vinyloxy or substituted vinyloxy group (substitution selected from ($C_1$–$C_4$)-alkyl, cyano, carboxy, or ($C_6$–$C_{10}$)aryl selected from phenyl, α-naphthyl or β-naphthyl); $R^aR^b$amino($C_1$–$C_4$)-alkoxy group, wherein $R^aR^b$ is a straight or branched ($C_1$–$C_4$)alkyl selected from methyl, ethyl, n-propyl, 1-methylethyl, n-butyl, 1-methylpropyl, or 2-methyl-propyl or $R^aR^b$ is $(CH_2)_n$, n=2–6, or —$(CH_2)_2W(CH_2)_2$— wherein W is selected from —N($C_1$–$C_3$)alkyl [straight or branched], —NH, —NOB [B is selected from hydrogen or ($C_1$–$C_3$)alkyl], O or S; or $R^aR^b$aminoxy group, wherein $R^aR^b$ is a straight or branched ($C_1$–$C_4$)alkyl selected from methyl, ethyl, n-propyl, 1-methylethyl, n-butyl, 1-methylpropyl, or 2-methylpropyl or $R^aR^b$ is $(CH_2)_n$, n=2-6, or -$(CH_2)_2W(CH_2)_2$—wherein W is selected from —N($C_1$–$C_3$)alkyl [straight or branched], —NH, —NOB [B is selected from hydrogen or ($C_1$–$C_3$)alkyl], O or S; and when R=$R^4(CH_2)_nCO$— and n=1–4, $R^4$ is selected from hydrogen; ($C_1$–$C_3$)alkyl group selected from methyl, ethyl, n-propyl or 1-methylethyl; amino; monosubstituted amino selected from straight or branched ($C_1$–$C_6$)alkylamino, cyclopropylamino, cyclobutylamino, benzylamino or phenylamino; disubstituted amino selected from dimethylamino, diethylamino, ethyl(1-methylethyl)amino, monomethylbenzylamino, piperidinyl, morpholinyl, 1-imidazolyl, 1-pyrrolyl, 1-(1,2,3-triazolyl) or 4-(1,2,4-triazolyl); ($C_6$–$C_{10}$)aryl group selected from phenyl, α-naphthyl or β-naphthyl; substituted ($C_6$–$C_{10}$) aryl group (substitution selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino or carboxy);

acyloxy or haloacyloxy group, selected from acetyl, propionyl, chloroacetyl, trichloroacetyl, $(C_3-C_6)$cycloalkylcarbonyl, $(C_6-C_{10})$aroyl selected from benzoyl or naphthoyl, halo substituted $(C_6-C_{10})$aroyl such as pentafluorobenzoyl, 4-chlorobenzoyl, 3-bromobenzoyl or 3,4-difluorobenzoyl, $(C_1-C_4)$alkylbenzoyl such as 4-toluoyl, 2-toluoyl, 4-(1-methylethyl)benzoyl or (heterocycle)carbonyl, the heterocycle selected from a five membered aromatic or saturated ring with one N, O, S or Se heteroatom optionaly having a benzo or pyrido ring fused thereto:

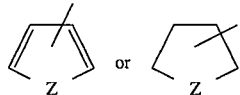

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

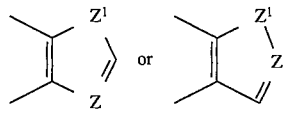

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

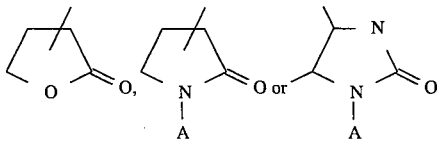

(A is selected from hydrogen; straight or branched $(C_1-C_4)$alkyl; $C_6$-aryl; substituted $C_6$-aryl (substitution selected from halo,$(C_1-C_4)$alkoxy, trihalo$(C_1-C_3)$alkyl, nitro, amino, cyano, $(C_1-C_4)$-alkoxycarbonyl, $(C_1-C_3)$alkylamino or carboxy); $(C_7-C_9)$-aralkyl group selected from benzyl, 1-phenylethyl, 2-phenylethyl or phenylpropyl)
such as γ-butyrolactam, γ-butyrolactone, imidazolidinone or N-aminoimidazolidinone, or a six membered aromatic ring with one to three N, O, S or Se heteroatoms such as pyridyl, pyridazinyl, pyrazinyl, sym-triazinyl, unsym-triazinyl, pyrimidinyl or $(C_1-C_3)$alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl; $(C_1-C_4)$alkoxy group such as allyloxy, methoxy, ethoxy, n-propoxy, n-butoxy or tert-butoxy; $C_6$-aryloxy group selected from phenoxy or substituted phenoxy (substitution selected from halo, $(C_1-C_4)$alkyl, nitro, cyano, thiol, amino, carboxy, di$(C_1-C_3)$alkylamino); $R^aR^b$amino$(C_1-C_4)$alkoxy group, wherein $R^aR^b$ is a straight or branched $(C_1-C_4)$alkyl selected from methyl, ethyl, n-propyl, 1-methylethyl, n-butyl, 1-methylpropyl, or 2-methylpropyl or $R^aR^b$ is $(CH_2)_n$, n=2-6, or $-(CH_2)_2W(CH_2)_2-$ wherein W is selected from $-N(C_1-C_3)$alkyl [straight or branched], $-NH$, $-NOB$ [B is selected from hydrogen or $(C_1-C_3)$alkyl], O or S; or $R^aR^b$aminoxy group, wherein $R^aR^b$ is a straight or branched $(C_1-C_4)$alkyl selected from methyl, ethyl, n-propyl, 1-methylethyl, n-butyl, 1-methylpropyl, or 2-methylpropyl or $R^aR^b$ is $(CH_2)_n$, n=2-6, or $-(CH_2)_2W(CH_2)_2-$ wherein W is selected from $-N(C_1-C_3)$alkyl [straight or branched], $-NH$, $-NOB$ [B is selected from hydrogen or $(C_1-C_3)$alkyl], O or S; $(C_1-C_3)$alkylthio group selected from methylthio, ethylthio, propylthio or allylthio; $C_6$-arylthio group selected from phenylthio or substituted phenylthio (substitution selected from halo, $(C_1-C_4)$alkyl, nitro, cyano, thiol, amino, carboxy, di$(C_1-C_3)$alkylamino); $C_6$-arylsulfonyl group selected from phenylsulfonyl or substituted phenylsulfonyl (substitution selected from halo, $(C_1-C_4)$-alkoxy, trihalo$(C_1-C_3)$alkyl, nitro, amino,-cyano, $(C_1-C_4)$alkoxycarbonyl, $(C_1-C_3)$alkylamino or carboxy); a heterocycle group selected from a five membered aromatic or saturated ring one N, O, S or Se heteroatom optionally having a benzo or pyrido ring fused thereto:

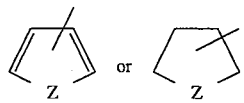

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

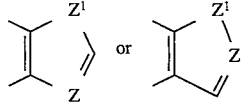

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

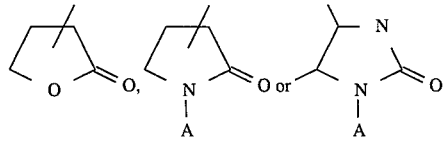

(A is selected from hydrogen; straight or branched $(C_1-C_4)$alkyl; $C_6$-aryl; substituted $C_6$-aryl (substitution selected from halo,$(C_1-C_4)$alkoxy, trihalo$(C_1-C_3)$alkyl, nitro, amino, cyano, $(C_1-C_4)$-alkoxycarbonyl, $(C_1-C_3)$alkylamino or carboxy); $(C_7-C_9)$-aralkyl group selected from benzyl, 1-phenylethyl, 2-phenylethyl or phenylpropyl)
such as γ-butyrolactam, γ-butyrolactone, imidazolidinone or N-aminoimidazolidinone, or a six membered aromatic ring with one to three N, O, S or Se heteroatoms such as pyridyl, pyridazinyl, pyrazinyl, sym-triazinyl, unsym-triazinyl, pyrimidinyl $(C_1-C_3)$alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl- 2-dioxo-1-piperazinyl, 2-dioxomorpholinyl or 2-dioxothiomorpholinyl; hydroxy group; α-hydroxy($C_1$–$C_3$)alkyl group selected from hydroxymethyl, α-hydroxyethyl or α-hydroxy-1-methylethyl or α-hydroxypropyl; halo($C_1$–$C_3$)alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoromethyl, 2-bromoethyl or 2-iodoethyl; acyl or haloacyl group selected from acetyl, propionyl, chloroacetyl, trifluoroacetyl, ($C_3$–$C_6$)cycloalkylcarbonyl, ($C_6$–$C_{10}$)aroyl selected from benzoyl or naphthoyl, halo substituted ($C_6$–$C_{10}$)aroyl such as pentafluorobenzoyl, 4-chlorobenzoyl, 3-bromophenylcarbonyl or 3,4-difluorobenzoyl, ($C_1$–$C_4$)alkylbenzoyl such as from 4-toluoyl, 2-toluoyl or 4-(1-methylethyl)benzoyl, or (heterocycle)carbonyl, the heterocycle selected from a five membered aromatic or saturated ring with one N, O, S or Se heteroatom optionally having a benzo or pyrido ring fused thereto:

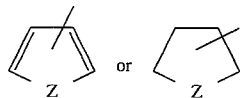

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

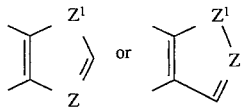

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

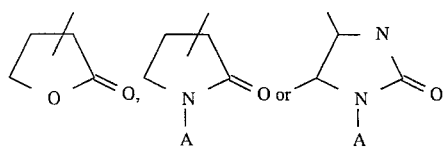

(A is selected from hydrogen; straight or branched ($C_1$–$C_4$)alkyl; $C_6$-aryl; substituted $C_6$-aryl (substitution selected from halo,($C_1$–$C_4$)alkoxy, trihalo($C_1$–$C_3$)alkyl, nitro, amino, cyano, ($C_1$–$C_4$)-alkoxycarbonyl, ($C_1$–$C_3$)alkylamino or carboxy); ($C_7$–$C_9$)-aralkyl group selected from benzyl, 1-phenylethyl, 2-phenylethyl or phenylpropyl) such as γ-butyrolactam, γ-butyrolactone, imidazolidinone or N-aminoimidazolidinone, or a six membered aromatic ring with one to three N, O, S or Se heteroatoms such as pyridyl, pyridazinyl, pyrazinyl, sym-triazinyl, unsym-triazinyl, pyrimidinyl or ($C_1$–$C_3$)alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl- 2-dioxo-1-piperazinyl, 2-dioxomorpholinyl or 2-dioxothiomorpholinyl; ($C_1$–$C_4$)alkoxycarbonylamino group selected from tert-butoxycarbonylamino, allyloxycarbonylamino, methoxycarbonylamino, ethoxycarbonylamino or propoxycarbonylamino; and when R=$R^{4'}$($CH_2$)$_n$$SO_2$— and n=0, $R^{4'}$ is selected from amino; monosubstituted amino selected from as straight or branched ($C_1$–$C_6$)alkylamino, cyclopropylamino, cyclobutylamino, benzylamino or phenylamino; disubstituted amino selected from dimethylamino, diethylamino, ethyl(1-methylethyl)amino, monomethylbenzylamino, piperidinyl, morpholinyl, 1-imidazolyl, 1-pyrrolyl, 1-(1,2,3-triazolyl) or 4-(1,2,4-triazolyl); straight or branched ($C_1$–$C_3$)alkyl group selected from methyl, ethyl, n-propyl or 1-methylethyl; ($C_6$–$C_{10}$)aryl group selected from phenyl, α-naphthyl or β-naphthyl; substituted ($C_6$–$C_{10}$)aryl group (substitution selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino or carboxy); a heterocycle group selected from a five membered aromatic or saturated ring with one N, O, S or Se heteroatom optionally having a benzo or pyrido ring fused thereto:

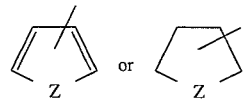

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

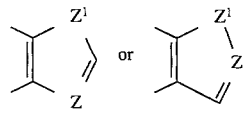

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

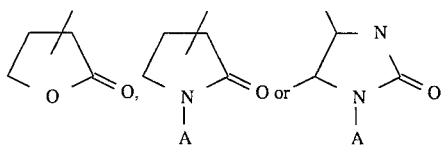

(A is selected from hydrogen; straight or branched ($C_1$–$C_4$)alkyl; $C_6$-aryl; substituted $C_6$-aryl (substitution selected from halo,($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino or carboxy); ($C_7$–$C_9$)aralkyl group selected from benzyl, 1-phenylethyl, 2-phenylethyl or phenylpropyl) such as γ-butyrolactam, γ-butyrolactone, imidazolidinone or N-aminoimidazolidinone, or a six membered aromatic ring with one to three N, O, S or Se heteroatoms such as pyridyl, pyridazinyl, pyrazinyl, sym-triazinyl, unsym-triazinyl, pyrimidinyl or (C₁-C₃)alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl- 2-dioxo-1-piperazinyl, 2-dioxomorpholinyl or 2-dioxo-thiomorpholinyl; and when R=R4' (CH₂)ₙSO₂—and n=1–4, R⁴' is selected from hydrogen; amino; monosubstituted amino selected from straight or branched (C₁-C₆)alkylamino, cyclopropylamino, cyclobutylamino, benzylamino or phenylamino; disubstituted amino selected from dimethylamino, diethylamino, ethyl(1-methylethyl)amino, monomethylbenzylamino, piperidinyl, morpholinyl, 1-imidazolyl, 1-pyrrolyl, 1-(1,2,3-triazolyl) or 4-(1,2,4-triazolyl); straight or branched (C₁-C₃)alkyl group selected from methyl, ethyl, n-propyl or 1-methylethyl; RᵃRᵇamino(C₁-C₄)alkoxy group, wherein RᵃRᵇ is a straight or branched (C₁-C₄)alkyl selected from methyl, ethyl, n-propyl, 1-methylethyl, n-butyl, 1-methylpropyl, or 2-methylpropyl or RᵃRᵇ is (CH₂)ₙ, n=2–6, or -(CH₂)₂W—(CH₂)₂—wherein W is selected from —N(C₁-C₃)alkyl [straight or branched], —NH, —NOB [B is selected from hydrogen or (C₁-C₃)alkyl], O or S; or RᵃRᵇaminoxy group, wherein RᵃRᵇ is a straight or branched (C₁-C₄)alkyl selected from methyl, ethyl, n-propyl, 1-methylethyl, n-butyl, 1-methylpropyl, or 2-methylpropyl or RᵃRᵇ is (CH₂)ₙ, n=2–6, or -(CH₂)₂W— (CH₂)₂—wherein W is selected from —N(C₁-C₃)alkyl [straight or branched], —NH, —NOB [B is selected from hydrogen or (C₁-C₃)alkyl], O or S; R⁵ is selected from hydrogen; straight or branched (C₁-C₃)alkyl group selected from methyl, ethyl, n-propyl or 1-methylethyl; (C₆-C₁₀)aryl group selected from phenyl, α-naphthyl or β-naphthyl; (C₇-C₉)aralkyl group such as benzyl, 1-phenylethyl, 2-phenylethyl or phenylpropyl; a heterocycle group selected from a five membered aromatic or saturated ring with one N, O, S or Se heteroatom optionally having a benzo or pyrido ring fused thereto:

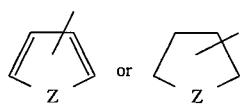

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

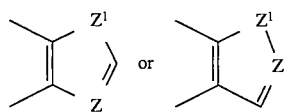

Z or Z¹ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended heteroatom:

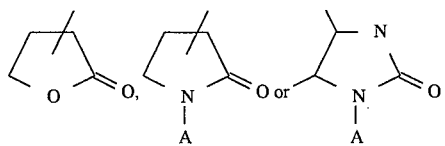

(A is selected from hydrogen; straight or branched (C₁-C₄)alkyl; C₆-aryl; substituted C₆-aryl (substitution selected from halo,(C₁-C₄)alkoxy, trihalo(C₁-C₃)alkyl, nitro, amino, cyano, (C₁-C₄)-alkoxycarbonyl, (C₁-C₃)alkylamino or carboxy); (C₇-C₉)-aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N, O, S or Se heteroatoms such as pyridyl, pyridazinyl, pyrazinyl, sym-triazinyl, unsym-triazinyl, pyrimidinyl or (C₁-C₃)alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl- 2-dioxo-1-piperazinyl, 2-dioxomorpholinyl, 2-dioxothiomorpholinyl; or —(CH₂)ₙCOOR⁷ where n=0–4 and R⁷ is selected from hydrogen; straight or branched (C₁-C₃)alkyl group selected from methyl, ethyl, n-propyl or 1-methylethyl; or (C₆-C₁₀)aryl group selected from phenyl, α-naphthyl or β-naphthyl; R⁶ is selected from hydrogen; straight or branched (C₁-C₃)alkyl group selected from methyl, ethyl, n-propyl or 1-methylethyl; (C₆-C₁₀)aryl group selected from phenyl, α-naphthyl or β-naphthyl; (C₇-C₉)aralkyl group such as benzyl, 1-phenylethyl, 2-phenylethyl or phenylpropyl; a heterocycle group selected from a five membered aromatic or saturated ring with one N, O, S or Se heteroatom optionally having a benzo or pyrido ring fused thereto:

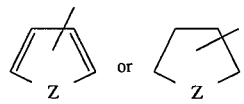

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

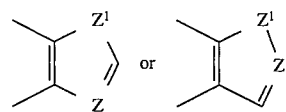

Z or Z¹ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended heteroatom:

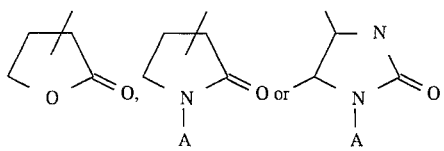

(A is selected from hydrogen; straight or branched ($C_1$–$C_4$)alkyl; $C_6$-aryl; substituted $C_6$-aryl (substitution selected from halo,($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino or carboxy); ($C_7$–$C_9$)aralkyl group selected from benzyl, 1-phenylethyl, 2-phenylethyl or phenylpropyl) such as γ-butyrolactam, γ-butyrolactone, imidazolidinone or N-aminoimidazolidinone, or a six membered aromatic ring with one to three N, O, S or Se heteroatoms such as pyridyl, pyridazinyl, pyrazinyl, sym-triazinyl, unsym-triazinyl, pyrimidinyl or ($C_1$–$C_3$)alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl- 2-dioxo-1-piperazinyl, 2-dioxomorpholinyl, 2-dioxothiomorpholinyl; or $(CH_2)_n COOR^7$ where n=0–4 and $R^7$ is selected from hydrogen; straight or branched ($C_1$–$C_3$)alkyl selected from methyl, ethyl, n-propyl or 1-methylethyl; or ($C_6$–$C_{10}$)aryl selected from phenyl, α-naphthyl or β-naphthyl; with the proviso that $R^5$ and $R^6$ cannot both be hydrogen; or $R^5$ and $R^6$ taken together are —$(CH_2)_2 W(CH_2)_2$—, wherein W is selected from $(CH_2)_n$ and n=0–1, —NH, —N($C_1$–$C_3$)alkyl [straight or branched], —N($C_1$–$C_4$)alkoxy, oxygen, sulfur or substituted congeners selected from (L or D)proline, ethyl(L or D)prolinate, morpholine, pyrrolidine or piperidine; and the pharmacologically acceptable organic and inorganic salts or metal complexes.

Most particularly preferred compounds are compounds according to the above formula I and II in which X is selected from amino, $NR^1R^2$, or halogen; the halogen is selected from bromine, chlorine, fluorine or iodine; and when $X=NR^1R^2$ and $R^1$=hydrogen, $R^2$ =methyl, ethyl, n-propyl, 1-methylethyl, n-butyl, 1-methylpropyl, 2-methylpropyl or 1,1-dimethylethyl; and when $R^1$ =methyl or ethyl, $R^2$ =methyl, ethyl, n-propyl, 1-methylethyl, n-butyl, 1-methylpropyl or 2-methylpropyl; R is selected from R4$(CH_2)_n$CO— or $R^{4'}$ $(CH_2)_n SO_2$—; and when R=$R^4(CH_2)_n$CO—and n=0, $R^4$ is selected from hydrogen; amino; monosubstituted amino selected from straight or branched ($C_1$–$C_6$)alkylamino, cyclopropylamino, cyclobutylamino, benzylamino or phenylamino; disubstituted amino selected from dimethylamino, diethylamino, ethyl(1-methylethyl)amino, monomethylbenzylamino, piperidinyl, morpholinyl, 1-imidazolyl, 1-pyrrollyl, 1-(1,2,3-triazolyl) or 4-(1,2,4-triazolyl); straight or branched ($C_1$–$C_2$)alkyl group selected from methyl or ethyl; ($C_6$–$C_{10}$)aryl group selected from phenyl, α-naphthyl or β-naphthyl; substituted ($C_6$–$C_{10}$)aryl group (substitution selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino or carboxy); carboxy($C_2$–$C_4$)alkylamino group selected from aminoacetic acid, α-aminobutyric acid or α-aminopropionic acid and their optical isomers; α-hydroxy($C_1$–$C_3$)alkyl group selected from hydroxymethyl, α-hydroxyethyl or α-hydroxy-1-methyl-ethyl or α-hydroxypropyl; halo($C_1$–$C_3$)alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-bromoethyl or 2-iodoethyl; a heterocycle group selected from a five membered aromatic or saturated ring with one N, O, S or Se heteroatom optionally having a benzo or pyrido ring fused thereto:

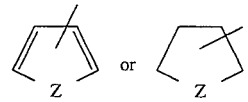

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

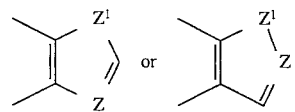

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

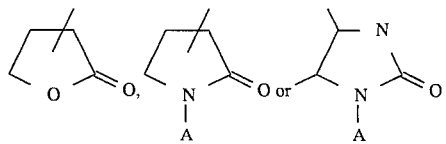

(A is selected from hydrogen; straight or branched ($C_1$–$C_4$)alkyl; $C_6$-aryl; substituted $C_6$-aryl (substitution selected from halo,($C_1$–$C_4$)alkoxy, trihalo($C_1$–$C_3$)alkyl, nitro, amino, cyano, ($C_1$–$C_4$)-alkoxycarbonyl, ($C_1$–$C_3$)alkylamino or carboxy); ($C_7$–$C_9$)aralkyl group selected from benzyl, 1-phenylethyl, 2-phenylethyl or phenylpropyl) such as γ-butyrolactam, γbutyrolactone, imidazolidinone or N-aminoimidazolidinone, or a six membered aromatic ring with one to three N, O, S or Se heteroatoms such as pyridyl, pyridazinyl, pyrazinyl, sym-triazinyl, unsym-triazinyl, pyrimidinyl or ($C_1$–$C_3$)alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyldioxo- 1-piperazinyl, 2-dioxomorpholinyl or 2-dioxothiomorpholinyl; ($C_1$–$C_4$)alkoxycarbonyl group selected from methoxycarbonyl, ethoxycarbonyl, straight or branched propoxylcarbonyl, straight or branched butoxycarbonyl or allyloxycarbonyl; vinyl or substituted vinyl group [substitution selected from ($C_1$–$C_3$)alkyl group, halogen, ($C_6$–$C_{10}$)aryl group selected from phenyl, α-naphthyl, β-naphthyl, substituted ($C_6$–$C_{10}$) aryl group (substitution selected from halo, ($C_1$–$C_4$)alkoxy trihalo($C_1$–$C_3$)alkyl, nitro, amino, cyano, ($C_1$–$C_4$)alkoxycarbonyl, ($C_1$–$C_3$)alkylamino or carboxy), halo($C_1$–$C_3$)alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-bromoethyl or 2-iodoethyl, a heterocycle group selected from a five membered aromatic or saturated ring with one N, O, S or Se heteroatom optionally having a benzo or pyrido ring fused thereto:

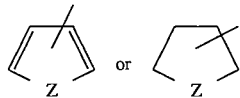

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl]; $(C_1-C_4)$alkoxy group such as allyloxy, methoxy, ethoxy, n-propoxy, n-butoxy or tert-butoxy; $C_6$-aryloxy group selected from phenoxy or substituted phenoxy (substitution selected from halo, $(C_1-C_4)$alkyl, nitro, cyano, thiol, amino, carboxy, di$(C_1-C_3)$alkylamino); $(C_7-C_{10})$aralkyloxy group such as benzyloxy, 1-phenylethyloxy or 2-phenylethyloxy; vinyloxy or substituted vinyloxy group (substitution selected from $(C_1-C_4)$alkyl, cyano, carboxy, or $(C_6-C_{10})$aryl selected from phenyl, α-naphthyl or βnaphthyl); $R^aR^b$amino$(C_1-C_4)$alkoxy group, wherein $R^aR^b$ is a straight or branched $(C_1-C_4)$alkyl selected from methyl, ethyl, n-propyl, 1-methylethyl, n-butyl, 1-methylpropyl, or 2-methylpropyl or $R^aR^b$ is $(CH_2)_n$, n=2–6, or —$(CH_2)_2W(CH_2)_2$— wherein W is selected from -N$(C_1-C_3)$alkyl [straight or branched], —NH, —NOB [B is selected from hydrogen or $(C_1-C_3)$alkyl], O or S; or $R^aR^b$aminoxy group, wherein $R^aR^b$ is a straight or branched $(C_1-C_4)$alkyl selected from methyl, ethyl, n-propyl, 1-methylethyl, n-butyl, 1-methylpropyl, or 2-methylpropyl or $R^aR^b$ is $(CH_2)_n$, n=2–6, or —$(CH_2)_2W$—$(CH_2)_2$—wherein W is selected from —N$(C_1-C_3)$alkyl [straight or branched], —NH, —NOB [B is selected from hydrogen or $(C_1-C_3$ ) alkyl ], O or S; and when R=$R^4$ $(CH_2)_nCO$— and n=1–4 $R^4$ is selected from hydrogen; $(C_1-C_2)$alkyl group selected from methyl or ethyl; amino; monosubstituted amino selected from straight or branched $(C_1-C_6)$alkylamino, cyclopropylamino, cyclobutylamino, benzylamino or phenylamino; disubstituted amino selected from dimethylamino, diethylamino, ethyl(1-methylethyl)amino, monomethylbenzylamino, piperidinyl, morpholinyl, 1-imidazolyl, 1-pyrrolyl, 1-(1,2,3-triazolyl) or 4-(1,2,4-triazolyl); $(C_6-C_{10})$aryl group selected from phenyl, α-naphthyl or β-naphthyl; substituted$(C_6-C_{10})$aryl group (substitution selected from halo, $(C_1-C_4)$alkoxy, trihalo$(C_1-C_3)$alkyl, nitro, amino, cyano, $(C_1-C_4)$alkoxycarbonyl, $(C_1-C_3)$alkylamino or carboxy); acyloxy or haloacyloxy group, selected from acetyl, propionyl, chloroacetyl, trichloroacetyl, $(C_3-C_6)$cycloalkylcarbonyl, $(C_6-C_{10})$aroyl selected from benzoyl or naphthoyl, halo substituted $(C_6-C_{10})$aroyl such as pentafluorobenzoyl, 4-chlorobenzoyl, 3-bromobenzoyl or 3,4-difluorobenzoyl, $(C_1-C_4)$alkylbenzoyl such as 4-toluoyl, 2-toluoyl, 4-(1-methylethyl)benzoyl or (heterocycle)carbonyl, the heterocycle selected from a five membered aromatic or saturated ring with one N, O, S or Se heteroatom optionally having a benzo or pyrido ring fused thereto:

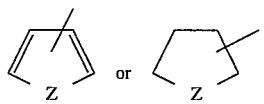

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

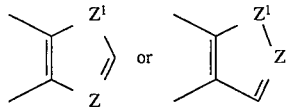

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

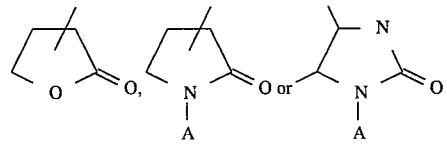

(A is selected from hydrogen; straight or branched $(C_1-C_4)$alkyl; $C_6$-aryl; substituted $C_6$-aryl (substitution selected from halo,$(C_1-C_4)$alkoxy, trihalo$(C_1-C_3)$alkyl, nitro, amino, cyano, $(C_1-C_4)$-alkoxycarbonyl, $(C_1-C_3)$alkylamino or carboxy); $(C_7-C_9)$-aralkyl group selected from benzyl, 1-phenylethyl, 2-phenylethyl or phenylpropyl) such as γ-butyrolactam, γ-butyrolactone, imidazolidinone or N-aminoimidazolidinone, or a six membered aromatic ring with one or two N, O, S or Se heteroatoms such as pyridyl, pyridazinyl, pyrazinyl, sym-triazinyl, unsym-triazinyl, pyrimidinyl or $(C_1-C_3)$alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl- 2-dioxo-1-piperazinyl, 2-dioxomorpholinyl or 2-dioxothiomorpholinyl; $(C_1-C_4)$alkoxy group such as allyloxy, methoxy, ethoxy, n-propoxy, n-butoxy or tert-butoxy; $R^aR^b$amino$(C_1-C_4)$alkoxy group, wherein $R^aR^b$ is a straight or branched $(C_1-C_4)$alkyl selected from methyl, ethyl, n-propyl, 1-methylethyl, n-butyl, 1-methylpropyl, or 2-methylpropyl or $R^aR^b$ is $(CH_2)_n$, n=2–6, or —$(CH_2)_2W(CH_2)_2$— wherein W is selected from —N$(C_1-C_3)$alkyl [straight or branched], —NH, —NOB [B is selected from hydrogen or $(C_1-C_3)$alkyl], O or S; or $R^aR^b$aminoxy group, wherein $R^aR^b$ is a straight or branched $(C_1-C_4)$—alkyl selected from methyl, ethyl, n-propyl, 1-methylethyl, n-butyl, 1-methylpropyl, or 2-methylpropyl or $R^aR^b$ is $(CH_2)$n, n=2–6, or —$(CH_2)_2W(CH_2)_2$—wherein W is selected from —N$(C_1-C_3)$alkyl [straight or branched], —NH, —NOB [B is selected from hydrogen or $(C_1-C_3)$alkyl], O or S; α-hydroxy$(C_1-C_3)$alkyl group selected from hydroxymethyl, α-hydroxyethyl or α-hydroxy-1-methylethyl or α-hydroxypropyl; halo$(C_1-C_3)$alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoromethyl, 2-bromoethyl or 2-iodoethyl; $(C_1-C_4)$alkoxycarbonylamino group selected from tert-butoxycarbonylamino, allyloxycarbonylamino, methoxycarbonylamino, ethoxycarbonylamino or propoxycarbonylamino; and when R=$R^{4'}$ $(CH_2)_nSO_2$— and n=0, $R^{4'}$ is-selected from amino; monosubstituted amino selected from as straight or branched $(C_1-C_6)$alkylamino, cyclopropylamino, cyclobutylamino, benzylamino or phenylamino; disubstituted amino selected from dimethylamino, diethylamino, ethyl(1-methylethyl)amino, monomethylbenzylamino, piperidinyl, morpholinyl, 1-imidazolyl, 1-pyrolyl, 1-(1,2,3-triazolyl) or 4-(1,2,4-triazolyl); straight or branched ($C_1$–$C_2$)alkyl group selected from methyl or ethyl; ($C_6$–$C_{10}$)aryl group selected from phenyl, α-naphthyl or β-naphthyl; substituted ($C_6$–$C_{10}$)aryl group (substitution selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino or carboxy); a heterocycle group selected from a five membered aromatic or saturated ring with one N, O, S or Se heteroatom optionally having a benzo or pyrido ring fused thereto:

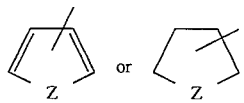

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

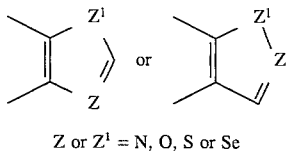

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

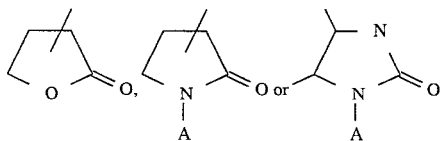

(A is selected from hydrogen; straight or branched ($C_1$–$C_4$)alkyl; $C_6$-aryl; substituted $C_6$-aryl (substitution selected from halo,($C_1$–$C_4$)alkoxy, trihalo($C_1$–$C_3$)alkyl, nitro, amino, cyano, ($C_1$–$C_4$)—alkoxycarbonyl, ($C_1$–$C_3$)alkylamino or carboxy); ($C_7$–$C_9$)—aralkyl group selected from benzyl, 1-phenylethyl, 2-phenylethyl or phenylpropyl)
such as γ-butyrolactam, γ-butyrolactone, imidazolidinone or N-aminoimidazolidinone, or a six membered aromatic ring with one to three N, O, S or Se heteroatoms such as pyridyl, pyridazinyl, pyrazinyl, sym-triazinyl, unsym-triazinyl, pyrimidinyl or ($C_1$–$C_3$)alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl- 2-dioxo-1-piperazinyl, 2-dioxomorpholinyl or 2-dioxothiomorpholinyl; and when R=R4' ($CH_2$)$_n$$SO_2$—and n=1–4, $R^{4'}$ is selected from hydrogen; straight or branched ($C_1$–$C_2$)alkyl group selected from methyl or ethyl; $R^5$ is selected from hydrogen; straight or branched ($C_1$–$C_3$)alkyl group selected from methyl, ethyl, n-propyl or 1-methylethyl; ($C_6$–$C_{10}$)aryl group selected from phenyl, α-naphthyl or p-naphthyl; ($C_7$–$C_9$)aralkyl group such as benzyl, 1-phenylethyl, 2-phenylethyl or phenylpropyl; a heterocycle group selected from a five membered aromatic or saturated ring with one N, O, S or Se heteroatom optionally having a benzo or pyrido ring fused thereto:

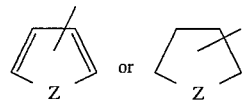

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

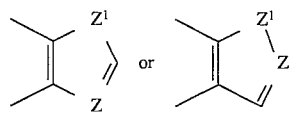

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

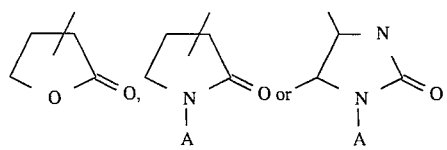

(A is selected from hydrogen; straight or branched ($C_1$–$C_4$) alkyl; $C_6$-aryl; substituted $C_6$-aryl (substitution selected from halo, ($C_1$–$C_4$) alkoxy, trihalo ($C_1$–$C_3$) alkyl, nitro, amino, cyano, ($C_1$–$C_4$)—alkoxycarbonyl, ($C_1$–$C_3$) alkylamino or carboxy); ($C_7$–$C_9$)—aralkyl group selected from benzyl, 1-phenylethyl, 2-phenylethyl or phenylpropyl)
such as γ-butyrolactam, γ-butyrolactone, imidazolidinone or N-aminoimidazolidinone, or a six membered aromatic ring with one to three N, O, S or Se heteroatoms such as pyridyl, pyridazinyl, pyrazinyl, sym-triazinyl, unsym-triazinyl, pyrimidinyl or ($C_1$–$C_3$)alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl- 2-dioxo-1-piperazinyl, 2-dioxomorpholinyl, 2-dioxothiomorpholinyl; or —($CH_2$)$_n$$COOR^7$ where n=0–4 and $R^7$ is selected from hydrogen; straight or branched ($C_1$–$C_3$)—alkyl group selected from methyl, ethyl, n-propyl or 1-methylethyl; or ($C_6$–$C_{10}$)aryl group selected from phenyl, α-naphthyl, β-naphthyl; $R^6$ is selected from hydrogen; straight or branched ($C_1$–$C_3$)alkyl group selected from methyl, ethyl, n-propyl or 1-methylethyl; ($C_6$–$C_{10}$)aryl group selected from phenyl, α-naphthyl or β-naphthyl; ($C_7$–$C_9$)aralkyl group such as benzyl, 1-phenylethyl, 2-phenylethyl or phenylpropyl; a heterocycle group selected from a five membered aromatic or saturated ring with one N, O, S or Se heteroatom optionally having a benzo or pyrido ring fused thereto:

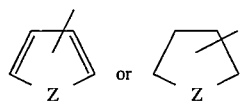

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

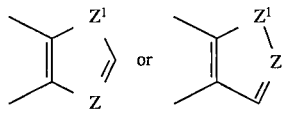

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

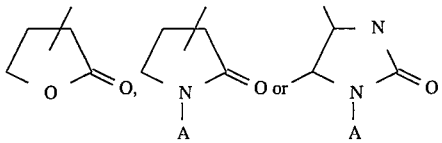

(A is selected from hydrogen; straight or branched $(C_1-C_4)$alkyl; $C_6$-aryl; substituted $C_6$-aryl (substitution selected from halo,$(C_1-C_4)$alkoxy, trihalo$(C_1-C_3)$alkyl, nitro, amino, cyano, $(C_1-C_4)$alkoxycarbonyl, $(C_1-C_3)$alkylamino or carboxy); $(C_7-C_9)$-aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N, O, S or Se heteroatoms such as pyridyl, pyridazinyl, pyrazinyl, sym-triazinyl, unsym-triazinyl, pyrimidinyl or $(C_1-C_3)$alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl- 2-dioxo-1-piperazinyl, 2-dioxomorpholinyl, 2-dioxothiomorpholinyl; or $(CH_2)_n$COOR7' where n=0–4 and $R^{7'}$ is selected from hydrogen; straight or branched $(C_1-C_3)$alkyl selected from methyl, ethyl, n-propyl or 1-methylethyl; or $(C_6-C_{10})$aryl selected from phenyl, α-naphthyl or β-naphthyl; with the proviso that $R^5$ and $R^6$ cannot both be hydrogen; or $R^5$ and $R^6$ taken together are —$(CH_2)_2W(CH_2)_2$—, wherein W is selected from $(CH_2)_n$ and n=0–1, —NH, —N$(C_1-C_3)$alkyl [straight or branched], —N$(C_1-C_4)$alkoxy, oxygen, sulfur or substituted congeners selected from (L or D)proline, ethyl(L or D)prolinate, morpholine, pyrrolidine or piperidine; and the pharmacologically acceptable organic and inorganic salts or metal complexes.

Compounds of special interest are compounds according to the above formula I and II in which X is selected from amino, $NR1R_2$ or halogen; the halogen is selected from bromine, chlorine, fluorine or iodine; and when X=$NR^1R^2$ and $R^1$=methyl or ethyl; $R^2$=methyl or ethyl, R is selected from $R^4(CH_2)_n$CO— or $R^{4'}$ $(CH_2)_n$SO$_2$—; and when R=$R^4(CH_2)_n$CO— and n=0, $R^4$ is selected from hydrogen; straight or branched $(C_1-C_2)$alkyl group selected from methyl or ethyl; a heterocycle group selected from a five membered aromatic or saturated ring with one N, O, or S heteroatom optionally having a benzo or pyrido ring fused thereto:

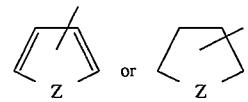

Z = N, O, or S such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O or S heteroatoms optionally having a benzo or pyrido ring fused thereto:

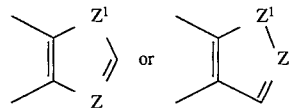

Z or $Z^1$ = N, O, or S such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O or S heteroatoms and an adjacent appended O heteroatom:

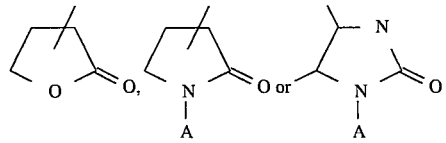

(A is selected from hydrogen; straight or branched $(C_1-C_2)$alkyl; $C_6$-aryl)

such as γ-butyrolactam, γ-butyrolactone, imidazolidinone or N-aminoimidazolidinone; $(C_1-C_4)$alkoxycarbonyl group selected from methoxycarbonyl, ethoxycarbonyl, straight or branched propoxylcarbonyl, straight or branched butoxycarbonyl or allyloxycarbonyl; vinyl or substituted vinyl group [substitution selected from $(C_1-C_2)$alkyl group, $(C_6-C_{10})$aryl group selected from phenyl, α-naphthyl, β-naphthyl, substituted $(C_6-C_{10})$aryl group (substitution selected from halo, $(C_1-C_4)$alkoxy, $(C_1-C_4)$alkoxycarbonyl), halo$(C_1-C_3)$alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-bromoethyl or 2-iodoethyl, $(C_1-C_4)$alkoxy group such as allyloxy, methoxy, ethoxy, n-propoxy, n-butoxy or tert-butoxy; $C_6$-aryloxy group selected from phenoxy or substituted phenoxy (substitution selected from halo, $(C_1-C_4)$alkyl); $(C_7-C_{10})$aralkyloxy group such as benzyloxy, 1-phenylethyloxy or 2-phenylethyloxy; vinyloxy or substituted vinyloxy group (substitution selected from $(C_1-C_2)$alkyl); $R^aR^b$amino$(C_1-C_4)$alkoxy group, wherein $R^aR^b$ is a straight or branched $(C_1-C_4)$alkyl selected from methyl, ethyl, n-propyl, 1-methylethyl, n-butyl; or $R^aR^b$aminoxy group, wherein $R^aR^b$ is a straight or branched $(C_1-C_4)$alkyl selected from methyl, ethyl, n-propyl, 1-methylethyl, n-butyl, 1-methylpropyl, or 2-methylpropyl; and when R=R4(CH$_2$)$_n$CO— and n=1–4, R$^4$ is selected from hydrogen; (C$_1$–C$_2$)alkyl group selected from methyl or ethyl; amino; monosubstituted amino selected from straight or branched (C$_1$–C$_6$)alkylamino, cyclopropylamino, cyclobutylamino, benzylamino or phenylamino; disubstituted amino selected from dimethylamino, diethylamino, ethyl(1-methylethyl)amino, monomethylbenzylamino, piperidinyl, morpholinyl, 1-imidazolyl, 1-pyrrolyl, or 1-(1,2,3-triazolyl); (C$_6$–C$_{10}$)aryl group selected from phenyl, α-naphthyl or β-naphthyl; substituted(C$_6$–C$_{10}$)aryl group (substitution selected from halo, (C$_1$–C$_4$)alkoxy, nitro, amino, (C$_1$–C$_4$)alkoxycarbonyl); acyloxy or haloacyloxy group selected from acetyl, propionyl or chloroacetyl; (C$_1$–C$_4$)alkoxy group such as allyloxy, methoxy, ethoxy, n-propoxy, n-butoxy or tert-butoxy; R$^a$R$^b$amino(C$_1$–C$_4$)alkoxy group, wherein R$^a$R$^b$ is a straight or branched (C$_1$–C$_4$)alkyl selected from methyl, ethyl, n-propyl, 1-methylethyl, n-butyl, 1-methylpropyl, or 2-methylpropyl or R$^a$R$^b$ is (CH$_2$)n, n=2–6, or —(CH$_2$)$_2$W(CH$_2$)$_2$— wherein W is selected from —N(C$_1$–C$_3$)alkyl [straight or branched], —NH, —NOB [B is selected from hydrogen or (C$_1$–C$_3$)alkyl], O or S; or R$^a$R$^b$aminoxy group, wherein R$^a$R$^b$ is a straight or branched (C$_1$–C$_4$)alkyl selected from methyl, ethyl, n-propyl, 1-methylethyl, n-butyl, 1-methylpropyl, or 2-methylpropyl or R$^a$R$^b$ is (CH$_2$)$_n$, n=2–6, or —(CH$_2$)$_2$W— (CH$_2$)$_2$—wherein W is selected from —N(C$_1$–C$_3$)alkyl [straight or branched], —NH, —NOB [B is selected from hydrogen or (C$_1$–C$_3$)alkyl], O or S; halo(C$_1$–C$_3$)alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoromethyl, 2-bromoethyl or 2-iodoethyl; (C$_1$–C$_4$)alkoxycarbonylamino group selected from tert-butoxycarbonylamino, allyloxycarbonylamino, methoxycarbonylamino, ethoxycarbonylamino or propoxycarbonylamino; and when R=R$^4'$ (CH$_2$)$_n$SO$_2$— and n=0, R$^{4'}$ is selected from straight or branched (C$_1$–C$_2$)alkyl group selected from methyl or ethyl; (C$_6$–C$_{10}$)aryl group selected from phenyl, α-naphthyl or β-naphthyl; substituted (C$_6$–C$_{10}$)aryl group (substitution selected from halo, (C$_1$–C$_4$)alkoxy, nitro, (C$_1$–C$_4$)alkoxycarbonyl); a heterocycle group selected from a five membered aromatic or saturated ring with one N, O or S heteroatom optionally having a benzo or pyrido ring fused thereto:

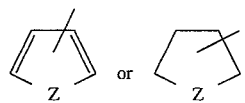

Z = N, O, or S such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O or S heteroatoms optionally having a benzo or pyrido ring fused thereto:

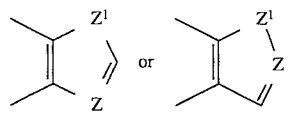

Z or Z$^1$ = N, O, or S such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl; and when R=R4' (CH$_2$)$_n$SO$_2$— and n=1–8, R$^{4'}$ is selected from hydrogen; straight or branched (C$_1$–C$_2$)alkyl group selected from methyl or ethyl; R$^5$ is selected from hydrogen; straight or branched (C$_1$–C$_3$)alkyl group selected from methyl, ethyl, n-propyl or 1-methylethyl; R$^6$ is selected from hydrogen; straight or branched (C$_1$–C$_3$)alkyl group selected from methyl, ethyl, n-propyl or 1-methylethyl; with the proviso that R$^5$ and R$^6$ cannot both be hydrogen; or R$^5$ and R$^6$ taken together are —(CH$_2$)$_2$W(CH$_2$)$_2$—, wherein W is selected from (CH$_2$)$_n$ and n=0–1, —NH, —N(C$_1$–C$_3$)alkyl [straight or branched], —N(C$_1$–C$_4$)alkoxy, oxygen, sulfur or substituted congeners selected from (L or D)proline, ethyl(L or D)prolinate, morpholine, pyrrolidine or piperidine;and the pharmacologically acceptable organic and inorganic salts or metal complexes.

Also included in the present invention are compounds useful as intermediates for producing the above compounds of formula I and II. Such intermediate compounds include those having the formula:

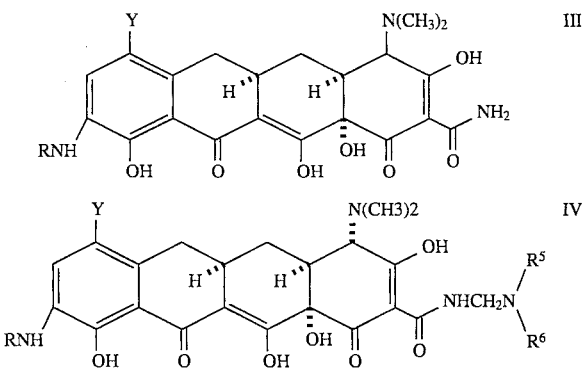

wherein formula III and IV, Y is NO$_2$; R is selected from R$^4$(CH$_2$)$_n$CO— or R$^{4'}$ (CH$_2$)$_n$SO$_2$; and when R=R$^4$ (CH$_2$)$_n$CO—and n=0, R$^4$ is selected from hydrogen; amino; monosubstituted amino selected from straight or branched (C$_1$–C$_6$)alkylamino, cyclopropylamino, cyclobutylamino, benzylamino or phenylamino; disubstituted amino selected from dimethylamino, diethylamino, ethyl(1-methylethyl)amino, monomethylbenzylamino, piperidinyl, morpholinyl, 1-imidazolyl, 1-pyrrolyl, 1-(1,2,3-triazolyl) or 4-(1,2,4-triazolyl); straight or branched (C$_1$–C$_4$)alkyl group selected from methyl, ethyl, n-propyl, 1-methylethyl, n-butyl, 1-methylpropyl, 2-methylpropyl or 1,1-dimethylethyl; (C$_3$–C$_6$)cycloalkyl group selected from cyclopropyl, cyclobutyl, cyclopentyl or cyclohexyl; substituted (C$_3$–C$_6$)cycloalkyl group (substitution selected from (C$_1$–C$_3$)alkyl, cyano, amino or (C$_1$–C$_3$)acyl); (C$_6$–C$_{10}$)aryl group selected from phenyl, α-naphthyl or β-naphthyl; substituted (C$_6$–C$_{10}$)aryl group (substitution selected from halo, (C$_1$–C$_4$)alkoxy, trihalo(C$_1$–C$_3$)alkyl, nitro, amino, cyano, (C$_1$–C$_4$)alkoxycarbonyl, (C$_1$–C$_3$)alkylamino or carboxy); (C$_7$–C$_9$)aralkyl group selected from benzyl, 1-phenylethyl, 2-phenylethyl or phenylpropyl; α-amino-(C$_1$–C$_4$)alkyl group selected from aminomethyl, α-aminoethyl, α-aminopropyl or α-aminobutyl; carboxy(C$_2$–C$_4$)-alkylamino group selected from aminoacetic acid, α-aminobutyric acid or α-aminopropionic acid and their optical isomers; (C$_7$–C$_9$)aralkylamino group such as phenylglycyl; (C$_1$–C$_4$)alkoxycarbonylamino substituted (C$_1$–C$_4$)alkyl group, substitution selected from phenyl or p-hydroxyphenyl; α-hydroxy(C$_1$–C$_3$)alkyl group selected from hydroxymethyl, α-hydroxyethyl or α-hydroxy-1-methylethyl or α-hydroxypropyl; α-mercapto(C$_1$–C$_3$)alkyl group selected from mercaptomethyl, α-mercaptoethyl, α-mercapto-1-methylethyl or α-mercaptopropyl; halo($C_1$–$C_3$)alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-bromoethyl or 2-iodoethyl; a heterocycle group selected from a five membered aromatic or saturated ring with one N, O, S or Se heteroatom optionally having a benzo or pyrido ring fused thereto:

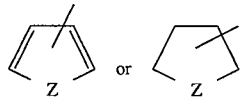

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

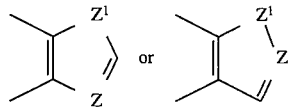

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

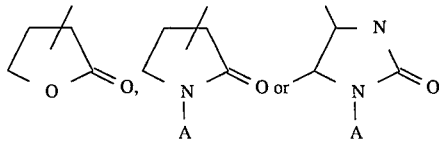

(A is selected from hydrogen; straight or branched ($C_1$–$C_4$)alkyl; $C_6$-aryl; substituted $C_6$-aryl (substitution selected from halo, ($C_1$–$C_4$)alkoxy, trihalo($C_1$–$C_3$)—alkyl, nitro, amino, cyano, ($C_1$–$C_4$)alkoxycarbonyl, ($C_1$–$C_3$)alkylamino or carboxy); ($C_7$–$C_9$)aralkyl group selected from benzyl, 1-phenylethyl, 2-phenylethyl or phenylpropyl) such as γ-butyrolactam, γ-butyrolactone, imidazolidinone or N-aminoimidazolidinone, or a six membered aromatic ring with one to three N, O, S or Se heteroatoms such as pyridyl, pyridazinyl, pyrazinyl, sym-triazinyl, unsym-triazinyl, pyrimidinyl or ($C_1$–$C_3$)alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl- 2-dioxo-1-piperazinyl, 2-dioxomorpholinyl or 2-dioxothiomorpholinyl; acyl or haloacyl group selected from acetyl, propionyl, chloroacetyl, trifluoroacetyl, ($C_3$–$C_6$)cycloalkylcarbonyl such as cyclopropylcarbonyl, cyclobutylcarbonyl, cyclopentylcarbonyl, cyclohexylcarbonyl, (2,3-dimethylcyclopropyl)carbonyl, (1,2-dimethylcyclopropyl)carbonyl, (2-ethylcyclopropyl)carbonyl, (2-methylcyclopentyl)carbonyl or (3-ethylcyclobutyl)carbonyl, ($C_6$–$C_{10}$)aroyl selected from benzoyl or naphthoyl, halo substituted ($C_6$–$C_{10}$)aroyl such as pentafluorobenzoyl, 4-chlorobenzoyl, 3-bromobenzoyl or 3,4-difluorobenzoyl, ($C_1$–$C_4$)alkylbenzoyl such as 4-toluoyl, 2-toluoyl or 4-(1-methylethyl)benzoyl, or (heterocycle)carbonyl, the heterocycle selected from a five membered aromatic or saturated ring with one N, O, S or Se heteroatom optionally having a benzo or pyrido ring fused thereto:

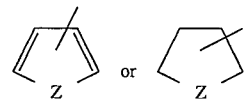

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

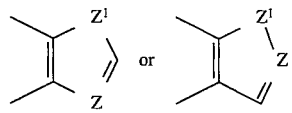

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

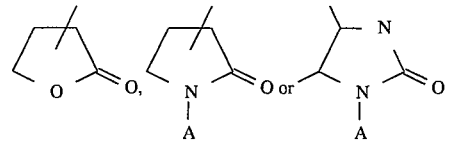

(A is selected from hydrogen; straight or branched ($C_1$–$C_4$)alkyl; $C_6$-aryl; substituted $C_6$-aryl (substitution selected from halo,($C_1$–$C_4$)alkoxy, trihalo ($C_1$–$C_3$)alkyl, nitro, amino, cyano, ($C_1$–$C_4$)alkoxycarbonyl, ($C_1$–$C_3$)alkylamino or carboxy); ($C_7$–$C_9$)aralkyl group selected from benzyl, 1-phenylethyl, 2-phenylethyl or phenylpropyl) such as γ-butyrolactam, γ-butyrolactone, imidazolidinone or N-aminoimidazolidinone, or a six membered aromatic ring with one to three N, O, S or Se heteroatoms such as pyridyl, pyridazinyl, pyrazinyl, sym-triazinyl, unsym-triazinyl, pyrimidinyl or ($C_1$–$C_3$)alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl- 2-dioxo-1-piperazinyl, 2-dioxomorpholinyl or 2-dioxothiomorpholinyl; ($C_1$–$C_4$)alkoxycarbonyl group selected from methoxycarbonyl, ethoxycarbonyl, straight or branched propoxylcarbonyl, straight or branched butoxycarbonyl or allyloxycarbonyl; vinyl or substituted vinyl group [substitution selected from ($C_1$–$C_3$)alkyl group, halogen, ($C_6$–$C_{10}$)aryl group selected from phenyl, α-naphthyl, β-naphthyl, substituted ($C_6$–$C_{10}$)aryl group (substitution selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino or carboxy), halo($C_1$–$C_3$)alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-bromoethyl or 2-iodoethyl, a heterocycle group selected from a five membered aromatic or saturated ring with one N, O, S or Se heteroatom optionally having a benzo or pyrido ring fused thereto:

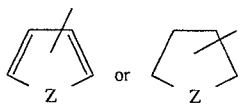

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl]; ($C_1$–$C_4$)alkoxy group such as allyloxy, methoxy, ethoxy, n-propoxy, n-butoxy or tert-butoxy; $C_6$-aryloxy group selected from phenoxy or substituted phenoxy (substitution selected from halo, ($C_1$–$C_4$)alkyl, nitro, cyano, thiol, amino, carboxy, di($C_1$–$C_3$)alkylamino); ($C_7$–$C_{10}$)aralkyloxy group such as benzyloxy, 1-phenylethyloxy or 2-phenylethyloxy; vinyloxy or substituted vinyloxy group (substitution selected from ($C_1$–$C_4$)alkyl, cyano, carboxy, or ($C_6$–$C_{10}$)aryl selected from phenyl, α-naphthyl or β-naphthyl); $R^aR^b$amino($C_1$–$C_4$)-alkoxy group, wherein $R^aR^b$ is a straight or branched ($C_1$–$C_4$)alkyl selected from methyl, ethyl, n-propyl, 1-methylethyl, n-butyl, 1-methylpropyl, or 2-methylpropyl or $R^aR^b$ is $(CH_2)n$, n=2–6, or —$(CH_2)_2W(CH_2)_2$—wherein W is selected from —N($C_1$–$C_3$)alkyl [straight or branched], —NH, —NOB [B is selected from hydrogen or ($C_1$–$C_3$)alkyl], O or S; or $R^aR^b$aminoxy group, wherein $R^aR^b$ is a straight or branched ($C_1$–$C_4$)alkyl selected from methyl, ethyl, n-propyl, 1-methylethyl, n-butyl, 1-methylpropyl, or 2-methylpropyl or $R^aR^b$ is $(CH_2)_n$, n=2–6, or —$(CH_2)_2W(CH_2)_2$—wherein W is selected from —N($C_1$–$C_3$)alkyl [straight or branched], —NH, —NOB [B is selected from hydrogen or ($C_1$–$C_3$)alkyl], O or S; and when R=$R^4(CH_2)_nCO$— and n=1–4, $R^4$ is selected from hydrogen; amino; straight or branched ($C_1$–$C_4$)alkyl group selected from methyl, ethyl, n-propyl, 1-methylethyl, n-butyl, 1-methylpropyl, 2-methylpropyl or 1,1-dimethylethyl; ($C_3$–$C_6$)cycloalkyl group selected from cyclopropyl, cyclobutyl, cyclopentyl or cyclohexyl; substituted ($C_3$–$C_6$)cycloalkyl group (substitution selected from ($C_1$–$C_3$)alkyl, cyano, amino or ($C_1$–$C_3$)acyl); ($C_6$–$C_{10}$)aryl group selected from phenyl, α-naphthyl or β-naphthyl; substituted($C_6$–$C_{10}$)aryl group (substitution selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino or carboxy); ($C_7$–$C_9$)aralkyl group such as benzyl, 1-phenylethyl, 2-phenylethyl or phenylpropyl; acyloxy or haloacyloxy group, selected from acetyl, propionyl, chloroacetyl, trichloroacetyl, ($C_3$–$C_6$)cycloalkylcarbonyl, ($C_6$–$C_{10}$)aroyl selected from benzoyl or naphthoyl, halo substituted ($C_6$–$C_{10}$)aroyl such as pentafluorobenzoyl, 4-chlorobenzoyl, 3-bromobenzoyl or 3,4-difluorobenzoyl, ($C_1$–$C_4$)alkylbenzoyl such as 4-toluoyl, 2-toluoyl or 4-(1-methylethyl)benzoyl, (heterocycle)carbonyl, the heterocycle selected from a five membered aromatic or saturated ring with one N, O, S or Se heteroatom optionally having a benzo or pyrido ring fused thereto:

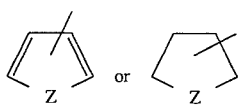

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

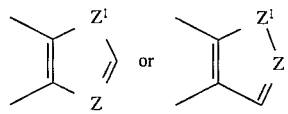

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended heteroatom:

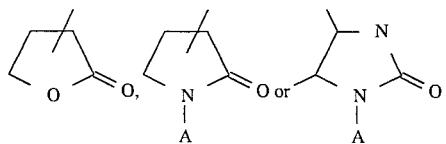

(A is selected from hydrogen; straight or branched ($C_1$–$C_4$)alkyl; $C_6$-aryl; substituted $C_6$-aryl (substitution selected from halo,($C_1$–$C_4$)alkoxy, trihalo($C_1$–$C_3$)alkyl, nitro, amino, cyano, ($C_1$–$C_4$)-alkoxycarbonyl, ($_1$–$C_3$)alkylamino or carboxy); ($C_7$–$C_9$)-aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N, O, S or Se heteroatoms such as pyridyl, pyridazinyl, pyrazinyl, sym-triazinyl, unsym-triazinyl, pyrimidinyl or ($C_{1-C3}$)-alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl; ($C_1$–$C_4$)alkoxy group such as allyloxy, methoxy, ethoxy, n-propoxy,n-butoxy or tert-butoxy; $C_6$-aryloxy group selected from phenoxy or substituted phenoxy (substitution selected from halo, ($C_1$–$C_4$)alkyl, nitro, cyano, thiol, amino, carboxy, di($C_1$–$C_3$)alkylamino); ($C_7$–$C_{10}$)aralkyloxy group such as benzyloxy, 1-phenylethyloxy or 2-phenylethyloxy; ($C_1$–$C_3$)alkylthio group selected from methylthio, ethylthio, propylthio or allylthio; $C_6$-arylthio group selected from phenylthio or substituted phenylthio (substitution selected from halo, ($C_1$–$C_4$)alkyl, nitro, cyano, thiol, amino, carboxy, di($C_1$–$C_3$)alkylamino); $C_6$-arylsulfonyl group selected from phenylsulfonyl or substituted phenylsulfonyl (substitution selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino or carboxy); ($C_7$–$C_8$)aralkylthio group such as benzylthio, 1-phenylethylthio or 2-phenylethylthio; a heterocycle group selected from a five membered aromatic or saturated ring with one N, O, S or Se heteroatom optionally having a benzo or pyrido ring fused thereto:

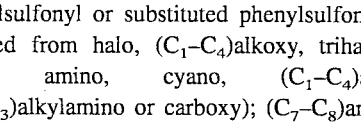

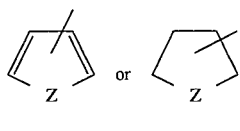

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl,
or a five membered aromatic ring with two N, O, S or Se heteroatoms optionally having a benzo or pyrido ring fused thereto:

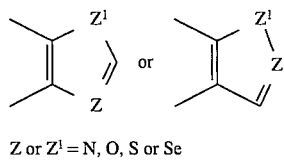

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

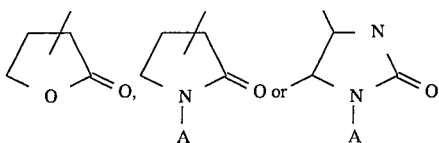

(A is selected from hydrogen; straight or branched $(C_1-C_4)$alkyl; $C_6$-aryl; substituted $C_6$-aryl (substitution selected from halo,$(C_1-C_4)$alkoxy, trihalo$(C_1-C_3)$alkyl, nitro, amino, cyano, $(C_1-C_4)$-alkoxycarbonyl, $(C_1-C_3)$alkylamino or carboxy); $(C_7-C_9)$aralkyl group selected from benzyl, 1-phenylethyl, 2-phenylethyl or phenylpropyl)
such as γ-butyrolactam, γ-butyrolactone, imidazolidinone or N-aminoimidazolidinone, or a six membered aromatic ring with one to three N, O, S or Se heteroatoms such as pyridyl, pyridazinyl, pyrazinyl, sym-triazinyl, unsym-triazinyl, pyrimidinyl or $(C_1-C_3$ )alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4 -cyclopropyl-2-dioxo-1-piperazinyl, 2-dioxomorpholinyl or 2-dioxothiomorpholinyl; hydroxy group; mercapto group; mono- or di-straight or branched chain $(C_1-C_6)$alkylamino group selected from methyl, ethyl, n-propyl, 1-methylethyl, n-butyl, 1-methylpropyl, 2-methylpropyl, 1,1-dimethylethyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 2-methylpentyl, 1,2-dimethylbutyl, 1,3-dimethylbutyl or 1-methyl-1-ethylpropyl amino; $(C_2-C_5)$azacycloalkyl group such as aziridinyl, azetidinyl, pyrrolidinyl, piperidinyl, morpholinyl or 2-methylpyrrolidinyl; carboxy$(C_2-C_4)$ alkylamino group selected from aminoacetic acid, α-aminopropionic acid, α-aminobutyric acid and their optical isomers; α-hydroxy$(C_1-C_3)$alkyl group selected from hydroxymethyl, α-hydroxyethyl or α-hydroxy-1 -methylethyl or α-hydroxypropyl; halo$(C_1-C_3)$alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoromethyl, 2-bromoethyl or 2-iodoethyl; acyl or haloacyl group selected from acetyl, propionyl, chloroacetyl, trifluoroacetyl, $(C_3-C_6)$cycloalkylcarbonyl, $(C_6-C_{10})$-aroyl selected from benzoyl or naphthoyl, halo substituted $(C_6-C_{10})$aroyl such as pentafluorobenzoyl, 4-chlorobenzoyl, 3-bromobenzoyl, 3,4-difluorobenzoyl, $(C_1-C_4)$alkylbenzoyl such as 4-toluoyl, 2-toluoyl or 4-(1-methylethyl)benzoyl, or (heterocycle)carbonyl, the heterocycle selected from a five membered aromatic or saturated ring with one N, O, S or Se heteroatom optionally having a benzo or pyrido ring fused thereto

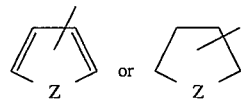

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl,benzofuranyl, tetrahydrothienyl, thienyl, benzothienyl or selenazolyl, or a five membered aromatic ring with two N, O, S or Se heteroatoms optionally having a benzo or pyrido ring fused thereto:

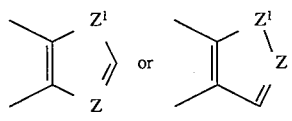

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

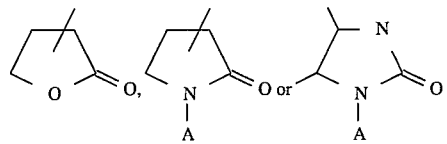

(A is selected from hydrogen; straight or branched $(C_1-C_4)$alkyl; $C_6$-aryl; substituted $C_6$-aryl (substitution selected from halo,$(C_1-C_4)$alkoxy, trihalo$(C_1-C_3)$alkyl, nitro, amino, cyano, $(C_1-C_4$ )alkoxycarbonyl, $(C_1-C_3)$alkylamino or carboxy); $(C_7-C_9$ )aralkyl group selected from benzyl, 1-phenylethyl, 2-phenylethyl or phenylpropyl)
such as γ-butyrolactam, γ-butyrolactone, imidazolidinone or N-aminoimidazolidinone, or a six membered aromatic ring with one to three N, O, S or Se heteroatoms such as pyridyl, pyridazinyl, pyrazinyl, sym-triazinyl, unsym-triazinyl, pyrimidinyl or $(C_1-C_3$ )alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1 -piperazinyl, 4-methyl-2,3-dioxo-1-piperazinyl, 4 -cyclopropyl- 2-dioxo-1-piperazinyl, 2-dioxomorpholinyl or 2-dioxothiomorpholinyl; $(C_1-C_4)$alkoxycarbonylamino group selected from tert-butoxycarbonylamino, allyloxycarbonylamino, methoxycarbonylamino, ethoxycarbonylamino or propoxycarbonylamino; $(C_1-C_4)$alkoxycarbonyl group selected from methoxycarbonyl, ethoxycarbonyl, straight or branched propoxycarbonyl, allyloxycarbonyl or straight or branched butoxycarbonyl; $R^aR^b$amino($C_1$-$C_4$)alkoxy group, wherein $R^aR^b$ is a straight or branched ($C_1$-$C_4$)alkyl selected from methyl, ethyl, n-propyl, 1-methylethyl, n-butyl, 1-methylpropyl, or 2-methylpropyl or $R^aR^b$ is $(CH_2)_n$, n=2–6, or —$(CH_2)_2W(CH_2)_2$— wherein W is selected from —N($C_1$-$C_3$)alkyl [straight or branched], —NH, —NOB [B is selected from hydrogen or ($C_1$-$C_3$)alkyl], O or S; or $R^aR^b$aminoxy group, wherein $R^aR^b$ is a straight or branched ($C_1$-$C_4$)alkyl selected from methyl, ethyl, n-propyl, 1-methylethyl, n-butyl, 1-methylpropyl, or 2-methylpropyl or $R^aR^b$ is $(CH_2)_n$, n=2–6, or —$(CH_2)_2W(CH_2)_2$— wherein W is selected from —N($C_1$-$C_3$)alkyl [straight or branched], —NH, —NOB [B is selected from hydrogen or ($C_1$-$C_3$)alkyl], O or S; and when $R=R^{4'}(CH_2)_nSO_2$— and n=0, $R^{4'}$ is selected from amino; monosubstituted amino selected from straight or branched ($C_1$-$C_6$)alkylamino, cyclopropylamino, cyclobutylamino, benzylamino or phenylamino; disubstituted amino selected from dimethylamino, diethylamino, ethyl(1-methylethyl)amino, monomethylbenzylamino, piperidinyl, morpholinyl, 1-imidazolyl, 1-pyrrolyl, 1-(1,2,3-triazolyl) or 4-(1,2,4-triazolyl); straight or branched ($C_1$-$C_4$)alkyl group selected from methyl, ethyl, n-propyl, 1-methylethyl, n-butyl, 1-methylpropyl, 2-methylpropyl or 1,1-dimethylethyl; ($C_3$-$C_6$)cycloalkyl group selected from cyclopropyl, cyclobutyl, cyclopentyl or cyclohexyl; substituted ($C_3$-$C_6$)cycloalkyl group (substitution selected from ($C_1$-$C_3$)alkyl, cyano, amino or ($C_1$-$C_3$)acyl); ($C_6$-$C_{10}$)aryl group selected from phenyl, α-naphthyl or β-naphthyl; substituted ($C_6$-$C_{10}$)aryl group (substitution selected from halo, ($C_1$-$C_4$)alkoxy, trihalo($C_1$-$C_3$)alkyl, nitro, amino, cyano, ($C_1$-$C_4$)alkoxycarbonyl, ($C_1$-$C_3$)alkylamino or carboxy); ($C_7$-$C_9$)aralkyl group such as benzyl, 1-phenylethyl, 2-phenylethyl or phenylpropyl; halo($C_1$-$C_3$)alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-chloroethyl, 2,2-dichloroethyl, 2,2,2-trichloroethyl, 2-bromoethyl or 2-iodoethyl; a heterocycle group selected from a five membered aromatic or saturated ring with one N, O, S or Se heteroatom optionally having a benzo or pyrido ring fused thereto:

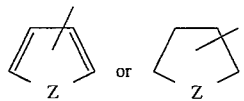

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

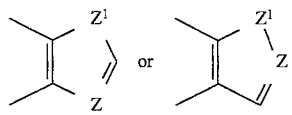

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

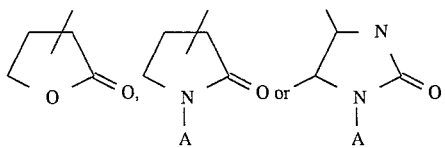

(A is selected from hydrogen; straight or branched ($C_1$-$C_4$)alkyl; $C_6$-aryl; substituted $C_6$-aryl (substitution selected from halo,($C_1$-$C_4$)alkoxy, trihalo($C_1$-$C_3$)alkyl, nitro, amino, cyano, ($C_1$-$C_4$)alkoxycarbonyl, ($C_1$-$C_3$)alkylamino or carboxy); ($C_7$-$C_9$)aralkyl group selected from benzyl, 1-phenylethyl, 2-phenylethyl or phenylpropyl) such as γ-butyrolactam, γ-butyrolactone, imidazolidinone or N-aminoimidazolidinone, or a six membered aromatic ring with one to three N, O, S or Se heteroatoms such as pyridyl, pyridazinyl, pyrazinyl, sym-triazinyl, unsym-triazinyl, pyrimidinyl or ($C_1$-$C_3$)alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl; $R^aR^b$amino($C_1$-$C_4$)alkoxy group, wherein $R^aR^b$ is a straight or branched ($C_1$-$C_4$)alkyl selected from methyl, ethyl, n-propyl, 1-methylethyl, n-butyl, 1-methylpropyl, or 2-methylpropyl or $R^aR^b$ is $(CH_2)_n$, n=2–6, or —$(CH_2)_2W(CH_2)_2$— wherein W is selected from —N($C_1$-$C_3$)alkyl [straight or branched], —NH, —NOB [B is selected from hydrogen or ($C_1$-$C_3$)alkyl], O or S; or $R^aR^b$aminoxy group, wherein $R^aR^b$ is a straight or branched ($C_1$-$C_4$)alkyl selected from methyl, ethyl, n-propyl, 1-methylethyl, n-butyl, 1-methylpropyl, or 2-methylpropyl or $R^aR^b$ is $(CH_2)_n$, n=2–6, or —$(CH_2)_2W(CH_2)_2$— wherein W is selected from —N($C_1$-$C_3$)alkyl [straight or branched], —NH, —NOB [B is selected from hydrogen or ($C_1$-$C_3$)alkyl], O or S;

and when $R=R^{4'}(CH_2)_nSO_2$— and n=1–4, $R^{4'}$ is selected from hydrogen; amino; straight or branched ($C_1$-$C_4$)alkyl group selected from methyl, ethyl, n-propyl, 1-methylethyl, n-butyl, 1-methylpropyl, 2-methylpropyl or 1,1-dimethylethyl; ($C_1$-$C_4$)carboxyalkyl group; ($C_3$-$C_6$)cycloalkyl group selected from cyclopropyl, cyclobutyl, cyclopentyl or cyclohexyl; substituted ($C_3$-$C_6$)cycloalkyl group (substitution selected from ($C_1$-$C_3$)alkyl, cyano, amino or ($C_1$-$C_3$)acyl); ($C_6$-$C_{10}$)aryl group selected from phenyl, α-naphthyl or β-naphthyl; substituted ($C_6$-$C_{10}$)aryl group (substitution selected from halo, ($C_1$-$C_4$)alkoxy, trihalo($C_1$-$C_3$)alkyl, nitro, amino, cyano, ($C_1$-$C_4$)alkoxycarbonyl, ($C_1$-$C_3$)alkylamino or carboxy); ($C_7$-$C_9$)aralkyl group selected from benzyl, 1-phenylethyl, 2-phenylethyl or phenylpropyl; ($C_1$-$C_4$)alkoxy group such as allyloxy, methoxy, ethoxy, n-propoxy or tert-butoxy; $C_6$-aryloxy group selected from phenoxy or substituted phenoxy (substitution selected from halo, ($C_1$-$C_3$)alkyl, nitro, cyano, thiol, amino, carboxy, di($C_1$-$C_3$)alkylamino); ($C_7$-$C_{10}$)aralkyloxy group such as benzyloxy, 1-phenylethyloxy or 2-phenylethyloxy; $R^aR^b$amino($C_1$-$C_4$)alkoxy group, wherein $R^aR^b$ is a straight or branched ($C_1$-$C_4$)alkyl selected from methyl, ethyl, n-propyl, 1-methylethyl, n-butyl, 1-methylpropyl, or 2-methylpropyl or $R^aR^b$ is $(CH_2)_n$, n=2–6, or —$(CH_2)_2W(CH_2)_2$— wherein W is selected from —N($C_1$-$C_3$)alkyl [straight or branched], —NH, —NOB [B is selected from hydrogen or ($C_1$-$C_3$)alkyl], O or S; or $R^aR^b$aminoxy group, wherein $R^aR^b$ is a straight or branched (C₁–C₄)alkyl selected from methyl, ethyl, n-propyl, 1-methylethyl, n-butyl, 1-methylpropyl, or 2-methylpropyl or $R^aR^b$ is $(CH_2)_n$, n=2–6, or —(CH₂)₂W(CH₂)₂— wherein W is selected from —N(C₁–C₃)alkyl [straight or branched], —NH, —NOB [B is selected from hydrogen or (C₁–C₃)alkyl], O or S; (C₁–C₃)alkylthio group selected from methylthio, ethylthio or n-propylthio; C₆-arylthio group selected from phenylthio or substituted phenylthio (substitution selected from halo, (C₁–C₃)alkyl, nitro, cyano, thiol, amino, carboxy, di(C₁–C₃)alkylamino); (C₇–C₈)aralkylthio group such as benzylthio, 1-phenylethylthio or 2-phenylethylthio; a heterocycle group selected from a five membered aromatic or saturated ring with one N, O, S or Se heteroatom optionally having a benzo or pyrido ring fused thereto:

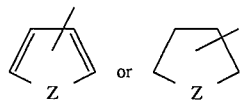

Z = N, O, S or Se such as pyrrolyl, N-methyl indolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

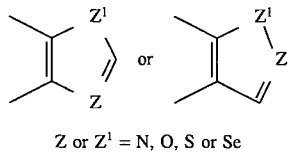

Z or Z¹ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

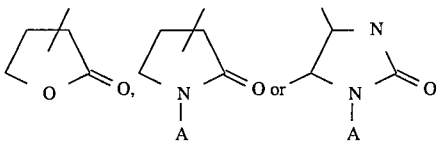

(A is selected from, hydrogen; straight or branched (C₁–C₄)alkyl; C₆-aryl; substituted C₆-aryl (substitution selected from halo, (C₁–C₄)alkoxy, trihalo(C₁–C₃)alkyl, nitro, amino, cyano, (C₁–C₄)alkoxycarbonyl, (C₁–C₃)alkylamino or carboxy); (C₇–C₉)aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N, O, S or Se heteroatoms such as pyridyl, pyridazinyl, pyrazinyl, sym-triazinyl, unsym-triazinyl, pyrimidinyl or (C₁–C₃)alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl; hydroxy group, mercapto group; mono- or di- straight or branched (C₁–C₆)alkylamino group selected from methyl, ethyl, n-propyl, 1-methylethyl, n-butyl, 1-methylpropyl, 2-methylpropyl, 1,1-dimethylethyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 2-methylpentyl, 1,2-dimethylbutyl, 1,3-dimethylbutyl or 1-methyl-1-ethylpropyl amino; halo(C₁–C₃)alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-chloroethyl, 2,2-dichloroethyl, 2,2,2-trichloroethyl, 2-bromoethyl or 2-iodoethyl; acyl or haloacyl group selected from acetyl, propionyl, chloroacetyl, trifluoroacetyl, (C₃–C₆)cycloalkylcarbonyl, (C₆–C₁₀)aroyl selected from benzoyl or naphthoyl, halo substituted (C₆–C₁₀)aroyl such as pentafluorobenzoyl, 4-chlorobenzoyl, 3-bromobenzoyl, or 3,4-difluorobenzoyl, (C₁–C₄)alkylbenzoyl such as 4-toluoyl, 2-toluoyl or 4-(1-methylethyl)benzoyl, or (heterocycle)carbonyl, the heterocycle selected from a five membered aromatic or saturated ring with one N, O, S or Se heteroatom optionally having a benzo or pyrido ring fused thereto:

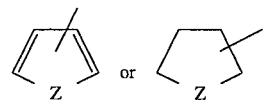

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

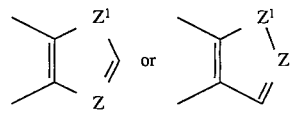

Z or Z¹ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

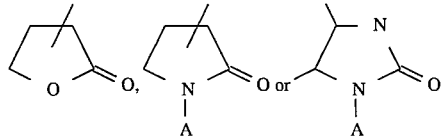

(A is selected from hydrogen; straight or branched (C₁–C₄)alkyl; C₆-aryl; substituted C₆-aryl (substitution selected from halo, (C₁–C₄)alkoxy, trihalo(C₁–C₃)alkyl, nitro, amino, cyano, (C₁–C₄)alkoxycarbonyl, (C₁–C₃)alkylamino or carboxy); (C₇–C₉)aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N, O, S or Se heteroatoms such as pyridyl, pyridazinyl, pyrazinyl, sym-triazinyl, unsym-triazinyl, pyrimidinyl or (C₁–C₃)alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl; (C₁–C₄)alkoxycarbonyl group selected from methoxycarbonyl, ethoxycarbonyl, straight or branched propoxycarbonyl, allyloxycarbonyl or straight or branched butoxycarbonyl; R⁵ is selected from hydrogen; straight or branched (C₁–C₃)alkyl group selected from methyl, ethyl, n-propyl or 1-methylethyl; (C₆–C₁₀)aryl group selected from phenyl, α-naphthyl or β-naphthyl; (C₇–C₉)aralkyl group such as benzyl, 1-phenylethyl, 2-phenylethyl or phenylpropyl; a heterocycle group selected from a five membered aromatic or saturated ring with one N, O, S or Se heteroatom optionally having a benzo or pyrido ring fused thereto:

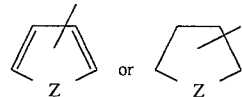

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

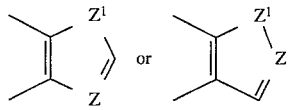

Z or Z¹ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

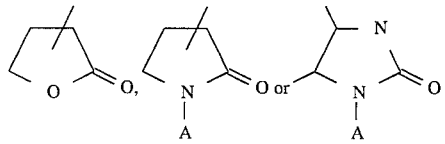

(A is selected from hydrogen; straight or branched (C₁–C₄)alkyl; C₆-aryl; substituted C₆-aryl (substitution selected from halo,(C₁–C₄)alkoxy, trihalo(C₁–C₃)alkyl, nitro, amino, cyano, (C₁–C₄)alkoxycarbonyl, (C₁–C₃)alkylamino or carboxy); (C₇–C₉)aralkyl group selected from benzyl, 1-phenylethyl, 2-phenylethyl or phenylpropyl)
such as γ-butyrolactam, γ-butyrolactone, imidazolidinone or N-aminoimidazolidinone, or a six membered aromatic ring with one to three N, O, S or Se heteroatoms such as pyridyl, pyridazinyl, pyrazinyl, sym-triazinyl, unsym-triazinyl, pyrimidinyl or (C₁–C₃) alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl, 2-dioxothiomorpholinyl; or —(CH₂)ₙCOOR⁷ where n=0–4 and R⁷ is selected from hydrogen; straight or branched (C₁–C₃)alkyl group selected from methyl, ethyl, n-propyl or 1-methylethyl; or (C₆–C₁₀)aryl group selected from phenyl, α-naphthyl, β-naphthyl; R⁶ is selected from hydrogen; straight or branched (C₁–C₃)alkyl group selected from methyl, ethyl, n-propyl or 1-methylethyl; (C₆–C₁₀)aryl group selected from phenyl, α-naphthyl or β-naphthyl; (C₇–C₉)aralkyl group such as benzyl, 1-phenylethyl, 2-phenylethyl or phenylpropyl; a heterocycle group selected from a five membered aromatic or saturated ring with one N, O, S or Se heteroatom optionally having a benzo or pyrido ring fused thereto:

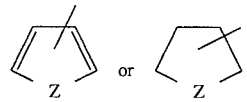

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

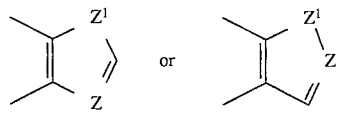

Z or Z¹ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

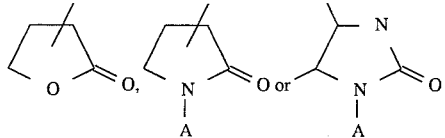

(A is selected from hydrogen; straight or branched (C₁–C₄)alkyl; C₆-aryl; substituted C₆-aryl (substitution selected from halo,(C₁–C₄)alkoxy, trihalo(C₁–C₃)alkyl, nitro, amino, cyano, (C₁–C₄)alkoxycarbonyl, (C₁–C₃)alkylamino or carboxy); (C₇–C₉)aralkyl group selected from benzyl, 1-phenylethyl, 2-phenylethyl or phenylpropyl)
such as γ-butyrolactam, γ-butyrolactone, imidazolidinone or N-aminoimidazolidinone, or a six membered aromatic ring with one to three N, O, S or Se heteroatoms such as pyridyl, pyridazinyl, pyrazinyl, sym-triazinyl, unsym-triazinyl, pyrimidinyl or (C₁–C₃)alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl, 2-dioxothiomorpholinyl; or —(CH₂)ₙCOOR⁷ where n=0–4 and R⁷ is selected from hydrogen; straight or branched (C₁–C₃)alkyl selected from methyl, ethyl, n-propyl or 1-methylethyl; or (C₆–C₁₀)aryl selected from phenyl, α-naphthyl or β-naphthyl; with the proviso that R⁵ and R⁶ cannot both be hydrogen;
or R⁵ and R⁶ taken together are —(CH₂)₂W(CH₂)₂—, wherein W is selected from (CH₂)ₙ and n=0–1, —NH, —N(C₁–C₃)alkyl [straight or branched], —N(C₁–C₄)alkoxy, oxygen, sulfur or substituted congeners selected from (L or D)proline, ethyl(L or D)prolinate, morpholine, pyrrolidine or piperidine; and the pharmacologically acceptable organic and inorganic salts or metal complexes.

Preferred compounds are compounds according to the above formula III and IV in which Y is $NO_2$; R is selected from $R^4(CH_2)_nCO-$ or $R^{4'}(CH_2)_nSO_2-$; and when $R=R^4(CH_2)_nCO-$ and n=0, $R^4$ is selected from hydrogen; amino; monosubstituted amino selected from straight or branched $(C_1-C_6)$alkylamino, cyclopropylamino, cyclobutylamino, benzylamino or phenylamino; disubstituted amino selected from dimethylamino, diethylamino, ethyl(1-methylethyl)amino, monomethylbenzylamino, piperidinyl, morpholinyl, 1-imidazolyl, 1-pyrrolyl, 1-(1,2,3-triazolyl) or 4-(1,2,4-triazolyl); straight or branched $(C_1-C_3)$alkyl group selected from methyl, ethyl, n-propyl or 1-methylethyl; $(C_3-C_6)$cycloalkyl group selected from cyclopropyl, cyclobutyl, cyclopentyl or cyclohexyl; substituted $(C_3-C_6)$cycloalkyl group (substitution selected from $(C_1-C_3)$alkyl, cyano, amino or $(C_1-C_3)$acyl); $(C_6-C_{10})$aryl group selected from phenyl, α-naphthyl or β-naphthyl; substituted $(C_6-C_{10})$aryl group (substitution selected from halo,$(C_1-C_4)$alkoxy, trihalo$(C_1-C_3)$alkyl, nitro, amino, cyano, $(C_1-C_4)$alkoxycarbonyl, $(C_1-C_3)$alkylamino or carboxy); α-amino$(C_1-C_4)$alkyl group selected from aminomethyl, α-aminoethyl, α-aminopropyl or α-aminobutyl; carboxy$(C_2-C_4)$alkylamino group selected from aminoacetic acid, α-aminobutyric acid or α-aminopropionic acid and their optical isomers; $(C_7-C_9)$aralkylamino group such as phenylglycyl; $(C_1-C_4)$alkoxycarbonylamino substituted $(C_1-C_4)$alkyl group, substitution selected from phenyl or p-hydroxyphenyl; α-hydroxy$(C_1-C_3)$alkyl group selected from hydroxymethyl, α-hydroxyethyl or α-hydroxy-1-methylethyl or α-hydroxypropyl; halo$(C_1-C_3)$alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-bromoethyl or 2-iodoethyl; a heterocycle group selected from a five membered aromatic or saturated ring with one N, O, S or Se heteroatom optionally having a benzo or pyrido ring fused thereto:

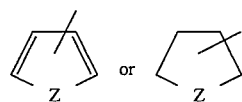

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

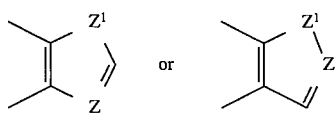

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

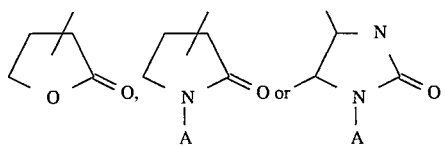

(A is selected from hydrogen; straight or branched $(C_1-C_4)$alkyl; $C_6$-aryl; substituted $C_6$-aryl (substitution selected from halo,$(C_1-C_4)$alkoxy, trihalo$(C_1-C_3)$alkyl, nitro, amino, cyano, $(C_1-C_4)$alkoxycarbonyl, $(C_1-C_3)$alkylamino or carboxy); $(C_7-C_9)$aralkyl group selected from benzyl, 1-phenylethyl, 2-phenylethyl or phenylpropyl) such as γ-butyrolactam, γ-butyrolactone, imidazolidinone or N-aminoimidazolidinone, or a six membered aromatic ring with one to three N, O, S or Se heteroatoms such as pyridyl, pyridazinyl, pyrazinyl, sym-triazinyl, unsym-triazinyl, pyrimidinyl or $(C_1-C_3)$alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl; acyl or haloacyl group selected from acetyl, propionyl, chloroacetyl, trifluoroacetyl, $(C_3-C_6)$cycloalkylcarbonyl such as cyclopropylcarbonyl, cyclobutylcarbonyl, cyclopentylcarbonyl, cyclohexylcarbonyl, (2,3-dimethylcyclopropyl)carbonyl, (1,2-dimethylcyclopropyl)carbonyl, (2-ethylcyclopropyl)carbonyl, (2-methylcyclopentyl)carbonyl or (3-ethylcyclobutyl)carbonyl, $(C_6-C_{10})$aroyl selected from benzoyl or naphthoyl, halo substituted $(C_6-C_{10})$aroyl such as pentafluorobenzoyl, 4-chlorobenzoyl, 3-bromobenzoyl or 3,4-difluorobenzoyl, $(C_1-C_4)$alkylbenzoyl such as 4-toluoyl, 2-methyltoluoyl or 4-(1-methylethyl)benzoyl, or (heterocycle)carbonyl, the heterocycle selected from a five membered aromatic or saturated ring with one N, O, S or Se heteroatom optionally having a benzo or pyrido ring fused thereto:

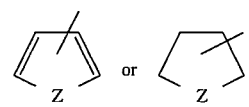

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

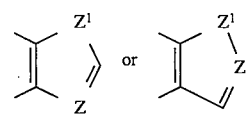

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

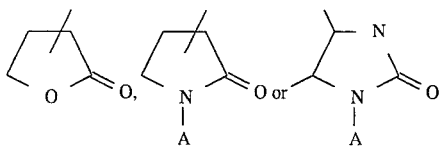

(A is selected from hydrogen; straight or branched (C$_1$–C$_4$)alkyl; C$_6$-aryl; substituted C$_6$-aryl (substitution selected from halo,(C$_1$–C$_4$)alkoxy, trihalo(C$_1$–C$_3$)alkyl, nitro, amino, cyano, (C$_1$–C$_4$)alkoxycarbonyl, (C$_1$–C$_3$)alkylamino or carboxy); (C$_7$–C$_9$)aralkyl group selected from benzyl, 1-phenylethyl, 2-phenylethyl or phenylpropyl) such as γ-butyrolactam, γ-butyrolactone, imidazolidinone or N-aminoimidazolidinone, or a six membered aromatic ring with one to three N, O, S or Se heteroatoms such as pyridyl, pyridazinyl, pyrazinyl, sym-triazinyl, unsym-triazinyl, pyrimidinyl or (C$_1$–C$_3$)alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl; (C$_1$–C$_4$)alkoxycarbonyl group selected from methoxycarbonyl, ethoxycarbonyl, straight or branched propoxylcarbonyl, straight or branched butoxycarbonyl or allyloxycarbonyl; vinyl or substituted vinyl group [substitution selected from (C$_1$–C$_3$)alkyl group, halogen, (C$_6$–C$_{10}$)aryl group selected from phenyl, α-naphthyl, β-naphthyl, substituted (C$_6$–C$_{10}$)aryl group (substitution selected from halo, (C$_1$–C$_4$)alkoxy, trihalo(C$_1$–C$_3$)alkyl, nitro, amino, cyano, (C$_1$–C$_4$)alkoxycarbonyl, (C$_1$–C$_3$)alkylamino or carboxy), halo(C$_1$–C$_3$)alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-bromoethyl or 2-iodoethyl, a heterocycle group selected from a five membered aromatic or saturated ring with one N, O, S or Se heteroatom optionally having a benzo or pyrido ring fused thereto:

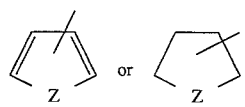

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl]; (C$_1$–C$_4$)alkoxy group such as allyloxy, methoxy, ethoxy, n-propoxy, n-butoxy or tert-butoxy; C$_6$-aryloxy group selected from phenoxy or substituted phenoxy (substitution selected from halo, (C$_1$–C$_4$)alkyl, nitro, cyano, thiol, amino, carboxy, di(C$_1$–C$_3$)alkylamino); (C$_7$–C$_{10}$)aralkyloxy group such as benzyloxy, 1-phenylethyloxy or 2-phenylethyloxy; vinyloxy or substituted vinyloxy group (substitution selected from (C$_1$–C$_4$)alkyl, cyano, carboxy, or (C$_6$–C$_{10}$)aryl selected from phenyl, α-naphthyl or β-naphthyl); R$^a$R$^b$amino(C$_1$–C$_4$)alkoxy group, wherein R$^a$R$^b$ is a straight or branched (C$_1$–C$_4$)alkyl selected from methyl, ethyl, n-propyl, 1-methylethyl, n-butyl, 1-methylpropyl, or 2-methylpropyl or R$^a$R$^b$ is (CH$_2$)$_n$, n=2–6, or —(CH$_2$)$_2$W(CH$_2$)$_2$— wherein W is selected from —N(C$_1$–C$_3$)alkyl [straight or branched], —NH, —NOB [B is selected from hydrogen or (C$_1$–C$_3$)alkyl], O or S; or R$^a$R$^b$aminoxy group, wherein R$^a$R$^b$ is a straight or branched (C$_1$–C$_4$)alkyl selected from methyl, ethyl, n-propyl, 1-methylethyl, n-butyl, 1-methylpropyl, or 2-methylpropyl or R$^a$R$^b$ is (CH$_2$)$_n$, n=2–6, or —(CH$_2$)$_2$W(CH$_2$)$_2$— wherein W is selected from —N(C$_1$–C$_3$)alkyl [straight or branched], —NH, —NOB [B is selected from hydrogen or (C$_1$–C$_3$)alkyl], O or S;

and when R=R$^4$(CH$_2$)$_n$CO— and n=1–4,

R$^4$ is selected from hydrogen; (C$_1$–C$_3$)alkyl group selected from methyl, ethyl, n-propyl or 1-methylethyl; amino; monosubstituted amino selected from straight or branched (C$_1$–C$_6$)alkylamino, cyclopropylamino, cyclobutylamino, benzylamino or phenylamino; disubstituted amino selected from dimethylamino, diethylamino, ethyl(1-methylethyl)amino, monomethylbenzylamino, piperidinyl, morpholinyl, 1-imidazolyl, 1-pyrrolyl, 1-(1,2,3-triazolyl) or 4-(1,2,4-triazolyl); (C$_6$–C$_{10}$)aryl group selected from phenyl, α-naphthyl or β-naphthyl; substituted (C$_6$–C$_{10}$)aryl group (substitution selected from halo, (C$_1$–C$_4$)alkoxy, trihalo(C$_1$–C$_3$)alkyl, nitro, amino, cyano, (C$_1$–C$_4$)alkoxycarbonyl, (C$_1$–C$_3$)alkylamino or carboxy); acyloxy or haloacyloxy group, selected from acetyl, propionyl, chloroacetyl, trichloroacetyl, (C$_3$–C$_6$)cycloalkylcarbonyl, (C$_6$–C$_{10}$)aroyl selected from benzoyl or naphthoyl, halo substituted (C$_6$–C$_{10}$)aroyl such as pentafluorobenzoyl, 4-chlorobenzoyl, 3-bromobenzoyl or 3,4-difluorobenzoyl, (C$_1$–C$_4$)alkylbenzoyl such as 4-toluoyl, 2-toluoyl, 4-(1-methylethyl)benzoyl or (heterocycle)carbonyl, the heterocycle selected from a five membered aromatic or saturated ring with one N, O, S or Se heteroatom optionally having a benzo or pyrido ring fused thereto:

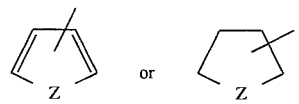

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

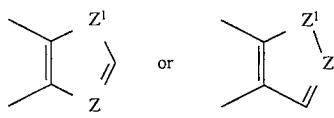

Z or Z$^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

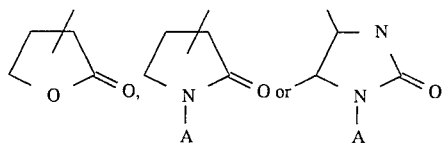

(A is selected from hydrogen; straight or branched (C$_1$–C$_4$)alkyl; C$_6$-aryl; substituted C$_6$-aryl (substitution selected from halo,(C$_1$–C$_4$)alkoxy, trihalo(C$_1$–C$_3$)alkyl, nitro, amino, cyano, (C$_1$–C$_4$)alkoxycarbonyl, ($C_1$–$C_3$)alkylamino or carboxy); ($C_7$–$C_9$)aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N, O, S or Se heteroatoms such as pyridyl, pyridazinyl, pyrazinyl, sym-triazinyl, unsym-triazinyl, pyrimidinyl or ($C_1$–$C_3$)alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl; ($C_1$–$C_4$)alkoxy group such as allyloxy, methoxy, ethoxy, n-propoxy, n-butoxy or tert-butoxy; $R^aR^b$amino($C_1$–$C_4$)alkoxy group, wherein $R^aR^b$ is a straight or branched ($C_1$–$C_4$)alkyl selected from methyl, ethyl, n-propyl, 1-methylethyl, n-butyl, 1-methylpropyl, or 2-methylpropyl or $R^aR^b$ is $(CH_2)_n$, n=2–6, or —$(CH_2)_2W(CH_2)_2$— wherein W is selected from —N($C_1$–$C_3$)alkyl [straight or branched], —NH, —NOB [B is selected from hydrogen or ($C_1$–$C_3$)alkyl], O or S; or $R^aR^b$aminoxy group, wherein $R^aR^b$ is a straight or branched ($C_1$–$C_4$)alkyl selected from methyl, ethyl, n-propyl, 1-methylethyl, n-butyl, 1-methylpropyl, or 2-methylpropyl or $R^aR^b$ is $(CH_2)_n$, n=2–6, or —$(CH_2)_2 W(CH_2)_2$— wherein W is selected from —N($C_1$–$C_3$)alkyl [straight or branched], —NH, —NOB [B is selected from hydrogen or ($C_1$–$C_3$)alkyl], O or S; $C_6$-aryloxy group selected from phenoxy or substituted phenoxy (substitution selected from halo, ($C_1$–$C_4$)alkyl, nitro, cyano, thiol, amino, carboxy, di($C_1$–$C_3$)alkylamino); ($C_1$–$C_3$)alkylthio group selected from methylthio, ethylthio, propylthio or allylthio; $C_6$-arylthio group selected from phenylthio or substituted phenylthio (substitution selected from halo, ($C_1$–$C_4$)alkyl, nitro, cyano, thiol, amino, carboxy, di($C_1$–$C_3$)alkylamino); $C_6$-arylsulfonyl group selected from phenylsulfonyl or substituted phenylsulfonyl (substitution selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino or carboxy); a heterocycle group selected from a five membered aromatic or saturated ring with one N, O, S or Se heteroatom optionally having a benzo or pyrido ring fused thereto:

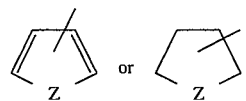

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

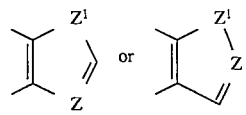

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

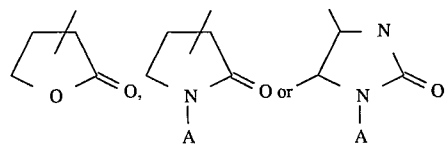

(A is selected from hydrogen; straight or branched ($C_1$–$C_4$)alkyl; $C_6$-aryl; substituted $C_6$-aryl (substitution selected from halo,($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino or carboxy); ($C_7$–$C_9$)aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N, O, S or Se heteroatoms such as pyridyl, pyridazinyl, pyrazinyl, sym-triazinyl, unsym-triazinyl, pyrimidinyl or ($C_1$–$C_3$)alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl; hydroxy group; α-hydroxy($C_1$–$C_3$)alkyl group selected from hydroxymethyl, α-hydroxyethyl or α-hydroxy-1-methylethyl or α-hydroxypropyl; halo($C_1$–$C_3$)alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoromethyl, 2-bromoethyl or 2-iodoethyl; acyl or haloacyl group selected from acetyl, propionyl, chloroacetyl, trifluoroacetyl, ($C_3$–$C_6$)cycloalkylcarbonyl, ($C_6$–$C_{10}$)aroyl selected from benzoyl or naphthoyl, halo substituted ($C_6$–$C_{10}$)aroyl such as pentafluorobenzoyl, 4-chlorobenzoyl, 3-bromobenzoyl or 3,4-difluorobenzoyl, ($C_1$–$C_4$)alkylbenzoyl such as 4-toluoyl, 2-toluoyl,or 4-(1-methylethyl)benzoyl, or (heterocycle)carbonyl, the heterocycle selected from a five membered aromatic or saturated ring with one N, O, S or Se heteroatom optionally having a benzo or pyrido ring fused thereto:

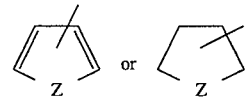

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl,
or a five membered aromatic ring with two N, O, S or Se heteroatoms optionally having a benzo or pyrido ring fused thereto:

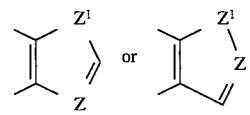

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

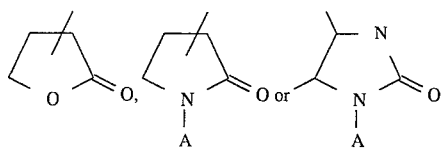

(A is selected from hydrogen; straight or branched $(C_1-C_4)$alkyl; $C_6$-aryl; substituted $C_6$-aryl (substitution selected from halo, $(C_1-C_4)$alkoxy, trihalo$(C_1-C_3)$alkyl, nitro, amino, cyano, $(C_1-C_4)$alkoxycarbonyl, $(C_1-C_3)$alkylamino or carboxy); $(C_7-C_9)$aralkyl group selected from benzyl, 1-phenylethyl, 2-phenylethyl or phenylpropyl)
such as γ-butyrolactam, γ-butyrolactone, imidazolidinone or N-aminoimidazolidinone, or a six membered aromatic ring with one to three N, O, S or Se heteroatoms such as pyridyl, pyridazinyl, pyrazinyl, sym-triazinyl, unsym-triazinyl, pyrimidinyl or $(C_1-C_3)$-alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl; $(C_1-C_4)$alkoxycarbonylamino group selected from tert-butoxycarbonylamino, allyloxycarbonylamino, methoxycarbonylamino, ethoxycarbonylamino or propoxycarbonylamino;
and when $R=R^{4'}(CH_2)_nSO_2$— and $n=0$,
$R^{4'}$ is selected from amino; monosubstituted amino selected from as straight or branched $(C_1-C_6)$alkylamino, cyclopropylamino, cyclobutylamino, benzylamino or phenylamino; disubstituted amino selected from dimethylamino, diethylamino, ethyl(1-methylethyl)amino, monomethylbenzylamino, piperidinyl, morpholinyl, 1-imidazolyl, 1-pyrrolyl, 1-(1,2,3-triazolyl) or 4-(1,2,4-triazolyl); straight or branched $(C_1-C_3)$alkyl group selected from methyl, ethyl, n-propyl or 1-methylethyl; $(C_6-C_{10})$aryl group from halo, $(C_1-C_4)$alkoxy, trihalo$(C_1-C_3)$alkyl, nitro, selected from phenyl, α-naphthyl or β-naphthyl; substituted $(C_6-C_{10})$aryl group (substitution selected amino, cyano, $(C_1-C_4)$alkoxycarbonyl, $(C_1-C_3)$alkylamino or carboxy); a heterocycle group selected from a five membered aromatic or saturated ring with one N, O, S or Se heteroatom optionally having a benzo or pyrido ring fused thereto:

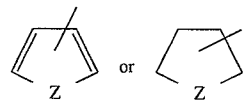

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl,
or a five membered aromatic ring with two N, O, S or Se heteroatoms optionally having a benzo or pyrido ring fused thereto:

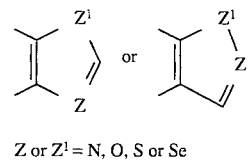

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended heteroatom:

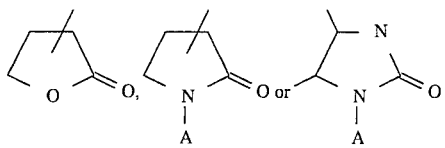

(A is selected from hydrogen; straight or branched $(C_1-C_4)$alkyl; $C_6$-aryl; substituted $C_6$-aryl (substitution selected from halo, $(C_1-C_4)$alkoxy, trihalo$(C_1-C_3)$alkyl, nitro, amino, cyano, $(C_1-C_4)$alkoxycarbonyl, $(C_1-C_3)$alkylamino or carboxy); $(C_7-C_9)$aralkyl group selected from benzyl, 1-phenylethyl, 2-phenylethyl or phenylpropyl)
such as γ-butyrolactam, γ-butyrolactone, imidazolidinone or N-aminoimidazolidinone, or a six membered aromatic ring with one to three N, O, S or Se heteroatoms such as pyridyl, pyridazinyl, pyrazinyl, sym-triazinyl, unsym-triazinyl, pyrimidinyl or $(C_1-C_3)$alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl;
and when $R=R^{4'}(CH_2)_nSO_2$— and $n=1-4$,
$R^{4'}$ is selected from hydrogen; amino; monosubstituted amino selected from straight or branched $(C_1-C_6)$alkylamino, cyclopropylamino, cyclobutylamino, benzylamino or phenylamino; disubstituted amino selected from dimethylamino, diethylamino, ethyl(1-methylethyl)amino, monomethylbenzylamino, piperidinyl, morpholinyl, 1-imidazolyl, 1-pyrrolyl, 1-(1,2,3-triazolyl) or 4-(1,2,4-triazolyl); straight or branched $(C_1-C_3)$alkyl group selected from methyl, ethyl, n-propyl or 1-methylethyl; $(C_6-C_{10})$aryl group selected from phenyl, α-naphthyl or β-naphthyl; substituted $(C_6-C_{10})$aryl group (substitution selected from halo, $(C_1-C_4)$alkoxy, trihalo$(C_1-C_3)$alkyl, nitro, amino, cyano, $(C_1-C_4)$alkoxycarbonyl, $(C_1-C_3)$alkylamino or carboxy); $(C_1-C_4)$alkoxy, group such as allyloxy, methoxy, ethoxy, n-propoxy, n-butoxy, iso-butoxy or tert-butoxy; $C_6$-aryloxy group selected from phenoxy or substituted phenoxy (substitution selected from halo, $(C_1-C_4)$alkyl, nitro cyano, thiol, amino, carboxy, di$(C_1-C_3)$alkylamino; $(C_7-C_{10})$aralkyloxy group such as benzyloxy, 1-phenylethyloxy or 2-phenylethyloxy; $(C_1-C_4)$carboxyalkyl group;
$R^5$ is selected from hydrogen; straight or branched $(C_1-C_3)$alkyl group selected from methyl, ethyl, n-propyl or 1-methylethyl; $(C_6-C_{10})$aryl group selected from phenyl, α-naphthyl or β-naphthyl; $(C_7-C_9)$aralkyl group such as benzyl, 1-phenylethyl, 2-phenylethyl or phenylpropyl; a heterocycle group selected from a five membered aromatic or saturated ring with one N, O, S or Se heteroatom optionally having a benzo or pyrido ring fused thereto:

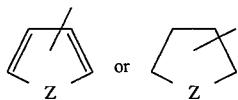

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

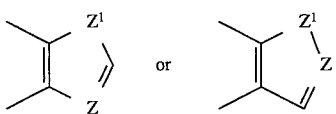

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

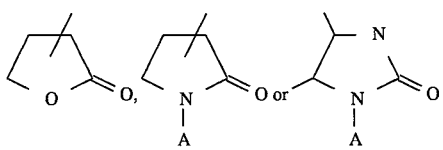

(A is selected from hydrogen; straight or branched $(C_1-C_4)$alkyl; $C_6$-aryl; substituted $C_6$-aryl (substitution selected from halo, $(C_1-C_4)$alkoxy, trihalo$(C_1-C_3)$alkyl, nitro, amino, cyano, $(C_1-C_4)$alkoxycarbonyl, $(C_1-C_3)$alkylamino or carboxy); $(C_7-C_9)$aralkyl group selected from benzyl, 1-phenylethyl, 2-phenylethyl or phenylpropyl) such as γ-butyrolactam, γ-butyrolactone, imidazolidinone or N-aminoimidazolidinone, or a six membered aromatic ring with one to three N, O, S or Se heteroatoms such as pyridyl, pyridazinyl, pyrazinyl, sym-triazinyl, unsym-triazinyl, pyrimidinyl or $(C_1-C_3)$alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl, 2-dioxothiomorpholinyl; or —$(CH_2)_n COOR^7$ where n=0–4 and $R^7$ is selected from hydrogen; straight or branched $(C_1-C_3)$alkyl group selected from methyl, ethyl, n-propyl or 1-methylethyl; or $(C_6-C_{10})$aryl group selected from phenyl, α-naphthyl or β-naphthyl;

$R^6$ is selected from hydrogen; straight or branched $(C_1-C_3)$alkyl group selected from methyl, ethyl, n-propyl or 1-methylethyl; $(C_6-C_{10})$aryl group selected from phenyl, α-naphthyl or β-naphthyl; $(C_7-C_9)$aralkyl group such as benzyl, 1-phenylethyl, 2-phenylethyl or phenylpropyl; a heterocycle group selected from a five membered aromatic or saturated ring with one N, O, S or Se heteroatom optionally having a benzo or pyrido ring fused thereto:

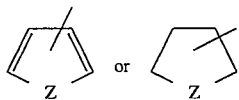

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

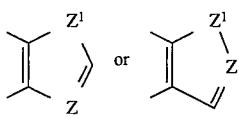

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

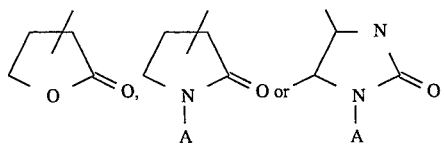

(A is selected from hydrogen; straight or branched $(C_1-C_4)$alkyl; $C_6$-aryl; substituted $C_6$-aryl (substitution selected from halo, $(C_1-C_4)$alkoxy, trihalo$(C_1-C_3)$alkyl, nitro, amino, cyano, $(C_1-C_4)$alkoxycarbonyl, $(C_1-C_3)$alkylamino or carboxy); $(C_7-C_9)$aralkyl group selected from benzyl, 1-phenylethyl, 2-phenylethyl or phenylpropyl) such as γ-butyrolactam, γ-butyrolactone, imidazolidinone or N-aminoimidazolidinone, or a six membered aromatic ring with one to three N, O, S or Se heteroatoms such as pyridyl, pyridazinyl, pyrazinyl, sym-triazinyl, unsym-triazinyl, pyrimidinyl or $(C_1-C_3)$alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl, 2-dioxothiomorpholinyl; or $(CH_2)_n COOR^{7'}$ wherein n=0–4 and $R^{7'}$ is selected from hydrogen; straight or branched $(C_1-C_3)$alkyl selected from methyl, ethyl, n-propyl or 1-methylethyl; or $(C_6-C_{10})$aryl selected from phenyl, α-naphthyl or β-naphthyl; with the proviso that $R^5$ and $R^6$ cannot both be hydrogen;

or $R^5$ and $R^6$ taken together are —$(CH_2)_2 W(CH_2)_2$—, wherein W is selected from $(CH_2)_n$ and n=0–1, —NH, —N$(C_1-C_3)$alkyl [straight or branched], —N$(C_1-C_4)$alkoxy, oxygen, sulfur or substituted congeners selected from (L or D)proline, ethyl(L or D)prolinate, morpholine, pyrrolidine or piperidine; and the pharmacologically acceptable organic and inorganic salts or metal complexes.

Particularly preferred compounds are compounds according to the above formula III and IV in which Y is $NO_2$; R is selected from $R^4(CH_2)_n CO$— or $R^{4'}(CH_2)_n SO_2$—; and when R=$R^4(CH_2)_n CO$— and n=0, R[4] is selected from hydrogen; amino; monosubstituted amino selected from straight or branched ($C_1$–$C_6$)alkylamino, cyclopropylamino, cyclobutylamino, benzylamino or phenylamino; disubstituted amino selected from dimethylamino, diethylamino, ethyl(1-methylethyl)amino, monomethylbenzylamino, piperidinyl, morpholinyl, 1-imidazolyl, 1-pyrrolyl, 1-(1,2,3-triazolyl) or 4-(1,2,4-triazolyl); straight or branched ($C_1$–$C_3$)alkyl group selected from methyl, ethyl, n-propyl or 1-methylethyl; ($C_3$–$C_6$)cycloalkyl group selected from cyclopropyl, cyclobutyl, cyclopentyl or cyclohexyl; substituted ($C_3$–$C_6$)cycloalkyl group (substitution selected from ($C_1$–$C_3$)alkyl, cyano, amino or ($C_1$–$C_3$)acyl); ($C_6$–$C_{10}$)aryl group selected from phenyl, α-naphthyl or β-naphthyl; substituted ($C_6$–$C_{10}$)aryl group (substitution selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino or carboxy); α-amino-($C_1$–$C_4$)alkyl group selected from aminomethyl, α-aminoethyl, α-aminopropyl or α-aminobutyl; carboxy($C_2$–$C_4$)alkylamino group selected from aminoacetic acid, α-aminobutyric acid or α-aminopropionic acid and their optical isomers; ($C_7$–$C_9$)aralkylamino group such as phenylglycyl; ($C_1$–$C_4$)alkoxycarbonylamino substituted ($C_1$–$C_4$)alkyl group, substitution selected from phenyl or p-hydroxyphenyl; α-hydroxy($C_1$–$C_3$)alkyl group selected from hydroxymethyl, α-hydroxyethyl or α-hydroxy-1-methylethyl or α-hydroxypropyl; halo($C_1$–$C_3$)alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-bromoethyl or 2-iodoethyl; a heterocycle group selected from a five membered aromatic or saturated ring with one N, O, S or Se heteroatom optionally having a benzo or pyrido ring fused thereto:

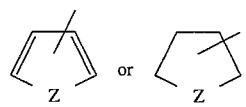

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

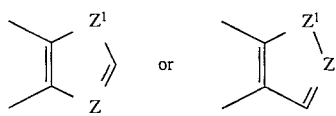

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended heteroatom:

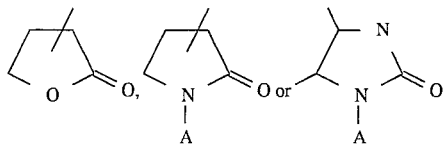

(A is selected from hydrogen; straight or branched ($C_1$–$C_4$)alkyl; $C_6$-aryl; substituted $C_6$-aryl (substitution selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino or carboxy); ($C_7$–$C_9$)aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N, O, S or Se heteroatoms such as pyridyl, pyridazinyl, pyrazinyl, sym-triazinyl, unsym-triazinyl, pyrimidinyl or ($C_1$–$C_3$)alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl; acyl or haloacyl group selected from acetyl, propionyl, chloroacetyl, trifluoroacetyl, ($C_3$–$C_6$)cycloalkylcarbonyl such as cyclopropylcarbonyl, cyclobutylcarbonyl, cyclopentylcarbonyl, cyclohexylcarbonyl, (2,3-dimethylcyclopropyl)carbonyl, (1,2-dimethylcyclopropyl)carbonyl, (2-ethylcyclopropyl)carbonyl, (2-methylcyclopentyl)carbonyl or (3-ethylcyclobutyl)carbonyl, ($C_6$–$C_{10}$)aroyl selected from benzoyl or naphthoyl, halo substituted ($C_6$–$C_{10}$)aroyl such as pentafluorobenzoyl, 4-chlorobenzoyl, 3-bromobenzoyl or 3,4-difluorobenzoyl, ($C_1$–$C_4$)alkylbenzoyl such as 4-toluoyl, 2-methylbenzoyl or 4-(1-methylethyl)benzoyl, or (heterocycle)carbonyl, the heterocycle selected from a five membered aromatic or saturated ring with one N, O, S or Se heteroatom optionally having a benzo or pyrido ring fused thereto:

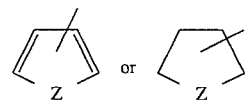

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

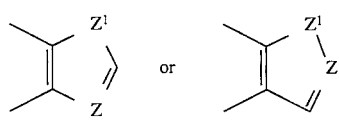

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

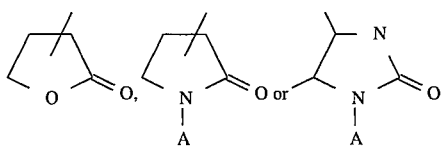

(A is selected from hydrogen; straight or branched $(C_1-C_4)$alkyl; $C_6$-aryl; substituted $C_6$-aryl (substitution selected from halo,$(C_1-C_4)$alkoxy, trihalo$(C_1-C_3)$alkyl, nitro, amino, cyano, $(C_1-C_4)$alkoxycarbonyl, $(C_1-C_3)$alkylamino or carboxy); $(C_7-C_9)$aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N, O, S or Se heteroatoms such as pyridyl, pyridazinyl, pyrazinyl, sym-triazinyl, unsym-triazinyl, pyrimidinyl or $(C_1-C_3)$alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1 -piperazinyl, 4-methyl-2,3-dioxo-1-piperazinyl, 4 -cyclopropyl- 2-dioxo-1-piperazinyl, 2-dioxomorpholinyl or 2 -dioxothiomorpholinyl; $(C_1-C_4)$alkoxycarbonyl group selected from methoxycarbonyl, ethoxycarbonyl, straight or branched propoxylcarbonyl, straight or branched butoxycarbonyl or allyloxycarbonyl; vinyl or substituted vinyl group [substitution selected from $(C_1-C_3)$alkyl group, halogen, $(C_6-C_{10})$aryl group selected from phenyl, α-naphthyl, β-naphthyl, substituted $(C_6-C_{10})$aryl group (substitution selected from halo, $(C_1-C_4)$alkoxy, trihalo$(C_1-C_3)$alkyl, nitro, amino, cyano, $(C_1-C_4)$alkoxycarbonyl, $(C_1-C_3)$alkylamino or carboxy), halo$(C_1-C_3)$alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-bromoethyl or 2-iodoethyl, a heterocycle group selected from a five membered aromatic or saturated ring with one N, O, S or Se heteroatom optionally having a benzo or pyrido ring fused thereto:

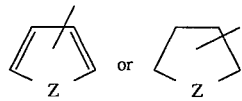

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl]; $(C_1-C_4)$alkoxy group such as allyloxy, methoxy, ethoxy, n-propoxy, n-butoxy or tert-butoxy; $C_6$-aryloxy group selected from phenoxy or substituted phenoxy (substitution selected from halo, $(C_1-C_4)$alkyl, nitro, cyano, thiol, amino, carboxy, di$(C_1-C_3)$alkylamino); $(C_7-C_{10})$aralkyloxy group such as benzyloxy, 1-phenylethyloxy or 2-phenylethyloxy; vinyloxy or substituted vinyloxy group (substitution selected from $(C_1-C_4)$alkyl, cyano, carboxy, or $(C_6-C_{10})$aryl selected from phenyl, α-naphthyl or β-naphthyl); $R^aR^b$amino$(C_1-C_4)$alkoxy group, wherein $R^aR^b$ is a straight or branched $(C_1-C_4)$alkyl selected from methyl, ethyl, n-propyl, 1-methylethyl, n-butyl, 1-methylpropyl, or 2-methylpropyl or $R^aR^b$ is $(CH_2)_n$, n=2-6, or —$(CH_2)_2W(CH_2)_2$— wherein W is selected from —N$(C_1-C_3)$alkyl [straight or branched], —NH, —NOB [B is selected from hydrogen or $(C_1-C_3)$alkyl], O or S; or $R^aR^b$aminoxy group, wherein $R^aR^b$ is a straight or branched $(C_1-C_4)$alkyl selected from methyl, ethyl, n-propyl, 1-methylethyl, n-butyl, 1-methylpropyl, or 2-methylpropyl or $R^aR^b$ is $(CH_2)_n$, n=2-6, or —$(CH_2)_2W(CH_2)_2$— wherein W is selected from —N$(C_1-C_3)$alkyl [straight or branched], —NH, —NOB [B is selected from hydrogen or $(C_1-C_3)$alkyl], O or S; and when R=$R^4(CH_2)_nCO$— and n=1-4, $R^4$ is selected from hydrogen; $(C_1-C_3)$alkyl group selected from methyl, ethyl, n-propyl or 1-methylethyl; amino; monosubstituted amino selected from straight or branched $(C_1-C_6)$alkylamino, cyclopropylamino, cyclobutylamino, benzylamino or phenylamino; disubstituted amino selected from dimethylamino, diethylamino, ethyl(1-methylethyl)amino, monomethylbenzylamino, piperidinyl, morpholinyl, 1-imidazolyl, 1-pyrrolyl, 1-(1,2,3-triazolyl) or 4-(1,2,4-triazolyl); $(C_6-C_{10})$aryl group selected from phenyl, β-naphthyl or β-naphthyl; substituted $(C_6-C_{10})$ aryl group (substitution selected from halo, $(C_1-C_4)$alkoxy, trihalo$(C_1-C_3)$alkyl, nitro, amino, cyano, $(C_1-C_4)$alkoxycarbonyl, $(C_1-C_3)$alkylamino or carboxy); acyloxy or haloacyloxy group, selected from acetyl, propionyl, chloroacetyl, trichloroacetyl, $(C_3-C_6)$cycloalkylcarbonyl, $(C_6-C_{10})$aroyl selected from benzoyl or naphthoyl, halo substituted $(C_6-C_{10})$aroyl such as pentafluorobenzoyl, 4-chlorobenzoyl, 3-bromobenzoyl or 3,4-difluorobenzoyl, $(C_1-C_4)$alkylbenzoyl such as 4-toluoyl, 2-toluoyl, 4-(1-methylethyl)benzoyl or (heterocycle)carbonyl, the heterocycle selected from a five membered aromatic or saturated ring with one N, O, S or Se heteroatom optionally having a benzo or pyrido ring fused thereto:

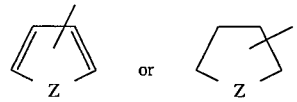

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

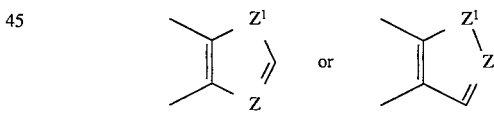

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

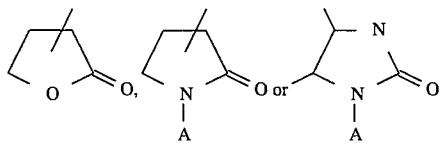

(A is selected from hydrogen; straight or branched $(C_1-C_4)$alkyl; $C_6$-aryl; substituted $C_6$-aryl (substitution selected from halo,$(C_1-C_4)$alkoxy, trihalo$(C_1-C_3)$alkyl, nitro, amino, cyano, $(C_1-C_4)$alkoxycarbonyl, ($C_1$–$C_3$)alkylamino or carboxy); ($C_7$–$C_9$)aralkyl group selected from benzyl, 1-phenylethyl, 2-phenylethyl or phenylpropyl) such as γ-butyrolactam, γ-butyrolactone, imidazolidinone or N-aminoimidazolidinone, or a six membered aromatic ring with one to three N, O, S or Se heteroatoms such as pyridyl, pyridazinyl, pyrazinyl, sym-triazinyl, unsym-triazinyl, pyrimidinyl or ($C_1$–$C_3$)alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl; ($C_1$–$C_4$)alkoxy group such as allyloxy, methoxy, ethoxy, n-propoxy, n-butoxy or tert-butoxy; $C_6$-aryloxy group selected from phenoxy or substituted phenoxy (substitution selected from halo, ($C_1$–$C_4$)alkyl, nitro, cyano, thiol, amino, carboxy, di($C_1$–$C_3$)alkylamino); $R^aR^b$amino($C_1$–$C_4$)alkoxy group, wherein $R^aR^b$ is a straight or branched ($C_1$–$C_4$)alkyl selected from methyl, ethyl, n-propyl, 1-methylethyl, n-butyl, 1-methylpropyl, or 2-methylpropyl or $R^aR^b$ is $(CH_2)_n$, n=2–6, or —$(CH_2)_2W(CH_2)_2$— wherein W is selected from —N($C_1$–$C_3$)alkyl [straight or branched], —NH, —NOB [B is selected from hydrogen or ($C_1$–$C_3$)alkyl], O or S; or $R^aR^b$ aminoxy group, wherein $R^aR^b$ is a straight or branched ($C_1$–$C_4$)alkyl selected from methyl, ethyl, n-propyl, 1-methylethyl, n-butyl, 1-methylpropyl, or 2-methylpropyl or $R^aR^b$ is $(CH_2)_n$, n=2–6, or —$(CH_2)_2W(CH_2)_2$— wherein W is selected from —N($C_1$–$C_3$)alkyl [straight or branched], —NH, —NOB [B is selected from hydrogen or ($C_1$–$C_3$)alkyl], O or S; ($C_1$–$C_3$)alkylthio group selected from methylthio, ethylthio, propylthio or allylthio; $C_6$-arylthio group selected from phenylthio or substituted phenylthio (substitution selected from halo, ($C_1$–$C_4$)alkyl, nitro, cyano, thiol, amino, carboxy, di($C_1$–$C_3$)alkylamino); $C_6$-arylsulfonyl group selected from phenylsulfonyl or substituted phenylsulfonyl (substitution selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino or carboxy); a heterocycle group selected from a five membered aromatic or saturated ring one N, O, S or Se heteroatom optionally having a benzo or pyrido ring fused thereto:

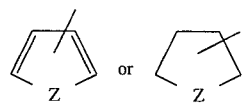

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo ring fused thereto:

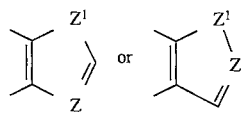

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

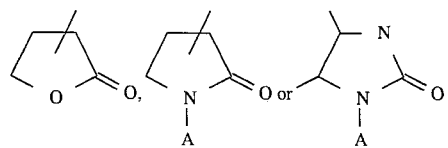

(A is selected from hydrogen; straight or branched ($C_1$–$C_4$)alkyl; $C_6$-aryl; substituted $C_6$-aryl (substitution selected from halo,($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino or carboxy); ($C_7$–$C_9$)aralkyl group selected from benzyl, 1-phenylethyl, 2-phenylethyl or phenylpropyl) such as γ-butyrolactam, γ-butyrolactone, imidazolidinone or N-aminoimidazolidinone, or a six membered aromatic ring with one to three N, O, S or Se heteroatoms such as pyridyl, pyridazinyl, pyrazinyl, sym-triazinyl, unsym-triazinyl, pyrimidinyl ($C_1$–$C_3$)alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl; hydroxy group; α-hydroxy($C_1$–$C_3$)alkyl group selected from hydroxymethyl, α-hydroxyethyl or α-hydroxy-1-methylethyl or α-hydroxypropyl; halo($C_1$–$C_3$)alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoromethyl, 2-bromoethyl or 2-iodoethyl; acyl or haloacyl group selected from acetyl, propionyl, chloroacetyl, trifluoroacetyl, ($C_3$–$C_6$)cycloalkylcarbonyl, ($C_6$–$C_{10}$)aroyl selected from benzoyl or naphthoyl, halo substituted ($C_6$–$C_{10}$)aroyl such as pentafluorobenzoyl, 4-chlorobenzoyl, 3-bromophenylcarbonyl or 3,4-difluorobenzoyl, ($C_1$–$C_4$)alkylbenzoyl such as from 4-toluoyl, 2-toluoyl or 4-(1-methylethyl)benzoyl, or (heterocycle)carbonyl, the heterocycle selected from a five membered aromatic or saturated ring with one N, O, S or Se heteroatom optionally having a benzo or pyrido ring fused thereto:

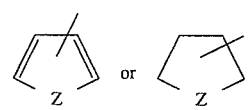

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo-or pyrido ring fused thereto:

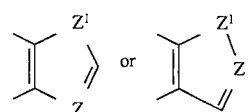

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

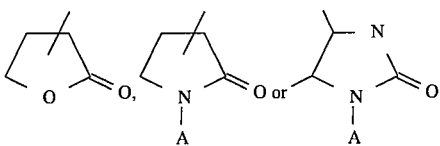

(A is selected from hydrogen; straight or branched $(C_1-C_4)$alkyl; $C_6$-aryl; substituted $C_6$-aryl (substitution selected from halo, $(C_1-C_4)$alkoxy, trihalo$(C_1-C_3)$alkyl, nitro, amino, cyano, $(C_1-C_4$ )alkoxycarbonyl, $(C_1-C_3)$alkylamino or carboxy); $(C_7-C_9$ )aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N, O, S or Se heteroatoms such as pyridyl, pyridazinyl, pyrazinyl, sym-triazinyl, unsym-triazinyl, pyrimidinyl or $(C_1-C_3)$alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1 -piperazinyl, 4-methyl-2,3-dioxo-1-piperazinyl, 4 -cyclopropyl-2-dioxo-1-piperazinyl, 2-dioxomorpholinyl or 2 -dioxothiomorpholinyl; $(C_1-C_4)$alkoxycarbonylamino group selected from tert-butoxycarbonylamino, allyloxycarbonylamino, methoxycarbonylamino, ethoxycarbonylamino or propoxycarbonylamino;

and when $R=R^{4'}(CH_2)_nSO_2$— and n=0, $R^{4'}$ is selected from amino; monosubstituted amino selected from as straight or branched $(C_1-C_6)$alkylamino, cyclopropylamino, cyclobutylamino, benzylamino or phenylamino; disubstituted amino selected from dimethylamino, diethylamino, ethyl(1-methylethyl)amino, monomethylbenzylamino, piperidinyl, morpholinyl, 1-imidazolyl, 1-pyrrolyl, 1-(1,2,3-triazolyl) or 4-(1,2,4-triazolyl); straight or branched $(C_1-C_3)$alkyl group selected from methyl, ethyl, n-propyl or 1-methylethyl; $(C_6-C_{10})$aryl group selected from phenyl, α-naphthyl or β-naphthyl; substituted $(C_6-C_{10})$aryl group (substitution selected from halo, $(C_1-C_4)$alkoxy, trihalo$(C_1-C_3)$alkyl, nitro, amino, cyano, $(C_1-C_4)$alkoxycarbonyl, $(C_1-C_3)$alkylamino or carboxy); a heterocycle group selected from a five membered aromatic or saturated ring with one N, O, S or Se heteroatom optionally having a benzo or pyrido ring fused thereto:

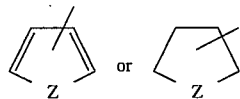

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

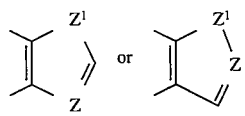

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

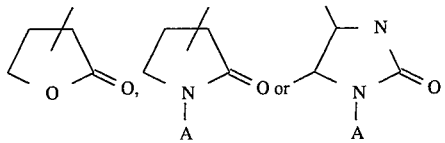

(A is selected from hydrogen; straight or branched $(C_1-C_4)$alkyl; $C_6$-aryl; substituted $C_6$-aryl (substitution selected from halo, $(C_1-C_4)$alkoxy, trihalo$(C_1-C_3)$alkyl, nitro, amino, cyano, $(C_1-C_4$ )alkoxycarbonyl, $(C_1-C_3)$alkylamino or carboxy); $(C_7-C_9$ )aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N, O, S or Se heteroatoms such as pyridyl, pyridazinyl, pyrazinyl, sym-triazinyl, unsym-triazinyl, pyrimidinyl or $(C_1-C_3)$alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1 -piperazinyl, 4-methyl-2,3-dioxo-1-piperazinyl, 4 -cyclopropyl-2-dioxo-1-piperazinyl, 2-dioxomorpholinyl or 2 -dioxothiomorpholinyl;

and when $R=R^{4'}(CH_2)_nSO_2$— and n=1–4, $R^{4'}$ is selected from hydrogen; amino; monosubstituted amino selected from straight or branched $(C_1-C_6)$alkylamino, cyclopropylamino, cyclobutylamino, benzylamino or phenylamino; disubstituted amino selected from dimethylamino, diethylamino, ethyl(1-methylethyl)amino, monomethylbenzylamino, piperidinyl, morpholinyl, 1-imidazolyl, 1-pyrrolyl, 1-(1,2,3-triazolyl) or 4-(1,2,4-triazolyl); straight or branched $(C_1-C_3)$alkyl group selected from methyl, ethyl, n-propyl or 1-methylethyl; $R^aR^b$amino$(C_1-C_4)$alkoxy group, wherein $R^aR^b$ is a straight or branched $(C_1-C_4)$alkyl selected from methyl, ethyl, n-propyl, 1-methylethyl, n-butyl, 1-methylpropyl, or 2-methylpropyl or $R^aR^b$ is $(CH_2)_n$, n=2–6, or —$(CH_2)_2W$—$(CH_2)_2$—wherein W is selected from —N$(C_1-C_3)$alkyl [straight or branched], —NH, —NOB [B is selected from hydrogen or $(C_1-C_3)$alkyl, O or S; or $R^aR^b$aminoxy group, wherein $R^aR^b$ is a straight or branched $(C_1-C_4)$alkyl selected from methyl, ethyl, n-propyl, 1-methylethyl, n-butyl, 1-methylpropyl, or 2-methylpropyl or $R^aR^b$ is $(CH_2)_n$, n=2–6, or —$(CH_2)_2W$—$(CH_2)_2$—wherein W is selected from —N$(C_1-C_3)$alkyl [straight or branched], —NH, —NOB [B is selected from hydrogen or $(C_1-C_3)$alkyl, O or S; $R^5$ is selected from hydrogen; straight or branched $(C_1-C_3)$alkyl group selected from methyl, ethyl, n-propyl or 1-methylethyl; $(C_6-C_{10})$aryl group selected from phenyl, α-naphthyl or β-naphthyl; $(C_7-C_9)$aralkyl group such as benzyl, 1-phenylethyl, 2-phenylethyl or phenylpropyl; a heterocycle group selected from a five membered aromatic or saturated ring with one N, O, S or Se heteroatom optionally having a benzo or pyrido ring fused thereto:

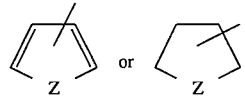

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

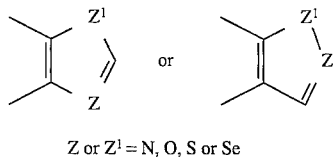

Z or Z¹ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

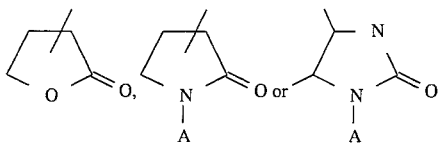

(A is selected from hydrogen; straight or branched ($C_1$–$C_4$)alkyl; $C_6$-aryl; substituted $C_6$-aryl (substitution selected from halo,($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino or carboxy); ($C_7$–$C_9$)aralkyl group selected from benzyl, 1-phenylethyl, 2-phenylethyl or phenylpropyl) such as γ-butyrolactam, γ-butyrolactone, imidazolidinone or N-aminoimidazolidinone, or a six membered aromatic ring with one to three N, O, S or Se heteroatoms such as pyridyl, pyridazinyl, pyrazinyl, sym-triazinyl, unsym-triazinyl, pyrimidinyl or ($C_1$–$C_3$)alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl- 2-dioxo-1-piperazinyl, 2-dioxomorpholinyl, 2-dioxothiomorpholinyl; or —($CH_2$)$_n$COOR$^7$ where n=0–4 and R$^7$ is selected from hydrogen; straight or branched ($C_1$–$C_3$)alkyl group selected from methyl, ethyl, n-propyl or 1-methylethyl; or ($C_6$–$C_{10}$)aryl group selected from phenyl, α-naphthyl or β-naphthyl; R$^6$ is selected from hydrogen; straight or branched ($C_1$–$C_3$)alkyl group selected from methyl, ethyl, n-propyl or 1-methylethyl; ($C_6$–$C_{10}$)aryl group selected from phenyl, α-naphthyl or β-naphthyl; ($C_7$–$C_9$)aralkyl group such as benzyl, 1-phenylethyl, 2-phenylethyl or phenylpropyl; a heterocycle group selected from a five membered aromatic or saturated ring with one N, O, S or Se heteroatom optionally having a benzo or pyrido ring fused thereto:

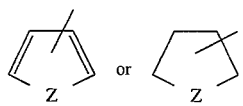

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

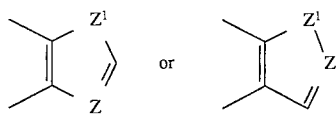

Z or Z¹ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

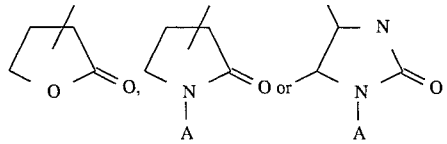

(A is selected from hydrogen; straight or branched ($C_1$–$C_4$)alkyl; $C_6$-aryl; substituted $C_6$-aryl (substitution selected from halo,($C_1$–$C_4$)alkoxy, trihalo($C_1$–$C_3$)alkyl, nitro, amino, cyano, ($C_1$–$C_4$)-alkoxycarbonyl, ($C_1$–$C_3$)alkylamino or carboxy); ($C_7$–$C_9$)-aralkyl group selected from benzyl, 1-phenylethyl, 2-phenylethyl or phenylpropyl) such as γ-butyrolactam, γ-butyrolactone, imidazolidinone or N-aminoimidazolidinone, or a six membered aromatic ring with one to three N, O, S or Se heteroatoms such as pyridyl, pyridazinyl, pyrazinyl, sym-triazinyl, unsym-triazinyl, pyrimidinyl or ($C_1$–$C_3$)alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl- 2-dioxo-1-piperazinyl, 2-dioxomorpholinyl, 2-dioxothiomorpholinyl; or ($CH_2$)$_n$COOR$^7$ where n=0–4 and R$^7$ is selected from hydrogen; straight or branched ($C_1$–$C_3$)-alkyl selected from methyl, ethyl, n-propyl or 1-methylethyl; or ($C_6$–$C_{10}$)aryl selected from phenyl, α-naphthyl or β-naphthyl; with the proviso that R$^5$ and wherein W is selected from ($CH_2$)$_n$ and n=0–1, —NH, R$^6$ cannot both be hydrogen; or R$^5$ and R$^6$ taken together are —($CH_2$)$_2$W($CH_2$)$_2$—, —N($C_1$–$C_3$)alkyl [straight or branched], —N($C_1$–$C_4$)alkoxy, oxygen, sulfur or substituted congeners selected from (L or D)proline, ethyl(L or D)prolinate, morpholine, pyrrolidine or piperidine; and the pharmacologically acceptable organic and inorganic salts or metal complexes.

Most particularly preferred compounds are compounds according to the above formula III and IV in which Y is NO$_2$; R is selected from R$^4$(CH$_2$)$_n$CO— or R$^{4'}$(CH$_2$)$_n$SO$_2$—; and when R=R$^4$(CH$_2$)$_n$CO— and n=0, R$^4$ is selected from hydrogen; amino; monosubstituted amino selected from straight or branched ($C_1$–$C_6$)alkylamino, cyclopropylamino, cyclobutylamino, benzylamino or phenylamino; disubstituted amino selected from dimethylamino, diethylamino, ethyl(1-methylethyl)amino, monomethylbenzylamino, piperidinyl, morpholinyl, 1-imidazolyl, 1-pyrrollyl, 1-(1,2,3-triazolyl) or 4-(1,2,4-triazolyl); straight or branched ($C_1$–$C_2$)alkyl group selected from methyl or ethyl; ($C_6$–$C_{10}$)aryl group selected from phenyl, α-naphthyl or β-naphthyl; substituted ($C_6$–$C_{10}$)aryl group (substitution selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino or carboxy); carboxy($C_2$–$C_4$)alkylamino group selected from aminoacetic acid, α-aminobutyric acid or α-aminopropionic acid and their optical isomers; α-hydroxy($C_1$–$C_3$)alkyl group selected from hydroxymethyl, α-hydroxyethyl or α-hydroxy-1-methylethyl or α-hydroxypropyl; halo($C_1$–$C_3$)alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-bromoethyl or 2-iodoethyl; a heterocycle group selected from a five membered aromatic or saturated ring with one N, O, S or Se heteroatom optionally having a benzo or pyrido ring fused thereto:

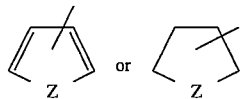

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

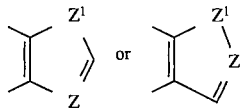

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, azolyl, or a five membered saturated ring with one or two N, O, S or Se heteroatoms and an adjacent appended O heteroatom:

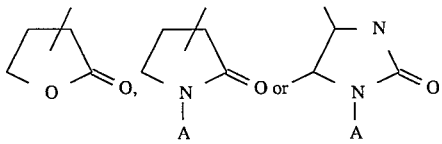

(A is selected from hydrogen; straight or branched ($C_1$–$C_4$)alkyl; $C_6$-aryl; substituted $C_6$-aryl (substitution selected from halo,($C_1$–$C_4$)alkoxy, trihalo($C_1$–$C_3$)alkyl, nitro, amino, cyano, ($C_1$–$C_4$)-alkoxycarbonyl, ($C_1$–$C_3$)alkylamino or carboxy); ($C_7$–$C_9$)aralkyl group selected from benzyl, 1-phenylethyl, 2-phenylethyl or phenylpropyl)
such as γ-butyrolactam, γ-butyrolactone, imidazolidinone or N-aminoimidazolidinone, or a six membered aromatic ring with one to three N, O, S or Se heteroatoms such as pyridyl, pyridazinyl, pyrazinyl, sym-triazinyl, unsym-triazinyl, pyrimidinyl or ($C_1$–$C_3$)alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl- 2-dioxo-1-piperazinyl, 2-dioxomorpholinyl or 2-dioxothiomorpholinyl; ($C_1$–$C_4$)alkoxycarbonyl group selected from methoxycarbonyl, ethoxycarbonyl, straight or branched propoxylcarbonyl, straight or branched butoxycarbonyl or allyloxycarbonyl; vinyl or substituted vinyl group [substitution selected from ($C_1$–$C_3$)alkyl group, halogen, ($C_6$–$C_{10}$)aryl group selected from phenyl, α-naphthyl, β-naphthyl, substituted ($C_6$–$C_{10}$)aryl group (substitution selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino or carboxy), halo($C_1$–$C_3$)alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-bromoethyl or 2-iodoethyl, a heterocycle group selected from a five membered aromatic or saturated ring with one N, O, S or Se heteroatom optionally having a benzo or pyrido ring fused thereto:

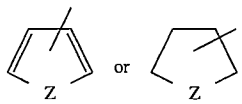

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl]; ($C_1$–$C_4$)alkoxy group such as allyloxy, methoxy, ethoxy, n-propoxy, n-butoxy or tert-butoxy; $C_6$-aryloxy group selected from phenoxy or substituted phenoxy (substitution selected from halo, ($C_1$–$C_4$)alkyl, nitro, cyano, thiol, amino, carboxy, di($C_1$–$C_3$)alkylamino); ($C_7$–$C_{10}$)aralkyloxy group such as benzyloxy, 1-phenylethyloxy or 2-phenylethyloxy; vinyloxy or substituted vinyloxy group (substitution selected from ($C_1$–$C_4$)alkyl, cyano, carboxy, or ($C_6$–$C_{10}$)aryl selected from phenyl, α-naphthyl or β-naphthyl); $R^a R^b$amino($C_1$–$C_4$)alkoxy group, wherein $R^a R^b$ is a straight or branched ($C_1$–$C_4$)alkyl selected from methyl, ethyl, n-propyl, 1-methylethyl, n-butyl, 1-methylpropyl, or 2-methylpropyl or $R^a R^b$ is $(CH_2)_n$, n=2–6, or —$(CH_2)_2 W(CH_2)_2$—wherein W is selected from —N($C_1$–$C_3$)alkyl [straight or branched], —NH, —NOB [B is selected from hydrogen or ($C_1$–$C_3$)alkyl], O or S; or $R^a R^b$aminoxy group, wherein is a straight or branched ($C_1$–$C_4$)alkyl selected from methyl, ethyl, n-propyl, 1-methylethyl, n-butyl, 1-methylpropyl, or 2-methylpropyl or $R^a R^b$ is $(CH_2)_n$, n=2–6, or —$(CH_2)_2 W$— $(CH_2)_2$—wherein W is selected from —N($C_1$–$C_3$)alkyl [straight or branched], —NH, —NOB [B is selected from hydrogen or ($C_1$–$C_3$)alkyl], O or S; and when R=$R^4 (CH_2)_n CO$— and n=1–4, $R^4$ is selected from hydrogen; ($C_1$–$C_2$)alkyl group selected from methyl or ethyl; amino; monosubstituted amino selected from straight or branched ($C_1$–$C_6$)alkylamino, cyclopropylamino, cyclobutylamino, benzylamino or phenylamino; disubstituted amino selected from dimethylamino, diethylamino, ethyl(1-methylethyl)amino, monomethylbenzylamino, piperidinyl, morpholinyl, 1-imidazolyl, 1-pyrrolyl, 1-(1,2,3-triazolyl) or 4-(1,2,4-triazolyl); ($C_6$–$C_{10}$)aryl group selected from phenyl, α-naphthyl or β-naphthyl; substituted($C_6$–$C_{10}$)aryl group (substitution selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino or carboxy); acyloxy or haloacyloxy group, selected from acetyl, propionyl, chloroacetyl, trichloroacetyl, ($C_3$–$C_6$)cycloalkylcarbonyl, ($C_6$–$C_{10}$)aroyl selected from benzoyl or naphthoyl, halo substituted ($C_6$–$C_{10}$)aroyl such as pentafluorobenzoyl, 4-chlorobenzoyl, 3-bromobenzoyl or 3,4-difluorobenzoyl, ($C_1$–$C_4$)alkylbenzoyl such as 4-toluoyl, 2-toluoyl, 4-(1-methylethyl)benzoyl or (heterocycle)carbonyl, the heterocycle selected from a five membered aromatic or saturated ring with one N, O, S or Se heteroatom optionally having a benzo or pyrido ring fused thereto:

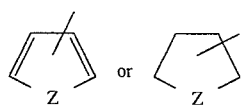

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

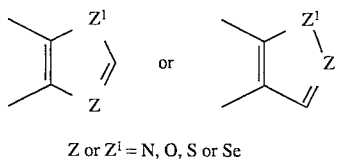

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

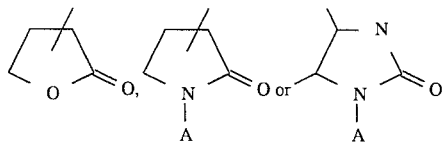

(A is selected from hydrogen; straight or branched $(C_1-C_4)$alkyl; $C_6$-aryl; substituted $C_6$-aryl (substitution selected from halo,$(C_1-C_4)$alkoxy, trihalo$(C_1-C_3)$alkyl, nitro, amino, cyano, $(C_1-C_4)$alkoxycarbonyl, $(C_1-C_3)$alkylamino or carboxy); $(C_7-C_9)$-aralkyl group selected from benzyl, 1-phenylethyl, 2-phenylethyl or phenylpropyl)
such as γ-butyrolactam, γ-butyrolactone, imidazolidinone or N-aminoimidazolidinone, or a six membered aromatic ring with one to three N, O, S or Se heteroatoms such as pyridyl, pyridazinyl, pyrazinyl, sym-triazinyl, unsym-triazinyl, pyrimidinyl or $(C_1-C_3)$alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl or 2-dioxothiomorpholinyl; $(C_1-C_4)$alkoxy group such as allyloxy, methoxy, ethoxy, n-propoxy, n-butoxy or tert-butoxy; $R^aR^b$amino$(C_1-C_4)$alkoxy group, wherein $R^aR^b$ is a straight or branched $(C_1-C_4)$alkyl selected from methyl, ethyl, n-propyl, 1-methylethyl, n-butyl, 1-methylpropyl, or 2-methylpropyl or $R^aR^b$ is $(CH_2)_n$, n=2–6, or —$(CH_2)_2W(CH_2)_2$—wherein W is selected from —$N(C_1-C_3)$alkyl [straight or branched], —NH, —NOB [B is selected from hydrogen or $(C_1-C_3)$alkyl], O or S; or $R^aR^b$aminoxy group, wherein $R^aR^b$ is a straight or branched $(C_1-C_4)$alkyl selected from methyl, ethyl, n-propyl, 1-methylethyl, n-butyl, 1-methylpropyl, or 2-methylpropyl or $R^aR^b$ is $(CH_2)_n$, n=2–6, or —$(CH_2)_2W(CH_2)_2$—wherein W is selected from —$N(C_1-C_3)$alkyl [straight or branched], —NH, —NOB [B is selected from hydrogen or $(C_1-C_3)$alkyl], O or S; α-hydroxy$(C_1-C_3)$alkyl group selected from hydroxymethyl, α-hydroxyethyl or α-hydroxy-1-methylethyl or α-hydroxypropyl; halo$(C_1-C_3)$alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoromethyl, 2-bromoethyl or 2-iodoethyl; $(C_1-C_4)$alkoxycarbonylamino group selected from tert-butoxycarbonylamino, allyloxycarbonylamino, methoxycarbonylamino, ethoxycarbonylamino or propoxycarbonylamino; and when R=$R^{4'}$ $(CH_2)_nSO_2$— and n=0, $R^{4'}$ is selected from amino; monosubstituted amino selected from as straight or branched $(C_1-C_6)$alkylamino, cyclopropylamino, cyclobutylamino, benzylamino or phenylamino; disubstituted amino selected from dimethylamino, diethylamino, ethyl(1-methylethyl)amino, monomethylbenzylamino, piperidinyl, morpholinyl, 1-imidazolyl, 1-pyrrolyl, 1-(1,2,3-triazolyl) or 4-(1,2,4-triazolyl); straight or branched $(C_1-C_2)$alkyl group selected from methyl or ethyl; $(C_6-C_{10})$aryl group selected from phenyl, α-naphthyl or β-naphthyl; substituted $(C_6-C_{10})$aryl group (substitution selected from halo, $(C_1-C_4)$alkoxy, trihalo$(C_1-C_3)$alkyl, nitro, amino, cyano, $(C_1-C_4)$alkoxycarbonyl, $(C_1-C_3)$alkylamino or carboxy); a heterocycle group selected from a five membered aromatic or saturated ring with one N, O, S or Se heteroatom optionally having a benzo or pyrido ring fused thereto:

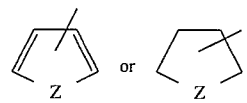

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

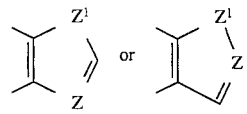

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended heteroatom:

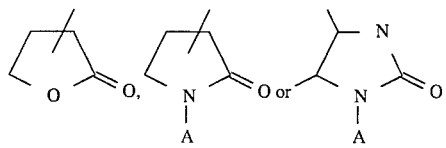

(A is selected from hydrogen; straight or branched $(C_1-C_4)$alkyl; $C_6$-aryl; substituted $C_6$-aryl (substitution selected from halo,$(C_1-C_4)$alkoxy, trihalo$(C_1-C_3)$alkyl, nitro, amino, cyano, $(C_1-C_4)$alkoxycarbonyl, $(C_1-C_3)$alkylamino or carboxy); $(C_7-C_9)$aralkyl group selected from benzyl, 1-phenylethyl, 2-phenylethyl or phenylpropyl)
such as γ-butyrolactam, γ-butyrolactone, imidazolidinone or N-aminoimidazolidinone, or a six membered aromatic ring with one to three N, O, S or Se heteroatoms such as pyridyl, pyridazinyl, pyrazinyl, sym-triazinyl, unsym-triazinyl, pyrimidinyl or ($C_1$–$C_3$)alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl- 2-dioxo-1-piperazinyl, 2-dioxomorpholinyl or 2-dioxothiomorpholinyl; and when R=R$^{4'}$ ($CH_2$)$_n$$SO_2$—and n=1–4, R$^{4'}$ is selected from hydrogen; straight or branched ($C_1$–$C_2$)alkyl group selected from methyl or ethyl; R$^5$ is selected from hydrogen; straight or branched ($C_1$–$C_3$)alkyl group selected from methyl, ethyl, n-propyl or 1-methylethyl; ($C_6$–$C_{10}$)aryl group selected from phenyl, α-naphthyl or β-naphthyl; ($C_7$–$C_9$)aralkyl group such as benzyl, 1-phenylethyl, 2-phenylethyl or phenylpropyl; a heterocycle group selected from a five membered aromatic or saturated ring with one N, O, S or Se heteroatom optionally having a benzo or pyrido ring fused thereto:

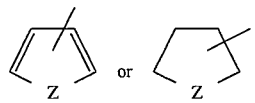

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

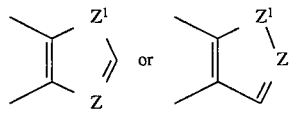

Z or Z$^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

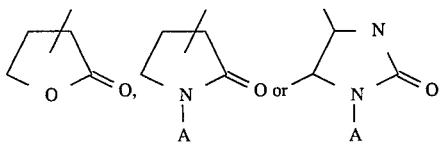

(A is selected from hydrogen; straight or branched ($C_1$–$C_4$)alkyl; $C_6$-aryl; substituted $C_6$-aryl (substitution selected from halo, ($C_1$–$C_4$)alkoxy, trihalo($C_1$–$C_3$)alkyl, nitro, amino, cyano, ($C_1$–$C_4$)-alkoxycarbonyl, ($C_1$–$C_3$)alkylamino or carboxy); ($C_7$–$C_9$)aralkyl group selected from benzyl, 1-phenylethyl, 2-phenylethyl or phenylpropyl) such as γ-butyrolactam, γ-butyrolactone, imidazolidinone or N-aminoimidazolidinone, or a six membered aromatic ring with one to three N, O, S or Se heteroatoms such as pyridyl, pyridazinyl, pyrazinyl, sym-triazinyl, unsym-triazinyl, pyrimidinyl or ($C_1$–$C_3$)alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl- 2-dioxo-1-piperazinyl, 2-dioxomorpholinyl, 2-dioxothiomorpholinyl; or —($CH_2$)$_n$COOR$^7$ where n=0–4 and R$^7$ is selected from hydrogen; straight or branched ($C_1$–$C_3$)-alkyl group selected from methyl, ethyl, n-propyl or 1-methylethyl; or ($C_6$–$C_{10}$)aryl group selected from phenyl, α-naphthyl, β-naphthyl; R$^6$ is selected from hydrogen; straight or branched ($C_1$–$C_3$)alkyl group selected from methyl, ethyl, n-propyl or 1-methylethyl; ($C_6$–$C_{10}$)aryl group selected from phenyl, α-naphthyl or β-naphthyl; ($C_7$–$C_9$)aralkyl group such as benzyl, 1-phenylethyl, 2-phenylethyl or phenylpropyl; a heterocycle group selected from a five membered aromatic or saturated ring with one N, O, S or Se heteroatom optionally having a benzo or pyrido ring fused thereto:

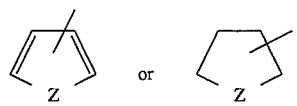

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

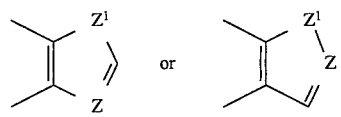

Z or Z$^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended heteroatom:

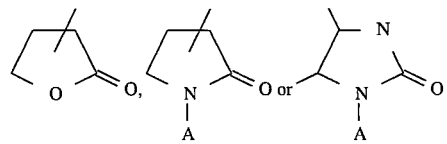

(A is selected from hydrogen; straight or branched ($C_1$–$C_4$)alkyl; $C_6$-aryl; substituted $C_6$-aryl (substitution selected from halo,($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino or carboxy); ($C_7$–$C_9$)-aralkyl group selected from benzyl, 1-phenylethyl, 2-phenylethyl or phenylpropyl) such as γ-butyrolactam, γ-butyrolactone, imidazolidinone or N-aminoimidazolidinone, or a six membered aromatic ring with one to three N, O, S or Se heteroatoms such as pyridyl, pyridazinyl, pyrazinyl, sym-triazinyl, unsym-triazinyl, pyrimidinyl or ($C_1$–$C_3$)alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl- 2-dioxo-1-piperazinyl, 2-dioxomorpholinyl, 2-dioxothiomorpholinyl; or ($CH_2$)$_n$COOR$^{7'}$ where n=0–4 and R$^{7'}$ is selected from hydrogen; straight or branched ($C_1$–$C_3$)alkyl selected from methyl, ethyl, n-propyl or 1-methylethyl; or ($C_6$–$C_{10}$)aryl selected from phenyl, α-naphthyl or β-naphthyl; with the proviso that R$^5$ and wherein W is selected from ($CH_2$)$_n$ and n=0–1, —NH, $R^6$ cannot both be hydrogen; or $R^5$ and $R^6$ taken together are —$(CH_2)_2W(CH_2)_2$—, —$N(C_1-C_3)$alkyl [straight or branched], —$N(C_1-C_4)$alkoxy, oxygen, sulfur or substituted congeners selected from (L or D)proline, ethyl(L or D)prolinate, morpholine, pyrrolidine or piperidine; and the pharmacologically acceptable organic and inorganic salts or metal complexes.

Compounds of special interest are compounds according to the above formula III and IV in which Y is $NO_2$; R is selected from $R^4(CH_2)_nCO$— or $R4'(CH_2)_nSO_2$—; and when R=R4$(CH_2)_nCO$— and n=0, $R^4$ is selected from hydrogen; straight or branched $(C_1-C_2)$alkyl group selected from methyl or ethyl; a heterocycle group selected from a five membered aromatic or saturated ring with one N, O, or S heteroatom optionally having a benzo or pyrido ring fused thereto:

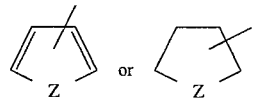

Z = N, O or S such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O or S heteroatoms optionally having a benzo or pyrido ring fused thereto:

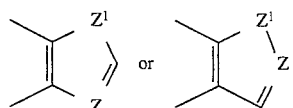

Z or $Z^1$ = N, O, or S such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O or S heteroatoms and an adjacent appended O heteroatom:

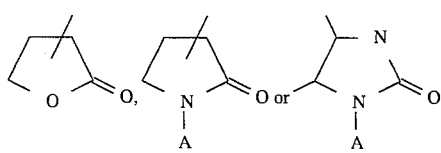

(A is selected from hydrogen; straight or branched $(C_1-C_2)$alkyl; $C_6$-aryl)

such as γ-butyrolactam, γ-butyrolactone, imidazolidinone or N-aminoimidazolidinone; $(C_1-C_4)$alkoxycarbonyl group selected from methoxycarbonyl, ethoxycarbonyl, straight or branched propoxylcarbonyl, straight or branched butoxycarbonyl or allyloxycarbonyl; vinyl or substituted vinyl group [substitution selected from $(C_1-C_2)$alkyl group, $(C_6-C_{10})$aryl group selected from phenyl, α-naphthyl, β-naphthyl, substituted $(C_6-C_{10})$aryl group (substitution selected from halo, $(C_1-C_4)$alkoxy, $(C_1-C_4)$alkoxycarbonyl), halo$(C_1-C_3)$alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-bromoethyl or 2-iodoethyl, $(C_1-C_4)$alkoxy group such as allyloxy, methoxy, ethoxy, n-propoxy, n-butoxy or tert-butoxy; $C_6$-aryloxy group selected from phenoxy or substituted phenoxy (substitution selected from halo, $(C_1-C_4)$alkyl); $(C_7-C_{10})$aralkyloxy group such as benzyloxy, 1-phenylethyloxy or 2-phenylethyloxy; vinyloxy or substituted vinyloxy group (substitution selected from $(C_1-C_2)$alkyl); $R^aR^b$amino$(C_1-C_4)$alkoxy group, wherein $R^aR^b$ is a straight or branched $(C_1-C_4)$alkyl selected from methyl, ethyl, n-propyl, 1-methylethyl, n-butyl; or $R^aR^b$aminoxy group, wherein $R^aR^b$ is a straight or branched $(C_1-C_4)$alkyl selected from methyl, ethyl, n-propyl, 1-methylethyl, n-butyl, 1-methylpropyl, or 2-methylpropyl; and when R=$R^4(CH_2)_n$CO— and n=1–4, $R^4$ is selected from hydrogen; $(C_1-C_2)$alkyl group selected from methyl or ethyl; amino; monosubstituted amino selected from straight or branched $(C_1-C_6)$alkylamino, cyclopropylamino, cyclobutylamino, benzylamino or phenylamino; disubstituted amino selected from dimethylamino, diethylamino, ethyl(1-methylethyl)amino, monomethylbenzylamino, piperidinyl, morpholinyl, 1-imidazolyl, 1-pyrrolyl, or 1-(1,2,3-triazolyl); $(C_6-C_{10})$aryl group selected from phenyl, α-naphthyl or β-naphthyl; substituted$(C_6-C_{10})$aryl group (substitution selected from halo, $(C_1-C_4)$alkoxy, nitro, amino, $(C_1-C_4)$alkoxycarbonyl); acyloxy or haloacyloxy group selected from acetyl, propionyl or chloroacetyl; $(C_1-C_4)$alkoxy group such as allyloxy, methoxy, ethoxy, n-propoxy, n-butoxy or tert-butoxy; $R^aR^b$amino$(C_1-C_4)$alkoxy group, wherein $R^aR^b$ is a straight or branched $(C_1-C_4)$alkyl selected from methyl, ethyl, n-propyl, 1-methylethyl, n-butyl, 1-methylpropyl, or 2-methylpropyl or $R^aR^b$ is $(CH_2)_n$, n=2–6, or —$(CH_2)_2W(CH_2)_2$—wherein W is selected from —$N(C_1-C_3)$alkyl [straight or branched], —NH, —NOB [B is selected from hydrogen or $(C_1-C_3)$alkyl], O or S; or $R^aR^b$aminoxy group, wherein $R^aR^b$ is a straight or branched $(C_1-C_4)$alkyl selected from methyl, ethyl, n-propyl, 1-methylethyl, n-butyl, 1-methylpropyl, or 2-methylpropyl or $R^aR^b$ is $(CH_2)_n$, n=2–6, or —$(CH_2)_2$W—$(CH_2)_2$—wherein W is selected from —$N(C_1-C_3)$alkyl [straight or branched], —NH, —NOB [B is selected from hydrogen or $(C_1-C_3)$alkyl], O or S; halo$(C_1-C_3)$alkyl group such as bromomethyl, fluoromethyl, difluoromethyl, trifluoromethyl, chloromethyl, dichloromethyl, trichloromethyl, 2-fluoroethyl, 2,2-difluoroethyl, 2,2,2-trifluoromethyl, 2-bromoethyl or 2-iodoethyl; $(C_1-C_4)$alkoxycarbonylamino group selected from tert-butoxycarbonylamino, allyloxycarbonylamino, methoxycarbonylamino, ethoxycarbonylamino or propoxycarbonylamino; and when R=$R^{4'}(CH_2)_nSO_2$— and n=0, $R^{4'}$ is selected from straight or branched $(C_1-C_2)$alkyl group selected from methyl or ethyl; $(C_6-C_{10})$aryl group selected from phenyl, α-naphthyl or β-naphthyl; substituted $(C_6-C_{10})$aryl group (substitution selected from halo, $(C_1-C_4)$alkoxy, nitro, $(C_1-C_4)$alkoxycarbonyl); a heterocycle group selected from a five membered aromatic or saturated ring with one N, O or S heteroatom optionally having a benzo or pyrido ring fused thereto:

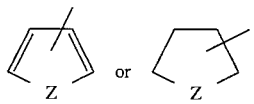

Z = N, O or S such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O or S heteroatoms optionally having a benzo or pyrido ring fused thereto:

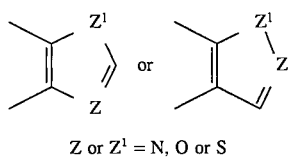

Z or $Z^1$ = N, O or S such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl; and when R=R4' $(CH_2)_nSO_2$— and n=1–4, $R^{4'}$ is selected from hydrogen; straight or branched $(C_1-C_2)$alkyl group selected from methyl or ethyl; $R^5$ is selected from hydrogen; straight or branched $(C_1-C_3)$alkyl group selected from methyl, ethyl, n-propyl or 1-methylethyl; $R^6$ is selected from hydrogen; straight or branched $(C_1-C_3)$alkyl group selected from methyl, ethyl, n-propyl or 1-methylethyl; with the proviso that $R^5$ and $R^6$ cannot both be hydrogen; or $R^5$ and $R^6$ taken together are —$(CH_2)_2W(CH_2)_2$-, wherein W is selected from $(CH_2)_n$ and n=0–1, —NH, —N($C_1-C_3$)alkyl [straight or branched], —N($C_1-C_4$)alkoxy, oxygen, sulfur or substituted congeners selected from (L or D)proline, ethyl(L or D)prolinate, morpholine, pyrrolidine or piperidine;and the pharmacologically acceptable organic and inorganic salts or metal complexes.

DESCRIPTION OF THE PREFERRED EMBODIMENTS

The novel compounds of the present invention may be readily prepared in accordance with the following schemes.

The starting 7-(substituted amino)-6-demethyl- 6-deoxytetracyclines described in formula 1, wherein X=$NR^1R^2$ and $R^1=R^2$ (1a) and X=$NHR^1$ (1b) or the salts thereof are prepared by procedures known to those skilled in the art including those described in U.S. Pat. Nos. 3,226,436 and 3,518,306.

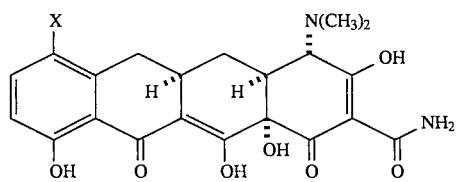

1a. x = $NR^1R^2$, $R^1 = R^2$
1b. x = $NHR^1$
1c. x = $NR^1R^2$, $R^1 \neq R^2$ The starting 7-(substituted amino)-6-demethyl- 6-deoxytetracyclines described in formula 1 wherein X=$NR^1R^2$ and $R^1= R^2$ (1c) are prepared according to Scheme 1.

Scheme I

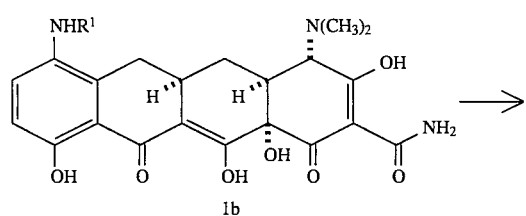

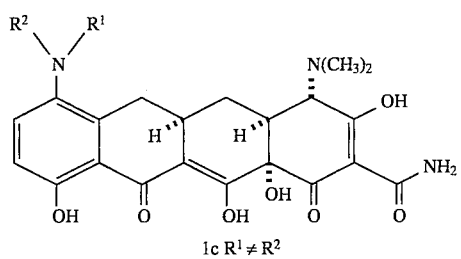

1c $R^1 \neq R^2$

In accordance with Scheme 1, a 7-(monoalkylamino)-6-demethyl- 6-deoxytetracycline 1b, in which X=$NHR^1$ is reductively alkylated with an aldehyde to give an unsymmetrical dialkylamino, 1c.

Scheme II

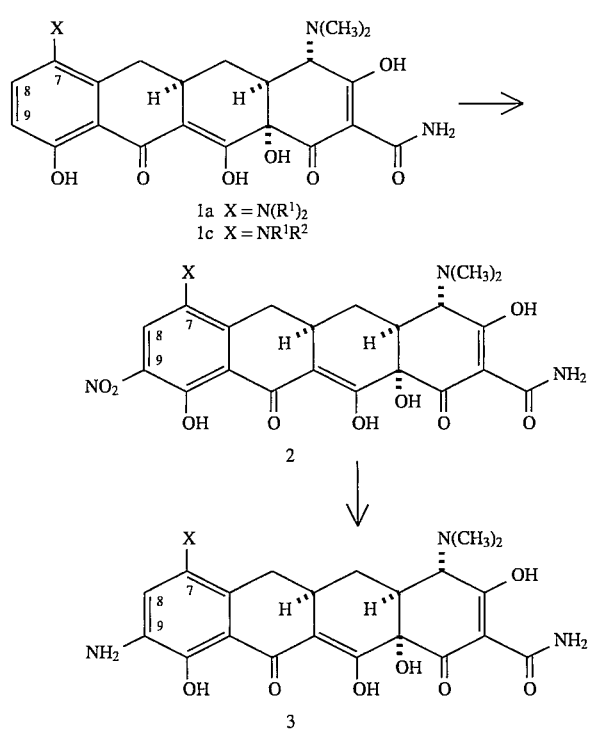

1a X = $N(R^1)_2$
1c X = $NR^1R^2$

In accordance with Scheme II, a 7-(substituted amino)-6-demethyl-6-deoxytetracycline or its salts, 1a or 1c, is treated with a) a metal nitrate salt; such as calcium, potassium or sodium; and a strong acid; such as sulfuric acid, trifluoroacetic acid, methanesulfonic acid or perchloric acid or b) nitric acid and a strong acid; such as sulfuric acid, trifluoroacetic acid, methanesulfonic acid or perchloric acid; to form the corresponding 7-(substituted amino)-9-nitro-6-demethyl-6-deoxytetracycline 2.

To produce the 9-(amino)-7-(substituted amino)-6-demethyl-6-deoxytetracyclines, 3, compound 2 or its salts is treated with hydrogen in an acidic alcohol solvent, in the presence of a suitable catalyst such as, for example:

a) any supported catalyst; such as 0.5–23% palladium-on-carbon, 0.5–25% palladium-on-barium, 0.5–25% platinum-on-carbon or 0.5-25% rhodium-on-carbon;

b) any reducible supported catalyst; such as Raney nickle or platinum oxide; or c) a homogeneous hydrogenation catalyst; such as tris(triphenylphosphine)rhodium (I) chloride; to obtain the 9-amino-7-(substituted amino)-6-demethyl- 6-deoxytetracycline, 3.

Alternatively, the 9-(amino)-7-(substituted amino)-6-demethyl-6-deoxytetracyclines, 3, are obtained by treating with:

a) stannous chloride dihydrate as described by R. B. Woodward, Org. Syn., Coll. Vol. 3,453 (1955);
b) a soluble metal sulfide, preferably sodium sulfide, in alcoholic solvents as described by G. R. Robertson, Org. Syn., Coll. Vol. 1, 52 (1941);
c) an active metal in mineral acid; such as iron, tin or zinc in dilute hydrochloric acid.;
d) active metal couples; such as copper-zinc, tin-mercury or aluminum amalgam in dilute acid; or
e) transfer hydrogenation using triethylammonium formate and a supported catalyst as described by I. D. Entwistle et al., J. Chem. Soc., Perkin 1, 443 (1977).

Preferably, the 9-(amino)-7-(substituted amino)-6-demethyl-6-deoxytetracyclines, 3, are obtained as inorganic salts such as hydrochloric, hydrobromic, hydroiodic, phosphoric, nitric or sulfate.

ethyl-3,4,5,6-tetrahydro- 2(1H)-pyrimidinone or 1,2-dimethoxyethane.

Alternatively, in accordance with Scheme III, a 9-(acylamino)-6-demethyl-6-deoxytetracycline, 5a, prepared by the procedures described in U.S. Pat. No. 3,239,499, or a 9-(sulfonylamino)-6-demethyl-6-deoxytetracycline, 5b, prepared by the procedures described in this invention, is treated with a halogenation agent such as bromine, N-bromoacetamide, N-bromosuccinimide, iodine monochloride, benzyltrimethylammonium chloride iodine monochloride complex or N-iodosuccinimide to give the corresponding 9-(acyl or sulfonylamino)-7-halo- 6-demethyl-6-deoxytetracycline, 6.

Similarly, compound 5a or 5b can be treated with:

a) a metal nitrate such as calcium, potassium or sodium; and a strong acid such as sulfuric, trifluoroacetic, methanesulfonic acid or trifluoromethanesulfonic; or
b) nitric acid and a strong acid such as sulfuric, trifluoroacetic, methanesulfonic, trifluoromethanesulfonic or perchloric acid to give the corresponding 9-(acyl or sulfonyl amino)-7-nitro-6-demethyl-6-deoxytetracycline, 7.

SCHEME III

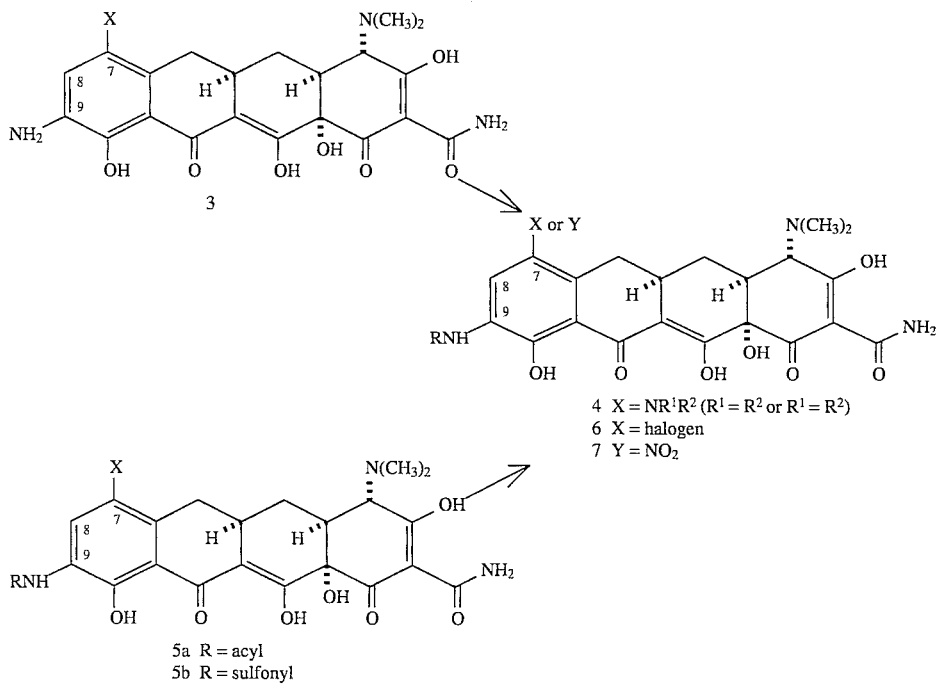

4  $X = NR^1R^2$ ($R^1 = R^2$ or $R^1 \neq R^2$)
6  X = halogen
7  Y = $NO_2$

5a  R = acyl
5b  R = sulfonyl

SCHEME III

In accordance with Scheme III, a 9-(amino)-7-(substituted amino)-6-demethyl-6-deoxytetracycline or its salts, 3, is treated with an acyl chloride, acyl anhydride, mixed acyl anhydride, sulfonyl chloride or sulfonyl anhydride in the presence of a suitable acid scavenger in a variety of solvents to form the corresponding 9-(acyl or sulfonyl amino)-7-(substituted amino)-6-demethyl-6-deoxytetracycline, 4. The acid scavenger is selected from sodium bicarbonate, sodium acetate, pyridine, triethylamine, N,O-bis(trimethylsilyl)acetamide, N,O-bis(trimethylsilyl)trifluoroacetamide or a basic ion-exchange resin. The solvents are selected from water-tetrahydrofuran, N-methylpyrrolidone, 1,3-dimethyl-2-imidazolidione, hexamethylphosphoramide, 1,3-dim-

SCHEME IV

SCHEME IV

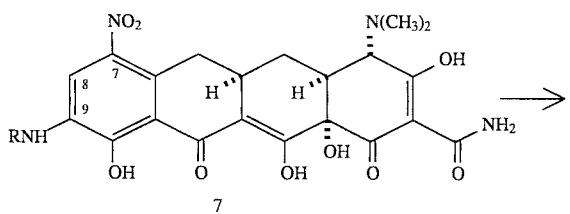

-continued
SCHEME IV

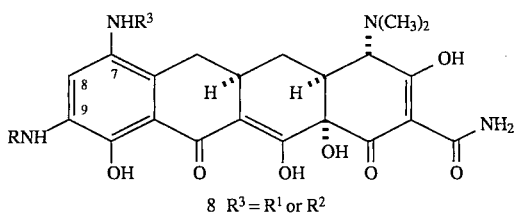

8  R³ = R¹ or R²

In accordance with Scheme IV, a 9-(acyl or sulfonyl amino)-7-nitro-6-demethyl-6-deoxytetracycline, Z, is selectively N-alkylated with aldehydes or ketones in the presence of acid and hydrogen to the corresponding 7,9-di(substituted amino)-6-demethyl- 6-deoxytetracycline, 8, by methodology known to those skilled in the art (U.S. Pat. Nos. 3,226,436 and 3,518,306).

SCHEME V

SCHEME V

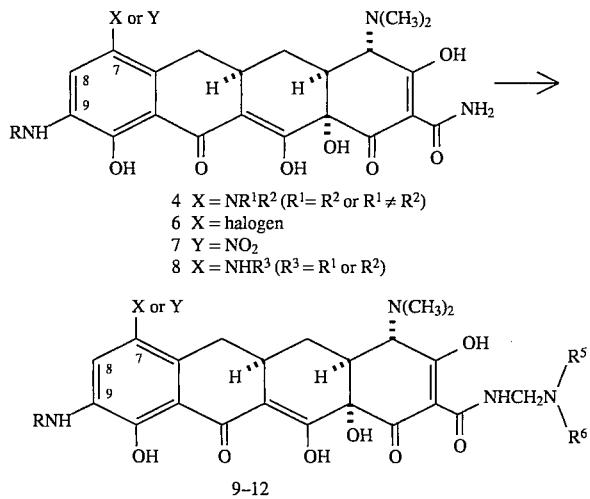

4  X = NR¹R² (R¹= R² or R¹ ≠ R²)
6  X = halogen
7  Y = NO₂
8  X = NHR³ (R³ = R¹ or R²)

9–12

In accordance with Scheme V, Compounds 4, 6, 7 or 8 are selectively N-alkylated in the presence of formaldehyde and either a primary amine such as methylamine, ethylamine, benzylamine, methyl glycinate, (L or D) lysine, (L or D)alanine or their substituted congeners; or a secondary amine such morpholine, pyrrolidine, piperidine or their substituted congeners to give the corresponding Mannich base adduct, 9, 10, 11 or 12, or the desired intermediate or of the biologically active 7-(substituted)-9-(substituted amino)-6-demethyl- 6-deoxytetracyclines. Contempleted equivalents include those substituted morpholine, pyrrolidine or piperidine moieties wherein the substituents are chosen to provide the requisite increase in solubility without adversely affecting antibacterial activity.

The 7-(substituted)-9-(substituted amino)-6-demethyl-6-deoxytetracyclines may be obtained as metal complexes such as aluminum, calcium, iron, magnesium, mamganese and complex salts; inorganic and organic salts and corresponding Mannich base adducts using methods known to those skilled in the art (Richard C. Larock, Comprehensive Organic Transformations, VCH Publishers, 411–415, 1989). Preferably, the 7-(substituted)- 9-(substituted amino)-6-demethyl-6-deoxytetracyclines are obtained as inorganic salts such as hydrochloric, hydrobromic, hydroiodic, phosphoric, nitric or sulfate; or organic salts such as acetate, benzoate, citrate, cysteine or other amino acids, fumarate, glycolate, maleate, succinate, tartrate alkylsulfonate or arylsulfonate. In all cases, the salt formation occurs with the C(4)-dimethylamino group. The salts are preferred for oral and parenteral administration.

BIOLOGICAL ACTIVITY

Methods for in Vitro antibacterial evaluation (Tables I–V)

The minimum inhibitory concentration (MIC), the lowest concentration of the antibiotic which inhibits growth of the test organism, is determined by the agar dilution method using 0.1 ml Muller-Hinton II agar (Baltimore Biological Laboratories) per well. An inoculum level of $1–5\times10^5$ CFU/ml, and a range of antibiotic concentrations (32–0.004 µg/ml) is used. MIC is determined after the plates are incubated for 18 hours at 35° C. in a forced air incubator. The test organisms comprise genetically defined strains that are sensitive to tetracycline and resistant strains that are insensitive to tetracycline, either by preventing the antibiotic from interacting with bacterial ribosomes (tetM) or by a tetK encoded membrane protein which confers tetracycline resistance by energy-dependent efflux of the antibiotic from the cell.

E. coli in Vitro Protein translation System (Table VI)

An in vitro, cell free, protein translation system using extracts from E. coli strain MRE 600 (tetracycline-sensitive) and a derivative of MRE 600 containing the tetM determinant has been developed based on literature methods. [J. M. Pratt, Coupled Transcription-translation in Prokaryotic Cell-free Systems, Transcription and Translation, a Practical Approach, (B. D. Hames and S. J. Higgins, eds.) p. 179–209, IRL Press, Oxford-Washington, 1984]

The antibiotics are added to exponentially growing cultures of tetracycline-susceptible E. coli at growth inhibitory concentrations. After 30 minutes, excess antibiotic is removed from the bacteria by centrifugation and the organism is resuspended in fresh growth medium. The ability of bacteria to resume growth is monitored. Washing of inhibited cells alleviates growth inhibition due to chlortetracycline, but not that caused by polymyxin. This reflects the different binding characteristics of the drugs. Chlortetracycline binds reversibly to bacterial ribosomes, while polymyxin remains tightly associated with its target, the cytoplasmic membrane, and continues to prevent bacterial growth even when excess antibiotic is removed.

In Vivo Antibacterial Evaluation (Table VII)

The therapeutic effects of tetracyclines are determined against acute lethal infections with various staphylococcal and E. coli strains. Female mice, strain CD-1 (Charles River Laboratories), 20±2 grams, are challenged by an intraperitoneal injection of sufficient bacteria (suspended in broth or hog mucin) to kill non-treated controls within 24–48 hours. Antibacterial agents, contained in 0.5 ml of 0.2% aqueous agar, are administered subcutaneously or orally 30 minutes after infection. When an oral dosing schedule is used, animals are deprived of food for 5 hours before and 2 hours after infection. Five mice are treated at each dose level. The 7 day survival ratios from 3 separate tests are pooled for calculation of median effective dose (ED50).

E. coli in Vitro Protein Translation System(Table VIII)

An in vitro, cell free, protein translation system using extracts from E. coli strain MRE600 (tetracycline sensitive) and a derivative of MRE600 containing the tetM determinant has been developed based on literature methods [J. M. Pratt, Coupled Transcription-translation in Prokaryotic Cell-free Systems, Transcription and Translation, a Practical Approach, (B. D. Hames and S. J. Higgins, eds) p. 179–209, IRL Press, Oxford-Washington, 1984].

Using the systems described above, the novel tetracycline compounds of the present invention are tested for their ability to inhibit protein synthesis in vitro. Briefly, each 10μl reaction contains S30 extract (a whole extract) made from either tetracycline sensitive cells or an isogenic tetracycline resistant (tetM) strain, low molecular weight components necessary for transcription and translation (i.e. ATP and GTP), a mix of 19 amino acids (no methionine), 35S labeled methionine, DNA template (either pBR322 or pUC119), and either DMSO (control) or the novel tetracycline compound to be tested ("Novel Tc") dissolved in DMSO.

The reactions are incubated for 20 minutes at 37° C. Timing is initiated with the addition of the S30 extract, the lase component to be added. After 30 minutes, 2.5 μl of the reaction is removed and mixed with 0.5 ml of 1N NaOH to destroy RNA and tRNA. Two ml of 25% trichloroacetic acid is added and the mixture incubated at room temperature for 15 minutes. The trichloracetic acid precipitated material is collected on Whatman GF/C filters and washed with a solution of 10% trichloracetic acid. The filters are dried and the retained radioactivity, representing incorporation of $^{35}$S-methionine into polypeptides, is counted using standard liquid scintillation methods.

The percent inhibition (P.I.) of protein synthesis is determined to be:

$$P.I. = 100 - \left[ \frac{\text{Retained radioactivity of Novel } TC \text{ containing sample}}{\text{Retained radioactivity of the } DMSO \text{ control reaction}} \right] \times 100$$

Testing Results

The claimed compounds exhibit antibacterial activity against a spectrum of tetracycline sensitive and resistant Gram-positive and Gram-negative bacteria, especially, strains of *E. coli, S. aureus* and *E. faecalis,* containing the tetM resistance determinants (Table I). Notable is 7-(dimethylamino)-9-(formylamino)- 6-demethyl-6-deoxytetracycline, as shown in Tables I and IV, which has good in vitro activity against tetracycline resistant strains containing the tetM resistance determinant (such as S. aureus UBMS 88-5, *S. aureus* UBMS 90-1 and 90-2, *E. coli* UBMS 89-1 and 90-4) and is equally as effective as minocycline against susceptible strains.

7-(Dimethylamino)-9-(formylamino)-6-demethyl-6-deoxytetracycline demonstrates effective activity against minocycline susceptible strains including a variety of recently isolated bacteria from clinical sources (Table V). With the exception of some Proteus spp., 7-(dimethylamino)-9-(formylamino)-6-demethyl-6-deoxytetracycline's activity is superior to that of minocycline against other isolates.

Protein synthesis, directed by cell-free extracts from the tetracycline susceptible strain MRE-600, are inhibited by tetracycline, minocycline and the 7-(dimethylamino)-9-(formylamino)-6-demethyl-6-deoxytetracycline of this invention (Table 6). Protein synthesis, directed by cell-free extracts from strain MRE 600 (tetM), is resistant to tetracycline and minocycline, since 50% inhibition of protein synthesis required addition of approximately 5-fold more antibiotic than in extracts prepared from strain MRE 600 (Table VI). However, in contrast, 7-(dimethylamino)-9-(formylamino)-6-demethyl-6-deoxytetracycline effectively inhibited protein synthesis in extracts prepared from either MRE 600 or MRE 600 (tetM) (Table VI). The evidence presented indicates that 7-(dimethylamino)-9-(formylamino)- 6-demethyl-6-deoxy-tetracycline is an inhibitor of protein synthesis at the ribosome level. The ability of 7-(dimethylamino)-9-(formylamino)-6-demethyl-6-deoxytetracycline to inhibit bacterial growth almost certainly reflects directed inhibition of bacterial synthesis. If so, then it is expected, like other tetracyclines, to exhibit a bacteriostatic effect against susceptible bacteria.

7-(Dimethylamino)-9-(formylamino)-6-demethyl-6-deoxytetracycline binds reversibly to its target (the ribosome) since bacterial growth resumed when the compound was removed from the cultures by washing of the organism. Therefore, the ability of 7-(dimethylamino)- 9-(formylamino)-6-demethyl-6-deoxytetracycline to inhibit bacterial growth appears to be a direct consequence of its ability to inhibit protein synthesis at the ribosome level.

The enhanced activity (Table VII) of 7-(dimethylamino)-9-(formylamino)-6-demethyl-6-deoxytetracycline against tetracycline susceptible and resistant organisms (tetM) is also demonstrated in vivo in animals infected with *S. aureus* UBMS 90-1 and 90-2. The $ED_{50}$'s (Table VII) obtained for 7-(dimethylamino)- 9-(formylamino)-6-demethyl-6-deoxytetracycline are lower than those of minocycline.

The improved efficacy of 7-(dimethylamino)- 9-(formylamino)-6-demethyl-6-deoxytetracycline is demonstrated by the in vitro activity against isogenic strains into which the resistance determinants, such as tetM, were cloned (Tables I-IV); the inhibition of protein synthesis by tetM ribosomes (Table VI); and the in vivo activity against experimental infections caused by strains resistant to the tetracyclines, due to the presence of resistance determinants, such as tetM (Table VII).

As can be seen from Tables I–V, compounds of the invention may be used to prevent or control important veterinary diseases such as mastitis, diarrhea, urinary tract infections, skin infections, ear infections, wound infections and the like.

| LEGEND FOR COMPOUNDS | |
|---|---|
| LETTER | NAME |
| A | 7-(Dimethylamino)-9-(formylamino)-6-demethyl-6-deoxytetracycline |
| B | 9-(Acetylamino)-7-(dimethylamino)-6-demethyl-6-deoxytetracycline |
| C | 7-(Diethylamino)-9-(formylamino)-6-demethyl-6-deoxytetracycline |
| D | 7-(Diethylamino)-9-(formylamino)-6-demethyl-6-deoxytetracycline disulfate |
| E | 9-(Acetylamino)-7-(diethylamino)-6-demethyl-6-deoxytetracycline disulfate |
| F | 9-(Acetylamino)-7-(diethylamino)-6-demethyl-6-deoxytetracycline |
| G | 9-(Formylamino)-7-iodo-6-demethyl-6-deoxytetracycline sulfate |
| H | 9-(Acetylamino)-7-iodo-6-demethyl-6-deoxytetracycline sulfate |
| I | 7-(Dimethylamino)-9[(trifluoroacetyl)amino]-6-demethyl-6-deoxytetracycline sulfate |
| J | 7-(Dimethylamino)-9-[[(phenylmethoxy)acetyl]amino]-6-demethyl-6-deoxytetracycline |
| K | 9-[[(Acetyloxy)acetyl]amino]-7-(dimethylamino)-6-demethyl-6-deoxytetracycline |
| L | 7-(Dimethylamino)-9-[(hydroxyacetyl)amino-6-demethyl-6-deoxytetracycline |
| M | 9-[(Aminoacetyl)amino]-7-(dimethylamino)-6-demethyl-6-deoxytetracycline mono(trifluoroacetate) |
| N | [7S-(7α, 10aα)]-[[9-(Aminocarbonyl)-7-(dimethylamino)-5,5a,6,6a,7,10,10a,12-octahydro-1,8,10a,11-tetrahydroxy-10,12-dioxo-2-naphthacenyl]amino]-oxoacetic acid ethyl ester |
| O | 7-(Dimethylamino)-6-demethyl-6-deoxytetracycline |

LEGEND FOR COMPOUNDS

| LETTER | NAME |
|---|---|
| P | hydrochloride (aminocycline hydrochloride)<br>9-(Benzoylamino)-7-(dimethylamino)-6-demethyl-6-deoxytetracycline |
| Q | 7-(Dimethylamino)-9-[(4-methoxybenzoyl)amino]-6-demethyl-6-deoxytetracycline |
| R | 7-(Dimethylamino)-9-[(2-methylbenzoyl)amino]-6-demethyl-6-deoxytetracycline |
| S | 7-(Dimethylamino)-9-[(2-fluorobenzoyl)amino]-6-demethyl-6-deoxytetracycline |
| T | 7-(Dimethylamino)-9-[(pentafluorobenzoyl)amino]-6-demethyl-6-deoxytetracycline |
| U | 7-(Dimethylamino)-9-[[3-(trifluoromethyl)benzoyl]amino]-6-demethyl-6-deoxytetracycline |
| V | 7-(Dimethylamino)-9-[(4-nitrobenzoyl)amino]-6-demethyl-6-deoxytetracycline |
| W | 7-(Dimethylamino)-9-[[(4-dimethylamino)benzoyl]amino]-6-demethyl-6-deoxytetracycline |
| X | 9-[(4-Aminobenzoyl)amino]-7-(dimethylamino)-6-demethyl-6-deoxytetracycline sulfate |
| Y | 7-(Dimethylamino)-9-[(2-furanylcarbonyl)amino]-6-demethyl-6-deoxytetracycline |
| Z | 7-(Dimethylamino)-9-[(2-thienylcarbonyl)amino]-6-demethyl-6-deoxytetracycline |
| AA | 7-(Dimethylamino)-9-[[(4-nitrophenyl)sulfonyl]amino]-6-demethyl-6-deoxytetracycline |
| BB | 7-(Dimethylamino)-9-[(3-nitrophenyl)sulfonyl]amino]-6-demethyl-6-deoxytetracycline |
| CC | 7-(Dimethylamino)-9-[(phenylsulfonyl)amino]-6-demethyl-6-deoxytetracycline |
| DD | 7-(Dimethylamino)-9-[(2-thienylsulfonyl]amino]-6-demethyl-6-deoxytetracycline |
| EE | 9-[[(4-Chlorophenyl)sulfonyl]amino]-7-(dimethylamino)-6-demethyl-6-deoxytetracycline |
| FF | 7-(Dimethylamino)-9-[(methylsulfonyl)amino]-6-demethyl-6-deoxytetracycline |
| GG | 9-[[[(2-Acetylamino)-4-methyl-5-thiazolyl]sulfonyl]amino]-7-(dimethylamino)-6-demethyl-6-deoxytetracycline |
| HH | [7S-(7α,10aα)]-[9-(Aminocarbonyl)-4,7-bis(dimethylamino)-5,5a,6,6a,7,10,10a,12-octahydro-1,8,10a,11-tetrahydroxy-10,12-dioxo-2-naphthacenyl]carbamic acid methyl ester |
| II | 7-(Dimethylamino)-9-[[(dimethylamino)acetyl]amino]-6-demethyl-6-deoxytetracycline sulfate |
| TC | Tetracycline hydrochloride |
| JJ | [4S-(4alpha,12aalpha)]-4,7-Bis(dimethylamino)-9-[[(dimethylamino)acetyl]amino]-1,4,4a,5,5a,6,11,12a-octahydro-3,10,12,12a-tetrahydroxy-1,11-dioxo-2-naphthacenecarboxamide disulfate |
| KK | [4S-(4alpha,12aalpha)]-4,7-Bis(dimethylamino)-9-[[(dimethylamino)acetyl]amino]-1,4,4a,5,5a,6,11,-12a-octahydro-3,10,12,12a-tetrahydroxy-1,11-dioxo-2-naphthacenecarboxamide dihydrochloride |
| LL | [4S-(4alpha,12aalpha)]-4,7-Bis(dimethylamino)-9-[[(dimethylamino)acetyl]amino]-1,4,4a,5,5a,6,11,-12a-octahydro-3,10,12,12a-tetrahydroxy-1,11-dioxo-2-naphthacenecarboxamide |
| MM | [4S-(4alpha,12aalpha)]-4,7-Bis(dimethylamino)-1,4,4a,5,5a,6,11,12a-octahydro-3,10,12,12a-tetrahydroxy-9-[[(methylamino)acetyl]amino]-1,11-dioxo-2-naphthacenecarboxamide dihydrochloride |
| NN | [7S-(7alpha,10aalpha)]-N-[9-(Aminocarbonyl)-4,7-bis(dimethylamino)-5,5a,6,6a,7,10,10a,12-octahydro-1,8,10a,11-tetrahydroxy-10,12-dioxo-2-naphthacenyl]-4-morpholineacetamide dihydrochloride |
| OO | [4S-(4alpha,12aalpha)]-4,7-Bis(dimethylamino)-9-[[(ethylamino)acetyl]amino]-1,4,4a,5,5a,6,11,12a-octahydro-3,10,12,12a-tetrahydroxy-1,11-dioxo-2-naphthacenecarboxamide dihydrochloride |
| PP | [4S-(4alpha,12aalpha)]-4,7-Bis(dimethylamino)-9-[[(butylamino)acetyl]amino]-1,4,4a,5,5a,6,11,12a-octahydro-3,10,12,12a-tetrahydroxy-1,11-dioxo-2-naphthacenecarboxamide dihydrochloride |
| QQ | [4S-(4alpha,12aalpha)]-9[[(Cyclopropylamino)acetyl]amino]-4,7-Bis(dimethylamino)-1,4,4a,5,5a,6,11,-12a-octahydro-3,10,12,12a-tetrahydroxy-1,11-dioxo-2-naphthacenecarboxamide dihydrochloride |
| RR | [4S-(4alpha,12aalpha)]-9-[[(Diethylamino)acetyl]amino]-4,7-Bis(dimethylamino)-1,4,4a,5,5a,6,11,-12a-octahydro-3,10,12,12a-tetrahydroxy-1,11-dioxo-2-naphthacenecarboxamide dihydrochloride |
| SS | [7S-(7alpha,10aalpha)]-N-[9-(Aminocarbonyl)-4,7-bis(dimethylamino)-5,5a,6,6a,7,10,10a,12-octahydro 1,8,10a,11-tetrahydroxy-10,12-dioxo-2-naphthacenyl]-1-pyrrolidineacetamide dihydrochloride |
| TT | [4S-(4alpha,12aalpha)]-4,7-Bis(dimethylamino)-1,4,4a,5,5a,6,11,12a-octahydro-3,10,12,12a-tetrahydroxy-9-[[[(2-methylpropyl)amino]acetyl]amino]-1,11-dioxo-2-naphthacenecarboxamide dihydrochloride |
| UU | [7S-(7alpha,10aalpha)]-N-[9-(Aminocarbonyl)-4,-7-bis(dimethylamino)-5,5a,6,6a,7,10,10a,12-octahydro-1,8,10a,11-tetrahydroxy-10,12-dioxo-2-naphthacenyl]-1-piperidineacetamide dihydrochloride |
| VV | [7S-(7alpha,10aalpha)]-N-[9-(Aminocarbonyl)-4,-7-bis(dimethylamino)-5,5a,6,6a,7,10,10a,12-octahydro-1,8,10a,11-tetrahydroxy-10,12-dioxo-2-naphthacenyl]-1H-imidazole-1-acetamide dihydrochloride |
| WW | [4S-(4alpha,12aalpha)]-4,7-bis(dimethylamino)-1,4,4a,5,5a,6,11,12a-octahydro-3,10,12,12a-tetrahydroxy-1,11-dioxo-9-[[(propylamino)acetyl]amino]-2-naphthacenecarboxamide dihydrochloride |
| XX | [4S-(4alpha,12aalpha)]-4,7-Bis(dimethylamino)-9-[[2-(dimethylamino)-1-oxopropyl]amino]-1,4,4a,5,5a,6,11,12a-octahydro-3,10,12,12a-tetrahydroxy-1,11-dioxo-2-naphthacenecarboxamide dihydrochloride |
| YY | [4S-(4alpha,12aalpha)]-4,7-Bis(dimethylamino)-1,4,4a,5,5a,6,11,12a-octahydro-3,10,12,12a-tetrahydroxy-9-[[2-(methylamino)-1-oxopropyl]amino]-1,11-dioxo-2-naphthacenecarboxamide dihydrochloride |
| ZZ | [4S-(4alpha,12aalpha)]-4,7-Bis(dimethylamino)-9-[[4-(dimethylamino)-1-oxobutyl]amino]-1,4,4a,5,5a,6,11,12a-octahydro-3,10,12,12a-tetrahydroxy-1,11-dioxo-2-naphthacenecarboxamide dihydrochloride |
| AAA | [7S-(7alpha,10aalpha)]-N-[9-(Aminocarbonyl)-4,7-bis(dimethylamino)-5,5a,6,6a,7,10,10a,12-octahydro-1,8,10a,11-tetrahydroxy-10,12-dioxo-2-naphthacenyl]-alpha-methyl-1-pyrrolidineacetamide dihydrochloride |
| BBB | [4S-(4alpha,12aalpha)]-4,7-Bis(dimethylamino)-9-[[(hexylamino)acetyl]amino]-1,4,4a,5,5a,6,11,12a-octahydro-3,10,12,12a-tetrahydroxy-1,11-dioxo-2-naphthacenecarboxamide dihydrochloride |
| CCC | [4S-(4alpha,12aalpha)]-9-[[(Butylmethylamino)-acetyl]amino]-4,7-Bis(dimethylamino)-1,4,4a,5,5a,6,11,12a-octahydro-3,10,12,12a-tetrahydroxy-1,11-dioxo-2-naphthacenecarboxamide dihydrochloride |
| DDD | [4S-(4alpha,12aalpha)]-4,7-Bis(dimethylamino)-1,4,4a,5,5a,6,11,12a-octahydro-3,10,12,12a-tetrahydroxy-1,11-dioxo-9-[[(pentylamino)acetyl]amino]-2-naphthacenecarboxamide dihydrochloride |
| EEE | [4S-(4alpha,12aalpha))-4,7-Bis(dimethylamino)-1,4,4a,5,5a,6,11,12a-octahydro-3,10,12,12a-tetrahydroxy-1,11-dioxo-9-[[[(phenylmethyl)amino]acetyl]-amino]-2-naphthacenecarboxamide dihydrochloride |
| FFF | (4S-(4alpha,12aalpha)]-4,7-Bis(dimethylamino)-9-[[(dimethylamino)acetyl]amino]-1,4,4a,5,5a,6,11,12a-octahydro-3,10,12,12a-tetrahydroxy-1,11-dioxo-N-(1-pyrrolidinylmethyl)-2-naphthacenecarboxamide |
| GGG | [4S-(4alpha,12aalpha))-4,7-Bis(dimethylamino)-9-[[[(dimethylamino)acetyl]amino]-1,4,4a,5,5a,6,11,12a-octahydro-3,10,12,12a-tetrahydroxy-1,11-dioxo-N-(4-morpholinylmethyl)-2-naphthacenecarboxamide |
| HHH | [4S-(4alpha,12aalpha))-4,7-Bis(dimethylamino)-9-[[(dimethylamino)acetyl]amino]-1,4,4a,5,5a,6,11,12a-octahydro-3,10,12,12a-tetrahydroxy-1,11-dioxo-N-(1-piperidinylmethyl)-2-naphthacenecarboxamide |
| III | [4S-(4alpha,12aalpha)]-9-[(Bromoacetyl)amino]-4,-7-bis(dimethylamino)-1,4,4a,5,5a,6,11,12a-octahydro-3,10,12,12a-tetrahydroxy-1,11-dioxo-2-naphthacenecarboxamide dihydrochloride |
| JJJ | [4S-(4alpha,12aalpha)]-9-[(2-Bromo-1-oxopropyl)-amino]-4,7-bis(dimethylamino)-1,4,4a,5,5a,6,11, |

| LEGEND FOR COMPOUNDS | |
|---|---|
| LETTER | NAME |
| | 12a-octahydro-3,10,12,12a-tetrahydroxy-1,11-dioxo-2-naphthacenecarboxamide hydrobromide |
| KKK | [7S-(7alpha,10aalpha]-N-(2-[[9-(Aminocarbonyl)-4,7-bis(dimethylamino)-5,5a,6,6a,7,10,10a,12-octahydro-1,8,10a,11-tetrahydroxy-10,12-dioxo-2-naphthacenyl]amino]-2-oxoethyl]glycine |
| LLL | [7S-(7alpha,10aalpha)]-N-[9-(Aminocarbonyl)-4,7-bis(dimethylamino)-5,5a,6,6a,7,10,10a,12-octahydro-1,8,10a,11-tetrahydroxy-10,12-dioxo-2-naphthacenyl]-1-azetidineacetamide |
| MMM | [4S-(4alpha,12aalpha)]-9-[[(Cyclobutylamino)acetyl]amino]-4,7-Bis(dimethylamino)-1,4,4a,5,5a,6,11,12a-octahydro-3,10,12,12a-tetrahydroxy-1,11-dioxo-2-naphthacenecarboxamide |

TABLE I

ANTIBACTERIAL ACTIVITY OF 9-(ACYLAMINO)-7-(SUBSTITUTED)-6-DEMETHYL-6-DEOXYTETRACYCLINES

| | MIC (µg/ml) COMPOUND | | | | | | | |
|---|---|---|---|---|---|---|---|---|
| ORGANISM | A | B | C | D | E | F | G | H |
| S. aureus UBMS 86-5 (tetM) | 0.06 | 0.12 | 0.12 | 0.25 | 4 | 0.5 | 1 | 1 |
| S. aureus UBMS 88-4 (Sensitive) | 0.015 | ≦0.06 | 0.03 | 0.12 | 0.5 | 0.25 | <0.015 | 0.25 |
| S. aureus UBMS 90-1 (tetM) | 0.06 | ND | 0.5 | 0.5 | 8 | 2 | 4 | 1 |
| S. aureus UBMS 90-2 (tetM) | 0.03 | ND | 0.12 | 0.12 | 2 | 0.5 | 0.5 | 0.5 |
| S. aureus UBMS 90-3 (Sensitive) | ≦0.015 | ND | 0.03 | 0.06 | 0.5 | 0.12 | 0.03 | 0.12 |
| S. aureus UBMS 88-7 (tetK) | 2 | 4 | 0.25 | 2 | 4 | 2 | 16 | 16 |
| S. aureus IVES 2943 (meth. resistant) | 4 | 64 | 1 | 4 | 8 | 2 | 32 | 32 |
| S. aureus IVES 1983 (meth. resistant) | 8 | ND | 1 | 4 | 16 | 4 | 32 | 32 |
| S. aureus ATCC 29213 (Sensitive) | ≦0.015 | 0.12 | ≦0.015 | ≦0.015 | ≦0.015 | ≦0.015 | ND | 0.12 |
| S. aureus Smith (Sensitive) | ≦0.015 | 0.12 | 0.03 | 0.03 | 0.5 | 0.12 | 0.03 | 0.12 |
| S. haemolyticus AVAH 88-3 | 0.03 | ND | 0.12 | ND | 8 | 2 | 0.06 | 2 |
| E. faecalis 12201 | 0.12 | 0.5 | 0.5 | 1 | 16 | 4 | 16 | 2 |
| E. faecalis ATCC 29212 | ≦0.015 | 0.12 | 0.06 | 0.12 | 2.0 | 0.25 | 0.25 | 0.25 |
| E. coli UBMS 88-1 (tetB) | 32 | >128 | 16 | >32 | >32 | >32 | >32 | >128 |
| E. coli UBMS 88-2 (Sensitive) | 0.12 | 2 | 0.25 | 0.5 | >32 | 32 | 1 | >128 |
| E. coli UBMS 89-1 (tetM) | 0.12 | ND | 1 | ND | 32 | 4 | 1 | 128 |
| E. coli UBMS 89-2 (Sensitive) | 0.12 | ND | 0.5 | 0.5 | >32 | 32 | 1 | 16 |
| E. coli ATCC 25922 | 0.06 | 2 | 0.25 | 0.5 | 32 | 4 | 0.5 | 16 |

| | MIC (µg/ml) COMPOUND | | | | | | | | |
|---|---|---|---|---|---|---|---|---|---|
| ORGANISM | I | J | K | L | M | N | O | HH | II |
| S. aureus UBMS 86-5 (tetM) | 16 | 4 | 0.25 | 4 | 1 | 32 | 2 | 0.25 | 0.12 |
| S. aureus UBMS 88-4 (Sensitive) | 8 | 2 | 0.12 | 4 | 1 | 2 | ≦0.015 | 0.03 | 0.06 |
| S. aureus UBMS 90-1 (tetM) | 16 | 4 | 0.25 | 8 | 2 | >32 | 4 | 1 | 0.25 |
| S. aureus UBMS 90-2 (tetM) | 16 | 2 | 0.06 | 2 | 0.5 | 32 | 2 | 0.25 | 0.06 |
| S. aureus UBMS 90-3 (Sensitive) | 4 | 0.5 | 0.03 | 1 | 0.5 | 1 | ≦0.015 | 0.03 | 0.06 |
| S. aureus UBMS 88-7 (tetK) | 16 | 2 | 32 | >32 | >32 | 8 | 0.06 | 0.5 | 1 |
| S. aureus IVES 2943 (meth. resistant) | ND | 4 | 32 | >32 | >32 | 32 | 1 | 2 | 1 |
| S. aureus IVES 1983 (meth. resistant) | 32 | 4 | 32 | >32 | >32 | >32 | 1 | 2 | 1 |
| S. aureus ATCC 29213 (Sensitive) | 1 | 0.06 | ≦0.015 | 0.5 | 0.5 | 0.25 | ≦0.015 | ≦0.015 | 0.03 |
| S. aureus Smith (Sensitive) | 8 | 0.5 | ≦0.015 | 0.5 | 1 | 2 | ≦0.015 | 0.03 | 0.12 |
| S. haemolyticus AVAH 88-3 | 0.5 | 4 | 0.5 | 16 | 1 | 4 | 0.03 | 0.25 | 0.25 |
| E. faecalis 12201 | 16 | 2 | 0.25 | 4 | 0.25 | 32 | 4 | 2 | 0.12 |
| E. faecalis ATCC 29212 | 8 | 4 | 0.06 | 2 | 0.25 | 32 | 0.5 | 0.25 | 0.03 |
| E. coli UBMS 88-1 (tetB) | >32 | >32 | 16 | >32 | 2 | >32 | 8 | 16 | 0.25 |
| E. coli UBMS 88-2 (Sensitive) | 32 | >32 | 4 | >32 | 2 | >32 | 0.5 | ND | ND |
| E. coli UBMS 89-1 (tetM) | 32 | >32 | 1 | >32 | 2 | >32 | 16 | 4 | 0.12 |
| E. coli UBMS 89-2 (Sensitive) | 32 | >32 | 8 | >32 | 2 | >32 | 0.5 | 4 | 0.25 |
| E. coli ATCC 25922 | 32 | 32 | 4 | 32 | 2 | 32 | 0.25 | 2 | 0.12 |

TABLE II

ANTIBACTERIAL ACTIVITY OF 9-(AROYLAMINO) AND 9-(HETEROYLAMINO)-7-(SUBSTITUTED)-6-DEMETHYL-6-DEOXYTETRACYCLINES

| | MIC (µg/ml) COMPOUND | | | | | | | | | | | |
|---|---|---|---|---|---|---|---|---|---|---|---|---|
| ORGANISM | P | Q | R | S | T | U | V | W | X | Y | Z | O |
| S. aureus UBMS 86-5 (tetM) | 4 | 8 | 4 | 2 | 4 | 1 | 2 | 32 | 8 | 16 | 8 | 2 |
| S. aureus UBMS 88-4 (Sensitive) | 4 | 8 | 2 | 2 | 4 | 0.5 | 2 | 8 | 1 | 4 | 8 | ≦0.015 |
| S. aureus UBMS 90-1 (tetM) | 4 | 8 | 8 | 4 | 4 | 1 | 2 | 16 | 16 | 32 | 4 | 4 |
| S. aureus UBMS 90-2 (tetM) | 4 | 8 | 2 | 1 | 2 | 1 | 1 | 8 | 8 | 8 | 4 | 2 |
| S. aureus UBMS 90-3 (Sensitive) | 1 | 4 | 1 | 1 | 2 | 0.5 | 0.5 | 8 | 1 | 2 | 2 | ≦0.015 |
| S. aureus UBMS 88-7 (tetK) | 8 | 16 | 4 | 8 | 4 | 1 | 4 | 16 | 8 | >32 | 32 | 0.06 |
| S. aureus IVES 2943 (meth. resistant) | 16 | 8 | 4 | 8 | 4 | 1 | 4 | 8 | >32 | >32 | 32 | 4 |
| S. aureus IVES 1983 (meth. resistant) | 8 | 16 | 8 | 4 | 4 | 1 | 8 | 8 | >32 | >32 | 32 | 4 |
| S. aureus ATCC 29213 (Sensitive) | 0.25 | 1 | 0.12 | 0.5 | 1 | 0.5 | 0.25 | 2 | 0.5 | 0.5 | 0.5 | ≦0.015 |
| S. aureus Smith (Sensitive) | 1 | 4 | 1 | 1 | 4 | 1 | 0.5 | 4 | 1 | 2 | 2 | ≦0.015 |
| S. haemolyticus AVAH 88-3 | 4 | 8 | 8 | 4 | 4 | 1 | 4 | 16 | 8 | >32 | 8 | 0.03 |
| E. faecalis 12201 | 8 | 8 | 2 | 4 | 4 | 1 | 4 | 16 | 32 | 32 | 8 | 4 |
| E. faecalis ATCC 29212 | 4 | 8 | 2 | 4 | 4 | 1 | 4 | 8 | 8 | 8 | 8 | 0.5 |
| E. coli UBMS 88-1 (tetB) | >32 | >32 | 2 | >32 | >32 | >32 | >32 | >32 | >32 | >32 | >32 | 8 |
| E. coli UBMS 88-2 (Sensitive) | >32 | >32 | >32 | >32 | >32 | >32 | >32 | >32 | >32 | >32 | >32 | 0.5 |
| E. coli UBMS 89-1 (tetM) | ND | ND | ND | ND | ND | >32 | >32 | >32 | >32 | >32 | >32 | 16 |
| E. coli UBMS 89-2 (Sensitive) | >32 | >32 | >32 | >32 | >32 | >32 | >32 | >32 | >32 | >32 | >32 | 0.5 |
| E. coli ATCC 25922 | >32 | >32 | >32 | >32 | >32 | >32 | >32 | >32 | >32 | >32 | >32 | 0.25 |

TABLE III

ANTIBACTERIAL ACTIVITY OF 9-(SULFONYLAMINO)-7-SUBSTITUTED)-6-DEMETHYL-6-DEOXYTETRACYCLINES

| | MIC (µg/ml) COMPOUND | | | | | | | |
|---|---|---|---|---|---|---|---|---|
| ORGANISM | AA | BB | CC | DD | EE | FF | GG | O |
| S. aureus UBMS 88-5 (tetM) | 0.12 | ND | 4 | 0.5 | 0.12 | 0.25 | 16 | 4 |
| S. aureus UBMS 88-4 (Sensitive) | 0.12 | 1 | 0.03 | 0.5 | 0.12 | 0.25 | 4 | 0.03 |
| S. aureus UBMS 90-1 (tetM) | 0.5 | 2 | 4 | 1 | 0.25 | 0.25 | 32 | 2 |
| S. aureus UBMS 90-2 (tetM) | 0.12 | 0.5 | 0.06 | 0.25 | 0.12 | 0.06 | 4 | 2 |
| S. aureus UBMS 90-3 (Sensitive) | 0.06 | 0.12 | 4 | 0.25 | 0.12 | 0.12 | 2 | ≦0.015 |
| S. aureus UBMS 88-7 (tetK) | 2 | 4 | 4 | 2 | 1 | 8 | 32 | 0.06 |
| S. aureus IVES 2943 (meth. resistant) | 4 | 4 | 4 | 4 | 0.5 | 16 | >32 | 2 |
| S. aureus IVES 1983 (meth. resistant) | 8 | 8 | 4 | 4 | 1 | 16 | 32 | 1 |
| S. aureus ATCC 29213 (Sensitive) | 0.12 | 0.06 | ≦0.015 | 0.03 | 0.03 | 0.03 | 0.5 | ≦0.015 |
| S. aureus Smith (Sensitive) | 0.12 | 0.25 | 4 | 0.03 | 0.12 | 0.12 | 2 | ≦0.015 |
| S. haemolyticus AVAH 88-3 | 2 | 4 | 4 | 2 | ND | ND | ND | 0.06 |
| E. faecalis 12201 | ND | ND | ND | ND | ND | ND | ND | 8 |
| E. faecalis ATCC 29212 | 0.12 | 0.12 | 0.06 | 0.25 | 0.06 | 0.06 | 1 | 0.5 |
| E. coli UBMS 88-1 (tetB) | 16 | >32 | 16 | 32 | >32 | 8 | >32 | 16 |
| E. coli UBMS 88-2 (Sensitive) | 8 | 4 | 8 | 8 | >32 | 2 | >32 | 0.5 |
| E. coli UBMS 89-1 (tetM) | 4 | ND | ND | ND | ND | ND | 32 | 16 |
| E. coli UBMS 89-2 (Sensitive) | 16 | 16 | 16 | 16 | >32 | 2 | >32 | 0.5 |
| E. coli ATCC 25922 | 4 | 2 | 2 | 4 | >32 | 2 | >32 | 0.5 |

TABLE IA

ANTIBACTERIAL ACTIVITY OF 9-(ACYLAMINO)-7-(SUBSTITITED)-6-DEMETHYL-6-DEOXYTETRACYCLINES

| | JJ | KK | LL | MM | NN | OO | PP | QQ | RR | SS | TT | UU | VV | WW |
|---|---|---|---|---|---|---|---|---|---|---|---|---|---|---|
| E. coli UBMS 88-1 TetB | 0.25 | 0.25 | 0.25 | 1 | >32 | 1 | 0.5 | 4 | 1 | 0.25 | 0.5 | 0.5 | >32 | 0.25 |
| E. coli J3272 Tet sens. | 0.25 | 0.12 | 0.12 | 1 | >32 | 1 | 0.5 | 2 | 1 | 0.25 | 0.5 | 0.5 | >32 | 0.25 |
| E. coli MC4100 Tet sens. | NT | NT | NT | NT | NT | NT | NT | NT | NT | NT | NT | NT | NT | NT |
| E. coli MC4100 TetB | 0.25 | 0.25 | 0.25 | 1 | >32 | 1 | 0.5 | 2 | 1 | 0.25 | 0.5 | 0.5 | >32 | 0.25 |
| E. coli PRP1 TetA | 2 | 1 | 1 | 16 | >32 | 2 | 1 | 32 | 2 | 0.5 | 2 | 1 | >32 | 1 |
| E. coli J3272 TetC | 1 | 1 | 0.5 | 8 | >32 | 2 | 0.5 | 8 | 1 | 0.25 | 0.5 | 0.5 | >32 | 0.25 |
| E. coli UBMS 89-1 TetM | 0.25 | 0.12 | 0.12 | 1 | 32 | 1 | 0.25 | 1 | 0.25 | 0.12 | 0.25 | 0.12 | >32 | 0.25 |
| E. coli UBMS 89-2 Tet Sens. | 0.25 | 0.25 | 0.12 | 1 | >32 | 1 | 0.5 | 2 | 1 | 0.25 | 0.5 | 0.5 | >32 | 0.25 |
| E. coli J2175 | 0.25 | 0.25 | 0.12 | 1 | >32 | 1 | 0.25 | 2 | 1 | 0.25 | 0.5 | 0.5 | >32 | 0.25 |
| E. coli BAJ9003 | 0.03 | 0.03 | NG | 0.25 | 0.5 | 0.12 | 0.12 | 0.25 | 0.06 | ≦0.015 | 0.06 | 0.06 | 1 | 0.06 |

TABLE IA-continued

ANTIBACTERIAL ACTIVITY OF 9-(ACYLAMINO)-7-(SUBSTITITED)-6-DEMETHYL-6-DEOXYTETRACYCLINES

| | | | | | | | | | | | | | |
|---|---|---|---|---|---|---|---|---|---|---|---|---|---|
| E. coli UBMS 90-4 TetM | 0.25 | 0.25 | 0.25 | CONT | CONT | 0.5 | 0.25 | 2 | 0.5 | 0.25 | 0.5 | 0.5 | >32 | 0.25 |
| E. coli UBMS 90-5 | 0.25 | 0.25 | 0.12 | 1 | >32 | 1 | 0.5 | 2 | 1 | 0.25 | 0.5 | 0.5 | >32 | 0.25 |
| E. coli #311 (MP) | 0.25 | 0.25 | 0.12 | 1 | >32 | 1 | 0.25 | 2 | 0.5 | 0.12 | 0.5 | 0.25 | >32 | 0.25 |
| E. coli ATCC 25922 | 0.25 | 0.25 | 0.12 | 1 | >32 | 1 | 0.25 | 2 | 0.5 | 0.25 | 0.5 | 0.25 | >32 | 0.25 |
| E. coli J3272 TetD | 0.12 | 0.12 | 0.06 | 0.05 | 32 | 0.5 | 0.25 | 2 | 0.25 | 0.12 | 0.12 | 0.25 | >32 | 0.12 |
| S. mariescens FPOR 8733 | 4 | 2 | 2 | 16 | >32 | 8 | 2 | >32 | 4 | 2 | 4 | 4 | >32 | 2 |
| X. maltophilia NEMC 87210 | 0.5 | 0.25 | 0.25 | 8 | 32 | 2 | 0.5 | 2 | 0.25 | 0.5 | 0.5 | 0.12 | >32 | 0.5 |
| Ps. acruginosa ATCC 27853 | 8 | 4 | 4 | 16 | >32 | 16 | 16 | >32 | 32 | 16 | 16 | 32 | >32 | 8 |
| S. aureus NEMC 8769/89-4 | 0.06 | 0.06 | ≦0.015 | 0.5 | 0.5 | 0.5 | 0.12 | 0.12 | 0.06 | 0.03 | 0.03 | 0.06 | 4 | 0.06 |
| S. aureus UBMS 88-4 | 0.25 | 0.12 | 0.06 | 0.5 | 2 | 1 | 0.25 | 0.5 | 0.25 | 0.12 | 0.25 | 0.25 | 8 | 0.25 |
| S. aureus UBMS 88-5 TetM | 0.25 | 0.25 | 0.12 | 0.5 | 4 | 1 | 0.5 | 0.5 | 0.25 | 0.25 | 0.25 | 0.25 | 32 | 0.25 |
| S. aureus UBMS 88-7 TetK | 1 | 0.25 | 0.5 | 16 | 32 | 8 | 2 | 4 | 0.5 | 0.5 | 2 | 0.25 | 32 | 1 |
| S. aureus UBMS 90-1 TetM | 0.25 | 0.25 | 0.12 | 1 | 4 | 1 | 0.5 | 0.5 | 0.25 | 0.12 | 0.25 | 0.25 | 32 | 0.12 |
| S. aureus UBMS 90-3 | 0.12 | 0.03 | 0.06 | 0.5 | 2 | 0.5 | 0.25 | 0.5 | 0.25 | 0.12 | 0.12 | 0.12 | 4 | 0.12 |
| S. aureus UBMS 90-2 TetM | 0.25 | 0.12 | 0.12 | 0.5 | 2 | 0.5 | 0.5 | 0.5 | 0.25 | 0.12 | 0.25 | 0.12 | 16 | 0.25 |
| S. aureus IVES 2943 | 2 | 1 | 1 | 32 | >32 | 8 | 2 | 16 | 1 | 1 | 2 | 0.25 | >32 | 2 |
| S. aureus ROSE (MP) | 2 | 1 | 1 | 32 | >32 | 8 | 2 | 16 | 1 | 1 | 2 | 0.5 | >32 | 2 |
| S. aureus SMITH (MP) | 0.12 | 0.06 | 0.06 | 0.5 | 2 | 0.5 | 0.12 | 0.25 | 0.25 | 0.12 | 0.12 | 0.12 | 4 | 0.12 |
| S. aureus IVES 1983 | 2 | 1 | 1 | 16 | >32 | 8 | 2 | 8 | 0.25 | 0.5 | 2 | 0.5 | >32 | 2 |
| S. aureus ATCC 29213 | 0.03 | ≦0.015 | 0.06 | 1 | 2 | 1 | 0.25 | 0.5 | 0.12 | 0.12 | 0.25 | 0.12 | 8 | 0.25 |
| S. hemolyticus AVHAH 88-3 | 0.25 | 0.12 | 0.12 | 1 | 32 | 1 | 0.25 | 2 | 0.5 | 0.25 | 0.5 | 0.12 | >32 | 0.25 |
| Enterococcus 12201 | 0.12 | 0.12 | 0.06 | 0.25 | 2 | 0.25 | 0.12 | 0.5 | 0.12 | 0.12 | 0.25 | 0.12 | 4 | 0.12 |
| E. faecalis ATCC 29212 | 0.12 | 0.06 | 0.06 | 0.25 | 2 | 0.25 | 0.12 | 0.25 | 0.12 | 0.12 | 0.25 | 0.06 | 4 | 0.25 |

| | XX | YY | ZZ | AAA | BBB | CCC | DDD | EEE | FFF | GGG | HHH | III | JJJ |
|---|---|---|---|---|---|---|---|---|---|---|---|---|---|
| E. coli UBMS 88-1 TetB | 0.5 | 0.5 | >32 | 0.5 | 0.5 | 1 | 0.5 | 2 | 0.25 | 0.25 | 0.25 | >32 | >32 |
| E. coli J3272 sens. | 0.5 | 0.5 | NT | NT | NT | NT | NT | NT | NT | NT | NT | 16 | >32 |
| E. coli MC4100 Tet sens. | NT | NT | 2 | 0.12 | 0.25 | 0.25 | 0.12 | 0.5 | 0.06 | 0.06 | 0.12 | NT | NT |
| E. coli MC4100 TetB | 1 | 0.5 | >32 | 0.5 | 0.5 | 2 | 0.5 | 4 | 0.25 | 0.25 | 0.25 | >32 | >32 |
| E. coli PRP1 TetA | 1 | 2 | >32 | 0.5 | 0.5 | 2 | 1 | 4 | 2 | 1 | 2 | >32 | >32 |
| E. coli J3272 TetC | 1 | 1 | 32 | 0.5 | 0.5 | 1 | 0.5 | 2 | 1 | 1 | 0.5 | >32 | >32 |
| E. coli UBMS 89-1 TetM | 0.12 | 0.5 | 32 | 0.12 | 0.25 | 0.25 | 0.25 | 0.5 | 0.12 | 0.12 | 0.25 | 4 | 32 |
| E. coli UBMS 89-2 Tet Sens. | 0.5 | 0.5 | 16 | 0.5 | 0.25 | 2 | 0.5 | 4 | 0.25 | 0.25 | 0.25 | 32 | >32 |
| E. coli J2175 | 0.5 | 0.5 | 16 | 0.5 | 0.25 | 2 | 0.5 | 4 | 0.25 | 0.25 | 0.25 | 32 | >32 |
| E. coli BAJ9003 | 0.06 | 0.06 | 1 | 0.06 | 0.06 | 0.12 | 0.12 | 0.25 | ≧0.015 | 0.03 | 0.03 | 0.25 | 4 |
| E. coli UBMS 90-4 TetM | 0.5 | 0.5 | 16 | 0.5 | 0.25 | 1 | 0.5 | 0.5 | 0.12 | 0.25 | 0.25 | — | >32 |
| E. coli UBMS 90-5 | 0.5 | 0.5 | 16 | 0.5 | 0.25 | 2 | 0.5 | 0,5 | 0.25 | 0.25 | 0.25 | 16 | >32 |
| E. coli #311 (MP) | 0.5 | 0.5 | 16 | 0.25 | 0.5 | 1 | 0.5 | 0.5 | 0.25 | 0.25 | 0.25 | 8 | >32 |
| E. coli ATCC 25922 | 0.5 | 0.5 | 8 | 0.25 | 0.12 | 1 | 0.5 | 0.5 | 0.12 | 0.25 | 0.25 | 16 | >32 |
| E. coli J3272 TetD | 0.25 | 0.25 | 4 | 0.12 | 0.12 | 0.5 | 0.25 | 0.5 | 0.12 | 0.12 | 0.12 | 32 | >32 |
| S. mariescens FPOR 8733 | 4 | 8 | >32 | 4 | 4 | 16 | 8 | 4 | 4 | 4 | 4 | >32 | >32 |
| X. maltophilia NEMC 87210 | 0.5 | 4 | 32 | 0.5 | 4 | 0.25 | 0.5 | 1 | 0.25 | 0.5 | 0.5 | 4 | 16 |
| Ps. acruginosa ATCC 27853 | 32 | 16 | >32 | >32 | 16 | >32 | 32 | 32 | 8 | 8 | 8 | >32 | >32 |
| S. aureus NEMC 8769/89-4 | 0.12 | 0.12 | 1 | 0.12 | 0.06 | 0.12 | 0.25 | 0.12 | 0.25 | 0.25 | 0.25 | 0.12 | 4 |
| S. aureus UBMS 88-4 | 0.25 | 0.5 | 2 | 0.25 | 0.25 | 0.5 | 0.5 | 0.25 | 0.12 | 0.12 | 0.25 | 0.5 | 8 |
| S. aureus UBMS 88-5 TetM | 0.25 | 0.5 | 8 | 0.25 | 0.5 | 0.5 | 0.5 | 0.5 | 0.12 | 0.12 | 0.25 | 1 | 8 |
| S. aureus UBMS 88-7 TetK | 1 | 4 | 16 | 0.5 | 2 | 1 | 2 | 2 | 1 | 1 | 0.5 | 2 | 16 |
| S. aureus UBMS 90-1 TetM | 0.25 | 0.25 | 8 | 0.5 | 0.25 | 1 | 1 | 0.5 | 0.12 | 0.25 | 0.25 | 1 | 16 |
| S. aureus UBMS 90-3 | 0.25 | 0.12 | 2 | 0.25 | 0.06 | 0.25 | 0.5 | 0.25 | 0.12 | 0.12 | 0.12 | 0.5 | 2 |
| S. aureus UBMS 90-2 TetM | 0.25 | 0.25 | 4 | 0.25 | 0.25 | 0.25 | 0.5 | 0.25 | 0.12 | 0.12 | 0.12 | 0.5 | 8 |
| S. aureus IVES 2943 | 1 | 8 | >32 | 0.5 | 4 | 1 | 4 | 2 | 2 | 2 | 2 | 4 | 32 |
| S. aureus ROSE (MP) | 1 | 8 | >32 | 2 | 16 | 2 | 4 | 8 | 2 | 2 | 2 | 8 | >32 |
| S. aureus SMITH (MP) | 0.25 | 0.25 | 2 | 0.25 | 0.12 | 0.5 | 0.25 | 0.25 | 0.12 | 0.12 | 0.12 | 0.5 | 4 |
| S. aureus IVES 1983 | 1 | 4 | >32 | 0.5 | 4 | 1 | 4 | 2 | 2 | 2 | 2 | 4 | 32 |
| S. aureus ATCC 29213 | 0.25 | 0.5 | 2 | 0.25 | 0.25 | 0.5 | 1 | 0.5 | 0.12 | 0.25 | 0.25 | 0.5 | 4 |
| S. hemolyticus AVHAH 88-3 | 0.5 | 0.5 | 8 | 0.5 | 0.5 | 0.5 | 0.5 | 2 | 0.25 | 0.5 | 0.5 | 2 | 16 |
| Enterococcus 12201 | 0.12 | 0.25 | 8 | 0.12 | 0.25 | 0.25 | 0.25 | 0.25 | 0.12 | 0.12 | 0.12 | 1 | 16 |
| E. faecalis ATCC 29212 | 0.12 | 0.12 | 4 | 0.12 | 0.12 | 0.12 | 0.25 | 0.25 | 0.06 | 0.06 | 0.06 | 0.5 | 16 |

| | KKK | LLL | MMM |
|---|---|---|---|
| E. coli UBMS 88-1 TetB | >32 | 0.5 | 0.5 |
| E. coli J3272 sens. | >32 | 0.25 | 0.06 |
| E. coli MC4100 Tet sens. | 32 | NT | NT |
| E. coli MC4100 TetB | >32 | 0.5 | 0.25 |
| E. coli PRP1 TetA | >32 | 1 | 4 |
| E. coli J3272 TetC | >32 | 0.5 | 0.5 |
| E. coli UBMS 89-1 TetM | >32 | 0.25 | 0.25 |
| E. coli UBMS 89-2 Tet Sens. | >32 | 0.5 | 0.5 |
| E. coli J2175 | >32 | 0.25 | 0.25 |
| E. coli BAJ9003 | 16 | 0.06 | 0.03 |
| E. coli UBMS 90-4 TetM | >32 | 0.25 | 0.25 |
| E. coli UBMS 90-5 | >32 | 0.25 | 0.5 |
| E. coli #311 (MP) | >32 | 0.25 | 0.25 |
| E. coli ATCC 25922 | >32 | 0.25 | 0.25 |

TABLE IA-continued

ANTIBACTERIAL ACTIVITY OF 9-(ACYLAMINO)-7-(SUBSTITITED)-6-DEMETHYL-6-DEOXYTETRACYCLINES

| | | | |
|---|---|---|---|
| E. coli J3272 TetD | >32 | 0.12 | 0.12 |
| S. mariescens FPOR 8733 | >32 | 2 | 8 |
| X. maltophilia NEMC 87210 | >32 | 1 | 0.5 |
| Ps. acruginosa ATCC 27853 | >32 | 8 | 32 |
| S. aureus NEMC 8769/89-4 | 32 | 0.12 | 0.5 |
| S. aureus UBMS 88-4 | 32 | 0.25 | 0.25 |
| S. aureus UBMS 88-5 TetM | >32 | 0.25 | 0.25 |
| S. aureus UBMS 88-7 TetK | >32 | 2 | 4 |
| S. aureus UBMS 90-1 TetM | >32 | 0.25 | 0.5 |
| S. aureus UBMS 90-3 | 16 | 0.12 | 0.12 |
| S. aureus UBMS 90-2 TetM | 32 | 0.25 | 0.25 |
| S. aureus IVES 2943 | >32 | 2 | 4 |
| S. aureus ROSE (MP) | >32 | 2 | 8 |
| S. aureus SMITH (MP) | 16 | 0.25 | 0.25 |
| S. aureus IVES 1983 | >32 | 2 | 4 |
| S. aureus ATCC 29213 | 32 | 0.25 | 0.25 |
| S. hemolyticus AVHAH 88-3 | >32 | 0.25 | 0.24 |
| Enterococcus 12201 | >32 | 0.25 | 0.24 |
| E. faecalis ATCC 29212 | 16 | 0.25 | 0.25 |

NG = No Growth
CONT = Contaminated
NT = Not Tested

TABLE IV

Susceptibility of Sensitive and Resistant (tetM) Organisms to Tetracyclines

| | MIC(µg/ml) | | |
|---|---|---|---|
| Organisms | A | O | TC |
| E. coli UBMS 88-2 (Sensitive) | 0.12 | 0.5 | ND |
| E. coli UBMS 90-4 (tetM) | 1 | 64 | 64 |
| S. aureus UBMS 88-4 (Sensitive) | <0.015 | 0.03 | 0.12 |
| S. aureus UBMS 88-5 (tetM) | 0.03 | 2 | 32 |
| S. aureus UBMS 90-3 (Sensitive) | <0.015 | 0.03 | 0.12 |
| S. aureus UBMS 90-1 (tetM) | 0.12 | 4 | 32 |
| N. gonorrhoeae IL 611 (Sensitive) | 0.06 | 0.5 | ND |
| N. gonorrhoeae 6418 (tetM) | 1 | >32 | >32 |
| E. faecalis UBMS 90-6 (tetM) | 0.12 | 8 | 32 |
| E. faecalis UBMS 90-7 (tetM) | 0.5 | 8 | 32 |

TABLE V

In vitro Activity of Compounds A and O Against Clinical Isolates

| Organism | No. Tested | Antibiotic | Range | MIC$_{50}$ | MIC$_{90}$ |
|---|---|---|---|---|---|
| Neisseria gonorrhoeae | (9) | A | 0.015–1.00 | 0.03 | 1.00 |
| | | O | 0.03–>32.00 | 0.25 | >32.00 |
| Haemophilus influenzae | (18) | A | <0.008–0.06 | 0.06 | 0.06 |
| | | O | 0.06–0.25 | 0.12 | 0.25 |
| Enterococcus faecalis | (14) | A | <0.015–2.00 | 0.12 | 1.00 |
| | | O | <0.015–16.00 | 4.00 | 16.00 |
| Enterococcus faecium | (11) | A | <0.015–2.00 | 0.06 | 2.00 |
| | | O | <0.015–16.00 | 8.00 | 16.00 |
| Escherichia coli | (10) | A | 0.06–>32.00 | 0.25 | >32.00 |
| | | O | 0.12–32.00 | 0.25 | 16.00 |
| Klebsiella pneumoniae | (10) | A | 0.25–>32.00 | 0.50 | 0.50 |
| | | O | 1.00–>32.00 | 1.00 | 4.00 |
| Proteus spp. indole + | (9) | A | 0.50–>32.00 | 2.00 | >32.00 |
| | | O | 1.00–>32.00 | 16.00 | >32.00 |
| Bacteroides spp. | (15) | A | <0.15–4.00 | 0.25 | 2.00 |
| | | O | <0.15–16.00 | 1.00 | 4.00 |

MIC(µg/ml)[+]

In Vitro Activity of KK and Comparative Antibiotics vs Recent Clinical and Agricultural Isolates

| | | MIC(µg/ml) | | |
|---|---|---|---|---|
| Organism | [No. Tested] | KK | O | TC |
| Staphylococcus aureus, | [15] | 0.12–2 | 0.06–4 | 0.25–>64 |

TABLE V-continued

| | | | | |
|---|---|---|---|---|
| methicillin-resistant | | | | |
| Staphylococcus aureus, methicillin-susceptible | [15] | 0.12–0.25 | 0.03–0.12 | 0.12–1 |
| Staphylococcus Coagulase-negative, methicillin-susceptible | [16] | 0.12–8 | 0.03–1 | 0.12–>64 |
| Enterococcus faecalis | [10] | 0.015–0.12 | 0.03–16 | 0.12–64 |
| Enterococcus faecium | [10] | 0.03–0.12 | 0.03–16 | 0.12–64 |
| Enterococcus spp. Vancomycin-resistant | [8] | 0.015–0.06 | 0.03–16 | 0.12–>64 |
| Streptococcus pyogenes | [10] | 0.06–0.12 | 0.03–2 | 0.12–16 |
| Streptococcus agalactiae | [10] | 0.06–0.25 | 0.12–16 | 0.25–64 |
| Streptococcus pneumoniae | [10] | 0.03–0.25 | 0.06–0.5 | 0.12–2 |
| Listeria monocytogenes | [8] | 0.06–0.12 | 0.015–0.03 | 0.12–0.5 |
| Escherichia coli (Clinical) | [30] | 0.12–4 | 0.25–32 | 0.5–>64 |
| Escherichia coli (Agricultural) | [15] | 0.12–4 | 1–16 | 2–>64 |
| Shigella spp. | [14] | 0.06–0.5 | 0.25–8 | 0.25–>64 |
| Klebsiella pneumoniae | [10] | 0.25–8 | 0.5–8 | 0.5–>64 |
| Klebsiella oxytoca | [10] | 0.5–1 | 0.5–4 | 0.5–1 |
| Citrobacter freundii | [10] | 0.25–8 | 0.03–32 | 0.5–16 |
| Citrobacter diversus | [10] | 0.25–1 | 0.25–4 | 0.5–4 |
| Salmonella spp. (Clinical) | [11] | 0.25–0.5 | 0.5–16 | 0.5–>64 |
| Salmonella cholerasuis (Agricultural) | [15] | 0.5–16 | 2–>64 | 1–>64 |
| Serratia mercescens | [10] | 2–8 | 1–8 | 8–>64 |
| Enterobacter cloacae | [10] | 0.5–1 | 0.25–4 | 0.5–2 |
| Enterobacter aerogenes | [10] | 0.5–1 | 0.5–1 | 0.5–1 |
| Providencia spp. | [13] | 2–8 | 4–>64 | 1–>64 |
| Proteus mirabilis | [26] | 1–32 | 1–32 | 0.5–64 |
| Proteus vulgaris | [18] | 0.5–4 | 0.5–16 | 0.25–64 |
| Morganella morganii | [16] | 0.5–4 | 0.25–32 | 0.25–>64 |
| Pseudomonas aeruginosa | [10] | 1–16 | 1–16 | 2–32 |
| Xanthomonas maltophilia | [10] | 0.5–2 | 0.12–1 | 8–16 |
| Moraxella catarrhalis | [18] | 0.06–0.12 | 0.03–0.12 | 0.06–0.5 |
| Neisseria gonorrhoeae | [14] | 0.25–1 | 0.5–64 | 1–>64 |
| Haemophilus influenzae | [15] | 0.5–2 | 0.5–2 | 1–32 |
| Pasturella multocida (Agricultural & Clinical) | [17] | 0.03–0.25 | 0.015–4 | 0.06–16 |
| Bordetella bronchiseptica (Agricultural) | [10] | 0.12 | 0.06–0.12 | 0.12–0.25 |
| Bacteroides fragilis | [11] | 0.06–0.2 | >0.008–16 | 0.25–>64 |
| Bacteroides fragilis group | [10] | 0.06–2 | >0.008–4 | 0.25–32 |
| Bacteroides spp. | [9] | 0.03–1 | 0.03–16 | 0.25–>64 |
| Clostridium difficile | [12] | 0.03 | 0.015–16 | 0.12–32 |
| Clostridium perfringens | [16] | 0.03–1 | >0.008–16 | 0.015–16 |
| Clostridium spp. | [9] | 0.015–0.12 | >0.008–16 | 0.015–64 |
| Anaerobic Gram (+) Cocci | [15] | 0.015–0.06 | 0.05–8 | 4–>64 |

[+]$MIC_{50}$ = minimum concentration required to inhibit 50% of strains tested.
$MIC_{90}$ = minimum concentration required to inhibit 90% of strains tested

TABLE VI

Inhibition of Protein Synthesis Directed by *E. coli* Cell-free Ribosomes with Tetracyclines

| | $IC_{50}(\mu g/ml)$[+] | |
|---|---|---|
| Antibiotic | TC Sensitive Host | Tet M Host |
| Tetracycline | 0.6 | 2.0 |
| Compound O | 0.4 | 2.0 |
| Compound A | <0.3 | 0.4 |

[+]Concentration of antibiotic required to inhibit protein synthesis by 50% compared to a drug-free control

TABLE VII

In vivo Protective Activity of Compounds A and O in Mice Infected with Staphylococci Containing the tetM Determinant

| Organism | Compound | $ED_{50}(mg/kg)$[+] |
|---|---|---|
| *S. aureus* UBMS 90-1 | A | 0.22 |
| | O | 1.7 |
| *S. aureus* UBMS 90-2 | A | 0.49 |
| | O | 3.0 |

[+]Median effective dose protecting 50% of the infected mice, single subcutaneous dosing.

TABLE VII (CONT)

In Vitro Protective Activity in Mice
Compounds (ED$_{50}$(mg/kg))

| Organism | Route of Antibiotic Administration | JJ | KK | LL | PP | RR | SS | TT | BBB | WW | XX | YY | AAA | DDD | EEE | O |
|---|---|---|---|---|---|---|---|---|---|---|---|---|---|---|---|---|
| *S. aureus* SMITH sens) | Oral | 9.6 | 8–16 | 4–8 | >16 | 8–16 | 8–16 | 8–26 | 4–8 | >16 | 8–26 | >16 | >16 | 8–16 | 8–16 | 0.74 |
| *S. aureus* SMITH (sens) | Intraveneous | 0.61 | 0.68 | 0.25–0.5 | 1–2 | — | 1–2 | 1–2 | 1.8 | 0.82 | 0.5–1 | 0.5–1 | — | — | — | 0.37 |
| *S. aureus* SMITH (sens) | Subcutaneous | 0.66 | — | — | — | — | — | — | — | — | — | — | — | — | — | — |
| *Escherichia coli* UBMS 90-4 (Tet-M) | Intraveneous | — | 2.49 | — | — | — | — | — | — | — | — | — | — | — | — | >32 |

TABLE VIII

In Vitro Transcription and Protein Translation
Sensitivity to Tetracycline Compounds

| COMPOUND | | % INHIBITION | |
|---|---|---|---|
| Organism | Concentration | Wild Type S30 | TetM S30 |
| KK | 1.0 mg/ml | 92 | 95 |
| | 0.5 mg/ml | 90 | 96 |
| | 0.25 mg/ml | 89 | 93 |
| | 0.12 mg/ml | 84 | 93 |
| | 0.06 mg/ml | 82 | 89 |
| | 0.03 mg/ml | 81 | 75 |
| MM | 1.0 mg/ml | 99 | 99 |
| | 0.2 mg/ml | 98 | 97 |
| | 0.06 mg/ml | 95 | 92 |
| OO | 1.0 mg/ml | 99 | 99 |
| | 0.2 mg/ml | 97 | 95 |
| | 0.06 mg/ml | 94 | 87 |
| QQ | 1.0 mg/ml | 99 | 99 |
| | 0.2 mg/ml | 97 | 95 |
| | 0.06 mg/ml | 92 | 85 |
| RR | 1.0 mg/ml | 99 | 99 |
| | 0.2 mg/ml | 97 | 97 |
| | 0.06 mg/ml | 93 | 90 |
| VV | 1.0 mg/ml | 99 | 98 |
| | 0.2 mg/ml | 93 | 92 |
| | 0.06 mg/ml | 91 | 79 |
| WW | 1.0 mg/ml | 99 | 98 |
| | 0.2 mg/ml | 99 | 97 |
| | 0.06 mg/ml | 93 | 88 |
| XX | 1.0 mg/ml | 98 | 97 |
| | 0.2 mg/ml | 96 | 89 |
| | 0.06 mg/ml | 85 | 78 |
| Minocycline | 1.0 mg/ml | 98 | 68 |
| | 0.2 mg/ml | 89 | 43 |
| | 0.06 mg/ml | 78 | 0 |

When the compounds are employed as antibacterials, they can be combined with one or more pharmaceutically acceptable carriers, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solutions or suspensions containing from about 0.05 to 5% suspending agent in an isotonic medium. Such pharmaceutical preparations may contain, for example, from about 25 to about 90% of the active ingredient in combination with the carrier, more usually between about 5% and 60% by weight.

An effective amount of compound from 2.0 mg/kg of body weight to 100.0 mg/kg of body weight should be administered one to five times per day via any typical route of administration including but not limited to oral, parenteral (including subcutaneous, intravenous, intramuscular, intrasternal injection or infusion techniques), topical or rectal, in dosage unit formulations containing conventional non-toxic pharmaceutically acceptable carriers, adjuvants and vehicles. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid, polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacterial and fungi. The carrier can be a solvent or dispersion medium containing, for example, water, ethanol, polyol (e.g., glycerol, propylene glycol and liquid polyethylene glycol), suitable mixtures thereof, and vegetable oil.

The invention will be more fully described in conjunction with the following specific examples which are not to be construed as limiting the scope of the invention.

EXAMPLE 1

[4S-(4α, 12aα)]-4,7-Bis(dimethylamino)-1,4,4a,5,5a,6, 11,12a-octahydro-3,10,12,12a-tetrahydroxy-9-nitro-1,11-dioxo-2-naphthacenecarboxamide sulfate (1:1)

To a stirred ice bath cooled solution of 0.444 g of [4S-(4α, 12aα)]-4,7 -bis(dimethylamino)-1,4,4a,5,5a,6,11,12a-octahydro-3,10,12,12a-tetrahydroxy-1,11-dioxo- 2-naphthacenecarboxamide hydrochloride, prepared by the procedure described in U.S. Pat. No. 3,226,436, dissolved in 15 ml of sulfuric acid is added 0.101 g of sodium nitrate. The mixture is stirred in the cold for 45 minutes followed by the dropwise addition to 500 ml of diethyl ether. The resulting solid is collected, washed with diethyl ether and dried to give 0.6 g of the desired product as a solid.
MS(FAB): m/z 503(M+H) and 601(M+$H_2SO_4$+H).

EXAMPLE 2

[4S-4α, 12aα]-9-Amino-4,7,bis(dimethylamino)-1,4,4a,5,5a,6,11,12a-octahydro-3,10,12,12a-tetrahydroxy-1,11-dioxo-2-naphthacenecarboxamide sulfate (1:1)

A mixture of 2.0 g of product from Example 1 in 20 ml of 2-methoxyethanol is stirred for 10 minutes and filtered. The filtrate is shaken, in a pressure bottle, with 1.0 g of 10% palladium-on-carbon and 5 ml of 2N sulfuric acid, under 30 lbs. of hydrogen pressure, for 1 hour. The reaction mixture is filtered and the filtrate concentrated in vacuo to half volume. The solution is poured into 100 ml of diethyl ether, the solid collected, washed with diethyl ether and dried to give 1.6 g of the desired product as a solid.
MS(FAB): m/z 473(M+H).

EXAMPLE 3

4S,(4α, 12aα)]-4,7-Bis(dimethylamino)-9-(formylamino)-1,4,4a,5,5a,6,11,12a-octahydro-3,10,12,12a-tetrahydroxy-1,11-dioxo-2-naphthacenecarboxamide To a stirring 0° C. solution of 3.0 g of product from Example 2, 0.451 g of anhydrous sodium acetate and ml of 98% formic acid is added, dropwise, 7.4 ml of acetic anhydride. The reaction is stirred at 0° C. for minutes followed by stirring at room temperature for hour. The mixture is poured into 500 ml of diethyl ether and the precipitate collected. The solid is washed with diethyl ether and dried to give 2.9 g of the desired product.
MS(FAB): m/z 501 (M+H).

EXAMPLE 4

[4S-(4α, 12aα)]-4,7-Bis(dimethylamino]-9-(formylamino]-1,4,4a,5,5a,6,11,12a-octahydro-3,10,12,12a-tetrahydroxy-1,11-dioxo-2-naphthacenecarboxamide sulfate To a solution of 3.5 g of product from Example 3 in 150 ml of distilled water is added sufficient 0.75N sulfuric acid to bring the reaction solution of pH 3.6. The solution is lyophilized to give 3.6 g of the desired salt.
MS (FAB): m/z 501 (M+H).

EXAMPLE 5

[4S-(4α, 12aα)]-4,7-Bis(dimethylamino)-9-(formylamino)-1,4,4a,5,5a,6,11,12a-octahydro-3,10,12,12a-tetrahydroxy-1,11-dioxo-2-naphthacenecarboxamide monohydrochloride To a solution of 3.5 g of product from Example 3 in 150 ml of distilled water is added sufficient 0.75N hydrochloric acid to bring the reaction solution of pH 3.6. The solution is lyophilized to give 3.6 g of the desired salt.
MS (FAB): m/z 501 (M+H).

EXAMPLE 6

[4S-(4α, 12aα)]-9-(Acetylamino)-4,7-bis(dimethylamino)-1,4,4a,5,5a,6,11,12a-octahydro-3, 10, 12, 12a-tetrahydroxy-1,11-dioxo-2-naphthacenecarboxamide To a stirring solution of 0.468 g of product from Example 2 in 5 ml of water is added 0.50 g of sodium acetate and 0.2 ml of acetic anhydride. The reaction is stirred at room temperature for 10 minutes followed by the addition of 0.2 ml of concentrated ammonium hydroxide. After stirring 5 hours at room temperature, the reaction is treated with. 0.5 ml of concentrated sulfuric acid. The reaction solution is extracted with 4 portions of n-butyl alcohol and the aqueous layer is concentrated in vacuo to dryness. The residue is triturated with 20 ml of methyl alcohol, filtered and the organic layer is concentrated in vacuo to give 0.35 g of the desired product.
MS (FAB): m/z 515 (M+H).

EXAMPLE 7

[4S-(4α, 12aα)]-4,7-Bis(dimethylamino)-1,4,4a,5,5a,6,11,12a-octahydro-3,10,12,12a-tetrahydroxy-1,11-dioxo-9-[(trifluoroacetyl)amino]-2-naphthacenecarboxamide sulfate A mixture of 0.20 g of product from Example 2 and 3.0 ml of trifluoroacetic anhydride is stirred at room temperature for 6 hours. The reaction liquid is decanted from the solid residue. The solid is dried, dissolved in 10 ml of methyl alcohol, stirred for 20 minutes and the mixture is poured into 100 ml of diethyl ether. The solid is collected and dried to give 0.16 g of the desired product.

MS(FAB): m/z 569 (M+H).

EXAMPLE 8

[4S-(4α, 12aα)]-7-(Diethylamino)-4-(dimethylamino)-1,4,4a,5,5a,6,11,12a-octahydro-3,10,12,12a-tetrahydroxy-9-nitro-1,11-dioxo-2-naphthacenecarboxamide sulfate (1:2.)

To a stirred ice cooled solution of 0.660 g of [4S-(4α, 12aα)]-7-(diethylamino)-4-(dimethylamino)-1,4,- 4a,5,5a,6,11,12a-octahydro-3,10,12,12a-tetrahydroxy-1,- 11-dioxo-2-naphthacenecarboxamide hydrochloride, prepared by the procedure described in U.S. Pat. No. 3,226,436, dissolved in 15 ml of sulfuric acid is added 0.151 g of sodium nitrate. The mixture is stirred in the cold followed by dropwise addition to 500 ml of diethyl ether. The resulting solid is collected, washed with diethyl ether and dried to give 0.8 g of the desired product as a solid.

MS(FAB): m/z 531(M+H) and 629(M+H$_2$SO$_4$+H).

EXAMPLE 9

[4S-(4α, 12aα)]-9-Amino-7-(diethylamino)-4-(dimethylamino)-1,4,4a,5,5a,6,11.12a-octahydro,3,10, 12,12a-tetrahydroxy-1,11-dioxo-2-naphthacenecarboxamide sulfate (1:2)

The title compound is prepared by the procedure of Example 2, using 0.82 g of product from Example 8, to give 0.65 g of the desired product as a solid. $^1$H NMR (CD$_3$SOCD$_3$): δ 4.25(s,1H,4-H) and 7.27(s,1H,8-H).

MS (FAB): m/z 501 (M+H) and 599 (M+H$_2$SO$_4$+H).

EXAMPLE 10

[4S-(4α, 12aα)]-7-(Diethylamino)-4-(dimethylamino)-9-(formylamino)-1,4,4a,5,5a,6,11,12a-octahydro-3,10,12 12a-tetrahydroxy-1,11-dioxo-2-naphthacenecarboxamide sulfate (1:2)

To a solution of 0.238 g of product from Example 9 in 6 ml of formic acid is added 0.035 g of sodium acetate and 0.75 ml of acetic anhydride. The reaction mixture is stirred at room temperature for 1.5 hours then poured into 200 ml of diethyl ether. The solid is collected and dried at 50° C. to give 0.125 g of the desired product.

MS(FAB): m/z 529 (M+H) and 627 (M+H$_2$SO$_4$+H).

EXAMPLE 11

[4S-(4α, 12aα)]-9-(Acetylamino)-7-(diethylamino)-4-(dimethylamino)- 1,4,4a,5,.5a,6,11,12a-octahydro-3,10,12,12a-tetrahydroxy-1,11-dioxo-2-naphthacenecarboxamide sulfate (1:2)

To a solution of 0.16 g of product from Example 9 in 0.6 ml of water is added 0.125 g of sodium acetate. After stirring for 5 minutes, 0.05 ml of acetic anhydride is added. The reaction is stirred for 15 minutes, 0.025 ml of ammonium hydroxide is added and the stirring continued for an additional 5 minutes. The mixture is acidified with 0.125 ml of sulfuric acid, extracted with n-butyl alcohol and concentrated in vacuo. The residue is dissolved in methyl alcohol and added to diethyl ether. The solid is collected and dried to give 0.10 g of the desired product.

MS(FAB): m/z 543 (M+H) and 641 (M+H$_2$SO$_4$+H).

EXAMPLE 12

[4S-(4α, 12aα)]-7-(Diethylamino)-4-(dimethylamino)-9-(formylamino)-1,4,4a,5,5a,6,11,12a-octahydro-3,10,12 12a-tetrahydroxy-1,11-dioxo-2-naphthacenecarboxamide A solution of 0.2 g of product from Example 10 in 10 ml of water is treated with sodium acetate to achieve pH 5–6. The mixture is extracted with chloroform. The organic extracts are dried with sodium acetate, concentrated in vacuo and the solid triturated with diethyl ether/hexane to give 0.11 g of the desired product.

MS (FAB): m/z 529 (M+H).

EXAMPLE 13

[4S-(4α, 12aα)]-9-(Acetylamino)-7-(diethylamino)-4-(dimethylamino)- 1,4,4a,5,5a,6,11,12a-octahydro-3,10,12,12a-tetrahydroxy-1,11-dioxo-2-naphthacenecarboxamide A solution of 0.25 g of product from Example 11 in 10 ml of water is treated with sodium acetate to achieve pH 6. The mixture is extracted with chloroform. The organic extracts are dried with sodium acetate, concentrated in vacuo and the solid triturated with diethyl ether/hexane to give 0.090 g of the desired product.

MS (FAB): m/z 543 (M+H).

EXAMPLE 14

[4S-(4α, 12aα)]-4-(Dimethylamino)-7-(ethylmethylamino)-1,4,4a,5,5a,6,11,12a-octahydro-3,10,12,12a-tetrahydroxy-1,11-dioxo-2-naphthacenecarboxamide hydrochloride A solution of 0.460 g of [4S-(4α, 12aα)]-4-(dimethylamino)- 7-(ethylamino)-1,4,4a,5,5a,6,11,12a-octahydro-3,10,12,12a-tetrahydroxy-1,11-dioxo-2-naphthacenecarboxamide hydrochloride, prepared by the procedure described in U.S. Pat. No. 3,226,436, in 0.5 ml of 97% formic acid and 0.75 ml of 40% aqueous formaldehyde is heated at reflux temperature for 2 hours, concentrated to ½ volume and poured into diethyl ether. The resulting solid is collected, washed with diethyl ether and dried to give 0.30 g of the desired product.

EXAMPLE 15

[4S-(4α, 12aα)]-4-(Dimethylamino)-7-(ethylmethylamino)-1,4,4a,5,5a,6,11,12a-octahydro-3,10,12,12a-tetrahydroxy-9-nitro-1,11-dioxo-2-naphthacenecarboxamide sulfate The title compound is prepared by the procedure of Example 8, using 0.460 g of product from Example 14, 15 ml of sulfuric acid and 0.101 g of sodium nitrate to give 0.5 g of the desired product.

EXAMPLE 16

[4S-(4α, 12aα)]-9-Amino-4-(dimethylamino)-7-(ethylmethylamino)- 1,4,4a,5,5a,6,11,12a-octahydro-3,10,12,12a-tetrahydroxy-1,11-dioxo-2-naphthacenecarboxamide sulfate The title compound is prepared by the procedure of Example 2, using 1.0 g of product from Example 15, 20 ml of 2-methoxyethanol, 1.0 g of 10% palladium-on-carbon and 5 ml of 2N sulfuric acid to give 0.8 g of the desired product.

EXAMPLE 17

[4S-(4α, 12aα)]-4-(Dimethylamino)-7-(ethylmethylamino)-9-(formylamino)-1,4,4a,5,5a,6,11,12a-octahydro-3,10,12, 12a-tetrahydroxy-1,11-dioxo-2-naphthacenecarboxamide sulfate The title compound is prepared by the procedure of Example 3, using 1.5 g of product from Example 16, 0.235 g of anhydrous sodium acetate, 25 ml of 98% formic acid and 3.7 ml of acetic anhydride to give 1.35 g of the desired product.

EXAMPLE 18

[4S-(4α, 12aα)]-9-(Acetylamino)-4-(dimethylamino)-1,4,4a,5,5a,6,11,12a-octahydro-3,10,12,12a-tetrahydroxy-1,11-dioxo-2-naphthacenecarboxamide sulfate To a solution of 3.2 g of [4S-(4α, 12aα)]-9-amino-4-dimethylamino-1,2,3,4,4a,5,5a,6,11,11a,12, 12a-dodecahydro-10,12aα-dihydroxy-1,3,11,12-tetraoxo-2-naphthacenecarboxamide, prepared by the procedure described in U.S. Pat. No. 3,239,499, in 50 ml of water is added a solution of 2.5 g of sodium acetate in 12 ml of water. The mixture is cooled to 0° C. and 1 ml of acetic anhydride is added with stirring. The reaction is stirred for 20 minutes, 0.5 ml of ammonium hydroxide is added and stirred for 5 minutes. Two and one half ml of sulfuric acid is added, the reaction is extracted twice with n-butyl alcohol, the combined organic layers are washed with water and concentrated in vacuo. The residue is dissolved in methyl alcohol and added dropwise to 500 ml of diethyl ether. The solid is collected and dried to give 2.3 g of the desired product. MS(FAB): m/z 472 (M+H) and 570 (M+H$_2$SO$_4$+H).

EXAMPLE 19

[4S-(4α, 12aα)]-4-(Dimethylamino)-9-(formylamino)-1,4,4a,5,5a,6,11,12a-octahydro-3,10,12,12a-tetrahydroxy-1,11-dioxo-2-naphthacenecarboxamide monohydrochloride To a 0° C. solution of 1.06 g of [4S-(4α, 12aα)]-9-amino-4-dimethylamino-1,2,3,4,5a, 6,11,11a,12,12a-dodecahydro-10,12aα-dihydroxy-1,3,11, 12-tetraoxo-2-naphthacenecarboxamide, prepared by the procedures described in U.S. Pat. No. 3,239,499, in 50 ml of formic acid is added 2.4 ml of acetic anhydride. After stirring for 5 minutes, the cooling bath is removed and the reaction is stirred for 55 minutes. The mixture is added to 400 ml of diethyl ether. The resulting solid is collected, washed with diethyl ether and dried to give 1.1 g of the desired product.
MS(FAB): m/z 458 (M+H). This procedure is a modification of U.S. Pat. No. 3,239,499.

EXAMPLE 20

[4S-(4α, 12aα)]-4-(Dimethylamino)-9-(formylamino)-1,4,4a,5,5a,6,11,12a-octahydro-3,10,12,12a-tetrahydroxy-7-iodo-1,11-dioxo-2-naphthacenecarboxamide sulfate To a well stirred 0° C. solution of 0.278 g of product from Example 19 in 10 ml of sulfuric acid is added, in portions, 0.1344 g of N-iodosuccinimide. The reaction is stirred at 0° C. for 20 minutes then poured into 500 ml of diethyl ether. The resulting solid is collected, washed with diethyl ether and dried to give 0.251 g of the desired product.
MS(FAB): m/z 584 (M+H).

EXAMPLE 21

[4S-(4α, 12aα)]-4-(Dimethylamino)-9-(formylamino)-1.4,4a,5,5a,6,11,12a-octahydro-3,10,12,12a-tetrahydroxy-7-nitro-1,11-dioxo-2-naphthacenecarboxamide sulfate To a well stirred 0° C. solution of 0.278 g of product from Example 19 in 10 ml of sulfuric acid is added 0.3 ml of 10% nitric acid in sulfuric acid. The reaction is stirred at 0° C. for 20 minutes then poured into 500 ml of diethyl ether. The resulting solid is collected, washed with diethyl ether and dried to give 0.26 g of the desired product.
MS (FAB): m/z 503 (M+H).

EXAMPLE 22

[4S-(4α, 12aα)]-4-(Dimethylamino)-9-(formylamino)-7-[(1-methylethyl)amino]-1,4,4a,5,5a,6,11,12a-octahydro- 3,10,12,12a-tetrahydroxy-1,11-dioxo-2-naphthacenecarboxamide sulfate A solution of 0.2 g of product from Example 21 (1:2 salt), 0.5 ml of acetone, 0.5 ml of 0.5N sulfuric acid and 10 ml of 2-methoxyethanol is shaken under 35 lbs. of hydrogen, in the presence of platinum oxide, for 2 hours. The catalyst is removed by filtration, the filtrate concentrated in vacuo to ½ volume and poured into diethyl ether. The resulting solid is collected and dried to give 0.135 g of the desired product.

EXAMPLE 23

[4S-(4α, 12aα)]-4,7-Bis(dimethylamino)-1,4,4a,5,5a,6, 11,12a-octahydro-3,10,12,12a-tetrahydroxy-9-[[(methoxyacetyl)amino]-1,11-dioxo-2-naphthacenecarboxamide To a well stirred solution of 0.055 g of product from Example 2, 0.200 g of sodium bicarbonate and 1 ml of N-methylpyrrolidone is added a solution of 0.011 g of methoxyacetyl chloride in 0.5 ml of acetonitrile. After 5 minutes, the suspension is filtered and the filtrate diluted with 50 ml of tert-butyl methyl ether. The resulting solid is collected and dried to give 0.040 g of the desired product.
MS (FAB): m/z 545 (M+H).

EXAMPLE 24

[4S-(4α, 12aα)]-4,7-Bis(dimethylamino)-9-(cyclopropylcarbonylamino)-1,4,4a,5,5a,6,11,12a-octahydro-3,10,12,12a-tetrahydroxy-1,11-dioxo-2-naphthacenecarboxamide The title compound is prepared by the procedure of Example 23, using 0.055 g of product from Example 2, 0.20 g of sodium bicarbonate, 1.0 ml N-methylpyrrolidone, 0.010 g of cyclopropanecarbonyl chloride and 0.5 ml of acetonitrile to give 0.030 g of the desired product.

EXAMPLE 25

[4S-(4α, 12aα)]-4,7-Bis(dimethylamino)-9-(chloroacetylamino)-1,4,4a,5,5a,6,11,12a-octahydro-3,10,12, 12a-tetrahydroxy-1,11-dioxo-2-naphthacenecarboxamide The title compound is prepared by the procedure of Example 23, using 0.055 g of product from Example 2, 0.20 g of sodium bicarbonate, 1 ml of N-methylpyrrolidone, 0.013 g of chloroacetyl chloride and 0.5 ml of acetonitrile to give 0.035 g of the desired product.

EXAMPLE 26

[4S-(4α, 12aα)]-9-[(4-Bromo-1-oxobutyl)amino]-4,7-bis(dimethylamino)- 1,4,4a,5,5a,6,11,12a-octahydro-3,10,12,12a-tetrahydroxy-1,11-dioxo-2-naphthacenecarboxamide The title compound is prepared by the procedure of Example 23, using 0.055 g of product from Example 2, 0.20 g of sodium bicarbonate, 1 ml of N-methylpyrrolidone, 0.025 g of 4-bromobutyryl chloride and 0.5 ml of acetonitrile to give 0.050 g of the desired product.
MS(FAB): m/z 622 (M+H).

EXAMPLE 27

[4S-(4α, 12aα)]-4,7-Bis(dimethylamino)-1,4,4a,5,5a,6,11,12a-octahydro-3,10,12,12a-tetrahydroxy-1,11-dioxo-9-[(1-oxo-2-propenyl)amino]-2-naphthacenecarboxamide The title compound is prepared by the procedure of Example 23, using 0.055 g of product from Example 2, 0.20 g of sodium bicarbonate, 1.0 ml N-methylpyrrolidone, 0.011 g of acryloyl chloride and 0.5 ml of acetonitrile to give 0.040 g of the desired product.
MS (FAB): 513 (M+H).

EXAMPLE 28

[4S-(4α, 12aα)]-9-[[(Acetyloxy]acetyl]amino]-4,7-Bis(dimethylamino)-1,4,4a,5,5a,6,11,12a-octahydro-3,10, 12,12a-tetrahydroxy-1,11-dioxo-2-naphthacenecarboxamide The title compound is prepared by the procedure of Example 23, using 0.055 g of product from Example 2, 0.20 g of sodium bicarbonate, 1.0 ml of N-methylpyrrolidone, 0.013 g of acetoxyacetyl chloride and 0.5 ml of acetonitrile to give 0.040 g of the desired product.
MS (FAB): m/z 573 (M+H).

EXAMPLE 29

[4S-(4α, 12aα)]-4,7-Bis(dimethylamino)-9-(phenylthioacetylamino)-1,4,4a,5,5a,11,12a-octahydro-3,10,12,12a-tetrahydroxy-1,11-dioxo-2-naphthacenecarboxamide The title compound is prepared by the procedure of Example 23, using 0.110 g of product from Example 2, 0.40 g of sodium bicarbonate, 4.0 ml of N-methylpyrrolidone, 0.035 g of phenylthioacetyl chloride and 0.5 ml of acetonitrile to give 0.075 g of the desired product.

EXAMPLE 30

[4S-(4α, 12aα)]-4,7-Bis(dimethylamino)-9-(pyruvylamino)-1,4,4a,5,5a,6,11,12a-octahydro-3,10,12,12a-tetrahydroxy-1,11-dioxo-2,naphthacenecarboxamide The title compound is prepared by the procedure of Example 23, using 0.110 g of product from Example 2, 0.40 g of sodium bicarbonate, 1.0 ml of N-methylpyrrolidone, 0.018 g of pyruvyl chloride and 0.5 ml of acetonitrile to give 0.060 g of the desired product.

EXAMPLE 31

[4S-(4α, 12aα)]-4,7-Bis(dimethylamino)-9-(ethoxycarbonylacetylamino)-1,4,4a,5,5a,6,11,12a-octahydro-3,10, 12,12a-tetrahydroxy-1,11-dioxo-2-naphthacenecarboxamide The title compound is prepared by the procedure of Example 23, using 0.055 g of product from Example 2, 0.20 g of sodium bicarbonate, 1.0 ml of N-methylpyrrolidone, 0.013 g of ethyl malonyl chloride and 0.5 ml of acetonitrile to give 0.035 g of the desired product.

EXAMPLE 32

[4S-(4α, 12aα)]-4,7-Bis(dimethylamino)-9-(4-bromophenylacetylamino)-1,4,4a,5,5a,6,11,12-octahydro-3,10,12,12a-tetrahydroxy-1,11-dioxo-2-naphthacenecarboxamide The title compound is prepared by the procedure of Example 23, using 0.055 g of product from Example 2, 0.20 g of sodium bicarbonate, 1.0 ml of N-methylpyrrolidone, 0.018 g of 4-bromophenylacetyl chloride and 0.5 ml of acetonitrile to give 0.040 g of the desired product.

EXAMPLE 33

[4S-(4α, 12aα)]-9-(Benzoylamino)-4,7-bis(dimethylamino)-1,4,4a,5,5a,6,11,12a-octahydro-3,10,12,12a-tetrahydroxy-1,11-dioxo-2-naphthacenecarboxamide To a vigorously stirring solution of 0.066 g of product from Example 2, 0.085 g of sodium acetate and 3 ml of tetrahydrofuran is added 0.015 ml of benzoyl chloride and 0.25 ml of water. The reaction is stirred for 1 hour. The organic layer is decanted, washed with saturated sodium chloride, dried and concentrated in vacuo. The residue is chromatographed on acid-washed diatomaceous earth using a two phase system of hexane- ethyl acetate:2-methoxyethanol:water (50:50:17:6) to give in the second void volume 0.030 g of the desired product as an orange solid.

MS (FAB): m/z 577 (M+H).

huH NMR ($d_6$-DMSO): δ 2.45 (s,6H,C(4)N(CH$_3$)$_2$), 2.57(s, 6-H,C( 7)N(CH$_3$)$_2$), 7.5–7.6(m,3H, benzoyl), 7.86(s,1H, H-8), 7.96 (d,J=7Hz, 2H, benzoyl).

EXAMPLES 34–41 (Table I)

Substantially following the method described in detail hereinabove in Example 33 using [4S-(4α, 12aα)]- 9-amino-4,7-bis(dimethylamino)-1,4,4a, 5,5a,6,11,12a-octahydro-3,10,12,12a-tetrahydroxy-1,11-dioxo-2-naphtacenecarboxamide sulfate (product from Example 2), the compounds of this invention listed below in Examples 34–41 are prepared.

TABLE I

| Ex. | Acid Chloride | Product | Spectra |
|---|---|---|---|
| 34 | 4-Methoxybenzoyl chloride | [4S-(4alpha,12aalpha))]-4,7-Bis(dimethylamino)-1,4,4a,5 5a,6,11,12a-octahydro-3,10, 12,12a-tetrahydroxy-9-[(4-methoxybenzoyl)amino]-1,11-dioxo-2-naphthacenecarbox-amide | MS(FAB):m/z 607 (M+H); $^1$H NMR ($d_6$-DMSO): delta 2.45(s,6H, C(4)NMe$_2$), 2.57(s,6H,C(7) NMe$_2$), 7.06(d,J = 9Hz,2H of 4-methoxybenzoyl), 7.84(s,1H, H-8), 7.97(d,J = 9Hz,2H of 4-methoxybenzoyl) |
| 35 | 2-Methylbenzoyl chloride | [4S-(4alpha,12aalpha))]-4,7-Bis(dimethylamino)-1,4,4a,5 5a,6,11,12a-octahydro-3,10, 12,12a-tetrahydroxy-9-[(2-methylbenzoyl)amino]-1,11-dioxo-2-naphthacenecarbox-amide | MS(FAB):m/z 591 (M+H); $^1$H NMR ($d_6$-DMSO): delta 2.52(m,12H, C(4)NMe$_2$ & C(7)NMe$_2$), 7.25-7.56(m,4H from 2-methylbenzoyl), 7.98(s,1H,H-8) |
| 36 | 2-Fluorobenzoyl chloride | [4S-(4alpha,12aalpha))]-4,7-Bis(dimethylamino)-9-[(2-fluorobenzoyl)amino]-1,4,4a, 5,5a,6,11,12a-octahydro-3,10, 12,12a-tetrahydroxy-1,11-dioxo-2-naphthacenecarbox-amide | MS(FAB):m/z 595 (M+H); $^1$H NMR ($d_6$-DMSO): delta 2.47–2.51 (m,6H,C(4)NMe$_2$), 2.57(bs,6H, C(7)NMe$_2$), 7.39(m,2H from 2-fluorobenzoyl), 7.63(m,1H from 2-fluorobenzoyl), (m, 1H from 2-fluorobenzoyl), 8.24(s,1H,H-8) |
| 37 | Pentafluoro-benzoyl chloride | [4S-(4alpha,12aalpha)]-4,7-Bis(dimethylamino)-1,4,4a, 5,5a,6,11,12a-octahydro-3,10, 12,12a-tetrahydroxy-9-[(pentafluorobenzoyl)amino]-1,11-dioxo-2-naphthacenecarbox-amide | MS(FAB):m/z 667 (M+H); $^1$H NMR ($d_6$-DMSO):delta 2.5(m,12H, C(4)NMe$_2$ & C(7)NMe$_2$), 8.08 (s,1H,H-8) |
| 38 | 3-Trifluoro-methylbenzoyl chloride | [4S-(4alpha,12aalpha)]-4,7-Bis(dimethylamino)-1,4,4a,5, 5a,6,11,12a-octahydro-3,10, 12,12a-tetrahydroxy-1,11-dioxo-9-[[3-(trifluoro-methyl)benzoyl]amino]-2-naphthacenecarboxamide | MS(FAB):m/z 645 (M+H); $^1$H NMR ($d_6$-DMSO):delta 2.50(m,6H, C(4)NMe$_2$), 2.57(m,6H,C(7) NMe$_2$), 7.85(m,2H of 3-trifluoromethylbenzoyl), 7.99 (m,1H of 3-trifluoromethyl-benzoyl), 8.28(1H of 3-trifluoromethylbenzoyl), 8.33 (s,1H,H-8), 8.31–8.42(m,2H) |
| 39 | 2-Furoyl chloride | [4S-(4alpha,12aalpha)]-4,7-Bis(dimethylamino)-9-[(2-furanylcarbonyl)amino]-1,4, 4a,5,5a,6,11,12a-octahydro- | MS(FAB):m/z 567 (M+H); $^1$H NMR ($d_6$-DMSO):delta 2.47(m,6H, C(4)NMe$_2$), 2.56(s,6H,C(7) NMe$_2$), 6.73(s,1H of furanyl) |

TABLE I-continued

| Ex. | Acid Chloride | Product | Spectra |
|---|---|---|---|
|  |  | 3,10,12,12a-tetrahydroxy-1,11-dioxo-2-naphthacene-carboxamide | 7.31(s,1H of furanyl), 7.95 (s,1H of furanyl), 8.00(s,1H,H-8) |
| 40 | 2-Thiophene-carbonyl chloride | [4S-(4alpha,12aalpha)]-4,7-Bis(dimethylamino)-1,4,4a,5,5a,6,11,12a-octahydro-3,10,12,12a-tetrahydroxy-1,11-dioxo-9-[(2-thienyl-carbonyl)amino]-2-naphthacenecarboxamide | MS(FAB):m/z 583 (M+H); $^1$H NMR ($d_6$-DMSO):delta 2.49(m,6H, C(4)NMe$_2$), 2.56(s,6H,C(7)NMe$_2$), 7.21(m,1H of thienyl), 7.70(s,1H,H-8), 7.85(m,1H of thienyl), 8.01(m,1H of thienyl) |
| 41 | 4-Nitro-benzoyl chloride | [4S-(4alpha,12aalpha)]-4,7-Bis(dimethylamino)-1,4,4a,5,5a,6,11,12a-octahydro-3,10,12,12a-tetrahydroxy-9-[(4-nitrobenzoyl)amino]-1,11-dioxo-2-naphthacene-carboxamide | MS(FAB):m/z 622 (M+H); $^1$H NMR ($d_6$-DMSO):delta 2.50(m,6H, C(4)NMe$_2$), 2.57(s,6H,C(7)NMe$_2$), 7.76(s,1H,H-8), 8.20 (d,J = 9Hz,2H of 4-nitrobenzoyl), 8.36(d,J = 9Hz,2H of 4-nitrobenzoyl) |

EXAMPLE 42

[4S-(4α, 12aα)]-9-[(4-Aminobenzoyl)amino]-4,7-Bis-dimethylamino)-1,4,4a,5,5a,6,11,12a-octahydro-3,10,12,12a-tetrahydroxy-1,11-dioxo-2-naphthacenecarboxamide sulfate A mixture of 0.030 g of product from Example 41, 0.010 g of 10% palladium-on-carbon, 1.5 ml of 2-methoxyethanol and 0.175 ml of 2N sulfuric acid, in a pressure bottle, is shaken under 30 lbs. of hydrogen pressure for 40 minutes. The catalyst is removed by filtration and the filtrate is concentrated in vacuo and codistilled with benzene. The oily residue is dissolved in 0.5 ml of 2-methoxyethanol, precipitated with diethyl ether and the solid collected to give 0.018 g of the desired product.
MS (FAB): m/z 592 (M+H).

EXAMPLE 43

[4S-(4α, 12aα)]-4,7-Bis(dimethylamino)-9-[[(4-dimethylamino)benzoyl]amino]-1,4,4a,5,5a,6,11,12a-octahydro- 3,10,12,12a-tetrahydroxy-1,11-dioxo-2-naphthacenecarboxamide A mixture of 0.065 g of product from Example 41, 2.0 ml of 2-methoxyethanol, 0.025 g of 10% palladium-on-carbon, 0.4 ml of 2N sulfuric acid and 0.3 ml of 37% aqueous formaldehyde, in a pressure bottle, is shaken under 30 lbs. of hydrogen pressure for 50 minutes. The catalyst is removed by filtration and the filtrate is concentrated in vacuo and codistilled with heptane. The oily residue is dissolved in 1.0 ml of 2-methoxyethanol, precipitated with diethyl ether to give 0.085 g of the desired product as the sulfate salt. The sulfate salt is dissolved in 0.5 ml of water and 6 ml of tetrahydrofuran followed by the addition of 0.10-g of sodium acetate. The organic layer is washed with saturated sodium chloride, dried and concentrated in vacuo. The residue is triturated with ethyl acetate/heptane to give 0.035 g of the desired product as the free base.
MS(FAB): m/z 620 (M+H)

1H NMR ($d_6$-DMSO): δ 2.50(m,6H,C(4)NMe$_2$), 2.57 (s,6H, C(7)NMe$_2$), 3.33 (s, 6H,NMe$_2$ of 4-dimethylaminobenzoyl), 7.76(s,1H,H-8), 8.20(d,J=9Hz,2H of 4-dimethylaminobenzoyl), 8.37(d,J=9Hz,2H of 4-dimethylaminobenzoyl).

EXAMPLE 44

[7S-(7α, 10aα)]-[2-[[9-(Aminocarbonyl)-4,7-Bis (dimethylamino)-5,5a,6,6a,7,10,10a,12-octahydro-1,8,10a,11-tetrahydroxy-10,12-dioxo-2-naphthacenyl]amino]-2-oxoethyl]carbamic acid 1,1-dimethylethyl ester A mixture of 0.850 g of product from Example 2 (as the disulfate), 0.680 g of sodium acetate in 25 ml of tetrahydrofuran and 5 ml of water is stirred at 25° C. for 5 minutes. The solution is treated with 0.359 g of (succinimyloxycarbonyl)methyl carbamic acid tert-butyl ester, stirred for 2 hours and extracted with chloroform. The organic layer is concentrated in vacuo to give 0.50 g of the desired product.
MS(FAB): m/z 630 (M+H).

EXAMPLE 45

[4S-(4α, 12aα)]-9-[(Aminoacetyl)amino]-4,7-Bisdimethylamino)-1,4,4a,5,5a,6,11,12a-octahydro-3,10,12,12a-tetrahydroxy-1,11-dioxo-2-naphthacenecarboxamide mono(trifluoroacetate)

A solution of 0.030 g of product from Example 44 and 1.0 ml of trifluoroacetic acid is maintained at 24° C. for 24 hours followed by concentrating in vacuo. The residue is triturated with methyl alcohol and the solid collected to give 0.024 g of the desired product.
MS (FAB): m/z 530 (M+H).

EXAMPLE 46

[4S-(4α, 12aα)]]-4,7-Bis(dimethylamino)-9-[[(dimethylamino)acetyl]amino]-1,4,4a,5,5a,6,11,12a-octahydro-3,10,12,12a-tetrahydroxy-1,11-dioxo-2-naphthacenecarboxamide sulfate A mixture of 0.030 g of product from Example 45, 0.020 g of 10% palladium-on-carbon, 0.5 ml of 37% formaldehyde, 1.5 ml of 2-methoxyethanol and 0.175 ml of 2N sulfuric acid, in a pressure bottle, is shaken under 30 lbs. of hydrogen pressure for 40 minutes. The catalyst is removed by filtration and the filtrate is concentrated in vacuo and codistilled with benzene. The oily residue is dissolved in 0.5 ml of 2-methoxyethanol, precipitated with diethyl ether and the precipitate collected to give 0.025 g of the desired product.

EXAMPLE 47

[4S-(4α, 12aα)]-4,7-Bis(dimethylamino)-1,4,4a,5,5a,6, 11,12a-octahydro-3,10,12,12a-tetrahydroxy-1,11-dioxo-9-[(phenylsulfonyl)amino]-2-naphthacenecarboxamide A mixture of 0.30 g of product from Example 2, 0.40 g of sodium acetate in 10 ml of tetrahydrofuran and 1.5 ml of water is stirred for 10 minutes under argon. The organic layer is separated, dried over anhydrous sodium sulfate and treated with 0.125 ml of benzenesulfonyl chloride and 0.60 g of sodium bicarbonate. The reaction is stirred vigorously for 1.5 hours. The organic layer is decanted and codistilled with heptane. The residue is dissolved in ethyl acetate, dried and concentrated in vacuo. The residue is chromatographed on diatomaceous earth using hexane: ethyl acetate:2-methoxyethanol:water (35:65:15:5) to give 0.036 g of the desired product as a yellow solid.

MS(FAB): m/z 613 (M+H).

$^1$H NMR (CDCl$_3$): δ 2.44(bs,6H,C(4)NMe$_2$), 2.55(s,6H, C(7)-NMe$_2$, 7.38–7.45(m,2H,m-H's from benzenesulfonyl), 7.52– 7.56(m, 1H,p-H from benzenesulfonyl), 7.58(s,1H,H-8), 7.78(d,J=7Hz,2H,o-H's from benzenesulfonyl).

EXAMPLES 48–53 (Table II)

Substantially following the method described in detail hereinabove in Example 47 using [4S-(4α, 12aα)]- 9-amino-4,7-bis(dimethylamino)-1,4,4a, 5,5a,6,11,12a-octahydro-3,10,12,12a-tetrahydroxy-1,11-dioxo-2-naphthacenecarboxamide sulfate (product from Example 2) and the appropriate alkyl, aryl or heteroarylsulfonyl chloride, the compounds of this invention listed below in Examples 48–53 are prepared.

TABLE II

| Ex. | Sulfonyl Chloride | Product | Spectra |
|---|---|---|---|
| 48 | 4-Chlorobenzenesulfonyl chloride | [4S-(4alpha,12aalpha))]-9-[[(4-chorophenyl)sulfonyl]-amino]-4,7-bis(dimethylamino)-1,4,4a,5,5a,6,11,12a-tetrahydroxy-1,11-dioxo-2-naphthacenecarboxamide | MS(FAB):m/z 622 (M+H); $^1$H NMR (d$_6$-DMSO):delta 2.48(m,12H, C(4)NME$_2$ & C(7)NMe$_2$), 7.16 (s,1H,H-8), 7.62(d,J = 9Hz,2H of 4-chlorobenzenesulfonyl), 7.75(d,J = 9Hz,2H of 4-chlorobenzenesulfonyl) |
| 49 | 3-Nitrobenzenesulfonyl chloride | [4S-(4alpha,12aalpha)) -4,7-Bis(dimethylamino)-1,4,4a,5 5a,6,11,12a-octahydro-3,10, 12,12a-tetrahydroxy-9-[(3-nitrophenyl)sulfonyl]amino]-1,11-dioxo-2-naphthacenecarboxamide | MS(FAB):m/z 658 (M+H); $^1$H NMR (d$_6$-DMSO): delta 2.44–2.45 (m,12H,C(4)NMe$_2$) & C(7)NMe$_2$) 7.51–7.62(m,3H of 3-nitrobenzenesulfonyl), 7.74–7.78 (m,1H of 3-nitrobenzenesulfonyl), 7.75(s,1H,H-8) |
| 50 | 4-Nitrobenzenesulfonyl chloride | [4S-(4alpha,12aalpha))]-4,7-Bis(dimethylamino)-1,4,4a,5, 5a,6,11,12a-octahydro-3,10, 12,12a-tetrahydroxy-9-[[(4-nitrophenyl)sulfonyl] amino]-1,11-dioxo-2-naphthacenecarboxamide | MS(FAB):m/z 658 (M+H); $^1$H NMR (CDCl$_3$):delta 2.46(s,6H,C(4) NMe$_2$), 2.58(s,6H,C(7)NMe$_2$), 7.59(s,1H,H-8), 7.96(d,J = 9Hz,2H of 4-nitrobenzenesulfonyl), 8.25(d,J = 9Hz, 2H of 4-nitrobenzenesulfonyl). |
| 51 | 2-Thiophene sulfonyl chloride | [4S-(4alpha,12aalpha)]-4,7-Bis(dimethylamino)-1,4,4a,5, 5a,6,11,12a-octahydro-3,10, 12,12a-tetrahydroxy-1,11-dioxo-9-[(2-thienylsulfonyl) amino]-2-naphthacenecarboxamide | MS(FAB):m/z 619 (M+H); $^1$H NMR (d$_6$-DMSO): delta 2.50(m,6H, C(4)NMe$_2$), 2.54(S,6H,C(7) NMe$_2$), 7.14(m,1H of thienyl), 7.29(m,1H of thienyl), 7.51 (s,1H of thienyl), 7.91(s, 1H,H-8) |
| 52 | 2-Acetamido-4-methyl-5-thiazole sulfonyl chloride | [4S-(4alpha,12aalpha)]-9-[[(2-(Acetylamino)-4-methyl-5-thiazolyl]sulfonyl]amino]-4,7-bis(dimethylamino)-1,4, 4a,5,5a,6,11,12a-octahydro-3,10,12,12a-tetrahydroxy-1, 11-dioxo-2-naphthacenecarboxamide | MS(FAB):m/z 691 (M+H); $^1$H NMR (CDCl$_3$) delta 2.21(s,3H,thiazoyl H$_3$CCONH), 2.40(s,3H, thiazoyl H$_3$C), 2.54(s,6H,C(4) NMe$_2$), 2.57(s,6H,C(7)NMe$_2$), 7.65(s,6H,C(7)NMe$_2$, 7.65(s, 1H,H-8) |
| 53 | Ethane sulfonyl chloride | [4S-(4alpha,12aalpha)]-4,7-Bis(dimethylamino)-9-[(ethylsulfonyl)amino]-1,4, 4a,5,5a,6,11,12a-octahydro-3,10,12,12a-tetrahydroxy-1,11-dioxo-2-naphthacenecarboxamide | MS(FAB):m/z 565 (M+H); $^1$H NMR (CDCl$_3$):delta 0.88(t,3H,CH$_3$ CH$_2$SO$_2$), 2.4–2.6(m,12H,C(4) NMe$_2$ & C(7)NMe$_2$), 3.34(q,2H, CH$_3$CH$_2$SO$_2$), 7.61(s,1H,H-8) |

EXAMPLE 54

[4S-(4α, 12aα)]-4,7-Bis(dimethylamino)-9-(formylamino)-1,4,4a,5a,6,11,12a-octahydro-3,10,12,12a-tetrahydroxy-1,11-dioxo-N-(1-pyrrolidinylmethyl)-2-naphthacenecarboxamide A solution of 0.30 g of product from Example 3 and 1.2 equivalents of 30% aqueous formaldehyde in 6.0 ml of 2-methoxyethanol is treated with 5.0 equivalents of pyrrolidine. The reaction is stirred vigorously at room temperature for 1.5 hours. The crystalline solid is collected and dried to give 0.25 g of the desired product.
MS (FAB): m/z 584 (M+H).

EXAMPLE 55

[4S-(4α, 12aα)]-4,7-Bis(dimethylamino)-1,4,4a,5a,6, 11,12a-octahydro-3,10,12,12a-tetrahydroxy-9-[(methanesulfonyl)amino]-1,11-dioxo-2-naphthacenecarboxamide A mixture of 0.30 g of product from Example 2, 0.40 g of sodium acetate in 10 ml of tetrahydrofuran and 1.5 ml of water is stirred for 10 minutes at room temperature under argon. The organic layer is separated, dried over sodium sulfate, filtered and treated with 0.10 ml of methanesulfonyl chloride and 0.60 g of sodium bicarbonate. The reaction is stirred vigorously for 1.5 hours. The organic layer is decanted and codistilled with heptane. The residue is dissolved in ethyl acetate, dried and concentrated in vacuo. The crude product is chromatographed on diatomaceous earth using hexane:ethyl acetate:2-methoxyethanol:water (35:65:15:5) to give 0.016 g of the desired product as a yellow solid.
MS (FAB): m/z 551 (M+H).

EXAMPLE 56

[4S-(4α, 12aα)]-4,7-Bis(dimethylamino)-9-[(methanesulfonyl)amino]- 1,4,4a,5a,6,11,12a-octahydro-3,10,12,12a-tetrahydroxy-1,11-dioxo-N-(pyrrolidinylmethyl)- 2-naphthacenecarboxamide A solution of 0.30 g of product from Example 55 and 1.2 equivalents of 30% aqueous formaldehyde in 6.0 ml of 2-methoxyethanol is treated with 5.0 equivalents of pyrrolidine. The reaction is stirred vigorously at room temperature for 1.5 hours. The crystalline solid is collected and dried to give 0.250 g of the desired product.
MS (FAB): m/z 634 (M+H).

EXAMPLE 57

[4S-(4α, 12aα) ]-4,7-Bis(dimethylamino)-1,4,4a, 5,5a, 6, 11,12a-octahydro, 3,10,12,12a-tetrahydroxy-1,11-dioxo-9-[[(phenylmethoxy)acetyl]amino]-2-naphthacenecarboxamide The title compound is prepared by the procedure of Example 23, using 0.055 g of product from Example 2, 0.20 g of sodium bicarbonate, 1.0 ml of N-methylpyrrolidine, 0.018 g of benzyloxyacetyl chloride and 0.5 ml of acetonitrile to give 0.060 g of the desired product.
MS (FAB): m/z 622 (M+H).

EXAMPLE 58

[7S-(7α, 10aα)]-[[9-(Aminocarbonyl),4,7-Bis(dimethylamino)-5,5a,6,6a,7,10,10a,12-octahydro-1,8,10a,11-tetrahydroxy-10,12-dioxo-2-naphthacenyl]amino]oxo-acetic acid ethyl ester The title compound is prepared by the procedure of Example 23, using 0.055 g of product from Example 2, 0.20 g of sodium bicarbonate, 1.0 ml of N-methylpyrrolidone, 0.015 g of ethyl oxalyl chloride and 0.5 ml of acetonitrile to give 0.030 g of the desired product.
MS (FAB): m/z 574 (M+H).

EXAMPLE 59

[4S-(4α, 12aα)]-4,7-Bis(dimethylamino)-,1,4,4a,5,5a, 6,11,12a-octahydro-3,10,12,12a-tetrahydroxy-9-[(hydroxyacetyl)amino]-1,11-dioxo-2-naphthacenecarboxamide A mixture of 0.048 g of product from Example 28 and 0.6 ml of concentrated sulfuric acid is stirred at room temperature for 2 hours, poured into diethyl ether and the precipitated salt collected. The salt is dissolved in 10 ml of tetrahydrofuran, 0.250 g of sodium acetate is added and the mixture stirred for 1 hour. The reaction is filtered and the filtrate is concentrated in vacuo. The residue is chromatographed on a poly(styrene-vinyl benzene)copolymer column with water:acetonitrile (1:1) to give 0.018 g of the desired product as a light yellow solid.
MS (FAB): m/z 532 (M+H).

EXAMPLE 60

[4s-(4α, 12aα)]-9-(Acetylamino)-4-(dimethylamino)-1,4,4a,5,5a,6,11,12a-octahydro-3,10,12,12a-tetrahydroxy-1,11-dioxo-2-naphthacenecarboxamide sulfate To a 0° C. solution of 1.06 g of [4S-(4α, 12aα)]-9-amino-4-(dimethylamino)-1,2,3,4,4a,5,5a,6,11,11a,12, 12a-dodecahydro-10,12aα-dihydroxy-1, 3,11,12-tetraoxo-2-naphthacenecarboxamide, prepared by the procedures described in U.S. Pat. No. 3,239,499, in 50 ml of acetic acid is added 2.4 ml of acetic anhydride. After 5 minutes, the reaction is allowed to warm to room temperature. The reaction mixture is poured into 500 ml of diethyl ether and the resulting precipitate is collected. The precipitate is washed with diethyl ether and dried to give 1.1 g of the desired product.
MS(FAB): m/z 472 (M+H).

EXAMPLE 61

[4S-(4α, 12aα)]-4-(Dimethylamino)-9-(acetylamino)- 1,4,4a,5,5a,6,11,12a-octahydro-3,10,12,12a- tetrahydroxy- 7-iodo-1,11-dioxo-2-naphthacenecarboxamide sulfate To a stirring 0° C. solution of 0.278 g of product from Example 60 in 10 ml of sulfuric acid is added, portionwise, 0.1344 g of N-iodosuccinimide. After stirring at 0° C. for 20 minutes, the reation mixture is poured into 400 ml of diethyl ether. The resultant precipitate is collected, washed with diethyl ether and dried to give 1.1 g of the desired product as a solid. MS(FAB): m/z 598 (M+H) and 696 (M+H$_2$SO$_4$+H).

EXAMPLE 62

[7S-(7α, 10aα)]-[9-(Aminocarbonyl)-4,7-Bis(dimethylamino)- 5,5a,6,6a,7,10,10a,12-octahydro-1,8,10a,11- tetrahydroxy- 10,12-dioxo-2-naphthacenyl]carbamic acid methyl ester To a room temperature mixture of 0.60 g of product from Example 2 in 2 ml of 1-methyl-2-pyrrolidinone is added 0.60 g of sodium bicarbonate. The mixture is stirred for 5 minutes followed by the addition of 0.12 ml of methyl chloroformate. The reaction is stirred at room temperature for 30 minutes and filtered into 200 ml of t-butyl methyl ether. The resulting solid is collected and dried to give 0.370 g of the desired product.
MS (FAB): m/z 531 (M+H).
$^1$H NMR (d$_6$DMSO): δ 2.6(s,12H,C(4)NMe$_2$ and C(7)NMe$_2$), 3.7(m,3H,o-CH$_3$), 7.8(s,1H,H-3), 8.7(s,1H, aromatic NH), 9.1(d,2H,CONH$_2$).

EXAMPLE 63

[7S-(7α, 10aα)]-[9-(Aminocarbonyl)-4,7-bis(dimethylamino)- 5,5a,6,6a,7,10,10a,12-octahydro-1,8,10a,11- tetrahydroxy- 10,12-dioxo-2-naphthacenyl]carbamic acid (2-diethylamino)ethyl ester The title compound is prepared by the procedure of Example 62, using 0.443 g of product from Example 2, 2 ml of 1-methyl-2-pyrrolidinone, 0.165 g of β-diethylaminoethyl chlorocarbonate hydrochloride and 0.443 g of sodium bicarbonate to give 0.350 g of the desired product.
$^1$H NMR (d$_6$DMSO): δ 1.2(m,6H,-N(CH$_2$CH$_3$)$_2$), 2.5(s,6H, C(7)NMe$_2$), 2–7(s,6H,C(4)NMe$_2$), 3–4(m,2H, OCH$_2$CH$_2$N), 3.51(m,4H,-N(C[2CH$_3$) 2) , 4-0(m,2H,- OCH$_2$CH2N), 6.8(s,1H,H-3), 9.0(d,2H,CONH$_2$).

EXAMPLE 64

[7S-(7α, 10aα)]-[9-(Aminocarbonyl)-4,7-bis(dimethylamino)- 5,5a,6,6a,7,10,10a,12-octahydro-1,8,10a,11-tetrahydroxy- 10,12-dioxo-2-naphthacenyl]carbamic acid ethenyl ester The title compound is prepared by the procedure of Example 62, using 0.189 g of product from Example 2, 1 ml of 1-methyl-2-pyrrolidone, 0.75 ml of acetonitrile, 0.20 g of sodium bicarbonate and 0.037 g of vinyl chloroformate to give 0.133 g of the desired product.
MS (FAB): m/z 548 (M+H).
$^1$H NMR (d$_6$DMSO+TFA): δ 4.35(s,1H,H-7), 4.6(d,1H, CH=CH$_2$cis) , 4.9 (d, 1H,CH=CH$_2$, trans), 7.2 (m,2H, —O—CH=CH$_2$), 8.1(s,1H,H-3), 9.6 & 9.1(s,2H, CONH$_2$), 9.61(s,H,aromatic NH)

EXAMPLE 65

[7S-(7α, 10aαe)]-[9-(Aminocarbonyl)-4,7-bis(dimethylamino)- 5,5a,6,6a,7,10,10a,12-octahydro-1,8,10a,11- tetrahydroxy- 10,12-dioxo-2-naphthacenyl]carbamic acid 2-propenyl ester The title compound is prepared by the procedure of Example 62, using 0.213 g of product from Example 2, 1 ml of 1-methyl-2-pyrrolidone, 0.75 ml of acetonitrile, 0.20 g of sodium bicarbonate and 0.054 g of allyl chloroformate to give 0.143 g of the desired product.
$^1$H NMR (d$_6$DMSO+TFA): δ 4.65(d,2H,=CHCH$_2$), 5.25(d, 1H, CH=CH$_2$cis), 5.4(d, 1H,CH=CH$_2$trans), 6.0(m, 1H,CH$_2$=CH—CH$_2$), 8.1(s,1H,H-3), 9.1(s,1H,aromatic NH), 9.6 & 9.0(s,2H,CONH$_2$).

Substantially following the methods described in detail hereinabove in Example 23, the compounds of this invention listed below in Examples 66–82 are prepared. Example 72 uses the appropriate anhydride rather than the acid chloride.

EXAMPLE 66

[4S-(4α,
12aα)]-4-(Dimethylamino)-9-[[(4-fluorophenoxy)
acetyl]amino]-1,4,4a,5,5a,6,11,12a-octahydro-3,10,12,
12a-tetrahydroxy-7-iodo-1,11-dioxo-2-
naphthacenecarboxamide.

EXAMPLE 67

[7S-(7α,
10aα)]-N-[9-(Aminocarbonyl)-4,7-Bis(dimethylamino-
5,5a,6,6a,7,10,10a,12-octahydro-1,8,10a,11-
tetrahydroxy-
10,12-dioxo-2-naphthacenyl]-2-thiopheneacetamide.

EXAMPLE 68

[4S-(4α,
12aα)]-9-[[(Diethylamino)acetyl]amino]-4,7-bis
(dimethylamino)- 1,4,4a,5,5a,6,11,12a-octahydro-3,
10,12,12a-tetrahydroxy-1,11-dioxo-2-
naphthacenecarboxamide.

EXAMPLE 69

[4S-(4α,
12aα)]-4-(Dimethylamino)-1,4,4a,5,5a,6,11,12a-
octahydro-
3,10,12,12a-tetrahydroxy-7-iodo-9-[[(methylthio)
acetyl]amino]-1,11-dioxo-2-naphthacenecarboxamide.

EXAMPLE 70

[4S-(4α,
12aα)]-4-(Dimethylamino)-1,4,4a,5,5a,6,11,12a-
octahydro-
3,10,12,12a-tetrahydroxy-7-[(1-methylethyl)
amino]-1,11-dioxo-9-[(3,3,3-trichloro-1-oxopropyl)
amino]-2-naphthacenecarboxamide.

EXAMPLE 71

[4S-(4α,
12aα)]-4,7-Bis(dimethylamino)-9-[(1,3-dioxo-3-
phenylpropyl)amino]-1,4,4a,5,5a,6,11,12a-octahydro-
3,10,12,12a-tetrahydroxy-1,12-dioxo-2-
naphthacenecarboxamide.

EXAMPLE 72

[4S-(4α,
12aα)]-4,7-Bis(dimethylamino)-9-[4-(dimethylamino)-
1-oxobutyl]-1,4,4a,5,5a,6,11,12a-octahydro-
3,10,12,12a-tetrahydroxy-1,11-dioxo-2-
naphthacenecarboxamide.

EXAMPLE 73

[4S-(4α,
12aα)]-4-(Dimethylamino)-1,4,4a,5,5a,6,11,12a-
octahydro- 3,10,12,12a-tetrahydroxy-1,11-dioxo-9-
[[(phenylsulfonyl)acetyl]amino]-2-
naphthacenecarboxamide.

EXAMPLE 74

[7S-(7α,
10aα)]-N-[9-(Aminocarbonyl)-7-(dimethylamino)-
5,5a,6,6a,7,10,10a-octahydro-1,8,10a,11-tetrahydroxy-
4-iodo-10,12-dioxo-2-naphthacenyl]-5-methyl-2-
furanacetamide.

EXAMPLE 75

[7S-(7α,
10aα)]-N-[9-(Aminocarbonyl)-4,7-bis(dimethylamino)-
5,5a,6,6a,7,10,10a,12-octahydro-1,8,10a,11-
tetrahydroxy-
10,12-dioxo-2-naphthacenyl]-2-thiazoleacetamide.

EXAMPLE 76

[7S-(7α,
10aα)]-2-[[[9-(Aminocarbonyl)-4,7-bis(dimethylamino-
5,5a,6,6a,7,10,10a,12-octahydro-1,8,10a,11-
tetrahydroxy-
10,12-dioxo-2-naphthacenyl]amino]carbonyl]benzoic
acid.

EXAMPLE 77

[7S-(7α,
10aα)]-N-[9-(Aminocarbonyl)-4,7-bis(dimethylamino-
5,5a,6,6a,7,10,10a,12-octahydro-1,8,10a,11-
tetrahydroxy-
10,12-dioxo-2-naphthacenyl]-3-methyl-2-oxo-
1-imidazolidineacetamide.

EXAMPLE 78

[7S-(7α,
10aα)]-N-[9-(Aminocarbonyl)-4,7-bis(dimethylamino)-
5,5a,6,6a,7,10,10a,12-octahydro-1,8,10a,11-
tetrahydroxy- 10,12-dioxo-2-naphthacenyl]-5,6-
dimethylpyrazinecarboxamide.

EXAMPLE 79

[7S-(7α,
10aα)]-N-[9-(Aminocarbonyl)-4,7-bis(dimethylamino)-
5,5a,6,6a,7,10,10a,12-octahydro-1,8,10a,11-tetrahydroxy
10,12-dioxo-2-naphthacenyl]-3-methyl-
3H-imidazo[4,5-b]pyridine-2-acetamide.

EXAMPLE 80

[4S-(4α,
12aα)]-4,7-Bis(dimethylamino)-1,4,4a,5,5a,6,
11,12a-octahydro-3,10,12,12a-tetrahydroxy-1,11-dioxo-
9-[[(pentafluorophenyl)acetyl]amino]-2-
naphthacenecarboxamide.

EXAMPLE 81

[7S-(7α,
10aα)]-N-[9-(Aminocarbonyl)-4,7-bis(dimethylamino)-
5,5a,6,6a,7,10,10a,12-octahydro-1,8,10a,11-
tetrahydroxy-
4-iodo-10,12-dioxo-2-naphthacenyl]-4-ethyl-
2,3-dioxo-1-piperazinecarboxamide.

EXAMPLE 82

[7S-(7α,
10aα)]-N-[9-(Aminocarbonyl)-4,7-bis(dimethylamino)-
5,5a,6,6a,7,10,10a,12-octahydro-1,8,10a,11-
tetrahydroxy-
10,12-dioxo-2-naphthacenyl]-4-ethyl-2,3-dioxo-
1-piperazinecarboxamide.

EXAMPLES 83–86

Substantially following the methods described in detail
hereinabove in Example 44, the compounds of this invention listed below in Examples 83–86 are prepared.

EXAMPLE 83

[7S-(7α,
10aα)]-[2-[[9-Aminocarbonyl-4,7-bis(dimethylamino)-
5,5a,6,6a,7,10,10a,12-octahydro-1,8,10a,11-
tetrahydroxy-
1,12-dioxo-2-naphthacenyl]amino]-2-oxoethyl]
carbamic acid 1,1-dimethylethyl ester.

EXAMPLE 84

[7S-[2 (S,), (7α, 10aα)]]-[2-[
[9-(Aminocarbonyl)-4-(diethylamino)-
7-(dimethylamino)-5,5a,6,6a,7,10,10a,12-octahydro-
1,8,10a,11-tetrahydroxy-10,12-dioxo-2-naphthacenyl]
amino]-1-methyl-2-oxoethyl]carbamic acid
1,1-dimethylethyl ester.

EXAMPLE 85

[7S-[2(S,), (7α, 10aα) ]]-[2-[
[9-(Aminocarbonyl)-4,7-bis
(dimethylamino)-5,5a,6,6a,7,10,10a,12-octahydro-1,8,
10a,11-tetrahydroxy-10,12-dioxo-2-naphthacenyl]
amino]- 2-oxo-1-phenylethyl]carbamic acid
1,1-dimethylethyl ester.

EXAMPLE 86

[7S-[2(S,), (7α, 10aα)
]]-[4-[[9-(Aminocarbonyl)-4,7-bis
(dimethylamino)-5,5a,6,6a,7,10,10a,12-octahydro-1,8,
10a,11-tetrahydroxy-10,12-dioxo-2-naphthacenyl]
amino]-
3-[[(1,1-dimethylethoxy)carbonyl]amino]-4-oxobutanoic
acid 1,1-dimethylethyl ester.

EXAMPLES 87–91

Substantially following the methods described in detail hereinabove in Example 45, the compounds of this invention listed below in Examples 87–91 are prepared.

EXAMPLE 87

[4S-(4α,
12aα)]-9-[(Aminoacetyl)amino]-7-(diethylamino)-
4-(dimethylamino)-1,4,4a,5,5a,6,11,12a-octahydro-3,10,
12,12a-tetrahydroxy-1,11-dioxo-2-
naphthacenecarboxamide.

EXAMPLE 88

[4S-(4α,
9(S,),12aα)]-9-[(2-Amino-1-oxopropyl)amino]-7-
diethylamino)-
4-(dimethylamino)-1,4,4a,5,5a,6,11,12a-octahydro-
3,10,12,12a-tetrahydroxy-1,11-dioxo-2-
naphthacenecarboxamide.

EXAMPLE 89

[4S-(4α,
9(S,),12aα)]-9-[(Aminophenylacetyl)amino]-4,7-
(bis(dimethylamino)-
1,4,4a,5,5a,6,11,12a-octahydro-
3,10,12,12a-tetrahydroxy-1,11-dioxo-2-
naphthacenecarboxamide.

EXAMPLE 90

[7S-[2(S,),7α,
10aα)]]-3-Amino-4-[[9-(aminocarbonyl)-
4,7-bis(dimethylamino)-5,5a,6,6a,7,10,10a,12-
octahydro-
1,8,10a,11-tetrahydroxy-10,12-dioxo-2-naphthacenyl]
amino]-4-oxobutanoic acid.

EXAMPLE 91

[7S-[2(S,),7α,
10aα)]]-4-[[9-(Aminocarbonyl)-4,7-bis
(dimethylamino)-
5,5a,6,6a,7,10,10a,12-octahydro-1,8,10,
10a-tetrahydroxy-10,12-dioxo-2-naphthacenyl]
amino]-3-(dimethylamino)- 4-oxobutanoic acid.

EXAMPLES 92–94

Substantially following the methods described in detail hereinabove in Example 47, the compounds of this invention listed below in Examples 92–94 are prepared.

EXAMPLE 92

[4S-(4α, 12aα)]-4-(Dimethylamino)-9-[[(2,2-dimethylpropyl) sulfonyl]amino]-',4,4a,5,5a,6,11,12a-octahydro-3,10,12,12a-tetrahydroxy-7-[(1-methylethyl)amino]-1,11-dioxo- 2-naphthacenecarboxamide.

EXAMPLE 93

[7S-(7α, 10aα)]-4-[[[9-(Aminocarbonyl)-4,7-bis(dimethylamino)-5,5a,6,6a,7,10,10a,12-octahydro-1,8,10,10a,11-tetrahydroxy-10,12-dioxo-2-naphthacenyl]amino]sulfonyl]butanoic acid.

EXAMPLE 94

[4S-(4α, 12aα)]-4-(Dimethylamino)-9-[[(1,1-dimethylethyl) sulfonyl-] amino]-1,4,4a,5,5a,6,11,12a-octahydro-3,10,12,12a-tetrahydroxy-7-iodo-1,11-dioxo-2-naphthacenecarboxamide.

EXAMPLE 95

[4S-(4α, 12aα)]-4,7-Bis(dimethylamino)-9-[[(diethylamino) acetyl]amino]-1,4,4a,5,5a,6,11,12a-octahydro-3,10,12,12a-tetrahydroxy-1,11-dioxo-2-naphthacenecarboxamide sulfate The title compound is prepared by the procedure of Example 46, using 0.030 g of product from Example 45, 0.020 g of 10% palladium-on-carbon, 2.5 equivalents of acetaldehyde, 1.5 ml of 2-methoxyethanol and 0.175 ml of 2N sulfuric acid to give the desired product as a solid.

EXAMPLE 96

Dimethylaminoacetyl chloride hydrochloride

A mixture of 15 g of N,N-dimethylglycine hydrochloride (pulverized and dried in a vacuum oven at 45°–50° C. for 24 hours) and 13.85 ml of thionyl chloride is heated, very slowly, in a sand bath to 78° C. and kept at this temperature for 1½ hours. Toluene is added to the mixture and the excess liquid is removed by pipette. This step is repeated several times. The solid is then transferred to a Buchner funnel, washed with methylene chloride and dried under vacuum at 50° C. for 24 hours to yield 14.2 g of the desired intermediate.

EXAMPLE 97

[4S-(4alpha,12aalpha)]-4,7-Bis(dimethylamino)-9-[[(dimethylamino)acetyl] amino]-1,4,4a,5,5a,6,11,12a-octahydro-3,10,12,12a-tetrahydroxy-1,11l-dioxo-2-naphthacenecarboxamide dihydrochloride To a mixture of 6.68 g of 9-amino-4,7-bis(dimethylamino)- 6-demethyl-6-deoxytetracycline in 120 ml of DMPU and acetonitrile is added 6.57 g of sodium carbonate. The mixture is stirred for 5 minutes, followed by the addition of 2.83 g of product from Example 96. The reaction is stirred for 1 hour, filtered and the filtrate is added slowly to a mixture of methylene chloride/diethyl ether (1200 ml/400 ml). The solid is collected, dissolved in 250 ml methyl alcohol and added slowly to 1600 ml of methylene chloride. The precipitate is collected, washed with diethyl ether and dried to give 5.75 g of the desired product.
MS (FAB): m/z 558 (M+H).

EXAMPLE 98

[4S-(4alpha,12aalpha)]-9-[(Chloroacetyl)amino]-4,7-bis(dimethylamino)-1,4,4a,5,5a,6,11,12a-octahydro-3,10,12,12a-tetrahydroxy-1,11-dioxo-2-naphthacenecarboxamide dihydrochloride To a room temperature solution of 0.334 g of 9-amino-4,7-bis(dimethyamino)-6-demethyl-6-deoxytetracycline sulfate, 6 ml of 1,3-dimethyl-3,4,5,6-tetrahydro- 2(1H)pyrimidinone, hereinafter called DMPU, and 2 ml of acetonitrile is added 0.318 g of sodium carbonate. The mixture is stirred for 5 minutes followed by the addition of 0.068 g of chloroacetyl chloride. The reaction is stirred for 30 minutes, filtered, and the filtrate added drowise to 100 ml of diethyl ether, containing 1 ml of 1M hydrochloric acid in diethyl ether. The resulting solid is collected and dried to give 0.340 g of the desired product.
MS (FAB): m/z 549 (M+H).

EXAMPLE 99

[4S-(4alpha,12aalpha]-9-[(Bromoacetyl)amino]-4,7-bis(dimethylamino)-1,4,4a,5,5a,6,11,12a-octahydro3,10,12,12a-tetrahydroxy-1,11-dioxo-2-naphthacenecarboxamide dihydrochloride The title compound is prepared by the procedure of Example 98, using 0.668 g of 9-amino-4,7-bis(dimethylamino)- 6-demethyl-6-deoxytetracycline sulfate, 6 ml of DMPU, 2 ml of acetonitrile, 0.636 g of sodium carbonate and 0.215 g of bromoacetyl chloride. Seven tenths of a gram of the desired product is obtained.
MS (FAB): m/z 593 (M+H).

EXAMPLE 100

[4S-(4alpha,12aalpha)]-9-[(Bromoacetyl) amino]-4,7-bis(dimethylamino)-1,4,4,5,5a,6,11,12a-octahydro-3,10,12,12a-tetrahydroxy-1,11-dioxo-2-naphthacenecarboxamide (free base)

To 0.20 g of product from Example 99 in 3 ml of 1,3-dimethyl-2-imidazolidenone is added 0.30 g of sodium bicarbonate. The reaction is stirred at room temperature for 15 minutes and filtered. The filtrate is added to 15 ml of diethyl ether and the resulting precipitate is collected to give 0.150 g of the desired product as the free base.

EXAMPLE 101

[4S-(4alpha,12aalpha)]-9-[(Bromoacetyl)amino]-4,7-bis(dimethylamino)-1,4,4a,5,5a,6,11,12a-octahydro-3,10,12,12a-tetrahydroxy-1,11-dioxo-2-naphthacenecarboxamide monohydrobromide To a solution of 5.01 g of 9-amino-4,7-bis(dimethylamino)- 6-demethyl-6-deoxytetracycline, 100 ml of DMPU and 25 ml of acetonitrile is added 5.0 g of sodium carbonate. The reaction is stirred, under argon, at room temperature for 5 minutes, followed by the addition of 3.03 g of bromoacetyl bromide. The stirring is continued for an additional hour. The solid is collected and the filtrate is added slowly to isopropyl alcohol/diethyl ether (200 ml/750 ml). The yellow solid is collected, washed with isopropanol and diethyl ether to give 5.77 g of the desired intermediate.
MS (FAB) :m/z 593 (M+H).

EXAMPLE 102

[4S-(4alpha,12aalpha)]-9-[(2-Bromo-1-oxopropyl)amino]-4,7-bis(dimethylamino)-1,4,4a,5,5a,6,11,12a-octahydro-3,10,12,12a-tetrahydroxy-1,11-dioxo-2-naphthacenecarboxamide hydrobromide The title compound is prepared by the procedure of Example 98, using 1.00 g of 9-amino-4,7-bis(dimethylamino)- 6-demethyl-6-deoxytetracycline, 1.0 g of sodium carbonate and 0.648 g of 2-bromopropionyl bromide to give 0.981 g of the desired product.
MS(FAB): m/z 607 (M+H).

EXAMPLE 103

[4S-(4alpha,12aalpha)]-9-[(4-Bromo-1-oxobutyl)amino]-4,7-bis(dimethylamino)-1,4,4a,5,5a,6,11,12a-octahydro-3,10,12,12a-tetrahydroxy-1,11-dioxo-2-naphthacenecarboxamide dihydrochloride The title compound is prepared by the procedure of Example 98, using 1.34 g of 9-amino-4,7-bis(dimethylamino)- 6-demethyl-6-deoxytetracycline sulfate, 1.3 g of sodium carbonate, 24 ml of DMPU, 8 ml of acetonitrile and 0.389 g of 4-bromobutyryl chloride to give 1.45 g of the desired product.

EXAMPLE 104

[4S-(4alpha,12aalpha)]-4,7-Bis(dimethylamino)-9-[[(dimethylamino)acetyl]amino]-1,4,4a,5,5a,6,11,12a-octahydro- 3,10,12,12a-tetrahydroxy-1,11-dioxo-2-naphthacenecarboxamide dihydrochloride To a solution of 0.15 g of product from Example 99 in 4 ml of DMPU is added 0.85 g of dimethylamine (40% in water). The reaction is stirred for 20 minutes followed by concentration in vacuo to remove any excess dimethylamine. The mixture is filtered and the filtrate added, dropwise, to 70 ml of isopropyl alcohol/diethyl ether (1:1). To this solution is added 1 ml of 1M hydrochloric acid/diethyl ether. The resulting precipitate is collected, washed with isopropyl alcohol and diethyl ether, and dried to give 0.11 g of the desired product.
MS (FAB): m/z 558 (M+H).

EXAMPLE 105

[4S-(4alpha,12aalpha)]-4,7-Bis(dimethylamino)-1,4,4a,-5,5a,6,11,12a-octahydro-3,10,12,12a-tetrahydroxy-9-[[(methylamino)acetyl]amino]-1,11-dioxo-2-naphthacenecarboxamide dihydrochloride
(331,256)

A mixture of 0.1258 g of product from Example 99, 5 ml of 40% methylamine in water and 5 ml of methyl alcohol, under Argon, is stirred at room temperature for 30 minutes. The excess methylamine is removed in vacuo and the residue diluted with a small volume of methyl alcohol. The diluted reaction solution is added dropwise to 100 ml of diethyl ether containing 1 ml of 1M hydrochloric acid in diethyl ether and 10 ml of isopropyl alcohol. The resulting solid is collected and dried to give 0.106 g of the desired product.
MS (FAB): m/z 544 (M+H).

Substantially following the methods described in detail herein above in Example 105, the compounds of this invention listed below in Examples 106–125 are prepared.

| Example # | Name | Starting Material Prod. of Exp. | Reactant | Rx Time | MS(FAB): m/z |
|---|---|---|---|---|---|
| 106 | [7S-(7alpha,10aalpha)]-N-[9-(Aminocarbonyl)-4,7-bis(dimethylamino)-5,5a,6,6a,7,10,10a,11-tetrahydroxy-10,12-dioxo-2-naphthacenyl]-4-morpholineacetamide dihydrochloride. | 99 | Morpholine | 0.5 hr. | 600(M+H) |
| 107 | [4S-(4alpha,12aalpha)]-4,7-Bis(dimethylamino)-9-[[(ethylamino)acetyl]amino]-1,4,4a,5,5a,6,11,12a-octahydro-3,10,-12,12a-tetrahydroxy-1,11-dioxo-2-naphthacenecarboxamide dihydrochloride. | 99 | Ethylamine (70% in water) | 2 hr. | 558(M+H) |
| 108 | [4S-(4,alpha,12aalpha)]-9-[[(Cyclopropylamino)acetyl]amino]-4,7-bis(dimethylamino)-1,4,4a,5,5a,6,11,12a-octahydro-3,10,-12,12a-tetrahydroxy-1,11-dioxo-2-naphthacenecarboxamide dihydrochloride. | 99 | Cyclopropylamine | 2 hr. | 570(M+H) |
| 109 | [4S-(4alpha,12aaytpha)]-4,7-Bis(dimethylamino)-9-[[(butylamino)acetyl]amino]-1,4,4a,5,5a,6,11,12a-octahydro-3,10,12,-12a-tetrahydroxy-1,11-dioxo-2-naphthacenecarboxamide dihydrochloride. | 99 | Butylamine | 2 hr. | 586(M+H) |
| 110 | [4S-(4,alpha,12aalpha)[-9-[[(Diethylamino)acetyl]amino]-4,7-bis(dimethylamino)-1,4,4a,5,5a,6,11,12a-octahydro-3,12,12-12a-tetrahydroxy-1,11-dioxo-2-naphthacenecarboxamide dihy- | 99 | Diethylamine | 2 hr. | 586(M+H) |

| Example # | Name | Starting Material Prod. of Exp. | Reactant | Rx Time | MS(FAB): m/z |
|---|---|---|---|---|---|
| 111 | drochloride.<br>[7S-(7alpha,10aalpha)]-N-[9-(Aminocarbonyl)-4,7-bis(dimethyl-amino)-5,5a,6,6a,7,10,10a,12-octahydro-1,8,10a,11-tetrahydroxy-10,12-dioxo-2-naphthacenyl]-1-pyrrolidineacetamide dihydrochloride. | 99 | Pyrrolidine | 0.5 hr. | 584(M+H) |
| 112 | [4S-(4,alpha,12aalpha)]-4,7-Bis(dimethylamino)-1,4,4a,5,5a-6,11,12a-octahydro-3,10,12,12a-tetrahydroxy-9-[[[(2-methylpropyl)amino]acetyl]amino]-1,11-dioxo-2-naphthacenecarboxamide dihydrochloride. | 99 | Isobutylamine | 2 hr. | 586(M+H) |
| 113 | [7S-(7alpha,10aalpha)]-N-[9-(Aminocarbonyl)-4,7-bis(dimethylamino)-5,5a,6,6a,7,10,10a,12-octahydro-1,8,10a,11-tetrahydroxy-10,12-dioxo-2-naphthacenyl]-1-piperidineacetamide dihydrochloride. | 99 | Piperidine | 1 hr. | 598(M+H) |
| 114 | [7S-(7alpha,10aalpha)]-N-[9-(Aminocarbonyl)-4,7-bis(dimethylamino)-5,5a,6,6a,7,10,10a,12-octahydro-1,8,10a,11-tetrahydroxy-10,12-dioxo-2-naphthacenyl]-1H-imidazole-1-acetamide dihydrochloride. | 99 | Imidazole | 1 hr. | 579(M+H) |
| 115 | [4S-(4alpha,12aalpha)]-4,7-Bis(dimethylamino)-1,4,4a,5,5a-6,11,12a-octahydro-3,10,12,12a-tetrahydroxy-1,11-dioxo-9-[[(propylamino)acetyl]amino]-2-naphthacenecarboxamide dihydrochloride. | 99 | Propylamine | 0.75 hr. | 570(M+H) |
| 116 | [4S-(4alpha,12aalpha)]-4,7-Bis(dimethylamino)-9-[[dimethylamino)acetyl]amino]-1,4,4a,5,5a,6,11,12a-octahydro-3,10,12,12a-tetrahydroxy-1,11-dioxo-2-naphthacenecarboxamide disulfate. | 99 | Dimethylamine | 0.5 hr. | 558(M+H) |
| 117 | [4S-(4alpha,12aalpha)]-4,7-Bis(dimethylamino)-9-[[dimethylamino)acetyl]amino]-1,4,4a,5,5a,6,11,12a-octahydro-3,10,12,12a-tetrahydroxy-1,11-dioxo-2-naphthacenecarboxamide. | 99 | Dimethylamine | 0.5 hr. | 558(M+H) |
| 118 | [4S-(4alpha,12aalpha)]-4,7-Bis(dimethylamino)-9-[[(hexyl-amino)acetyl]amino]-1,4,4a,5,5a,6,11,12a-octahydro-3,10,12,-12a-tetrahydroxy-1,11-dioxo-2-naphthacenecarboxamide dihydrochloride. | 99 | n-Hexylamine | 2 hr. | 614(M+H) |
| 119 | [4S-(4alpha,12aalpha)]-4,7-Bis(dimethylamino)-9-[[2-(dimethylamino)-1-oxopropyl]amino]-1,4,4a,5,5a,6,11,12s-octahydro-3,10,12,12a-tetrahydroxy-1,11-dioxo-2-napthacenecarboxamide dihydrochloride. | 102 | Dimethylamine (40% in water) | 2.5 hr. | 572(M+H) |
| 120 | [4S-(4alpha,12aalpha)]-4,7-Bis(dimethylamino)-1,4,4a,5,5a,6,11,12a-octahydro-3,10,12,12a-tetrahydroxy-9-[[2-(methylamino)-1-oxopropyl]amino]-1,11-dioxo-2-naphthacenecarboxamide dihydrochloride. | 102 | Methylamine (40% in water) | 2 hr. | 558(M+H) |
| 121 | [7S-(7alpha,10aalpha)]-N-[9-(Aminocarbonyl)-4,7-bis(dimethylamino)-5,5a,6,6a,7,10,10a,12-octahydro-1,8,10a,11-tetrahydroxy-10,12-dioxo-2-naphthacenyl]-alpha-methyl-1-pyrrolidineacetamide dihydrochloride. | 102 | Pyrrolidine | 1 hr. | 598(M+H) |
| 122 | [4S-(4alpha,12aalpha)]-4,7-Bis(dimethylamino)-9-[[4-(dimethylamino)-1-oxobutyl[amino]-1,4,4a,5,5a,6,11,12a-octahydro-3,10,12,12a-tetrahydroxy-1,11-dioxo-2-napthacenecarboxamide dihydrochloride. | 103 | Dimethylamine (40% in water) | 2 hr. | 586(M+H) |
| 123 | [4S-(4alpha,12aalpha)]-9-[[(Butylmethylamino)acetyl]amino]-4,7-bis(dimethylamino)-1,4,4a,5,5a,6,11,12a-octahydro-3,10,12,12a-tetrahydroxy-1,11-dioxo-2-naphthacenecarboxamide dihydrochloride | 99 | N-Methylbutyl-amine | 2 hr. | 600(M+H) |
| 124 | [4S-(4alpha,12aalpha)]-4,7-Bis(dimethylamino)-1,4,4a,5,5a-6,11,12a-octahydro-3,10,12,12a-tetrahydroxy-1,11-dioxo-9-[[[(pentylamino)acetyl]amino]-2-naphthacenecarboxamide dihydrochloride. | 99 | Amylamine | 2 hr. | 600(M+H) |
| 125 | [4S-(4alpha,12aalpha)]-4,7-Bis(dimethylamino)-1,4,4a,5,5a-6,11,12a-octahydro-3,10,12,12a-tetrahydroxy-1,11-dioxo-9-[[[(phenylmethyl)amino]acetyl]amino]-2-naphthacenecarboxamide dihydrochloride. | 99 | Benzylamine | 1 hr. | 620(M+H) |

EXAMPLE 126

[7S-(7alpha,10aalpha)]-N-[2-[[9-(Aminocarbonyl)-4,7-bis(dimethylamino)-5,5a,6,6a,7,10a,12-octahydro-1,8,10a,11-tetrahydroxy-10,12-dioxo-2-naphthacenyl]amino]- 2-oxoethyl]glycine phenylmethyl ester To 0.30 g of benzylglycine hydrochloride in 3 ml of 1,3-dimethyl-2-imidazolidinone is added 0.60 g of sodium bicarbonate. The mixture is stirred at room temperature for 15 minutes and filtered. To the filtrate is added 0.20 g of product from Example 100. The reaction mixture is stirred at room temperature for 1 hour and then added to diethyl ether. The resulting solid is collected.

EXAMPLE 127

[7S-(7alpha,10aalpha)]-N-[2-[[9-(Aminocarbonyl)-4,7-bis (dimethylamino)- 5,5a,6,6a,7,10a,12-octahydro-1,8,10a,11-tetrahydroxy-10,12-dioxo,2-naphthacenyl]amino]- 2-oxoethyl]glycine One-tenth of a gram of product from Example 126 in 10 ml of monomethyl ethylene glycol is reduced catalytically, in a Parr shaker, with 0.10 g of 10% palladium on carbon, at 30 psi of hydrogen, for 2 hours. The reaction mixture is filtered and the filtrate concentrated to give 0.050 g of the desired product.
CI-MS: m/z 588 (M+H).

General Procedure for the Preparation of Mannich Bases

A mixture of 0.5 g of product from Example 117, 3 ml of t-butyl alcohol, 0.55 ml of 37% formaldehyde, and 0.55 ml of pyrrolidine, morpholine or piperidine is stirred at room temperature for 30 minutes followed by heating at 100° C. for 15 minutes. The reaction mixture is cooled to room temperature and triturated with diethyl ether and hexane. The solid is collected, washed with diethyl ether and hexane, and dried to give the desired product.
In this manner the following compounds are made:

EXAMPLE 128

S-(4alpha, 10aalpha]-4,7-Bis(dimethylamino)-9-[[(dimethylamino)acetyl]amino]-1,4,4a,5,5a,6,11,12a-octahydro- 3,10,12,12a-tetrahydroxy-1,11-dioxo-N-(1-pyrrolidinyl-methyl)- 2-naphthacenecarboxamide

EXAMPLE 129

[4S-(4alpha, 12aalpha)]-4,7-Bis (dimethylamino)-9-[[(dimethylamino)acetyl] amino]-1,4,4a, 5,5a, 6,11,12a-octahydro-3,10,12,12a-tetrahydroxy-1,11-dioxo-N-(4-morpholinyl-methyl)- 2-naphthacenecarboxamide

EXAMPLE 130

4S- (4alpha, 12aalpha)]-4,7-Bis (dimethylamino)9-[[(dimethylamino)acetyl] amino]-1,4,4a, 5,5a, 6,11,12a-octahydro-3,10,12,12a-tetrahydroxy-1,11-dioxo-N-(1-piperidinylmethyl)- 2-naphthacenecarboxamide

EXAMPLE 131

7s-(7alpha, 10aalpha)]-N-[9-(Aminocarbonyl)-4,7-bis (dimethylamino)- 5,5a, 6,6a,7,10,10a,12-octahydro-1,8, 10a, 11-tetrahydroxy-10, 12-dioxo-2-napthacenyl] -1-azetidineacetamide The title compound is prepared by the procedure of Example 105 using 0.20 g of product form Example 99, 0.50 g of azetidine and 5 ml of DMPU to give 0. 126 g of the desired product.
MS (FAB): m/z 570 (M+H).

EXAMPLE 132

[4S-(4alpha, 12aalpha)]-9-[[(Cyclobutylamino)acetyl]amino]-4,7-bis (dimethylamino),1,4,4a, 5,5a, 6,11,12a-octahydro-3,10,12,12a-tetrahydroxy-1,11-dioxo-2-naphthacenecarboxamide hydrochloride To a solution of 0.200 g of 9-(bromoacetylamino)- 7-dimethylamino-6-demethyl-6-deoxytetracycline in 2 ml of 1,3-demethyl-2-imidazolidinone is added 0.1 ml of cyclobutylamine. The resulting solution is stirred at room temperature for 45 minutes and then added to 50 ml of diethyl ether. An oil layer is formed and the diethyl ether layer is decanted and the oil is dissolved in 5 ml of 0.1N methanolic hydrogen chloride. The resulting solution is added to 50 ml of diethyl ether, yielding 0.050 g of solid.
MS(FAB): m/z 584(M+H)

We claim:

1. A compound of the formula:

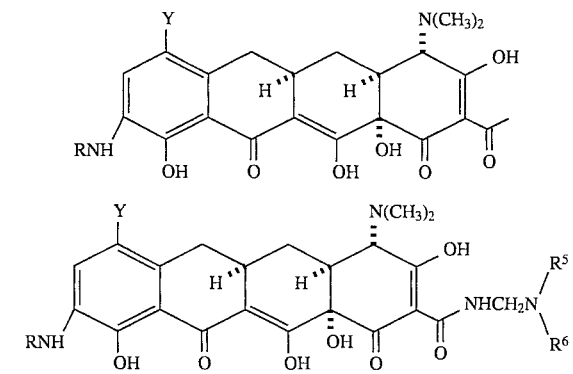

wherein

Y is $NO_2$;

R is selected from $R^4(CH_2)_nCO-$ or $R^{4'}(CH_2)_nSO_2-$; n is an integer between 0 and 4; and when $R=R^4(CH_2)_nCO-$ and n=0, $R^4$ is selected from amino; monosubstituted amino selected from straight or branched $(C_1-C_6)$alkylamino, cyclopropylamino, cyclobutylamino, benzylamino, and phenylamino; disubstituted amino selected from dimethylamino, diethylamino, ethyl(1-methylethyl)amino, monomethylbenzylamino, piperidinyl, morpholinyl, 1-imidazolyl, 1-pyrrolyl, 1-(1,2,3-triazolyl) and 4-( 1,2,4-triazolyl); $(C_3-C_6)$cycloalkyl group selected from cyclopropyl, cyclobutyl, cyclopentyl, and cyclohexyl; substituted $(C_3-C_6)$cycloalkyl group wherein the substitution is selected from $(C_1-C_3)$alkyl, cyano, amino and $(C_1-C_3)$acyl; $(C_6-C_{10})$aryl group selected from phenyl, α-napthyl or β-napthyl; substituted $(C_6-C_{10})$aryl wherein the substitution is selected from halo, $(C_1-C_4)$alkoxy, trihalo$(C_1-C_3)$alkyl, nitro, amino, cyano, $(C_1-C_4)$alkoxycarbonyl, $(C_1-C_3)$alkylamino and carboxy; $(C_7-C_9)$aralkyl group selected from benzyl, 1-phenylethyl, 2-phenylethyl and phenylpropyl; α-amino$(C_1-C_4)$alkyl group selected from α-aminomethyl, α-aminoethyl, α-aminopropyl and α-aminobutyl; carboxy$(C_2-C_4)$alkylamino group selected from aminoacetic acid, α-aminobutyric acide, α-aminoproprionic acid, and their optical isomers; $(C_7-C_9)$aralkylamino group; substituted $(C_1-C_4)$alkoxycarbonylamino group wherein the substitution is selected from phenyl or p-hydroxyphenyl; α-hydroxy$(C_1-C_3)$alkyl group selected from hydroxymethyl, α-hydroxyethyl, α-hydroxy-1-methylethyl and α-hydroxypropyl; α-mercapto$(C_1-C_3)$alkyl group selected from mercaptomethyl, α-mercaptoethyl, α-mercapto-1-methylethyl and α-mercaptopropyl; halo $(C_1-C_3)$alkyl group; a heterocycle group selected from a five membered aromatic or saturated ring with one N, O, S, or Se heteroatom optinally having a benzo or pyrido ring fused thereto selected from

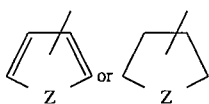

wherein Z is N, O, S, or Se;

a five membered aromatic ring with two N, O, S, or Se heteroatoms optionally having a benzo or pyrido ring fused thereto selected from

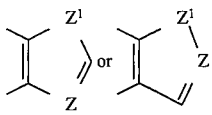

wherein Z and $Z_1$ are independently selected from N, O, S, and Se;

a five membered saturated ring with one or two N, O, S, or Se heteroatoms and an adjacent appended O heteroatom selected from

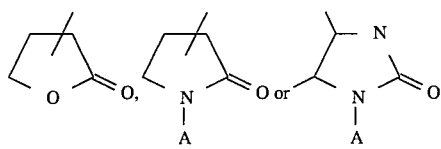

wherein A is selected from hydrogen; straight or branched ($C_1$–$C_4$)alkyl; $C_6$-aryl; substituted $C_6$-aryl wherein the substitution is selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino and carboxy; and ($C_7$–$C_9$)aralkyl group selected from benzyl, 1-phenylethyl, 2-phenylethyl and phenylpropyl;

a six membered aromatic ring with one to three N, O, S, or Se heteroatoms;

a six membered saturated ring with one or two N, O, S or Se heteroatoms and an adjacent appended O heteroatom; acyl or haloacyl group selected from acetyl, propionyl, chloroacetyl, trifluoroacetyl, ($C_3$–$C_6$)cycloalkylcarbonyl, ($C_6$–$C_{10}$)aroyl selected from benzoyl or napthoyl, halo-substituted ($C_6$–$C_{10}$)aroyl, ($C_1$–$C_4$)alkylbenzoyl, and (heterocycle)carbonyl wherein the heterocycle is selected from a five membered aromatic or saturated ring with one N, O, S, or Se heteroatom optinally having a benzo or pyrido ring fused thereto selected from

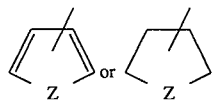

wherein Z is N, O, S, or Se;

a five membered aromatic ring with two N, O, S, or Se heteroatoms optionally having a benzo or pyrido ring fused thereto selected from

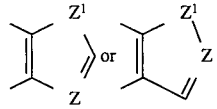

wherein Z and $Z_1$ are independently selected from N, O, S, and Se;

a five membered saturated ring with one or two N, O, S, or Se heteroatoms and an adjacent appended O heteroatom selected from

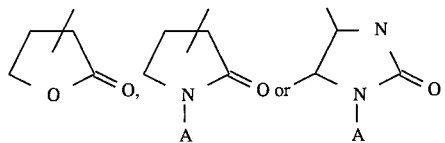

wherein A is selected from hydrogen; straight or branched ($C_1$–$C_4$)alkyl; $C_6$-aryl; substituted $C_6$-aryl wherein the substitution is selected from halo, ($C_1$–$C_4$)alkoxy, trihalo ($C_1$–$C_3$)alkyl, nitro, amino, cyano, ($C_1$–$C_4$)alkoxycarbonyl, ($C_1$–$C_3$)alkylamino and carboxy; and ($C_7$–$C_9$)aralkyl group selected from benzyl, 1-phenylethyl, 2-phenylethyl and phenylpropyl;

a six membered aromatic ring with one to three N, O, S, or Se heteroatoms;

a six membered saturated ring with one or two N, O, S or Se heteroatoms and an adjacent appended O heteroatom; ($C_1$–$C_4$)alkoxycarbonyl group selected from methoxycarbonyl, ethoxycarbonyl, straght or branched propoxycarbonyl, straight or branched butoxycarbonyl and allyloxycarbonyl; vinyl or substituted vinyl wherein the substitution is selected from ($C_1$–$C_3$)alkyl group; halogen; ($C_6$–$C_{10}$)aryl group selected from phenyl, α-napthyl, β-napthyl; substituted ($C_6$–$C_{10}$)aryl group wherein the substitution is selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino and carboxy; halo($C_1$–$C_3$)alkyl group; a heterocycle group selected from a five membered aromatic or saturated ring with one N, O, S, or Se heteroatom optionally having a benzo or pyrido ring fused thereto selected from

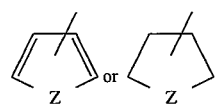

wherein Z is N, O, S, or Se; ($C_1$–$C_4$)alkoxy group; $C_6$-aryloxy group selected from phenoxy or substituted phenoxy where the substitution is selected from halo, ($C_1$–$C_4$)alkyl, nitro, cyano, thiol, amino, carboxy, and di($C_1$–$C_3$)alkylamino; ($C_7$–$C_{10}$)aralkoxy group; vinyloxy or substituted vinyloxy group wherein the substitution is selected from ($C_1$–$C_4$)alkyl, cyano, carboxy, and ($C_6$–$C_{10}$)aryl selected from phenyl, α-napthyl, and β-napthyl; $R^aR^b$amino($C_1$–$C_4$)alkoxy or $R^aR^b$aminoxy group wherein $R^aR^b$ is selected from a straight or branched ($C_1$–$C_4$)alkyl selected from methyl, ethyl, n-propyl, 1-methylethyl, n-butyl, 1-methylpropyl, 2-methylpropyl, 1,1-dimethylethyl, $(CH_2)_n$ where n is from 2 to 6, and —$(CH_2)_2W(CH_2)_2$— wherein W is selected from —N($C_1$–$C_3$)alkyl wherein alkyl is straight or branched, —NH, NOB where B is selected from hydrogen or ($C_1$–$C_4$)alkyl, O, and S; and when R=$R^4(CH_2)_n$CO— and n=1–4, $R^4$ is selected from amino; ($C_3$–$C_6$)cycloalkyl group selected from cyclopropyl, cyclobutyl, cyclopentyl, and cyclohexyl; substituted ($C_3$–$C_6$)cycloalkyl group wherein the substitution is selected from ($C_1$–$C_3$)alkyl, cyano, amino and ($C_1$–$C_3$)acyl; ($C_6$–$C_{10}$)aryl group selected from phenyl, α-napthyl or β-napthyl; substituted ($C_6$–$C_{10}$)aryl wherein the substitution is selected from halo, ($C_1$–$C_4$)alkoxy, trihalo ($C_1$–$C_3$)alkyl, nitro, amino, cyano, ($C_1$–$C_4$)alkoxycarbonyl, ($C_1$–$C_3$)alkylamino and carboxy; ($C_7$–C9)aralkyl group; acyloxy or haloacyloxy group wherein the acyl or haloacyl is selected from acetyl, propionyl, chloroacetyl, trifluoroacetyl, ($C_3$–$C_6$)cycloalkylcarbonyl,($C_6$–$C_{10}$)aroyl selected from benzoyl or napthoyl, halo-substituted($C_6$–$C_{10}$)aroyl, ($C_1$–$C_4$)alkylbenzoyl, and (heterocycle)carbonyl wherein the heterocycle is selected from a five membered aromatic or saturated ring with one N, O, S, or Se heteroatom optinally having a benzo or pyrido ring fused thereto selected from

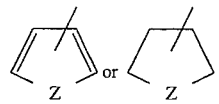

wherein Z is N, O, S, or Se;

a five membered aromatic ring with two N, O, S, or Se heteroatoms optionally having a benzo or pyrido ring fused thereto selected from

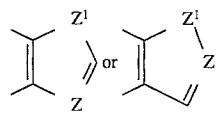

wherein Z and $Z_1$ are independently selected from N, O, S, and Se;

a five membered saturated ring with one or two N, O, S, or Se heteroatoms and an adjacent appended O heteroatom selected from

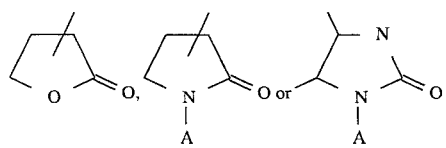

wherein A is selected from hydrogen; straight or branched ($C_1$–$C_4$)alkyl; $C_6$-aryl; substituted $C_6$-aryl wherein the substitution is selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino and carboxy; and ($C_7$–$C_9$)aralkyl group selected from benzyl, 1-phenylethyl, 2-phenylethyl and phenylpropyl;

a six membered aromatic ring with one to three N, O, S, or Se heteroatoms;

a six membered saturated ring with one or two N, O, S or Se heteroatoms and an adjacent appended O heteroatom; ($C_1$–$C_4$)alkoxy group; $C_6$-aryloxy group selected from phenoxy or substituted phenoxy where the substitution is selected from halo, ($C_1$–$C_4$)alkyl, nitro, cyano, thiol, amino, carboxy, and di($C_1$–$C_3$)alkylamino; ($C_7$–$C_{10}$)aralkoxy group; ($C_1$–$C_3$)alkylthio group selected from methylthio, ethylthio, propylthio or allylthio; $C_6$-arylthio group selected from phenylthio or substituted phenylthio wherein the substitution is selected from halo, ($C_1$–$C_4$)alkyl, nitro, cyano, thiol, amino, carboxy, and di($C_1$–$C_3$)alkylamino; $C_6$-arylsulfonyl group selected from phenylsulfonyl or substituted phenylsulfonyl wherein the substitution is selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino, and carboxy; ($C_7$–$C_8$)aralkylthio group; a heterocycle group selected from a five membered aromatic or saturated ring with one N, O, S, or Se heteroatom optinally having a benzo or pyrido ring fused thereto selected from

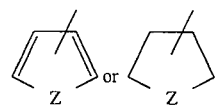

wherein Z is N, O, S, or Se;

a five membered aromatic ring with two N, O, S, or Se heteroatoms optionally having a benzo or pyrido ring fused thereto selected from

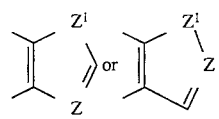

wherein Z and $Z_1$ are independently selected from N, O, S, and Se;

a five membered saturated ring with one or two N, O, S, or Se heteroatoms and an adjacent appended O heteroatom selected from

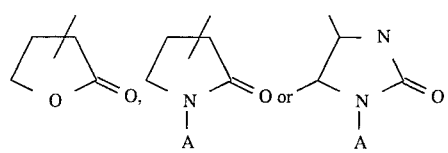

wherein A is selected from hydrogen; straight or branched ($C_1$–$C_4$)alkyl; $C_6$-aryl; substituted $C_6$-aryl wherein the substitution is selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino and carboxy; and ($C_7$–$C_9$)aralkyl group selected from benzyl, 1-phenylethyl, 2-phenylethyl and phenylpropyl;

a six membered aromatic ring with one to three N, O, S, or Se heteroatoms;

a six membered saturated ring with one or two N, O, S or Se heteroatoms and an adjacent appended O heteroatom; hydroxy group; mercapto group; mono- or di- straight or branched chain ($C_1$–$C_6$)alkylamino group wherein alkyl is selected from methyl, ethyl, n-propyl, 1-methylethyl, n-butyl, 1-methylpropyl, 2-methylpropyl, 1,1-dimethylethyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 2-methylpentyl, 1,2-dimethylbutyl, 1,3-dimethylbutyl, and 1-methyl-1-ethylpropyl; ($C_2$–$C_5$)azacycloalkyl group; carboxy($C_2$–$C_4$)alkylamino group selected from aminoacetic acid, α-aminopropionic acid, α-aminobutyric acid and their optical isomers; α-hydroxy($C_1$–$C_3$)alkyl group selected from hydroxymethyl, α-hydroxyethyl, α-hydroxy-1-methylethyl, and α-hydroxypropyl; halo($C_1$–$C_3$)alkyl group; acyl or haloacyl group selected from acetyl, propionyl, chloroacetyl, trifluoroacetyl, ($C_3$–$C_6$)cycloalkylcarbonyl, ($C_6$–$C_{10}$)aroyl selected from benzoyl or napthoyl, halo-substituted($C_6$–$C_{10}$)aroyl, ($C_1$–$C_4$)alkylbenzoyl, and (heterocycle)carbonyl wherein the heterocycle is selected from a five membered aromatic or saturated ring with one N, O, S, or Se heteroatom optinally having a benzo or pyrido ring fused thereto selected from

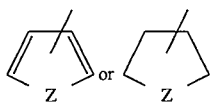

wherein Z is N, O, S, or Se;

a five membered aromatic ring with two N, O, S, or Se heteroatoms optionally having a benzo or pyrido ring fused thereto selected from

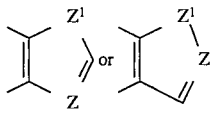

wherein Z and $Z_1$ are independently selected from N, O, S, and Se;

a five membered saturated ring with one or two N, O, S, or Se heteroatoms and an adjacent appended O heteroatom selected from

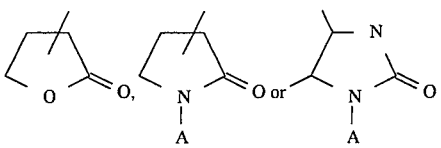

wherein A is selected from hydrogen; straight or branched ($C_1$–$C_4$)alkyl; $C_6$-aryl; substituted $C_6$-aryl wherein the substitution is selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino and carboxy; and ($C_7$–$C_9$)aralkyl group selected from benzyl, 1-phenylethyl, 2-phenylethyl and phenylpropyl;

a six membered aromatic ring with one to three N, O, S, or Se heteroatoms;

a six membered saturated ring with one or two N, O, S or Se heteroatoms and an adjacent appended O heteroatom; ($C_1$–$C_4$)alkoxycarbonylamino group selected from tert-butoxycarbonylamino, allyloxycarbonylamino, methoxycarbonylamino, ethoxycarbonylamino, and propoxycarbonylamino; ($C_1$–$C_4$)alkoxycarbonyl group selected from methoxycarbonyl, ethoxycarbonyl, straight or branched propoxycarbonyl, allyloxycarbonyl, and straight or branched butoxycarbonyl; $R^aR^b$amino($C_1$–$C_4$)alkoxy or $R^aR^b$aminoxy group wherein $R^aR^b$ is selected from a straight or branched ($C_1$–$C_4$)alkyl selected from methyl, ethyl, n-propyl, 1-methylethyl, n-butyl, 1-methylpropyl, 2-methylpropyl, 1,1-dimethylethyl, $(CH_2)_n$ where n is from 2 to 6, and —$(CH_2)_2W(CH_2)_2$— wherein W is selected from —N($C_1$–$C_3$)alkyl wherein alkyl is straight or branched, —NH, NOB where B is selected from hydrogen or ($C_1$–$C_4$)alkyl, O, and S; and when R=$R^{4'}(CH_2)_nSO_2$— and n=0, $R^{4'}$ is selected from amino; monosubstituted amino selected from straight or branched ($C_1$–$C_6$)alkylamino, cyclopropylamino, cyclobutylamino, benzylamino, and phenylamino; disubstituted amino selected from dimethylamino, diethylamino, ethyl(1-methylethyl)amino, monomethylbenzylamino, piperidinyl, morpholinyl, 1-imidazolyl, 1-pyrrolyl, 1-(1,2,3-triazolyl) and 4-( 1,2,4-triazolyl); straight or branched ($C_1$–$C_4$)alkyl group selected from methyl, ethyl, n-propyl, 1-methylethyl, n-butyl, 1-methylpropyl, 2-methylpropyl, and 1,1-dimethylethyl; ($C_3$–$C_6$)cycloalkyl group selected from cyclopropyl, cyclobutyl, cyclopentyl, and cyclohexyl; substituted ($C_3$–$C_6$)cycloalkyl group wherein the substitution is selected from ($C_1$–$C_3$)alkyl, cyano, amino and ($C_1$–$C_3$)acyl; ($C_6$–$C_{10}$)aryl group selected from phenyl, α-napthyl or β-napthyl; substituted ($C_6$–$C_{10}$)aryl wherein the substitution is selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino and carboxy; ($C_7$–$C_9$)aralkyl group; halo ($C_1$–$C_3$)alkyl group; a heterocycle group selected from a five membered aromatic or saturated ring with one N, O, S, or Se heteroatom optinally having a benzo or pyrido ring fused thereto selected from

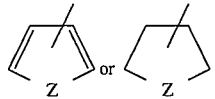

wherein Z is N, O, S, or Se;

a five membered aromatic ring with two N, O, S, or Se heteroatoms optionally having a benzo or pyrido ring fused thereto selected from

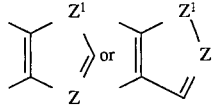

wherein Z and $Z_1$ are independently selected from N, O, S, and Se;

a five membered saturated ring with one or two N, O, S, or Se heteroatoms and an adjacent appended O heteroatom selected from

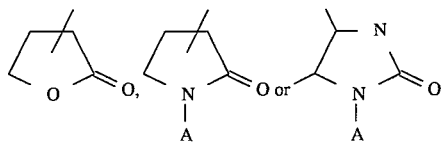

wherein A is selected from hydrogen; straight or branched ($C_1$–$C_4$)alkyl; $C_6$-aryl; substituted $C_6$-aryl wherein the substitution is selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino and carboxy; and ($C_7$–$C_9$)aralkyl group selected from benzyl, 1-phenylethyl, 2-phenylethyl and phenylpropyl;

a six membered aromatic ring with one to three N, O, S, or Se heteroatoms;

a six membered saturated ring with one or two N, O, S or Se heteroatoms and an adjacent appended O heteroatom; $R^aR^b$amino($C_1$–$C_4$)alkoxy or $R^aR^b$aminoxy group wherein $R^aR^b$ is selected from a straight or branched ($C_1$–$C_4$)alkyl selected from methyl, ethyl, n-propyl, 1-methylethyl, n-butyl, 1-methylpropyl, 2-methylpropyl, 1,1-dimethylethyl, $(CH_2)_n$ where n is from 2 to 6, and —$(CH_2)_2W(CH_2)_2$— wherein W is selected from —N($C_1$–$C_3$)alkyl wherein alkyl is straight or branched, —NH, NOB where B is selected from hydrogen or ($C_1$–$C_4$)alkyl, O, and S; and when R=$R^{4'}(CH_2)_nSO_2$— and n=1–4, $R^4$ is selected from hydrogen; amino; straight or branched ($C_1$–$C_4$)alkyl group selected from methyl, ethyl, n-propyl, 1-methylethyl, n-butyl, 1-methylpropyl, 2-methylpropyl, and 1,1-dimethylethyl; ($C_1$–$C_4$)carboxyalkyl group; ($C_3$–$C_6$)cycloalkyl group selected from cyclopropyl, cyclobutyl, cyclopentyl, and cyclohexyl; substituted ($C_3$-$C_6$)cycloalkyl group wherein the substitution is selected from ($C_1$-$C_3$)alkyl, cyano, amino and ($C_1$-$C_3$)acyl; ($C_6$-$C_{10}$)aryl group selected from phenyl, α-napthyl or β-napthyl; substituted ($C_6$-$C_{10}$)aryl wherein the substitution is selected from halo, ($C_1$-$C_4$)alkoxy, trihalo($C_1$-$C_3$)alkyl, nitro, amino, cyano, ($C_1$-$C_4$)alkoxycarbonyl, ($C_1$-$C_3$)alkylamino and carboxy; ($C_7$-$C_9$)aralkyl group selected from benzyl, 1-phenylethyl, 2-phenylethyl and phenylpropyl; ($C_1$-$C_4$)alkoxy group; $C_6$-aryloxy group selected from phenoxy or substituted phenoxy where the substitution is selected from halo, ($C_1$-$C_4$)alkyl, nitro, cyano, thiol, amino, carboxy, and di($C_1$-$C_3$)alkylamino; ($C_7$-$C_{10}$)aralkoxy group; $R^aR^b$amino($C_1$-$C_4$)alkoxy or $R^aR^b$aminoxy group wherein $R^aR^b$ is selected from a straight or branched ($C_1$-$C_4$)alkyl selected from methyl, ethyl, n-propyl, 1-methylethyl, n-butyl, 1-methylpropyl, 2-methylpropyl, 1,1-dimethylethyl, $(CH_2)_n$ where n is from 2 to 6, and —$(CH_2)_2W(CH_2)_2$— wherein W is selected from —$N(C_1$-$C_3)$alkyl wherein alkyl is straight or branched, —NH, NOB where B is selected from hydrogen or ($C_1$-$C_4$)alkyl, O, and S; ($C_1$-$C_3$)alkylthio group selected from methylthio, ethylthio, propylthio or allylthio; $C_6$-arylthio group selected from phenylthio or substituted phenylthio wherein the substitution is selected from halo, ($C_1$-$C_4$)alkyl, nitro, cyano, thiol, amino, carboxy, and di($C_1$-$C_3$)alkylamino; ($C_7$-$C_8$)aralkylthio group; a heterocycle group selected from a five membered aromatic or saturated ring with one N, O, S, or Se heteroatom optinally having a benzo or pyrido ring fused thereto selected from

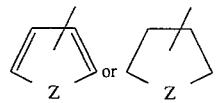

wherein Z is N, O, S, or Se;

a five membered aromatic ring with two N, O, S, or Se heteroatoms optionally having a benzo or pyrido ring fused thereto selected from

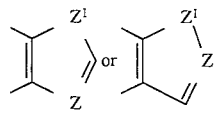

wherein Z and $Z_1$ are independently selected from N, O, S, and Se;

a five membered saturated ring with one or two N, O, S, or Se heteroatoms and an adjacent appended O heteroatom selected from

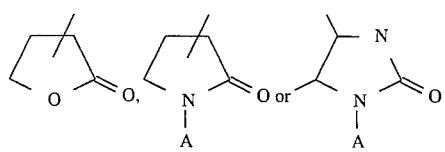

wherein A is selected from hydrogen; straight or branched ($C_1$-$C_4$)alkyl; $C_6$-aryl; substituted $C_6$-aryl wherein the substitution is selected from halo, ($C_1$-$C_4$)alkoxy, trihalo($C_1$-$C_3$)alkyl, nitro, amino, cyano, ($C_1$-$C_4$)alkoxycarbonyl, ($C_1$-$C_3$)alkylamino and carboxy; and ($C_7$-$C_9$)aralkyl group selected from benzyl, 1-phenylethyl, 2-phenylethyl and phenylpropyl;

a six membered aromatic ring with one to three N, O, S, or Se heteroatoms;

a six membered saturated ring with one or two N, O, S or Se heteroatoms and an adjacent appended O heteroatom; hydroxy group; mercapto group; mono- or distraight or branched chain ($C_1$-$C_6$)alkylamino group wherein alkyl is selected from methyl, ethyl, n-propyl, 1-methylethyl, n-butyl, 1-methylpropyl, 2-methylpropyl, 1,1-dimethylethyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 2-methylpentyl, 1,2-dimethylbutyl, 1,3-dimethylbutyl, and 1-methyl-1-ethylpropyl; acyl or haloacyl group selected from acetyl, propionyl, chloroacetyl, trifluoroacetyl, ($C_3$-$C_6$)cycloalkylcarbonyl, ($C_6$-$C_{10}$)aroyl selected from benzoyl or napthoyl, halo-substituted($C_6$-$C_{10}$)aroyl, ($C_1$-$C_4$)alkylbenzoyl, and (heterocycle)carbonyl wherein the heterocycle is selected from a five membered aromatic or saturated ring with one N, O, S, or Se heteroatom optinally having a benzo or pyrido ring fused thereto selected from

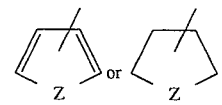

wherein Z is N, O, S, or Se;

a five membered aromatic ring with two N, O, S, or Se heteroatoms optionally having a benzo or pyrido ring fused thereto selected from

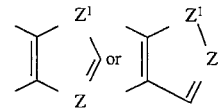

wherein Z and $Z_1$ are independently selected from N, O, S, and Se;

a five membered saturated ring with one or two N, O, S, or Se heteroatoms and an adjacent appended O heteroatom selected from

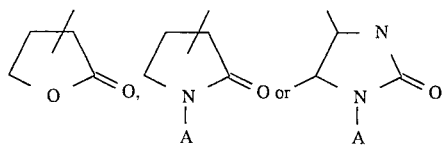

wherein A is selected from hydrogen; straight or branched ($C_1$-$C_4$)alkyl; $C_6$-aryl; substituted $C_6$-aryl wherein the substitution is selected from halo, ($C_1$-$C_4$)alkoxy, trihalo($C_1$-$C_3$)alkyl, nitro, amino, cyano, ($C_1$-$C_4$)alkoxycarbonyl, ($C_1$-$C_3$)alkylamino and carboxy; and ($C_7$-$C_9$)aralkyl group selected from benzyl, 1-phenylethyl, 2-phenylethyl and phenylpropyl;

a six membered aromatic ring with one to three N, O, S, or Se heteroatoms;

a six membered saturated ring with one or two N, O, S or Se heteroatoms and an adjacent appended O heteroatom; ($C_1$-$C_4$)alkoxycarbonyl group selected from methoxycarbonyl, ethoxycarbonyl, straght or branched propoxycarbonyl, straight or branched butoxycarbonyl and allyloxycarbonyl;

147

$R^5$ is selected from hydrogen; straight or branched ($C_1$–$C_3$)alkyl group selected from methyl, ethyl, n-propyl, or 1-methylethyl; ($C_6$–$C_{10}$)aryl group selected from phenyl, α-napthyl, or β-napthyl; ($C_7$–$C_9$)aralkyl group; a heterocycle group selected from a five membered aromatic or saturated ring with one N, O, S, or Se heteroatom optionally having a benzo or pyrido ring fused thereto selected from

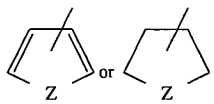

wherein Z is N, O, S, or Se;

a five membered aromatic ring with two N, O, S, or Se heteroatoms optionally having a benzo or pyrido ring fused thereto selected from

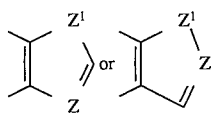

wherein Z and $Z_1$ are independently selected from N, O, S, and Se;

a five membered saturated ring with one or two N, O, S, or Se heteroatoms and an adjacent appended O heteroatom selected from

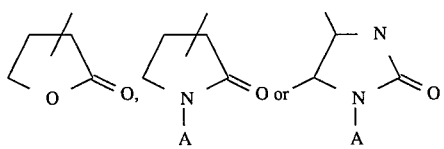

wherein A is selected from hydrogen; straight or branched ($C_1$–$C_4$)alkyl; $C_6$-aryl; substituted $C_6$-aryl wherein the substitution is selected from halo, ($C_1$–$C_4$)alkoxy, trihalo($C_1$–$C_3$)alkyl, nitro, amino, cyano, ($C_1$–$C_4$)alkoxycarbonyl, $C_1$–$C_3$)alkylamino and carboxy; and ($C_7$–$C_9$)aralkyl group selected from benzyl, 1-phenylethyl, 2-phenylethyl and phenylpropyl;

a six membered aromatic ring with one to three N, O, S, or Se heteroatoms;

a six membered saturated ring with one or two N, O, S or Se heteroatoms and an adjacent appended O heteroatom; —$(CH_2)_n COOR^7$ where n=0–4 and $R^7$ is selected from hydrogen; straight or branched ($C_1$–$C_3$)alkyl group selected from methyl, ethyl, n-propyl, or 1-methylethyl; and ($C_6$–$C_{10}$)aryl group selected from phenyl, α-naphthyl, or β-naphthyl;

$R^6$ is selected from hydrogen; straight or branched ($C_1$–$C_3$)alkyl group selected from methyl, ethyl, n-propyl, or 1-methylethyl; ($C_6$–$C_{10}$)aryl group selected from phenyl, α-napthyl, or β-napthyl; ($C_7$–$C_9$)aralkyl group; a heterocycle group selected from a five membered aromatic or saturated ring with one N, O, S, or Se heteroatom optinally having a benzo or pyrido ring fused thereto selected from

148

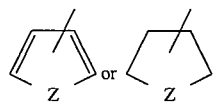

wherein Z is N, O, S, or Se;

a five membered aromatic ring with two N, O, S, or Se heteroatoms optionally having a benzo or pyrido ring fused thereto selected from

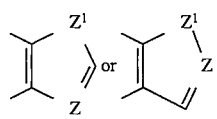

wherein Z and $Z_1$ are independently selected from N, O, S, and Se;

a five membered saturated ring with one or two N, O, S, or Se heteroatoms and an adjacent appended O heteroatom selected from

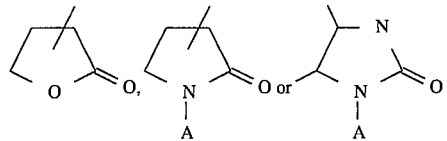

wherein A is selected from hydrogen; straight or branched ($C_1$–$C_4$)alkyl; $C_6$-aryl; substituted $C_6$-aryl wherein the substitution is selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino and carboxy; and ($C_7$–$C_9$)aralkyl group selected from benzyl, 1-phenylethyl, 2-phenylethyl and phenylpropyl;

a six membered aromatic ring with one to three N, O, S, or Se heteroatoms;

a six membered saturated ring with one or two N, O, S or Se heteroatoms and an adjacent appended O heteroatom; —$(CH_2)_n COOR^{7'}$ where n=0–4 and $R^{7'}$ is selected from hydrogen; straight or branched ($C_1$–$C_3$)alkyl group selected from methyl, ethyl, n-propyl, or 1-methylethyl; and ($C_6$–$C_{10}$)aryl group selected from phenyl, α-naphthyl, or β-naphthyl; with the proviso that $R^5$ and $R^6$ cannot both be hydrogen; or $R^5$ and $R^6$ taken together are —$(CH_2)_2 W(CH_2)_2$— wherein W is selected from $(CH_2)_n$ where n=0–1; —NH; —N($C_1$–$C_3$)alkyl where alkyl is straight or branched; —N($C_1$–$C_4$)alkoxy; O; S; and congeners selected from (L or D)proline, ethyl(L or D)prolinate, morphiline, pyrrolidine and piperidine; or a pharmacologically acceptable organic or inorganic salt or metal complex thereof.

2. The compound according to claim 1, wherein

Y is $NO_2$;

R is selected from $R^4$ $(CH_2)_n CO$— or $R^{4'}(CH_2)_n SO_2$—; n is an integer between 0 and 4; and when R=$R^4(CH_2)_n CO$— and n=0, $R^4$ is selected from amino; monosubstituted amino selected from straight or branched ($C_1$–$C_6$)alkylamino, cyclopropylamino, cyclobutylamino, benzylamino, and phenylamino; disubstituted amino selected from dimethylamino, diethylamino, ethyl(1-methylethyl)amino, monomethylbenzylamino, piperidinyl, morpholinyl, 1-imidazolyl, 1-pyrrolyl, 1-(1,2,3-triazolyl) and 4-( 1,2,4-triazolyl); ($C_3$–$C_6$)cycloalkyl group selected from cyclopropyl, cyclobutyl, cyclopentyl, and cyclohexyl; substituted ($C_3$–$C_6$)cycloalkyl group wherein the substitution is selected from ($C_1$–$C_3$)alkyl, cyano, amino and ($C_1$–$C_3$)acyl; ($C_6$–$C_{10}$)aryl group selected from phenyl, α-napthyl or β-napthyl; substituted ($C_6$–$C_{10}$)aryl wherein the substitution is selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino and carboxy; α-amino($C_1$–$C_4$)alkyl group selected from α-aminomethyl, α-aminoethyl, α-aminopropyl and α-aminobutyl; carboxy($C_2$–$C_4$)alkylamino group selected from aminoacetic acid, α-aminobutyric acide, α-aminoproprionic acid, and their optical isomers; ($C_7$–$C_9$)aralkylamino group; substituted ($C_1$–$C_4$)alkoxycarbonylamino group wherein the substitution is selected from phenyl or p-hydroxyphenyl; α-hydroxy($C_1$–$C_3$)alkyl group selected from hydroxymethyl, α-hydroxyethyl, α-hydroxy-1-methylethyl and α-hydroxypropyl; halo $C_1$–$C_3$)alkyl group; a heterocycle group selected from a five membered aromatic or saturated ring with one N, O, S, or Se heteroatom optinally having a benzo or pyrido ring fused thereto selected from

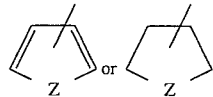

wherein Z is N, O, S, or Se;

a five membered aromatic ring with two N, O, S, or Se heteroatoms optionally having a benzo or pyrido ring fused thereto selected from

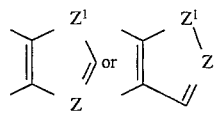

wherein Z and $Z_1$ are independently selected from N, O, S, and Se;

a five membered saturated ring with one or two N, O, S, or Se heteroatoms and an adjacent appended O heteroatom selected from

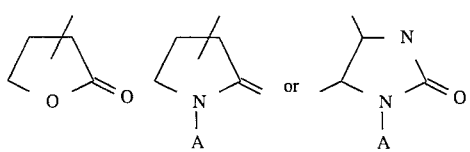

wherein A is selected from hydrogen; straight or branched ($C_1$–$C_4$)alkyl; $C_6$-aryl; substituted $C_6$-aryl wherein the substitution is selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino and carboxy; and ($C_7$–$C_9$)aralkyl group selected from benzyl, 1-phenylethyl, 2-phenylethyl and phenylpropyl;

a six membered aromatic ring with one to three N, O, S, or Se heteroatoms;

a six membered saturated ring with one or two N, O, S or Se heteroatoms and an adjacent appended O heteroatom; acyl or haloacyl group selected from acetyl, propionyl, chloroacetyl, trifluoroacetyl, ($C_3$–$C_6$)cycloalkylcarbonyl, ($C_6$–$C_{10}$)aroyl selected from benzoyl or napthoyl, halo-substituted($C_6$–$C_{10}$)aroyl, ($C_1$–$C_4$)alkylbenzoyl, and (heterocycle)carbonyl wherein the heterocycle is selected from a five membered aromatic or saturated ring with one N, O, S, or Se heteroatom optinally having a benzo or pyrido ring fused thereto selected from

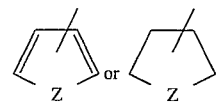

wherein Z is N, O, S, or Se;

a five membered aromatic ring with two N, O, S, or Se heteroatoms optionally having a benzo or pyrido ring fused thereto selected from

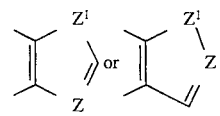

wherein Z and $Z_1$ are independently selected from N, O, S, and Se;

a five membered saturated ring with one or two N, O, S, or Se heteroatoms and an adjacent appended O heteroatom selected from

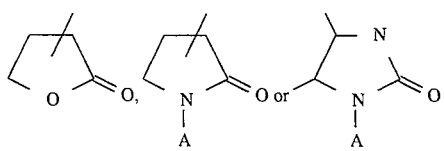

wherein A is selected from hydrogen; straight or branched ($C_1$–$C_4$)alkyl; $C_6$-aryl; substituted $C_6$-aryl wherein the substitution is selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino and carboxy; and ($C_7$–$C_9$)aralkyl group selected from benzyl, 1-phenylethyl, 2-phenylethyl and phenylpropyl;

a six membered aromatic ring with one to three N, O, S, or Se heteroatoms;

a six membered saturated ring with one or two N, O, S or Se heteroatoms and an adjacent appended O heteroatom; ($C_1$–$C_4$)alkoxycarbonyl group selected from methoxycarbonyl, ethoxycarbonyl, straght or branched propoxycarbonyl, straight or branched butoxycarbonyl and allyloxycarbonyl; vinyl or substituted vinyl wherein the substitution is selected 649 from ($C_1$–$C_3$)alkyl group; halogen; ($C_6$–$C_{10}$)aryl group selected from phenyl, α-napthyl, β-napthyl; substituted ($C_6$–$C_{10}$)aryl group wherein the substitution is selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino and carboxy; halo($C_1$–$C_3$)alkyl group; a heterocycle group selected from a five membered aromatic or saturated ring with one N, O, S, or Se heteroatom optionally having a benzo or pyrido ring fused thereto selected from

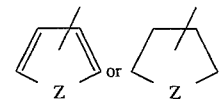

wherein Z is N, O, S, or Se; ($C_1$–$C_4$)alkoxy group; $C_6$-aryloxy group selected from phenoxy or substituted phenoxy where the substitution is selected from halo, $(C_1-C_4)$alkyl, nitro, cyano, thiol, amino, carboxy, and di$(C_1-C_3)$alkylamino; $(C_7-C_{10})$aralkoxy group; vinyloxy or substituted vinyloxy group wherein the substitution is selected from $(C_1-C_4)$alkyl, cyano, carboxy, and $(C_6-C_{10})$aryl selected from phenyl, α-napthyl, and β-napthyl; $R^aR^b$amino$(C_1-C_4)$alkoxy or $R^aR^b$aminoxy group wherein $R^aR^b$ is selected from a straight or branched $(C_1-C_4)$alkyl selected from methyl, ethyl, n-propyl, 1-methylethyl, n-butyl, 1-methylpropyl, 2-methylpropyl, 1,1-dimethylethyl, $(CH_2)_n$ where n is from 2 to 6, and —$(CH_2)_2W(CH_2)_2$— wherein W is selected from —N$(C_1-C_3)$alkyl wherein alkyl is straight or branched, —NH, NOB where B is selected from hydrogen or $(C_1-C_4)$alkyl, O, and S; and when R=$R^4(CH_2)_nCO$— and n=1–4, $R^4$ is selected from amino; $(C_6-C_{10})$aryl group selected from phenyl, α-napthyl or β-napthyl; substituted $(C_6-C_{10})$aryl wherein the substitution is selected from halo, $(C_1-C_4)$alkoxy, trihalo$(C_1-C_3)$alkyl, nitro, amino, cyano, $(C_1-C_4)$alkoxycarbonyl, $(C_1-C_3)$alkylamino and carboxy; acyloxy or haloacyloxy group wherein the acyl or haloacyl is selected from acetyl, propionyl, chloroacetyl, trifluoroacetyl, $(C_3-C_6)$cycloalkylcarbonyl, $(C_6-C_{10})$aroyl selected from benzoyl or napthoyl, halo-substituted$(C_6-C_{10})$aroyl, $(C_1-C_4)$alkylbenzoyl, and (heterocycle)carbonyl wherein the heterocycle is selected from a five membered aromatic or saturated ring with one N, O, S, or Se heteroatom optinally having a benzo or pyrido ring fused thereto selected from

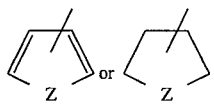

wherein Z is N, O, S, or Se;

a five membered aromatic ring with two N, O, S, or Se heteroatoms optionally having a benzo or pyrido ring fused thereto selected from

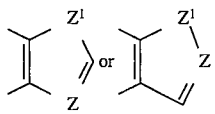

wherein Z and $Z_1$ are independently selected from N, O, S, and Se;

a five membered saturated ring with one or two N, O, S, or Se heteroatoms and an adjacent appended O heteroatom selected from

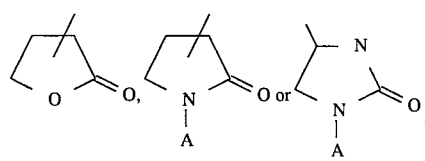

wherein A is selected from hydrogen; straight or branched $(C_1-C_4)$alkyl; $C_6$-aryl; substituted $C_6$-aryl wherein the substitution is selected from halo, $(C_1-C_4)$alkoxy, trihalo$(C_1-C_3)$alkyl, nitro, amino, cyano, $(C_1-C_4)$alkoxycarbonyl, $(C_1-C_3)$alkylamino and carboxy; and $(C_7-C_9)$aralkyl group selected from benzyl, 1-phenylethyl, 2-phenylethyl and phenylpropyl;

a six membered aromatic ring with one to three N, O, S, or Se heteroatoms;

a six membered saturated ring with one or two N, O, S or Se heteroatoms and an adjacent appended O heteroatom; $(C_1-C_4)$alkoxy group; $C_6$-aryloxy group selected from phenoxy or substituted phenoxy where the substitution is selected from halo, $(C_1-C_4)$alkyl, nitro, cyano, thiol, amino, carboxy, and di$(C_1-C_3)$alkylamino; $(C_1-C_3)$alkylthio group selected from methylthio, ethylthio, propylthio or allylthio; $C_6$-arylthio group selected from phenylthio or substituted phenylthio wherein the substitution is selected from halo, $(C_1-C_4)$alkyl, nitro, cyano, thiol, amino, carboxy, and di$(C_1-C_3)$alkylamino; $C_6$-arylsulfonyl group selected from phenylsulfonyl or substituted phenylsulfonyl wherein the substitution is selected from halo, $(C_1-C_4)$alkoxy, trihalo$(C_1-C_3)$alkyl, nitro, amino, cyano, $(C_1-C_4)$alkoxycarbonyl, $(C_1-C_3)$alkylamino, and carboxy; a heterocycle group selected from a five membered aromatic or saturated ring with one N, O, S, or Se heteroatom optinally having a benzo or pyrido ring fused thereto selected from

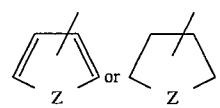

wherein Z is N, O, S, or Se;

a five membered aromatic ring with two N, O, S, or Se heteroatoms optionally having a benzo or pyrido ring fused thereto selected from

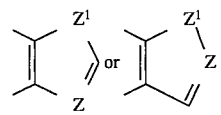

wherein Z and $Z_1$ are independently selected from N, O, S, and Se;

a five membered saturated ring with one or two N, O, S, or Se heteroatoms and an adjacent appended O heteroatom selected from

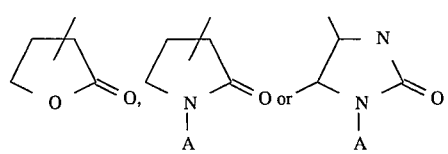

wherein A is selected from hydrogen; straight or branched $(C_1-C_4)$alkyl; $C_6$-aryl; substituted $C_6$-aryl wherein the substitution is selected from halo, $(C_1-C_4)$alkoxy, trihalo$(C_1-C_3)$alkyl, nitro, amino, cyano, $(C_1-C_4)$alkoxycarbonyl, $(C_1-C_3)$alkylamino and carboxy; and $(C_7-C_9)$aralkyl group selected from benzyl, 1-phenylethyl, 2-phenylethyl and phenylpropyl;

a six membered aromatic ring with one to three N, O, S, or Se heteroatoms;

a six membered saturated ring with one or two N, O, S or Se heteroatoms and an adjacent appended O heteroatom; hydroxy group; α-hydroxy$(C_1-C_3)$alkyl group selected from hydroxymethyl, α-hydroxyethyl, α-hydroxy-1-methylethyl, and α-hydroxypropyl; halo $(C_1-C_3)$alkyl group; acyl or haloacyl group selected from acetyl, propionyl, chloroacetyl, trifluoroacetyl, $(C_3-C_6)$cycloalkylcarbonyl, $(C_6-C_{10})$aroyl selected from benzoyl or napthoyl, halo-substituted$(C_6-C_{10})$aroyl, $(C_1-C_4)$alkylbenzoyl, and (heterocycle)carbonyl wherein the heterocycle is selected from a five membered aromatic or saturated ring with one N, O, S, or Se heteroatom optionally having a benzo or pyrido ring fused thereto selected from

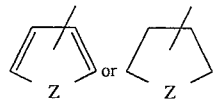

wherein Z is N, O, S, or Se;

a five membered aromatic ring with two N, O, S, or Se heteroatoms optionally having a benzo or pyrido ring fused thereto selected from

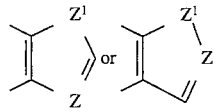

wherein Z and $Z_1$ are independently selected from N, O, S, and Se;

a five membered saturated ring with one or two N, O, S, or Se heteroatoms and an adjacent appended O heteroatom selected from

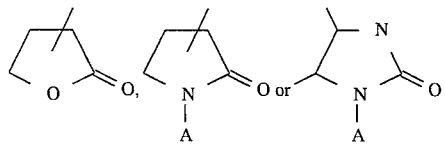

wherein A is selected from hydrogen; straight or branched $(C_1-C_4)$alkyl; $C_6$-aryl; substituted $C_6$-aryl wherein the substitution is selected from halo, $(C_1-C_4)$alkoxy, trihalo$(C_1-C_3)$alkyl, nitro, amino, cyano, $(C_1-C_4)$alkoxycarbonyl, $(C_1-C_3)$alkylamino and carboxy; and $(C_7-C_9)$aralkyl group selected from benzyl, 1-phenylethyl, 2-phenylethyl and phenylpropyl;

a six membered aromatic ring with one to three N, O, S, or Se heteroatoms;

a six membered saturated ring with one or two N, O, S or Se heteroatoms and an adjacent appended O heteroatom; $(C_1-C_4)$alkoxycarbonylamino group selected from tert-butoxycarbonylamino, allyloxycarbonylamino, methoxycarbonylamino, ethoxycarbonylamino, and propoxycarbonylamino; $R^aR^b$amino$(C_1-C_4)$alkoxy or $R^aR^b$aminoxy group wherein $R^aR^b$ is selected from a straight or branched $(C_1-C_4)$alkyl selected from methyl, ethyl, n-propyl, 1-methylethyl, n-butyl, 1-methylpropyl, 2-methylpropyl, 1,1-dimethylethyl, $(CH_2)_n$ where n is from 2 to 6, and —$(CH_2)_2W(CH_2)_2$— wherein W is selected from —N$(C_1-C_3)$alkyl wherein alkyl is straight or branched, —NH, NOB where B is selected from hydrogen or $(C_1-C_4)$alkyl, O, and S; and when R=$R^{4'}$(CH$_2$)$_n$SO$_2$— and n=0, $R^{4'}$ is selected from amino; monosubstituted amino selected from straight or branched $(C_1-C_6)$alkylamino, cyclopropylamino, cyclobutylamino, benzylamino, and phenylamino; disubstituted amino selected from dimethylamino, diethylamino, ethyl(1-methylethyl)amino, monomethylbenzylamino, piperidinyl, morpholinyl, 1-imidazolyl, 1-pyrrolyl, 1-(1,2,3-triazolyl) and 4-(1,2,4-triazolyl); straight or branched $(C_1-C_4)$alkyl group selected from methyl, ethyl, n-propyl, and 1-methylethyl; $(C_6-C_{10})$aryl group selected from phenyl, α-napthyl or β-napthyl; substituted $(C_6-C_{10})$aryl wherein the substitution is selected from halo, $(C_1-C_4)$alkoxy, trihalo$(C_1-C_3)$alkyl, nitro, amino, cyano, $(C_1-C_4)$alkoxycarbonyl, $(C_1-C_3)$alkylamino and carboxy; a heterocycle group selected from a five membered aromatic or saturated ring with one N, O, S, or Se heteroatom optionally having a benzo or pyrido ring fused thereto selected from

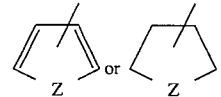

wherein Z is N, O, S, or Se;

a five membered aromatic ring with two N, O, S, or Se heteroatoms optionally having a benzo or pyrido ring fused thereto selected from

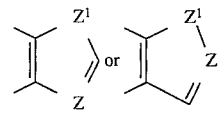

wherein Z and $Z_1$ are independently selected from N, O, S, and Se;

a five membered saturated ring with one or two N, O, S, or Se heteroatoms and an adjacent appended O heteroatom selected from

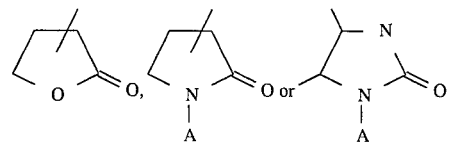

wherein A is selected from hydrogen; straight or branched $(C_1-C_4)$alkyl; $C_6$-aryl; substituted $C_6$-aryl wherein the substitution is selected from halo, $(C_1-C_4)$alkoxy, trihalo$(C_1-C_3)$alkyl, nitro, amino, cyano, $(C_1-C_4)$alkoxycarbonyl, $(C_1-C_3)$alkylamino and carboxy; and $(C_7-C_9)$aralkyl group selected from benzyl, 1-phenylethyl, 2-phenylethyl and phenylpropyl;

a six membered aromatic ring with one to three N, O, S, or Se heteroatoms;

a six membered saturated ring with one or two N, O, S or Se heteroatoms and an adjacent appended O heteroatom; and when R=$R^{4'}$(CH$_2$)$_n$SO$_2$— and n=1–4, $R^4$ is selected from hydrogen; amino; straight or branched $(C_1-C_4)$alkyl group selected from methyl, ethyl, n-propyl, and 1-methylethyl; $(C_1-C_4)$carboxyalkyl group; $(C_6-C_{10})$aryl group selected from phenyl, α-napthyl or β-napthyl; substituted $(C_6-C_{10})$aryl wherein the substitution is selected from halo, $(C_1-C_4)$alkoxy, trihalo$(C_1-C_3)$alkyl, nitro, amino, cyano, $(C_1-C_4)$alkoxycarbonyl, $C_1-C_3)$alkylamino and carboxy; $(C_1-C_4)$alkoxy group; $C_6$-aryloxy group selected from phenoxy or substituted phenoxy where the substitution is selected from halo, $(C_1-C_4)$alkyl, nitro, cyano, thiol, amino, carboxy, and di$(C_1-C_3)$alkylamino; $(C_7-C_{10})$aralkoxy group;

$R^5$ is selected from hydrogen; straight or branched $(C_1-C_3)$alkyl group selected from methyl, ethyl, n-propyl, or 1-methylethyl; $(C_6-C_{10})$aryl group selected from phenyl, α-napthyl, or β-napthyl; $(C_7-C_9)$aralkyl group; a heterocycle group selected from a five membered aromatic or saturated ring with one N, O, S, or Se heteroatom optinally having a benzo or pyrido ring fused thereto selected from

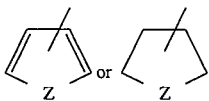

wherein Z is N, O, S, or Se;

a five membered aromatic ring with two N, O, S, or Se heteroatoms optionally having a benzo or pyrido ring fused thereto selected from

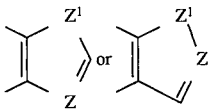

wherein Z and $Z_1$ are independently selected from N, O, S, and Se;

a five membered saturated ring with one or two N, O, S, or Se heteroatoms and an adjacent appended O heteroatom selected from

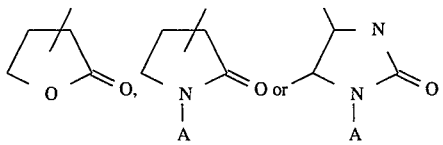

wherein A is selected from hydrogen; straight or branched $(C_1-C_4)$alkyl; $C_6$-aryl; substituted $C_6$-aryl wherein the substitution is selected from halo, $(C_1-C_4)$alkoxy, trihalo$(C_1-C_3)$alkyl, nitro, amino, cyano, $(C_1-C_4)$alkoxycarbonyl, $(C_1-C_3)$alkylamino and carboxy; and $(C_7-C_9)$aralkyl group selected from benzyl, 1-phenylethyl, 2-phenylethyl and phenylpropyl;

a six membered aromatic ring with one to three N, O, S, or Se heteroatoms;

a six membered saturated ring with one or two N, O, S or Se heteroatoms and an adjacent appended O heteroatom; —$(CH_2)_n COOR^7$ where n=0–4 and $R^7$ is selected from hydrogen; straight or branched $(C_1-C_3)$alkyl group selected from methyl, ethyl, n-propyl, or 1-methylethyl; and $(C_6-C_{10})$aryl group selected from phenyl, α-naphthyl, or β-naphthyl;

$R^6$ is selected from hydrogen; straight or branched $(C_1-C_3)$alkyl group selected from methyl, ethyl, n-propyl, or 1-methylethyl; $(C_6-C_{10})$aryl group selected from phenyl, α-napthyl, or β-naphthyl; $(C_7-C_9)$aralkyl group; a heterocycle group selected from a five membered aromatic or saturated ring with one N, O, S, or Se heteroatom optinally having a benzo or pyrido ring fused thereto selected from

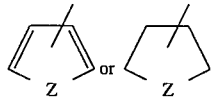

wherein Z is N, O, S, or Se;

a five membered aromatic ring with two N, O, S, or Se heteroatoms optionally having a benzo or pyrido ring fused thereto selected from

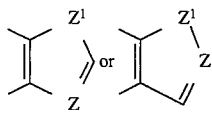

wherein Z and $Z_1$ are independently selected from N, O, S, and Se;

a five membered saturated ring with one or two N, O, S, or Se heteroatoms and an adjacent appended O heteroatom selected from

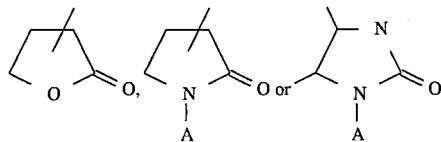

wherein A is selected from hydrogen; straight or branched $(C_1-C_4)$alkyl; $C_6$-aryl; substituted $C_6$-aryl wherein the substitution is selected from halo, $(C_1-C_4)$alkoxy, trihalo$(C_1-C_3)$alkyl, nitro, amino, cyano, $(C_1-C_4)$alkoxycarbonyl, $(C_1-C_3)$alkylamino and carboxy; and $(C_7-C_9)$aralkyl group selected from benzyl, 1-phenylethyl, 2-phenylethyl and phenylpropyl;

a six membered aromatic ring with one to three N, O, S, or Se heteroatoms;

a six membered saturated ring with one or two N, O, S or Se heteroatoms and an adjacent appended O heteroatom; —$(CH_2)_n COOR^{7'}$ where n=0–4 and $R^{7'}$ is selected from hydrogen; straight or branched $(C_1-C_3)$alkyl group selected from methyl, ethyl, n-propyl, or 1-methylethyl; and $(C_6-C_{10})$aryl group selected from phenyl, α-naphthyl, or β-naphthyl; with the proviso that $R^5$ and $R^6$ cannot both be hydrogen; or $R^5$ and $R^6$ taken together are —$(CH_2)_2 W(CH_2)_2$— wherein W is selected from $(CH_2)_n$ where n=0–1; —NH; —N$(C_1-C_3)$alkyl where alkyl is straight or branched; —N$(C_1-C_4)$alkoxy; O; S; and congeners selected from (L or D)proline, ethyl(L or D)prolinate, morphiline, pyrrolidine and piperidine; or a pharmacologically acceptable organic or inorganic salt or metal complex thereof.

3. The compound of claim 1 wherein

Y is $NO_2$;

R is selected from $R^4(CH_2)_n CO$— or $R^{4'}(CH_2)_n SO_2$—; n is an integer between 0 and 4; and when R=$R^4(CH_2)_n CO$— and n=0, $R^4$ is selected from amino; monosubstituted amino selected from straight or branched $(C_1-C_6)$alkylamino, cyclopropylamino, cyclobutylamino, benzylamino, and phenylamino; disubstituted amino selected from dimethylamino, diethylamino, ethyl(1-methylethyl)amino, monomethylbenzylamino, piperidinyl, morpholinyl, 1-imidazolyl, 1-pyrrolyl, 1-(1,2,3-triazolyl) and 4-( 1,2,4-triazolyl); $(C_3-C_6)$cycloalkyl group selected from cyclopropyl, cyclobutyl, cyclopentyl, and cyclohexyl; substituted $(C_3-C_6)$cycloalkyl group wherein the substitution is selected from $(C_1-C_3)$alkyl, cyano, amino and $C_1-C_3)$acyl; $(C_6-C_{10})$aryl group selected from phenyl, α-napthyl or β-napthyl; substituted $(C_6-C_{10})$aryl wherein the substitution is selected from halo, $(C_1-C_4)$alkoxy, trihalo$(C_1-C_3)$alkyl, nitro, amino, cyano, $(C_1-C_4)$alkoxycarbonyl, $(C_1-C_3)$alkylamino and carboxy; α-amino$(C_1-C_4)$alkyl group selected from α-aminomethyl, α-aminoethyl, α-aminopropyl and α-aminobutyl; carboxy($C_2$–$C_4$)alkylamino group selected from aminoacetic acid, α-aminobutyric acide, α-aminoproprionic acid, and their optical isomers; ($C_7$–$C_9$)aralkylamino group; substituted ($C_1$–$C_4$)alkoxycarbonylamino group wherein the substitution is selected from phenyl or p-hydroxyphenyl; α-hydroxy($C_1$–$C_3$)alkyl group selected from hydroxymethyl, α-hydroxyethyl, α-hydroxy-1-methyl-ethyl and α-hydroxypropyl; halo $C_1$–$C_3$ alkyl group; a heterocycle group selected from a five membered aromatic or saturated ring with one N, O, S, or Se heteroatom optinally having a benzo or pyrido ring fused thereto selected from

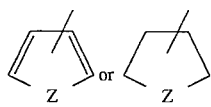

wherein Z is N, O, S, or Se;

a five membered aromatic ring with two N, O, S, or Se heteroatoms optionally having a benzo or pyrido ring fused thereto selected from

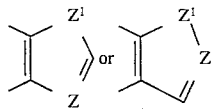

wherein Z and $Z_1$ are independently selected from N, O, S, and Se;

a five membered saturated ring with one or two N, O, S, or Se heteroatoms and an adjacent appended O heteroatom selected from

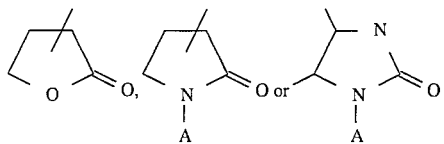

wherein A is selected from hydrogen; straight or branched $C_1$–$C_4$ alkyl; $C_6$-aryl; substituted $C_6$-aryl wherein the substitution is selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino and carboxy; and ($C_7$–$C_9$)aralkyl group selected from benzyl, 1-phenyl-ethyl, 2-phenylethyl and phenylpropyl;

a six membered aromatic ring with one to three N, O, S, or Se heteroatoms;

a six membered saturated ring with one or two N, O, S or Se heteroatoms and an adjacent appended O heteroatom; acyl or haloacyl group selected from acetyl, propionyl, chloroacetyl, trifluoroacetyl, ($C_3$–$C_6$)cycloalkylcarbonyl, ($C_6$–$C_{10}$)aroyl selected from benzoyl or napthoyl, halo-substituted($C_6$–$C_{10}$)aroyl, ($C_1$–$C_4$)alkylbenzoyl, and (heterocycle)carbonyl wherein the heterocycle is selected from a five membered aromatic or saturated ring with one N, O, S, or Se heteroatom optionally having a benzo or pyrido ring fused thereto selected from

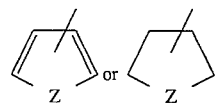

wherein Z is N, O, S, or Se;

a five membered aromatic ring with two N, O, S, or Se heteroatoms optionally having a benzo or pyrido ring fused thereto selected from

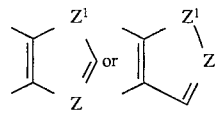

wherein Z and $Z_1$ are independently selected from N, O, S, and Se;

a five membered saturated ring with one or two N, O, S, or Se heteroatoms and an adjacent appended O heteroatom selected from

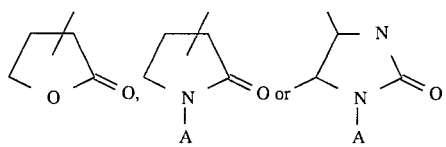

wherein A is selected from hydrogen; straight or branched ($C_1$–$C_4$)alkyl; $C_6$-aryl; substituted $C_6$-aryl wherein the substitution is selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino and carboxy; and ($C_7$–$C_9$)aralkyl group selected from benzyl, 1-phenyl-ethyl, 2-phenylethyl and phenylpropyl;

a six membered aromatic ring with one to three N, O, S, or Se heteroatoms;

a six membered saturated ring with one or two N, O, S or Se heteroatoms and an adjacent appended O heteroatom; ($C_1$–$C_4$)alkoxycarbonyl group selected from methoxycarbonyl, ethoxycarbonyl, straght or branched propoxycarbonyl, straight or branched butoxycarbonyl and allyloxycarbonyl; vinyl or substituted vinyl wherein the substitution is selected from ($C_1$–$C_3$)alkyl group; halogen; ($C_6$–$C_{10}$)aryl group selected from phenyl, α-napthyl, β-napthyl; substituted ($C_6$–$C_{10}$)aryl group wherein the substitution is selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino and carboxy; halo($C_1$–$C_3$)alkyl group; a heterocycle group selected from a five membered aromatic or saturated ring with one N, O, S, or Se heteroatom optionally having a benzo or pyrido ring fused thereto selected from

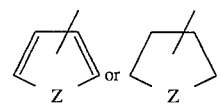

wherein Z is N, O, S, or Se; ($C_1$–$C_4$)alkoxy group; $C_6$-aryloxy group selected from phenoxy or substituted phenoxy where the substitution is selected from halo, ($C_1$–$C_4$)alkyl, nitro, cyano, thiol, amino, carboxy, and di($C_1$–$C_3$)alkylamino; ($C_7$–$C_{10}$)aralkoxy group; vinyloxy or substituted vinyloxy group wherein the substitution is selected from ($C_1$–$C_4$)alkyl, cyano, carboxy, and ($C_6$–$C_{10}$)aryl selected from phenyl, α-napthyl, and β-napthyl; $R^aR^b$amino($C_1$–$C_4$)alkoxy or $R^aR^b$aminoxy group wherein $R^aR^b$ is selected from a straight or branched ($C_1$–$C_4$)alkyl selected from methyl, ethyl, n-propyl, 1-methylethyl, n-butyl, 1-methylpropyl, 2-methylpropyl, 1,1-dimethylethyl, $(CH_2)_n$ where n is from 2 to 6, and —$(CH_2)_2W(CH_2)_2$— wherein W is selected from —N($C_1$–$C_3$)alkyl wherein alkyl is straight or branched, —NH, NOB where B is selected from hydrogen or ($C_1$–$C_4$)alkyl, O, and S; and when R=$R^4(CH_2)_nCO$— and n=1–4, $R^4$ is selected from amino; ($C_6$–$C_{10}$)aryl group selected from phenyl, α-napthyl or β-napthyl; substituted ($C_6$–$C_{10}$)aryl wherein the substitution is selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino and carboxy; acyloxy or haloacyloxy group wherein the acyl or haloacyl is selected from acetyl, propionyl, chloroacetyl, trifluoroacetyl, ($C_3$–$C_6$)cycloalkylcarbonyl,($C_6$–$C_{10}$)aroyl selected from benzoyl or napthoyl, halo-substituted($C_6$–$C_{10}$)aroyl, ($C_1$–$C_4$)alkylbenzoyl, and (heterocycle)carbonyl wherein the heterocycle is selected from a five membered aromatic or saturated ring with one N, O, S, or Se heteroatom optinally having a benzo or pyrido ring fused thereto selected from

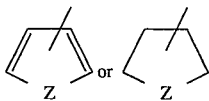

wherein Z is N, O, S, or Se;

a five membered aromatic ring with two N, O, S, or Se heteroatoms optionally having a benzo or pyrido ring fused thereto selected from

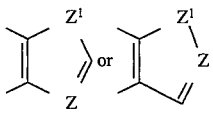

wherein Z and $Z_1$ are independently selected from N, O, S, and Se;

a five membered saturated ring with one or two N, O, S, or Se heteroatoms and an adjacent appended O heteroatom selected from

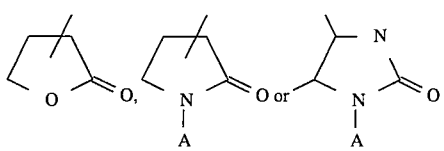

wherein A is selected from hydrogen; straight or branched ($C_1$–$C_4$)alkyl; $C_6$-aryl; substituted $C_6$-aryl wherein the substitution is selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino and carboxy; and ($C_7$–$C_9$)aralkyl group selected from benzyl, 1-phenylethyl, 2-phenylethyl and phenylpropyl;

a six membered aromatic ring with one to three N, O, S, or Se heteroatoms;

a six membered saturated ring with one or two N, O, S or Se heteroatoms and an adjacent appended O heteroatom; ($C_1$–$C_4$)alkoxy group; $C_6$-aryloxy group selected from phenoxy or substituted phenoxy where the substitution is selected from halo, ($C_1$–$C_4$)alkyl, nitro, cyano, thiol, amino, carboxy, and di($C_1$–$C_3$)alkylamino; ($C_1$–$C_3$)alkylthio group selected from methylthio, ethylthio, propylthio or allylthio; $C_6$-arylthio group selected from phenylthio or substituted phenylthio wherein the substitution is selected from halo, ($C_1$–$C_4$)alkyl, nitro, cyano, thiol, amino, carboxy, and di($C_1$–$C_3$)alkylamino; $C_6$-arylsulfonyl group selected from phenylsulfonyl or substituted phenylsulfonyl wherein the substitution is selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino, and carboxy; a heterocycle group selected from a five membered aromatic or saturated ring with one N, O, S, or Se heteroatom optinally having a benzo or pyrido ring fused thereto selected from

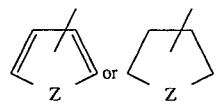

wherein Z is N, O, S, or Se;

a five membered aromatic ring with two N, O, S, or Se heteroatoms optionally having a benzo or pyrido ring fused thereto selected from

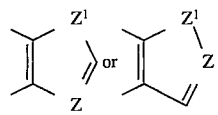

wherein Z and $Z_1$ are independently selected from N, O, S, and Se;

a five membered saturated ring with one or two N, O, S, or Se heteroatoms and an adjacent appended O heteroatom selected from

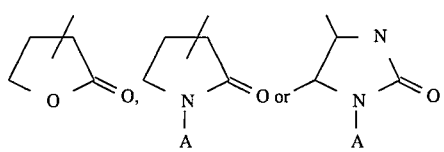

wherein A is selected from hydrogen; straight or branched ($C_1$–$C_4$)alkyl; $C_6$-aryl; substituted $C_6$-aryl wherein the substitution is selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino and carboxy; and ($C_7$–$C_9$)aralkyl group selected from benzyl, 1-phenylethyl, 2-phenylethyl and phenylpropyl;

a six membered aromatic ring with one to three N, O, S, or Se heteroatoms;

a six membered saturated ring with one or two N, O, S or Se heteroatoms and an adjacent appended O heteroatom; hydroxy group; α-hydroxy($C_1$–$C_3$)alkyl group selected from hydroxymethyl, α-hydroxyethyl, α-hydroxy-1-methylethyl, and α-hydroxypropyl; halo($C_1$–$C_3$)alkyl group; acyl or haloacyl group selected from acetyl, propionyl, chloroacetyl, trifluoroacetyl, ($C_3$–$C_6$)cycloalkylcarbonyl, ($C_6$–$C_{10}$)aroyl selected from benzoyl or napthoyl, halo-substituted($C_6$–$C_{10}$)aroyl, ($C_1$–$C_4$)alkylbenzoyl, and (heterocycle)carbonyl wherein the heterocycle is selected from a five membered aromatic or saturated ring with one N, O, S, or Se heteroatom optinally having a benzo or pyrido ring fused thereto selected from

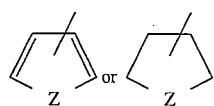

wherein Z is N, O, S, or Se;

a five membered aromatic ring with two N, O, S, or Se heteroatoms optionally having a benzo or pyrido ring fused thereto selected from

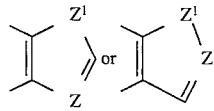

wherein Z and $Z_1$ are independently selected from N, O, S, and Se;

a five membered saturated ring with one or two N, O, S, or Se heteroatoms and an adjacent appended O heteroatom selected from

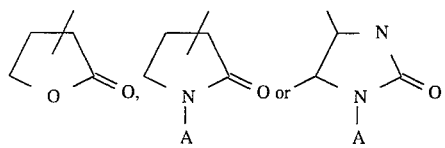

wherein A is selected from hydrogen; straight or branched ($C_1$–$C_4$)alkyl; $C_6$-aryl; substituted $C_6$-aryl wherein the substitution is selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino and carboxy; and ($C_7$–$C_9$)aralkyl group selected from benzyl, 1-phenylethyl, 2-phenylethyl and phenylpropyl;

a six membered aromatic ring with one to three N, O, S, or Se heteroatoms;

a six membered saturated ring with one or two N, O, S or Se heteroatoms and an adjacent appended O heteroatom; ($C_1$–$C_4$)alkoxycarbonylamino group selected from tert-butoxycarbonylamino, allyloxycarbonylamino, methoxycarbonylamino, ethoxycarbonylamino, and propoxycarbonylamino; $R^aR^b$amino($C_1$–$C_4$)alkoxy or $R^aR^b$aminoxy group wherein $R^aR^b$ is selected from a straight or branched ($C_1$–$C_4$)alkyl selected from methyl, ethyl, n-propyl, 1-methylethyl, n-butyl, 1-methylpropyl, 2-methylpropyl, 1,1-dimethylethyl, $(CH_2)_n$ where n is from 2 to 6, and —$(CH_2)_2W(CH_2)_2$— wherein W is selected from —N($C_1$–$C_3$)alkyl wherein alkyl is straight or branched, —NH, NOB where B is selected from hydrogen or ($C_1$–$C_4$)alkyl, O, and S; and when R=$R^{4'}(CH_2)_nSO_2$— and n=0, $R^{4'}$ is selected from amino; monosubstituted amino selected from straight or branched ($C_1$–$C_6$)alkylamino, cyclopropylamino, cyclobutylamino, benzylamino, and phenylamino; disubstituted amino selected from dimethylamino, diethylamino, ethyl(1-methylethyl)amino, monomethylbenzylamino, piperidinyl, morpholinyl, 1-imidazolyl, 1-pyrrolyl, 1-(1,2,3-triazolyl) and 4-( 1,2,4-triazolyl); straight or branched ($C_1$–$C_4$)alkyl group selected from methyl, ethyl, n-propyl, and 1-methylethyl; ($C_6$–$C_{10}$)aryl group selected from phenyl, α-napthyl or β-napthyl; substituted ($C_6$–$C_{10}$)aryl wherein the substitution is selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino and carboxy; a heterocycle group selected from a five membered aromatic or saturated ring with one N, O, S, or Se heteroatom optinally having a benzo or pyrido ring fused thereto selected from

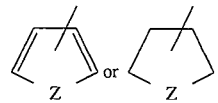

wherein Z is N, O, S, or Se;

a five membered aromatic ring with two N, O, S, or Se heteroatoms optionally having a benzo or pyrido ring fused thereto selected from

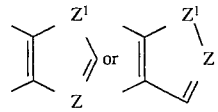

wherein Z and $Z_1$ are independently selected from N, O, S, and Se;

a five membered saturated ring with one or two N, O, S, or Se heteroatoms and an adjacent appended O heteroatom selected from

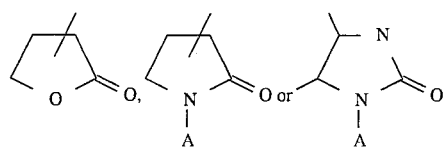

wherein A is selected from hydrogen; straight or branched ($C_1$–$C_4$)alkyl; $C_6$-aryl; substituted $C_6$-aryl wherein the substitution is selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino and carboxy; and ($C_7$–$C_9$)aralkyl group selected from benzyl, 1-phenylethyl, 2-phenylethyl and phenylpropyl;

a six membered aromatic ring with one to three N, O, S, or Se heteroatoms;

a six membered saturated ring with one or two N, O, S or Se heteroatoms and an adjacent appended O heteroatom; and when R=$R^{4'}(CH_2)_nSO_2$— and n=1–4, $R^4$ is selected from hydrogen; amino; straight or branched ($C_1$–$C_4$)alkyl group selected from methyl, ethyl, n-propyl, and 1-methylethyl; $R^aR^b$amino($C_1$–$C_4$)alkoxy or $R^aR^b$aminoxy group wherein $R^aR^b$ is selected from a straight or branched ($C_1$–$C_4$)alkyl selected from methyl, ethyl, n-propyl, 1-methylethyl, n-butyl, 1-methylpropyl, 2-methylpropyl, 1,1-dimethylethyl, $(CH_2)_n$ where n is from 2 to 6, and —$(CH_2)_2W(CH_2)_2$— wherein W is selected from —N($C_1$–$C_3$)alkyl wherein alkyl is straight or branched, —NH, NOB where B is selected from hydrogen or ($C_1$–$C_4$)alkyl, O, and S;

$R^5$ is selected from hydrogen; straight or branched ($C_1$–$C_3$)alkyl group selected from methyl, ethyl, n-propyl, or 1-methylethyl; ($C_6$–$C_{10}$)aryl group selected from phenyl, α-napthyl, or β-napthyl; ($C_7$–$C_9$)aralkyl group; a heterocycle group selected from a five membered aromatic or saturated ring with one N, O, S, or Se heteroatom optinally having a benzo or pyrido ring fused thereto selected from

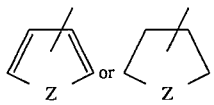

wherein Z is N, O, S, or Se;

a five membered aromatic ring with two N, O, S, or Se heteroatoms optionally having a benzo or pyrido ring fused thereto selected from

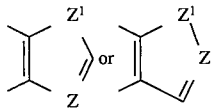

wherein Z and $Z_1$ are independently selected from N, O, S, and Se;

a five membered saturated ring with one or two N, O, S, or Se heteroatoms and an adjacent appended O heteroatom selected from

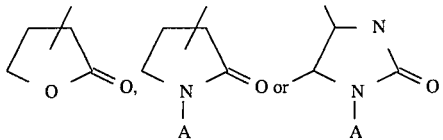

wherein A is selected from hydrogen; straight or branched ($C_1$–$C_4$)alkyl; $C_6$-aryl; substituted $C_6$-aryl wherein the substitution is selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino and carboxy; and ($C_7$–$C_9$)aralkyl group selected from benzyl, 1-phenylethyl, 2-phenylethyl and phenylpropyl;

a six membered aromatic ring with one to three N, O, S, or Se heteroatoms;

a six membered saturated ring with one or two N, O, S or Se heteroatoms and an adjacent appended O heteroatom; —$(CH_2)_n COOR^7$ where n=0–4 and $R^7$ is selected from hydrogen; straight or branched ($C_1$–$C_3$)alkyl group selected from methyl, ethyl, n-propyl, or 1-methylethyl; and ($C_6$–$C_{10}$)aryl group selected from phenyl, α-naphthyl, or β-naphthyl;

$R^6$ is selected from hydrogen; straight or branched ($C_1$–$C_3$)alkyl group selected from methyl, ethyl, n-propyl, or 1-methylethyl; ($C_6$–$C_{10}$)aryl group selected from phenyl, α-napthyl, or β-napthyl; ($C_7$–$C_9$)aralkyl group; a heterocycle group selected from a five membered aromatic or saturated ring with one N, O, S, or Se heteroatom optinally having a benzo or pyrido ring fused thereto selected from

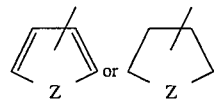

wherein Z is N, O, S, or Se;

a five membered aromatic ring with two N, O, S, or Se heteroatoms optionally having a benzo or pyrido ring fused thereto selected from

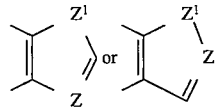

wherein Z and $Z_1$ are independently selected from N, O, S, and Se;

a five membered saturated ring with one or two N, O, S, or Se heteroatoms and an adjacent appended O heteroatom selected from

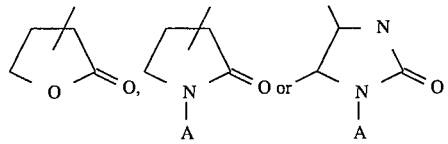

wherein A is selected from hydrogen; straight or branched ($C_1$–$C_4$)alkyl; $C_6$-aryl; substituted $C_6$-aryl wherein the substitution is selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino and carboxy; and ($C_7$–$C_9$)aralkyl group selected from benzyl, 1-phenylethyl, 2-phenylethyl and phenylpropyl;

a six membered aromatic ring with one to three N, O, S, or Se heteroatoms;

a six membered saturated ring with one or two N, O, S or Se heteroatoms and an adjacent appended O heteroatom; —$(CH_2)_n COOR^7$ where n=0–4 and $R^7$ is selected from hydrogen; straight or branched ($C_1$–$C_3$)alkyl group selected from methyl, ethyl, n-propyl, or 1-methylethyl; and ($C_6$–$C_{10}$)aryl group selected from phenyl, α-naphthyl, or β-naphthyl; with the proviso that $R^5$ and $R^6$ cannot both be hydrogen; or $R^5$ and $R^6$ taken together are —$(CH_2)_2 W(CH_2)_2$— wherein W is selected from $(CH_2)_n$ where n=0–1; —NH; —N($C_1$–$C_3$)alkyl where alkyl is straight or branched; —N($C_1$–$C_4$)alkoxy; O; S; and congeners selected from (L or D)proline, ethyl(L or D)prolinate, morphiline, pyrrolidine and piperidine; or a pharmacologically acceptable organic or inorganic salt or metal complex thereof.

4. The compound of claim 1 wherein

Y is $NO_2$;

R is selected from $R^4(CH_2)_n CO$— or $R^{4'}(CH_2)_n SO_2$—; n is an integer between 0 and 4; and when R=$R^4(CH_2)_n CO$— and n=0, $R^4$ is selected from amino; monosubstituted amino selected from straight or branched ($C_1$–$C_6$)alkylamino, cyclopropylamino, cyclobutylamino, benzylamino, and phenylamino; disubstituted amino selected from dimethylamino, diethylamino, ethyl(1-methylethyl)amino, monomethylbenzylamino, piperidinyl, morpholinyl, 1-imidazolyl, 1-pyrrolyl, 1-(1,2,3-triazolyl) and 4-( 1,2,4-triazolyl); ($C_6$–$C_{10}$)aryl group selected from phenyl, α-napthyl or β-napthyl; substituted ($C_6$–$C_{10}$)aryl wherein the substitution is selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino and carboxy; carboxy($C_2$–$C_4$)alkylamino group selected from aminoacetic acid, α-aminobutyric acide, α-aminoproprionic acid, and their optical isomers; α-hydroxy($C_1$–$C_3$)alkyl group selected from hydroxymethyl, α-hydroxyethyl, α-hydroxy-1-methylethyl and α-hydroxypropyl; halo ($C_1$–$C_3$)alkyl group; a heterocycle group selected from a five membered aromatic or saturated ring with one N, O, S, or Se heteroatom optinally having a benzo or pyrido ring fused thereto selected from

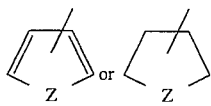

wherein Z is N, O, S, or Se;

a five membered aromatic ring with two N, O, S, or Se heteroatoms optionally having a benzo or pyrido ring fused thereto selected from

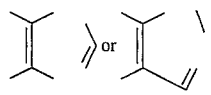

wherein Z and $Z_1$ are independently selected from N, O, S, and Se;

a five membered saturated ring with one or two N, O, S, or Se heteroatoms and an adjacent appended O heteroatom selected from

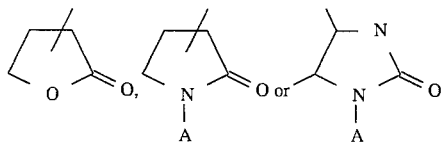

wherein A is selected from hydrogen; straight or branched $(C_1-C_4)$alkyl; $C_6$-aryl; substituted $C_6$-aryl wherein the substitution is selected from halo, $(C_1-C_4)$alkoxy, trihalo$(C_1-C_3)$alkyl, nitro, amino, cyano, $(C_1-C_4)$alkoxycarbonyl, $(C_1-C_3)$alkylamino and carboxy; and $(C_7-C_9)$aralkyl group selected from benzyl, 1-phenylethyl, 2-phenylethyl and phenylpropyl;

a six membered aromatic ring with one to three N, O, S, or Se heteroatoms;

a six membered saturated ring with one or two N, O, S or Se heteroatoms and an adjacent appended O heteroatom; $(C_1-C_4)$alkoxycarbonyl group selected from methoxycarbonyl, ethoxycarbonyl, straght or branched propoxycarbonyl, straight or branched butoxycarbonyl and allyloxycarbonyl; vinyl or substituted vinyl wherein the substitution is selected from $(C_1-C_3)$alkyl group; halogen; $(C_6-C_{10})$aryl group selected from phenyl, α-napthyl, β-napthyl; substituted $(C_6-C_{10})$aryl group wherein the substitution is selected from halo, $(C_1-C_4)$alkoxy, trihalo$(C_1-C_3)$alkyl, nitro, amino, cyano, $(C_1-C_4)$alkoxycarbonyl, $(C_1-C_3)$alkylamino and carboxy; halo$(C_1-C_3)$alkyl group; a heterocycle group selected from a five membered aromatic or saturated ring with one N, O, S, or Se heteroatom optionally having a benzo or pyrido ring fused thereto selected from

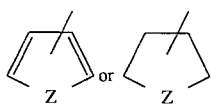

wherein Z is N, O, S, or Se; $(C_1-C_4)$alkoxy group; $C_6$-aryloxy group selected from phenoxy or substituted phenoxy where the substitution is selected from halo, $(C_1-C_4)$alkyl, nitro, cyano, thiol, amino, carboxy, and di$(C_1-C_3)$alkylamino; $(C_7-C_{10})$aralkoxy group; vinyloxy or substituted vinyloxy group wherein the substitution is selected from $(C_1-C_4)$alkyl, cyano, carboxy, and $(C_6-C_{10})$aryl selected from phenyl, α-napthyl, and β-napthyl; $R^aR^b$amino$(C_1-C_4)$alkoxy or $R^aR^b$aminoxy group wherein $R^aR^b$ is selected from a straight or branched $(C_1-C_4)$alkyl selected from methyl, ethyl, n-propyl, 1-methylethyl, n-butyl, 1-methylpropyl, 2-methylpropyl, 1,1-dimethylethyl, $(CH_2)_n$ where n is from 2 to 6, and —$(CH_2)_2W(CH_2)_2$— wherein W is selected from —$N(C_1-C_3)$alkyl wherein alkyl is straight or branched, —NH, NOB where B is selected from hydrogen or $(C_1-C_4)$alkyl, O, and S; and when $R=R^4(CH_2)_nCO$— and n=1-4, $R^4$ is selected from amino; $(C_6-C_{10})$aryl group selected from phenyl, α-napthyl or β-napthyl; substituted $(C_6-C_{10})$aryl wherein the substitution is selected from halo, $(C_1-C_4)$alkoxy, trihalo$(C_1-C_3)$alkyl, nitro, amino, cyano, $(C_1-C_4)$alkoxycarbonyl, $(C_1-C_3)$alkylamino and carboxy; acyloxy or haloacyloxy group wherein the acyl or haloacyl is selected from acetyl, propionyl, chloroacetyl, trifluoroacetyl, $(C_3-C_6)$cycloalkylcarbonyl,$(C_6-C_{10})$aroyl selected from benzoyl or napthoyl, halo-substituted$(C_6-C_{10})$aroyl, $(C_1-C_4)$alkylbenzoyl, and (heterocycle)carbonyl wherein the heterocycle is selected from a five membered aromatic or saturated ring with one N, O, S, or Se heteroatom optinally having a benzo or pyrido ring fused thereto selected from

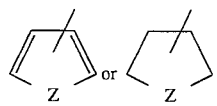

wherein Z is N, O, S, or Se;

a five membered aromatic ring with two N, O, S, or Se heteroatoms optionally having a benzo or pyrido ring fused thereto selected from

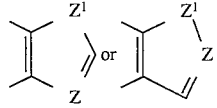

wherein Z and $Z_1$ are independently selected from N, O, S, and Se;

a five membered saturated ring with one or two N, O, S, or Se heteroatoms and an adjacent appended O heteroatom selected from

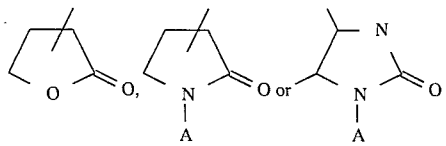

wherein A is selected from hydrogen; straight or branched $(C_1-C_4)$alkyl; $C_6$-aryl; substituted $C_6$-aryl wherein the substitution is selected from halo, $(C_1-C_4)$alkoxy, trihalo$(C_1-C_3)$alkyl, nitro, amino, cyano, $(C_1-C_4)$alkoxycarbonyl, $(C_1-C_3)$alkylamino and carboxy; and $(C_7-C_9)$aralkyl group selected from benzyl, 1-phenylethyl, 2-phenylethyl and phenylpropyl;

a six membered aromatic ring with one to three N, O, S, or Se heteroatoms;

a six membered saturated ring with one or two N, O, S or Se heteroatoms and an adjacent appended O heteroatom; $(C_1-C_4)$alkoxy group; α-hydroxy$(C_1-C_3)$alkyl group selected from hydroxymethyl, α-hydroxyethyl, α-hydroxy-1-methylethyl, and α-hydroxypropyl; halo($C_1$–$C_3$)alkyl group; ($C_1$–$C_4$)alkoxycarbonylamino group selected from tert-butoxycarbonylamino, allyloxycarbonylamino, methoxycarbonylamino, ethoxycarbonylamino, and propoxycarbonylamino; and when R=$R^{4'}$($CH_2$)$_n$$SO_2$— and n=0, $R^{4'}$ is selected from amino; monosubstituted amino selected from straight or branched ($C_1$–$C_6$)alkylamino, cyclopropylamino, cyclobutylamino, benzylamino, and phenylamino; disubstituted amino selected from dimethylamino, diethylamino, ethyl(1-methylethyl)amino, monomethylbenzylamino, piperidinyl, morpholinyl, 1-imidazolyl, 1-pyrrolyl, 1-(1,2,3-triazolyl) and 4-(1,2,4-triazolyl); straight or branched ($C_1$–$C_4$)alkyl group selected from methyl and ethyl; ($C_6$–$C_{10}$)aryl group selected from phenyl, α-napthyl or β-napthyl; substituted ($C_6$–$C_{10}$)aryl wherein the substitution is selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino and carboxy; ($C_7$–$C_9$)aralkyl group; halo ($C_1$–$C_3$)alkyl group; a heterocycle group selected from a five membered aromatic or saturated ring with one N, O, S, or Se heteroatom optinally having a benzo or pyrido ring fused thereto selected from

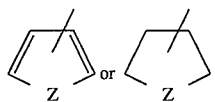

wherein Z is N, O, S, or Se;

a five membered aromatic ring with two N, O, S, or Se heteroatoms optionally having a benzo or pyrido ring fused thereto selected from

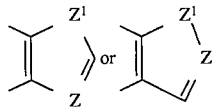

wherein Z and $Z_1$ are independently selected from N, O, S, and Se;

a five membered saturated ring with one or two N, O, S, or Se heteroatoms and an adjacent appended O heteroatom selected from

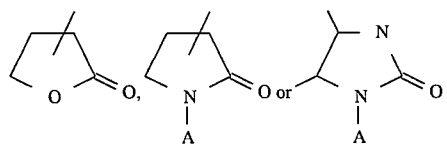

wherein A is selected from hydrogen; straight or branched ($C_1$–$C_4$)alkyl; $C_6$-aryl; substituted $C_6$-aryl wherein the substitution is selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino and carboxy; and ($C_7$–$C_9$)aralkyl group selected from benzyl, 1-phenylethyl, 2-phenylethyl and phenylpropyl;

a six membered aromatic ring with one to three N, O, S, or Se heteroatoms;

a six membered saturated ring with one or two N, O, S or Se heteroatoms and an adjacent appended O heteroatom; and when R=$R^{4'}$($CH_2$)$_n$$SO_2$— and n=1–4, $R^4$ is selected from hydrogen; straight or branched ($C_1$–$C_4$)alkyl group selected from methyl and ethyl;

$R^5$ is selected from hydrogen; straight or branched ($C_1$–$C_3$)alkyl group selected from methyl, ethyl, n-propyl, or 1-methylethyl; ($C_6$–$C_{10}$)aryl group selected from phenyl, α-napthyl, or β-napthyl; ($C_7$–$C_9$)aralkyl group; a heterocycle group selected from a five membered aromatic or saturated ring with one N, O, S, or Se heteroatom optinally having a benzo or pyrido ring fused thereto selected from

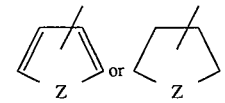

wherein Z is N, O, S, or Se;

a five membered aromatic ring with two N, O, S, or Se heteroatoms optionally having a benzo or pyrido ring fused thereto selected from

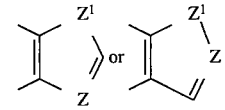

wherein Z and $Z_1$ are independently selected from N, O, S, and Se;

a five membered saturated ring with one or two N, O, S, or Se heteroatoms and an adjacent appended O heteroatom selected from

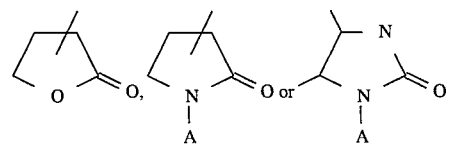

wherein A is selected from hydrogen; straight or branched ($C_1$–$C_4$)alkyl; $C_6$-aryl; substituted $C_6$-aryl wherein the substitution is selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino and carboxy; and ($C_7$–$C_9$)aralkyl group selected from benzyl, 1-phenylethyl, 2-phenylethyl and phenylpropyl;

a six membered aromatic ring with one to three N, O, S, or Se heteroatoms;

a six membered saturated ring with one or two N, O, S or Se heteroatoms and an adjacent appended O heteroatom; —($CH_2$)$_n$$COOR^7$ where n=0–4 and $R^7$ is selected from hydrogen; straight or branched $C_1$–$C_3$)alkyl group selected from methyl, ethyl, n-propyl, or 1-methylethyl; and ($C_6$–$C_{10}$)aryl group selected from phenyl, α-naphthyl, or β-naphthyl;

$R^6$ is selected from hydrogen; straight or branched ($C_1$–$C_3$)alkyl group selected from methyl, ethyl, n-propyl, or 1-methylethyl; ($C_6$–$C_{10}$)aryl group selected from phenyl, α-napthyl, or β-napthyl; ($C_7$–$C_9$)aralkyl group; a heterocycle group selected from a five membered aromatic or saturated ring with one N, O, S, or Se heteroatom optinally having a benzo or pyrido ring fused thereto

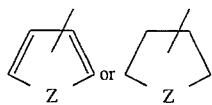

wherein Z is N, O, S, or Se;

a five membered aromatic ring with two N, O, S, or Se heteroatoms optionally having a benzo or pyrido ring fused thereto selected from

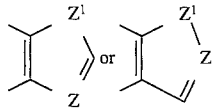

wherein Z and $Z_1$ are independently selected from N, O, S, and Se;

a five membered saturated ring with one or two N, O, S, or Se heteroatoms and an adjacent appended O heteroatom selected from

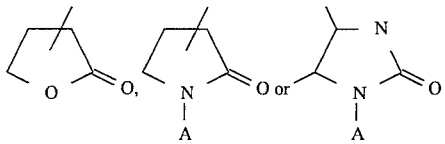

wherein A is selected from hydrogen; straight or branched $(C_1-C_4)$alkyl; $C_6$-aryl; substituted $C_6$-aryl wherein the substitution is selected from halo, $(C_1-C_4)$alkoxy, trihalo$(C_1-C_3)$alkyl, nitro, amino, cyano, $(C_1-C_4)$alkoxycarbonyl, $(C_1-C_3)$alkylamino and carboxy; and $(C_7-C_9)$aralkyl group selected from benzyl, 1-phenylethyl, 2-phenylethyl and phenylpropyl;

a six membered aromatic ring with one to three N, O, S, or Se heteroatoms;

a six membered saturated ring with one or two N, O, S or Se heteroatoms and an adjacent appended O heteroatom; —$(CH_2)_n COOR^{7'}$ where n=0–4 and $R^{7'}$ is selected from hydrogen; straight or branched $(C_1-C_3)$alkyl group selected from methyl, ethyl, n-propyl, or 1-methylethyl; and $(C_6-C_{10})$aryl group selected from phenyl, α-naphthyl, or β-naphthyl; with the proviso that $R^5$ and $R^6$ cannot both be hydrogen; or $R^5$ and $R^6$ taken together are —$(CH_2)_2 W(CH_2)_2$— wherein W is selected from $(CH_2)_n$ where n=0–1; —NH; —N$(C_1-C_3)$alkyl where alkyl is straight or branched; —N$(C_1-C_4)$alkoxy; O; S; and congeners selected from (L or D)proline, ethyl(L or D)prolinate, morphiline, pyrrolidine and piperidine; or a pharmacologically acceptable organic or inorganic salt or metal complex thereof.

5. The compound of claim 1 wherein

Y is $NO_2$;

R is selected from $R^4(CH_2)_n CO$— or $R^{4'}(CH_2)_n SO_2$—; n is an integer between 0 and 4; and when $R=R^4(CH_2)_n CO$— and n=0, $R^4$ is selected from $(C_6-C_{10})$aryl group selected from phenyl, α-napthyl or β-napthyl; substituted $(C_6-C_{10})$aryl wherein the substitution is selected from halo, $(C_1-C_4)$alkoxy, nitro, amino, and $(C_1-C_4)$alkoxycarbonyl; a heterocycle group selected from a five membered aromatic or saturated ring with one N, O, S, or Se heteroatom optinally having a benzo or pyrido ring fused thereto selected from

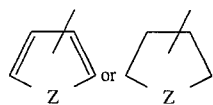

wherein Z is N, O, S, or Se;

a five membered aromatic ring with two N, O, S, or Se heteroatoms optionally having a benzo or pyrido ring fused thereto selected from

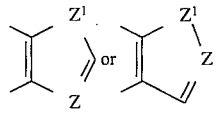

wherein Z and $Z_1$ are independently selected from N, O, S, and Se;

a five membered saturated ring with one or two N, O, S, or Se heteroatoms and an adjacent appended O heteroatom selected from

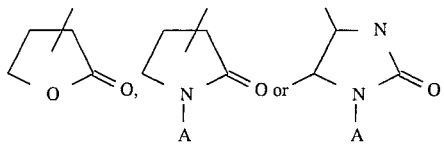

wherein A is selected from hydrogen; straight or branched $(C_1-C_2)$alkyl and $C_6$-aryl; $(C_1-C_4)$alkoxycarbonyl group selected from methoxycarbonyl, ethoxycarbonyl, straght or branched propoxycarbonyl, straight or branched butoxycarbonyl and allyloxycarbonyl; vinyl or substituted vinyl wherein the substitution is selected from $(C_1-C_2)$alkyl group; halogen; $(C_6-C_{10})$aryl group selected from phenyl, α-napthyl, β-napthyl; substituted $(C_6-C_{10})$aryl group wherein the substitution is selected from halo, $(C_1-C_4)$alkoxy, and $(C_1-C_4)$alkoxycarbonyl; halo$(C_1-C_3)$alkyl group; $(C_1-C_4)$alkoxy group; $C_6$-aryloxy group selected from phenoxy or substituted phenoxy where the substitution is selected from halo, and $(C_1-C_4)$alkyl; $(C_7-C_{10})$aralkoxy group; vinyloxy or substituted vinyloxy group wherein the substitution is selected from $(C_1-C_2)$alkyl; $R^a R^b$amino$(C_1-C_4)$alkoxy or $R^a R^b$aminoxy group wherein $R^a R^b$ is selected from a straight or branched $(C_1-C_4)$alkyl selected from methyl, ethyl, n-propyl, 1-methylethyl, n-butyl, 1-methylpropyl, and 2-methylpropyl and when $R=R^4(CH_2)_n CO$— and n=1–4, $R^4$ is selected from amino; $(C_6-C_{10})$aryl group selected from phenyl, α-napthyl or β-napthyl; substituted $(C_6-C_{10})$aryl wherein the substitution is selected from halo, $(C_1-C_4)$alkoxy, trihalo$(C_1-C_3)$alkyl, nitro, amino, cyano, and $(C_1-C_4)$alkoxycarbonyl; acyloxy or haloacyloxy group wherein the acyl or haloacyl is selected from acetyl, propionyl, and chloroacetyl; $(C_1-C_4)$alkoxy group; halo$(C_1-C_3)$alkyl group; $(C_1-C_4)$alkoxycarbonylamino group selected from tert-butoxycarbonylamino, allyloxycarbonylamino, methoxycarbonylamino, ethoxycarbonylamino, and propoxycarbonylamino; $R^a R^b$amino$(C_1-C_4)$alkoxy or $R^a R^b$aminoxy group wherein $R^a R^b$ is selected from a straight or branched $(C_1-C_4)$alkyl selected from methyl, ethyl, n-propyl, 1-methylethyl, n-butyl, 1-methylpropyl, and 2-methylpropyl, $(CH_2)_n$ where n is from 2 to 6, and —$(CH_2)_2 W(CH_2)_2$— wherein W is selected from —N$(C_1-C_3)$alkyl wherein alkyl is straight or branched, —NH, NOB where B is selected from hydrogen or $(C_1-C_4)$alkyl, O, and S; and when $R=R^{4'}(CH_2)_n SO_2$— and n=0, $R^{4'}$ is selected from straight or branched $(C_1-C_2)$alkyl group selected from methyl and ethyl; $(C_6-C_{10})$aryl group selected from phenyl, α-napthyl or β-napthyl; substituted $(C_6-C_{10})$aryl wherein the substitution is selected from halo, $(C_1-C_4)$alkoxy, nitro, and $(C_1-C_4)$alkoxycarbonyl; a heterocycle group selected from a five membered aromatic or saturated ring with one N, O, S, or Se heteroatom optinally having a benzo or pyrido ring fused thereto selected from

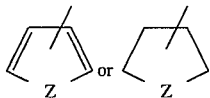

wherein Z is N, O, S, or Se;

a five membered aromatic ring with two N, O, S, or Se heteroatoms optionally having a benzo or pyrido ring fused thereto selected from

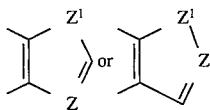

wherein Z and $Z_1$ are independently selected from N, O, S, and Se; and when $R=R^{4'}(CH_2)_nSO_2$— and n=1–4, $R^4$ is selected from hydrogen; straight or branched $(C_1-C_2)$alkyl group selected from methyl and ethyl;

$R^5$ is selected from hydrogen; straight or branched $(C_1-C_3)$alkyl group selected from methyl, ethyl, n-propyl, or 1-methylethyl;

$R^6$ is selected from hydrogen; straight or branched $(C_1-C_3)$alkyl group selected from methyl, ethyl, n-propyl, or 1-methylethyl; with the proviso that $R^5$ and $R^6$ cannot both be hydrogen; or $R^5$ and $R^6$ taken together are —$(CH_2)_2W(CH_2)_2$— wherein W is selected from $(CH_2)_n$ where n=0–1; —NH; —$N(C_1-C_3)$alkyl where alkyl is straight or branched; —$N(C_1-C_4)$alkoxy; O; S; and congeners selected from (L or D)proline, ethyl(L or D)prolinate, morphiline, pyrrolidine and piperidine; or a pharmacologically acceptable organic or inorganic salt or metal complex thereof.

6. The compound according to claim 1 wherein said inorganic salts comprise hydrochloric, hydrobromic, hydroiodic, phosphoric, nitric or sulfate.

7. The compound according to claim 1 wherein said organic salts comprise acetate, benzoate, citrate, cysteine or other amino acids, fumarate, glycolate, maleate, succinate, tartrate, alkylsulfonate or arylsulfonate.

8. The compound according to claim 1 wherein said metal complexes comprise aluminium, calcium, iron, magnesium, manganese and complex salts.

* * * * *